United States Patent
Huang

(10) Patent No.: US 9,511,150 B2
(45) Date of Patent: Dec. 6, 2016

(54) CROSSLINKING REAGENTS, MACROMOLECULES, THERAPEUTIC BIOCONJUGATES, AND SYNTHETIC METHODS THEREOF

(71) Applicant: CellMosaic, Inc., Worcester, MA (US)

(72) Inventor: Yumei Huang, Lexington, MA (US)

(73) Assignee: CellMosaic, Inc., Woburn, MA (US)

( * ) Notice: Subject to any disclaimer, the term of this patent is extended or adjusted under 35 U.S.C. 154(b) by 0 days.

(21) Appl. No.: 14/156,224

(22) Filed: Jan. 15, 2014

(65) Prior Publication Data

US 2015/0017246 A1    Jan. 15, 2015

Related U.S. Application Data

(63) Continuation-in-part of application No. PCT/US2012/047255, filed on Jul. 18, 2012.

(60) Provisional application No. 61/509,296, filed on Jul. 19, 2011, provisional application No. 61/754,571, filed on Jan. 19, 2013.

(51) Int. Cl.
*C07K 17/10* (2006.01)
*A61K 47/48* (2006.01)
*C12N 11/06* (2006.01)
*C07C 43/23* (2006.01)
*C07K 17/14* (2006.01)

(52) U.S. Cl.
CPC ..... *A61K 47/4823* (2013.01); *A61K 47/48092* (2013.01); *A61K 47/48238* (2013.01); *A61K 47/48369* (2013.01); *C07C 43/23* (2013.01); *C07K 17/10* (2013.01); *C07K 17/14* (2013.01); *C12N 11/06* (2013.01)

(58) Field of Classification Search
USPC .............................. 536/43, 44, 47
See application file for complete search history.

(56) References Cited

U.S. PATENT DOCUMENTS

| | | | |
|---|---|---|---|
| 2,258,892 | A | 10/1941 | Harris |
| 7,468,458 | B2 | 12/2008 | Tian et al. |
| 8,907,079 | B2 | 12/2014 | Huang |
| 2004/0157247 | A1 | 8/2004 | Bergmann et al. |
| 2011/0082090 | A1* | 4/2011 | Haag et al. .................. 514/19.3 |
| 2012/0322978 | A1 | 12/2012 | Huang |

FOREIGN PATENT DOCUMENTS

| | | |
|---|---|---|
| GB | 723244 | 2/1955 |
| WO | 2004/031244 A1 | 4/2004 |
| WO | 2004/032971 A | 4/2004 |
| WO | 2006/115312 A1 | 11/2006 |
| WO | 2008/073463 A2 | 6/2008 |
| WO | 2010/080817 A2 | 7/2010 |

OTHER PUBLICATIONS

Trinh; Macromolecular Chemistry and physics; 2015, pp. 1-9.*
Veerkamp, J. H., et al., The Structure of a Mannitol Teichoic Acid from *Bifidobacterium bifidum* ssp. *pennsylvanicum*, Biochimica er Biophysica Acta (BBA)—General Subjects, vol. 755, No. 3, pp. 439-451 (Feb. 22, 1983).
Grazu, V., et al., Novel Bifunctional Epoxy/Thiol-Reactive Support to Immobilize Thiol Containing Proteins by the Epoxy Chemistry, Biomacromolecules, vol. 4, No. 6, pp. 1495-1501 (Nov.-Dec. 2003).
Park, T.E., et al., Selective Stimulation of Caveolae-Mediated Endocytosis by an Osmotic Polymannitol-Based Gene Transporter, Biomaterials, vol. 33, No. 29, pp. 7272-7281 (Oct. 2012).
Mancera, M., et al., New Derivatives of D-Mannaric and Galactaric Acids. Synthesis of a New Stereoregular Nylon 66 Analog from Carbohydrate-Based Monomers Having the D-Manno Configuration, Carbohydr. Res., vol. 338, No. 10, pp. 1115-1119 (May 1, 2003).
Chaveriat, Ludovic, et al., The Direct Synthesis of 6-amino-6-deoxyaldonic Acids as Monomers for the Preparation of Polyhydroxylated Nylon 6, Tetrahedron: Asymmetry, vol. 17, No. 9, pp. 1349-1354 (May 16, 2006).
Hu, Jun, et al., "Sweet Polyesters": Lipase-Catalyzed Condensation-Polymerizations of Alditols, Macromolecules, vol. 39, No. 20, pp. 6789-6792 (Sep. 9, 2006).
Satoh, T., et al., Synthesis of Hyperbranched Carbohydrate Polymers by Ring-Opening Multibranching Polymerization of Anhydro Sugar, Macromol. Biosci., vol. 7, No. 8, pp. 999-1009 (Aug. 7, 2007).
Zhang, Shiyong, et al., Facile Synthesis of Multivalent Water-Soluble Organic Nanoparticles via "Surface Clicking" of Alkynylated Surfactant Micelles, Macromolecules, vol. 43, No. 9, pp. 4020-4022 (2010).
Glacon, V., et al., A New Efficient Way to Alpha, Omega-Diaminoitols by Direct Azidation of Unprotected Itols, Tetrahedron Letters, vol. 37, No. 21, 5 pgs. (1996).

(Continued)

*Primary Examiner* — Pancham Bakshi
(74) *Attorney, Agent, or Firm* — Milstein Zhang & Wu LLC

(57) ABSTRACT

The invention provides novel chemical entities based on sugar alcohols. These new chemical entities are biocompatible and biodegradable. The molecules can be made in a single and pure form. The molecular weights of these molecules range from small (<1000 Da) to large (1000-120,000 Da). The sugar alcohol-based molecules can have functional groups throughout the molecule for crosslinking compounds, such as the preparation of antibody-drug conjugates, or to facilitate the delivery of therapeutic proteins, peptides, siRNA, and chemotherapeutic drugs. Also provided are new conjugate entities prepared through sugar alcohol molecules. Methods of synthesizing sugar alcohol-based molecules and conjugates are also within the scope of the invention.

16 Claims, 12 Drawing Sheets

(56) References Cited

OTHER PUBLICATIONS

Mancera, Manuel, et al., Synthesis of D-Mannitol and L-Iditol Derivatives as Monomers for the Preparation of New Regioregular AABB-Type Polyamides, Carbohydrate Research, vol. 337, No. 7, pp. 607-611 (Apr. 2, 2002).

International Application Serial No. PCT/US2012/047255, International Search Report dated Jun. 6, 2013, 9 pgs.

International Application Serial No. PCT/US2012/047255, International Search Report dated Jun. 6, 2013, 10 pgs.

Clave et al., "A novel heterotrifunctional peptide-based cross-linking reagent for facile access to bioconjugates. Applications to peptide fluorescent labelling and immobilisation," Org. Biomol. Chem., vol. 6, pp. 3065-3078 (2008).

Fancy, "Elucidation of protein-protein interactions using chemical crosslinking or label transfer techniques," Current Opinion in Chemical Biology, vol. 4, pp. 28-33 (2000).

Hecker et al., "A Flexible Method for the Conjugation of Aminooxy Ligands to Preformed Complexes of Nucleic Acids and Lipods," ChemMedChem, vol. 3, pp. 1356-1361 (2008).

Ingallinella et al., "A New Method for Chemoselective Conjugation of Unprotected Peptides to Dauno- and Doxorubicin," Bioorganic & Medicinal Chemistry Letters, vol. 11, pp. 1343-1346 (2001).

International Preliminary Report on Patentability for PCT/US2012/047255 dated Jan. 21, 2014 (28 pages).

Kanoh et al., "Photo-cross-linked small-moleculemicroarrays as chemical genomic tools for dissecting protein-ligand interactions," Chem. Asian. J., pp. 789-797 (2006).

Kurth et al., "Site-Specific Conjugation of a Radioiodinated Phenethylamine Derivative to a Monoclonal Antibody Results in Increased Radioactivity Localization in Tumor," J. Med. Chem., vol. 36, pp. 1255-1261 (1993).

Mikola et al., "Introduction of Aliphatic Amino and Hydroxy Groups to Keto Steroids Using O-Substituted Hydroxylamines," Bioconjugate Chem., vol. 3, pp. 182-186 (1992).

Nishiyama et al., "Synthesis of Fluorescence-Labeled Galβ1-3Fuc and Galβ1-4Fuc as Probes for the Endogenous Glyco-Epitope Recognized by Galectins in Caenorhaditis elegans," Chem. Pharm. Bull., vol. 58, pp. 495-500 (2010).

Resek et al., "A New Photo-Cross-Linking Reagent for the Study of Protein-Protein Interactions," J. Org. Chem., vol. 58, pp. 7598-7601 (1993).

Rose et al., "Natural Peptides as Building Blocks for the Synthesis of Large Protein-like Molecules with Hydrazone and Oxime Linkages," Bioconjugate Chem., vol. 7, pp. 552-556 (1996).

Webb et al., "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," Bioconjugate Chem., vol. 1, pp. 96-99 (1990).

* cited by examiner

FIG. 1. Chemical structures of SA linker and PEG linker
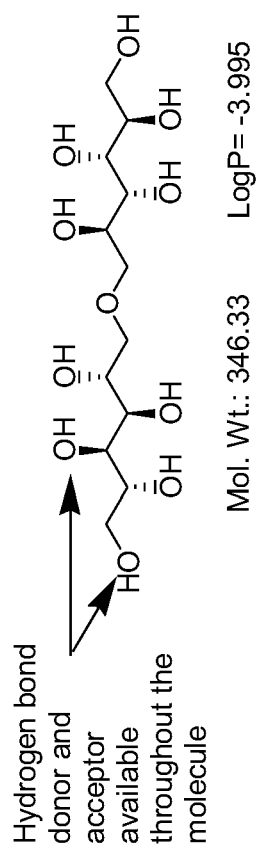
Sugar alcohol based linker or molecule
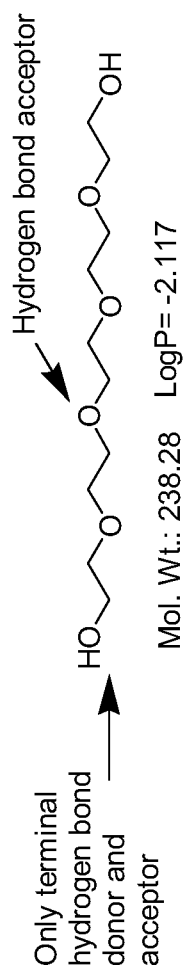
Comparable PEG linker

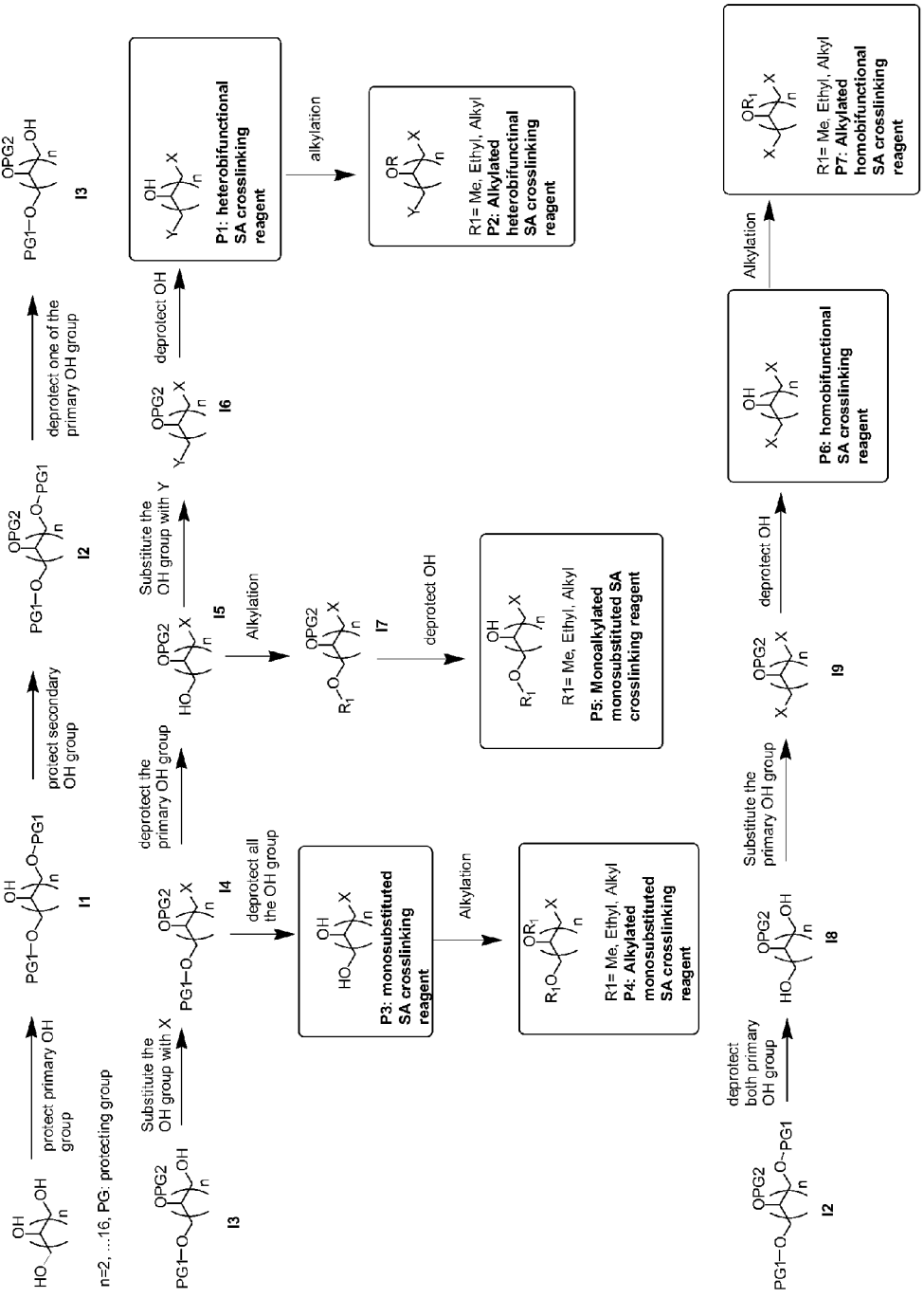
FIG. 2. Methods of synthesizing mono, homobifunctional, and heterobifunctional SA crosslinking reagent

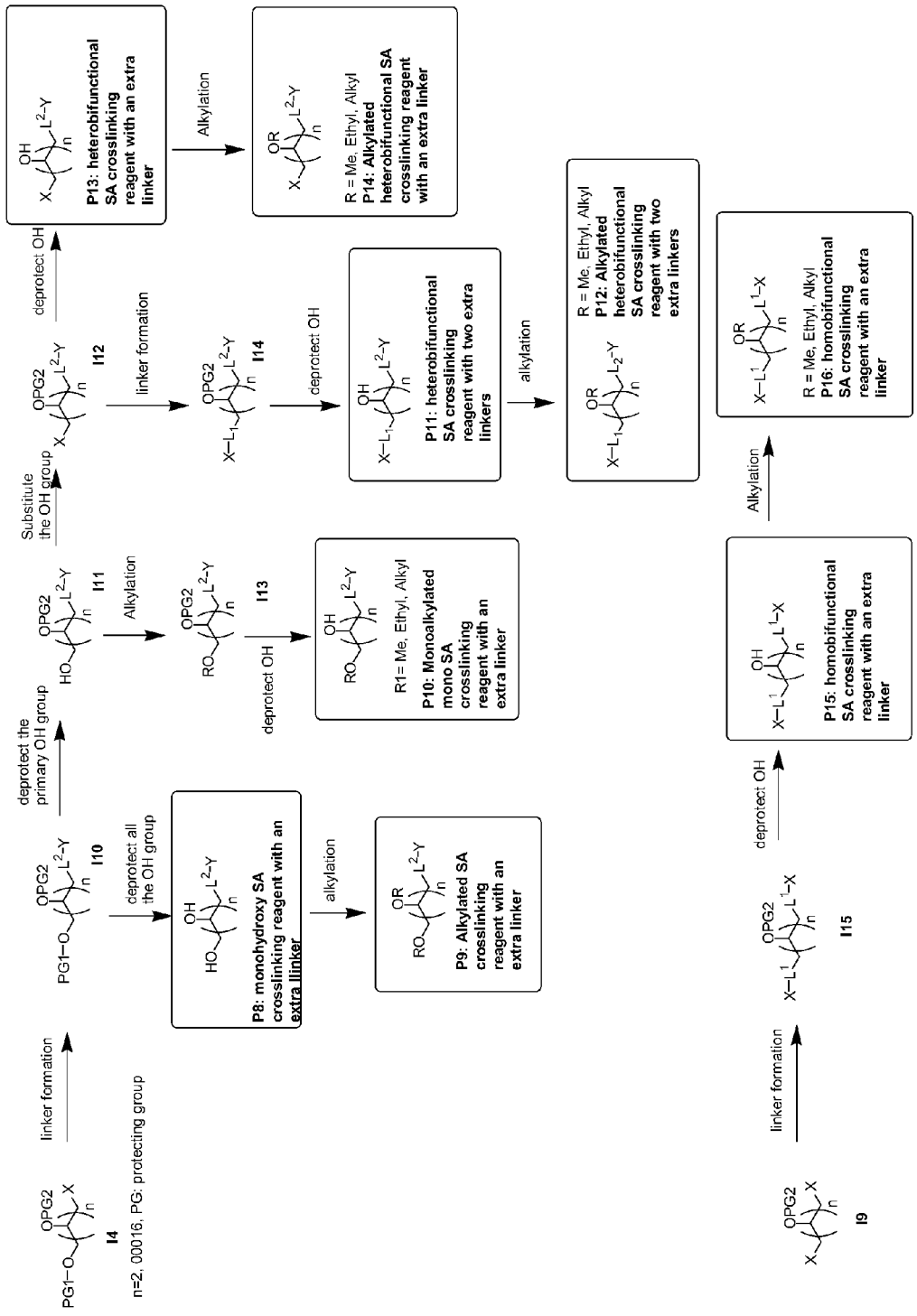
FIG. 3. Methods of synthesizing mono, homobifunctional, and heterobifunctional SA crosslinking reagent with extra linkers

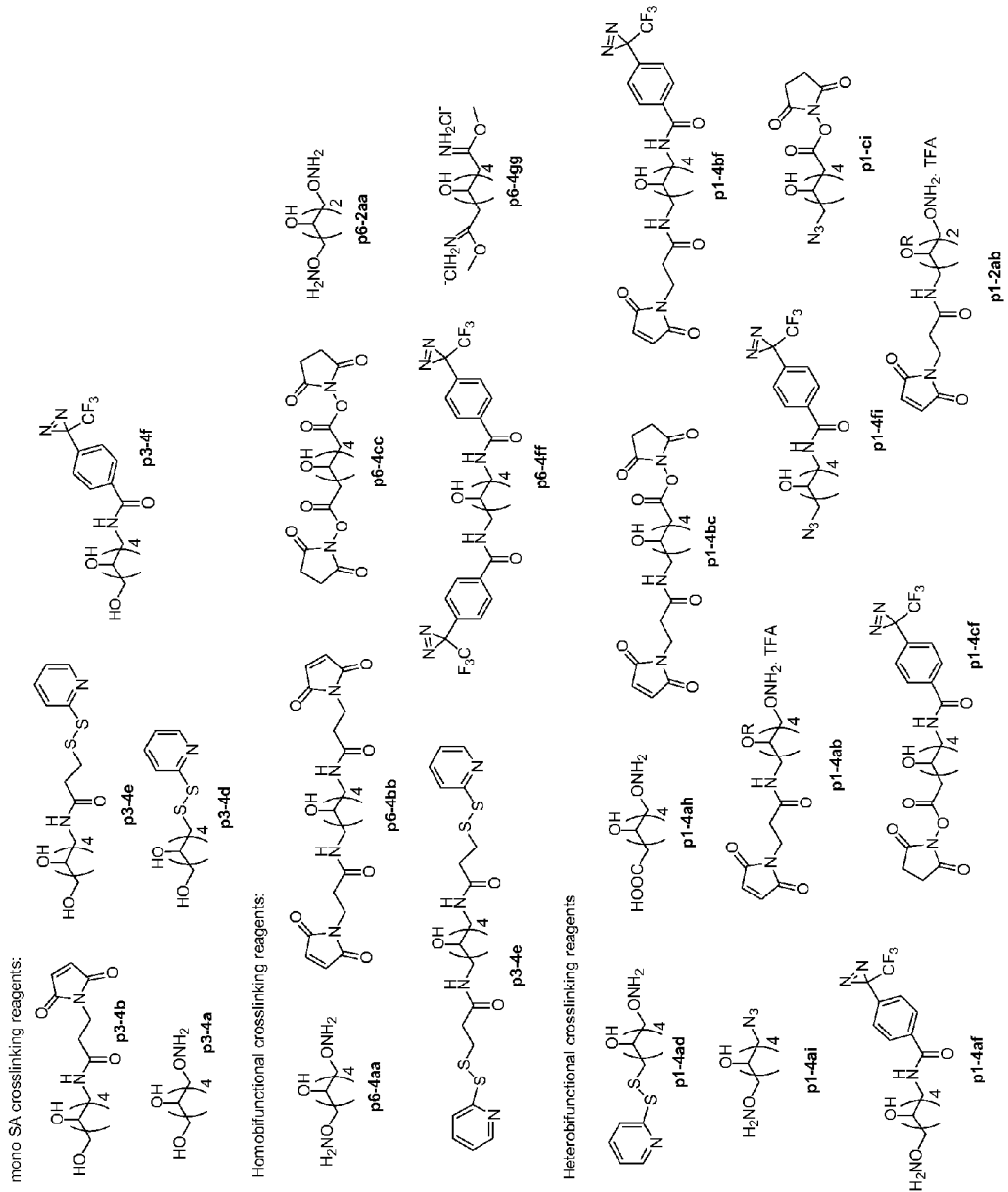
FIG. 4. Examples of useful SA crosslinking reagents

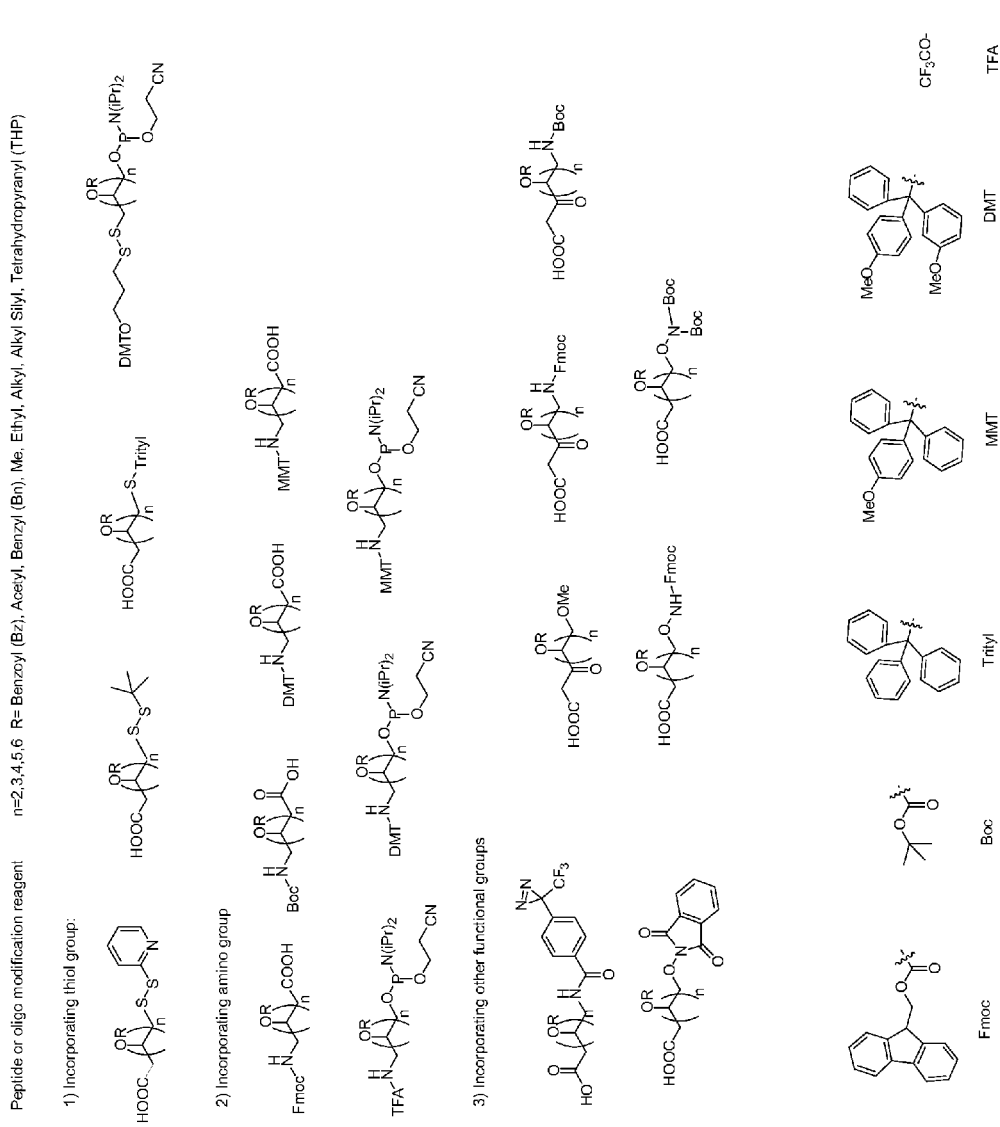
FIG. 5. Examples of useful SA reagents for solid phase peptide and oligo synthesis

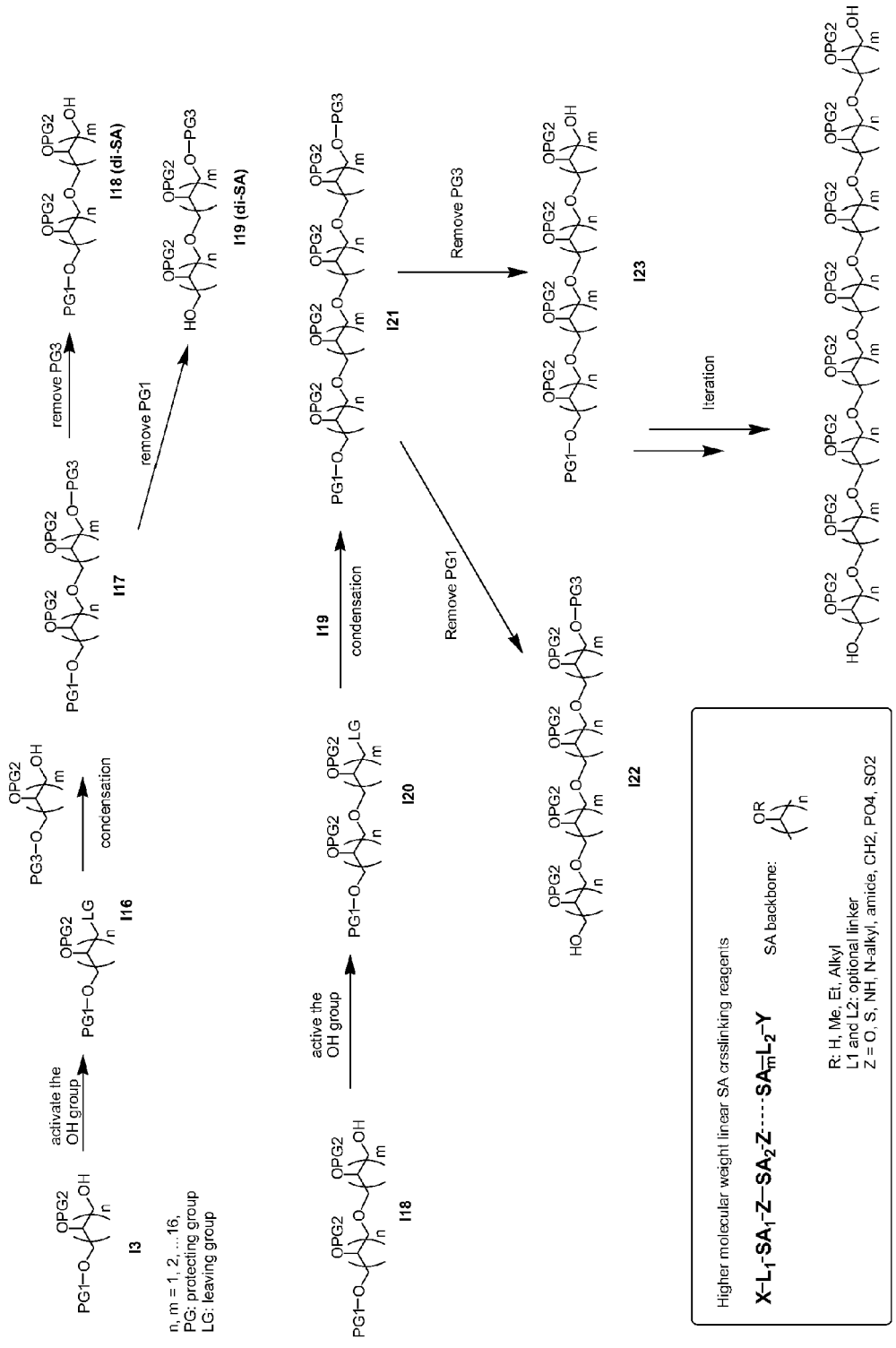
FIG. 6. Methods of synthesizing di-, tetra, and higher molecular weight SA molecule

FIG. 7. MW of linear macro SA molecules based on D-mannitol

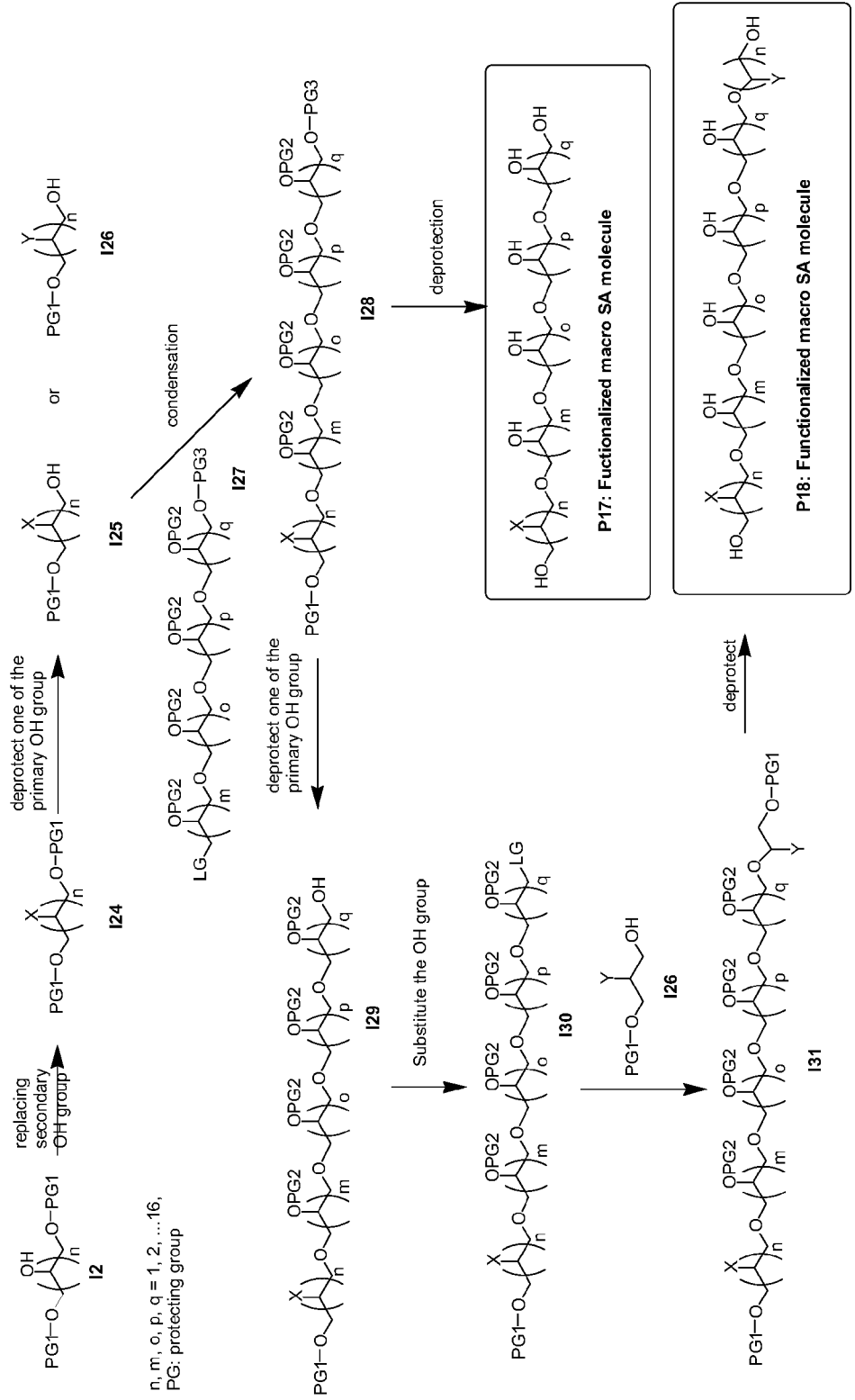
FIG. 8. Incorporating crosslinking group at the side chain of macro SA molecule

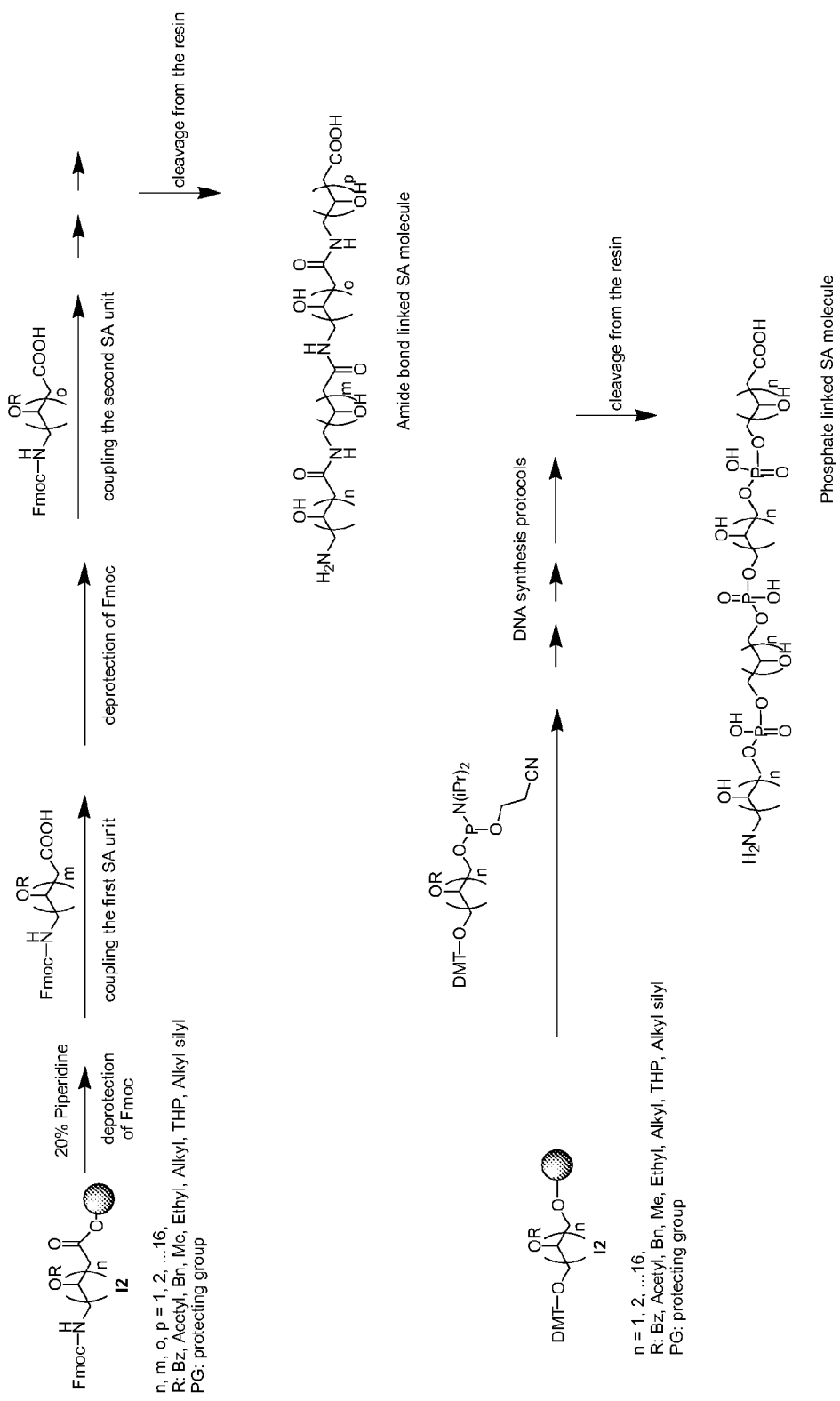
FIG. 9. Examples of linear macro SA molecules synthesized by solid phase

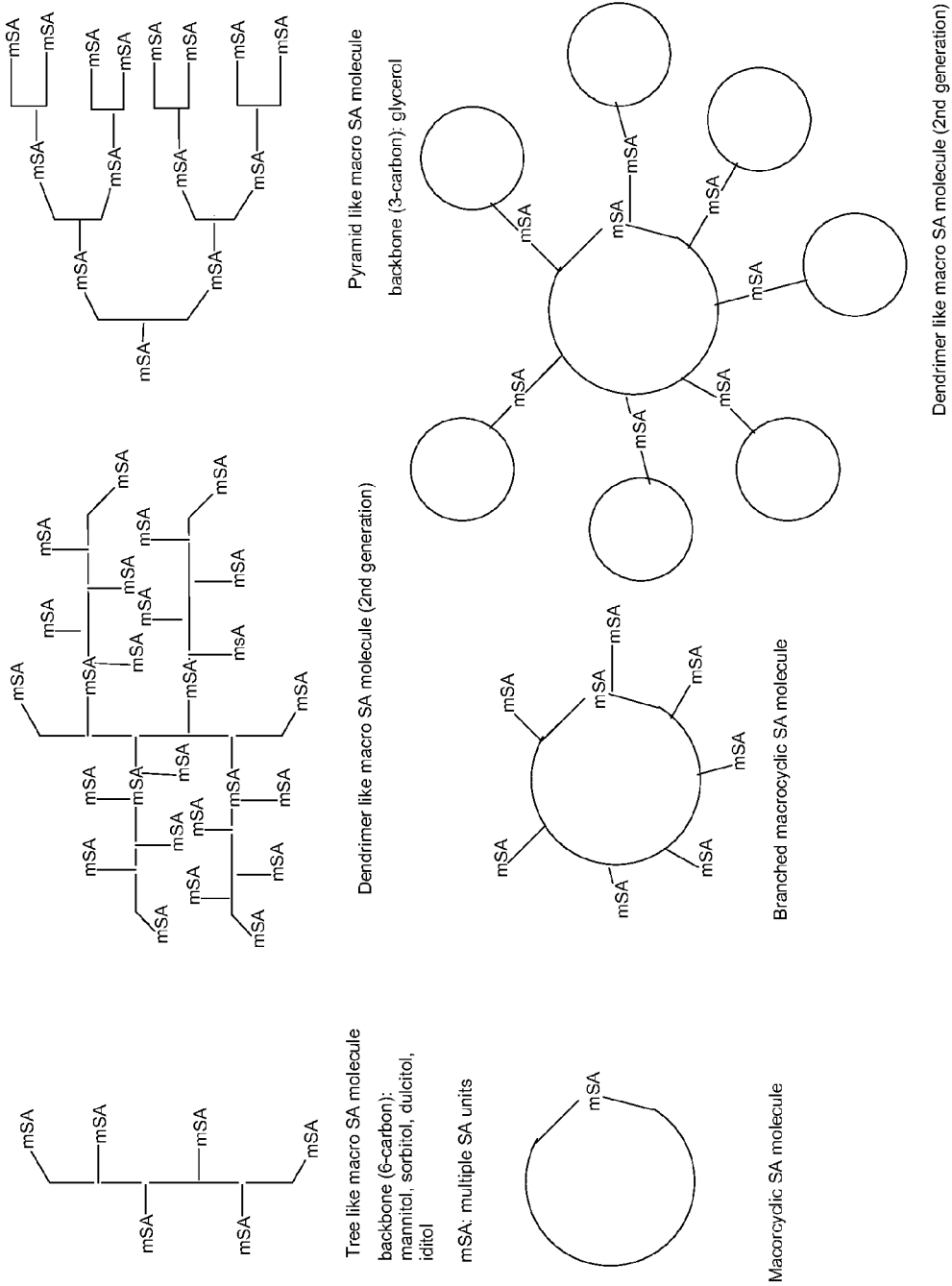
FIG. 10. Configuration of hyperbranched SA macromolecule

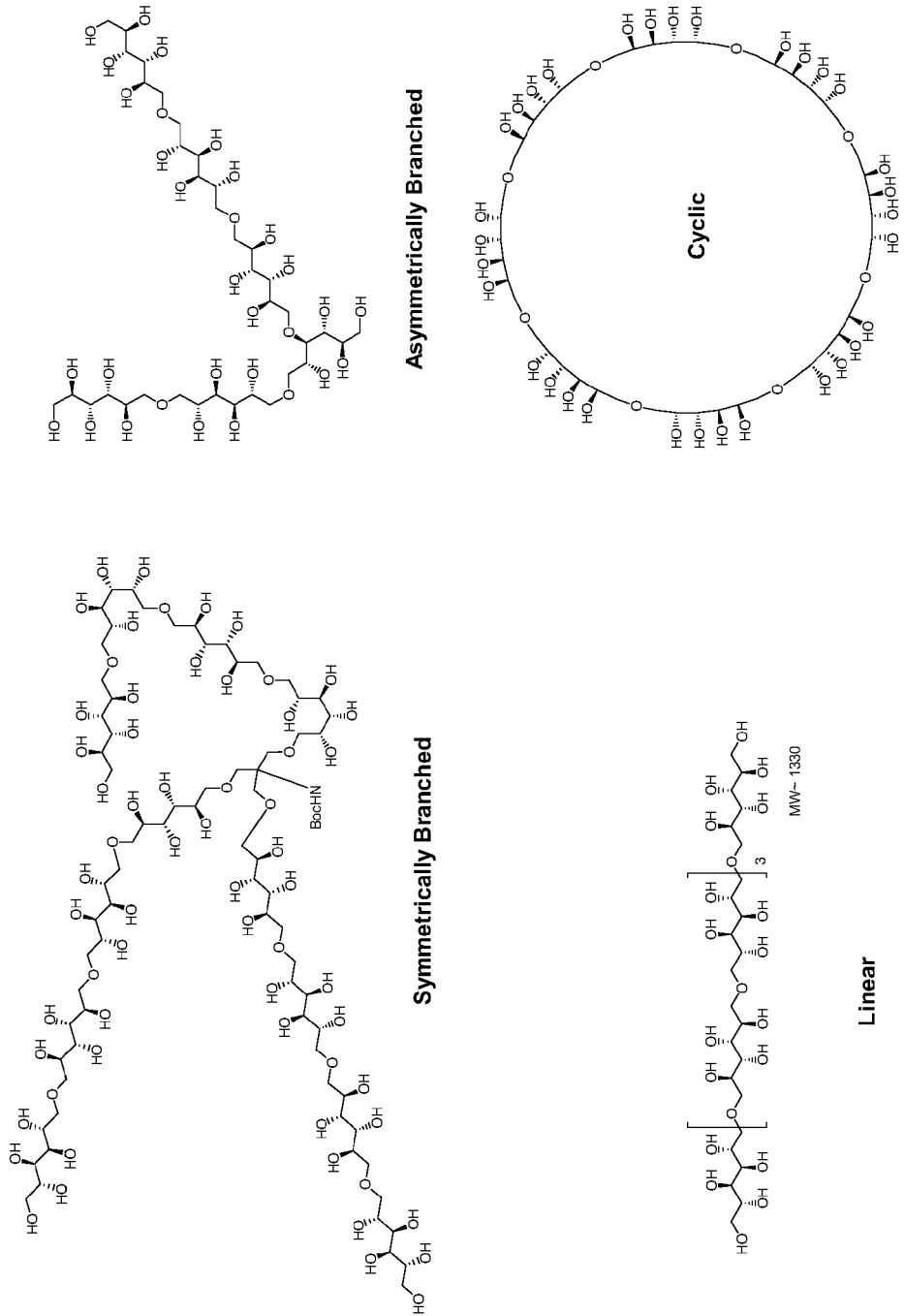
FIG. 11. Some examples of macro SA molecules based on D-mannitol

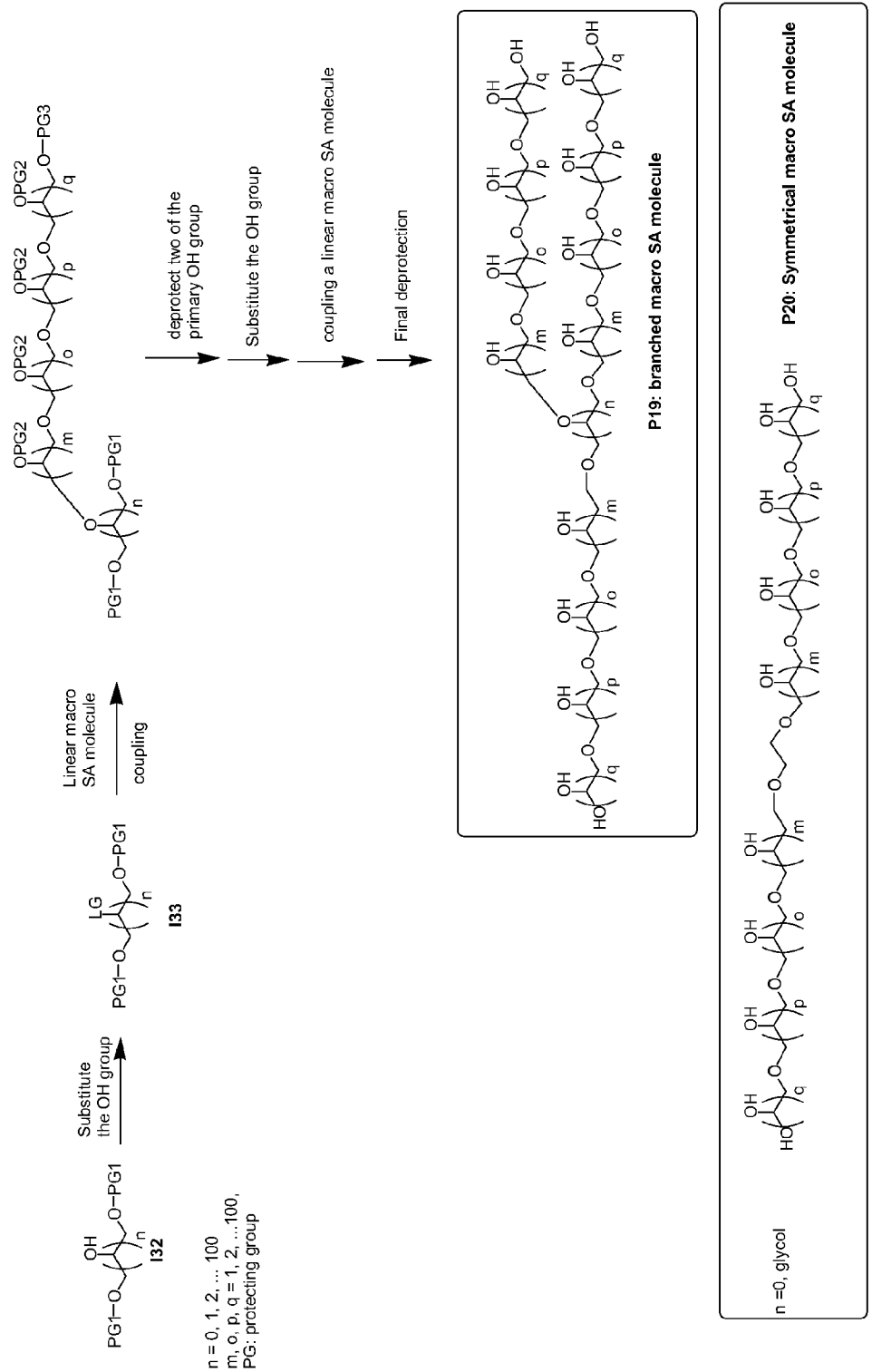
FIG. 12. Synthesis of branched macro SA molecule

CROSSLINKING REAGENTS, MACROMOLECULES, THERAPEUTIC BIOCONJUGATES, AND SYNTHETIC METHODS THEREOF

This application is a Continuation-In-Part of PCT/US2012/047255, filed Jul. 18, 2012, which claims the benefit of U.S. Provisional Application Ser. No. 61/509,296, filed on Jul. 19, 2011. This application also claims the benefit of U.S. Provisional Application Ser. No. 61/754,571, filed Jan. 19, 2013. These applications are hereby incorporated by reference in their entireties.

FIELD OF THE INVENTION

The invention relates to novel sugar alcohol-based crosslinking reagents, macromolecules, therapeutic conjugates, and synthetic methods. More specifically, the invention relates to novel chemical entities that may be used for labeling, conjugation, modification, molecule immobilization, therapeutic or diagnostic agents, and in drug delivery. Furthermore, the invention relates to novel conjugates prepared through new sugar alcohol-based crosslinking reagents and macromolecules.

BACKGROUND

Bioconjugation technologies have been adapted in the biotechnology and pharmaceutical industries for the preparation of drug entities, detection reagents, and formulation strategies (Greg T. Hermanson "Bioconjugate Techniques", 2008, Elsevier Inc.; Christof M. Niemeyer "Bioconjugation Protocols: Strategies and Methods", 2004, Humana Press, Inc.). Bioconjugation is a chemical process that links together two or more biomolecules, including conjugation, labeling, modification, or immobilization of the biomolecules.

SUMMARY OF THE INVENTION

The present invention provides a novel class of molecules based on sugar alcohol (SA), their applications in conjugate preparation, and methods for synthesizing these SA-based molecules. The invention is based, in part, on SAs with better hydrophilicity and higher hydrodynamic volume than polyethyleneglycol (PEG). The invention is also based, in part, on SAs that can be derivatized and modified to allow for the incorporation of various functional groups and activation groups to produce SA crosslinking reagents. The invention is also based, in part, on SAs that can be further reacted with various other SAs to prepare single and pure high molecular weight (MW) compounds (SA macromolecules), including, for example, linear SA macromolecules and sophisticated two- or three-dimensional architectures, such as branched, cyclic, and hyperbranched SA macromolecules.

The advantages of SA macromolecule compounds of the invention compared to existing compounds include, for example, (i) super hydrophilicity conferred from SAs that can be used to modulate biomolecule properties after conjugation; (ii) the ability to make crosslinking reagents with versatile functional groups; (iii) the availability of single and pure higher MW compounds; (iv) multivalent conjugation sites allowing higher loading of drug molecules; (v) an improved hydrodynamic radius; (vi) biodegradablity and biocompatibility; and (vii) natural, inexpensive starting materials.

In one aspect, the invention generally relates to a conjugate having a chemical structure selected from the group consisting of:

$$M_1\text{-}(L\text{-}B)_u \qquad \text{Formula (I), and}$$

$$B\text{-}(L\text{-}M_1)_u \qquad \text{Formula (II)}$$

wherein
each $M_1$ is independently selected from the group consisting of a protein, an enzyme, an antibody, an antibody fragment, a polypeptide, an oligonucleotide, an oligonucleotide analog, a polysaccharide;
each B is a single MW modified sugar alcohol polymer, comprising:
from 2 to about 2000 sugar alcohol monomer(s);
wherein each monomer has from 3 to about 14 —$OR^1$ groups;
wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of:
a $R^2$ and, a structure of —$V_1$—$R^2$—$V_2$—, wherein:
$V_1$ and $V_2$ are independently selected from the group consisting of:
Diels-Alder adduct, a 1,3-dipolar adduct, —C(=$G^2$)-$G^1$-, -$G^1$-C(=$G^2$)-, -$G^3$-, $G^1$-C(=$G^2$)-$G^1$-, —S—S—, —S—($CH_2$)$_2$—S($O$)$_2$—, —S($O$)$_2$—($CH_2$)$_2$—S—, —S($O$)$_2$—N($R^3$)—, —N($R^3$)—S($O$)$_2$—, —C(O)—NH—NH—$CH_2$—, —C(O)—NH—N=CH—, —CH=N—NH—C(O)—, —$CH_2$—NH—NH—C(O)—, —N($R^3$)—S($O$)$_2$—N($R^3$)—, —C(O)—NH—CH($CH_2$SH)—, —N=CH—, —NH—$CH_2$—, —NH—C(O) —$CH_2$—C(O)—NH—, —CH=N-$G^4$-, —$CH_2$—NH-$G^4$-, -$G^4$—NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

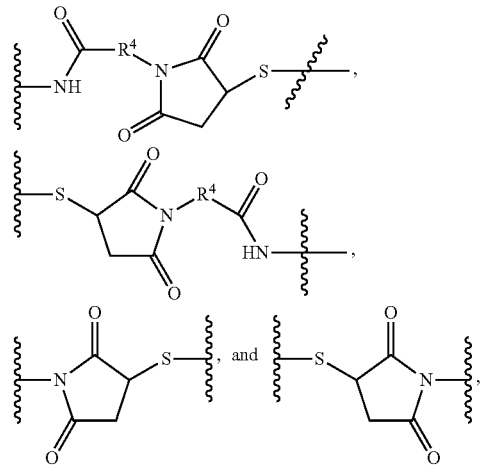

wherein:
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$—$CH_2$—, optionally substituted alicyclyl, heteroalicyclyl, aryl, a peptide, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl;
each $R^8$ is independently $C_1$-$C_8$ alkyl;
u is an integer from 1 to about 20; and, In another aspect, the invention generally relates to a conjugate A conjugate having chemical structural Formula (III):

$$(M_2\text{-}L)_q\text{-}B \quad \quad \text{(III)}$$

wherein
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, and a small molecule,
each B is a single MW modified sugar alcohol polymer, comprising:
from 2 to about 2000 sugar alcohol monomer(s);
wherein each monomer has from 3 to about 14 —$OR^1$ groups;
wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of:
a $R^2$ and, a structure of —$V_1$—$R^2$—$V_1$—, wherein:
$V_1$ and $V_2$ are independently selected from the group consisting of:
Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—$(CH_2)_2$—$S(O)_2$—, —$S(O)_2$—$(CH_2)_2$—S—, —$S(O)_2$—$N(R^3)$—, —$N(R^3)$—$S(O)_2$—, —C(O)—NH—NH—$CH_2$—, —C(O)—NH—N=CH—, —CH=N—NH—C(O)—, —$CH_2$—NH—NH—C(O)—, —$N(R^3)$—$S(O)_2$—$N(R^3)$—, —C(O)—NH—CH($CH_2SH$)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

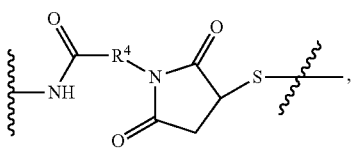

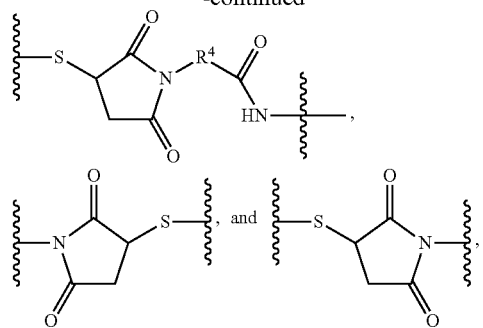

wherein:
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$—$CH_2$—, optionally substituted alicyclyl, heteroalicyclyl, aryl, a peptide, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl;
each $R^8$ is independently $C_1$-$C_8$ alkyl;
q is an integer from 1 to about 100.

In yet another aspect, the invention generally relates a conjugate having a chemical structure selected from the group consisting of:

$$(M_1)_q\text{-}L\text{-}(B\text{-}(L\text{-}M_2)_k)_u \quad \quad \text{(IV) and}$$

$$(M_1\text{-}L)_q\text{-}(B\text{-}(L\text{-}M_2)_k)_u \quad \quad \text{(V) and}$$

$$M_1\text{-}(L\text{-}B\text{-}(L\text{-}M_2)_k)_u \quad \quad \text{(VI)}$$

wherein
each $M_1$ is independently selected from the group consisting of a protein, an enzyme, an antibody, an antibody fragment, a polypeptide, avidin, streptavidin, an oligonucleotide, an oligonucleotide analog, a polysaccharide;
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a small molecule, and another biologically active molecule;
each B is a single MW modified sugar alcohol polymer, comprising:
from 2 to about 2000 sugar alcohol monomer(s);
wherein each monomer has from 3 to about 14 —$OR^1$ groups;
wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

each L is independently selected from the group consisting of:
a $R^2$ and, a structure of —$V_1$—$R^2$—$V_2$—, wherein:
  $V_1$ and $V_2$ are independently selected from the group consisting of:
    Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—, wherein:
each $G^1$ is independently selected from NH, O, and S;
each $G^2$ is independently O or S;
each $G^3$ is independently selected from S, O, N$R^3$, and SO$_2$;
each $G^4$ is independently O or N$R^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;
each R8 is independently $C_1$-$C_8$ alkyl;
u is an integer from 1 to about 100;
q is an integer from 1 to about 100; and,
k is 0 or an integer from 1 to about 20.

In yet another aspect, the invention generally relates to a conjugate having chemical selected from the group consisting of:

S-(L-B-(L-$M_1$)$_k$)$_u$ (VII)

S-(L-B-L-($M_1$)$_k$)$_u$ (VIII)

S-(L-B-(L-$M_2$)$_k$)$_u$ (IX)

S-(L-B-L-($M_2$)$_k$)$_u$ (X)

wherein
S comprises a solid support;
each $M_1$ is independently selected from the group consisting of a protein, an enzyme, an antibody, an antibody fragment, a polypeptide, avidin, streptavidin, an oligonucleotide, an oligonucleotide analog, a polysaccharide;
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a small molecule, and another biologically active molecule;
each B is a modified sugar alcohol polymer, comprising:
  from 2 to about 2000 sugar alcohol monomer(s);
    wherein each sugar alcohol monomer has from 3 to about 14 —O$R^1$ groups;
      wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
wherein each L is independently selected from the group consisting of a $R^2$ and —$V_1$—$R^2$—$V_2$—, wherein:
  $V_1$ and $V_2$ are independently selected from the group consisting of:
    Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—, wherein:
  each $G^1$ is independently selected from NH, O, and S;
  each $G^2$ is independently O or S;
  each $G^3$ is independently selected from S, O, $NR^3$, and $SO_2$;
  each $G^4$ is independently O or $NR^3$;
  each $R^2$ is independently selected from a bond, $C_1$-$C_{12}$ alkyl, —$(CH_2CH_2O)_{1-10}$—, —$(CH_2CH_2O)_{1-10}$—$CH_2$—, optionally substituted alicyclyl, heteroalicyclyl, aryl, a peptide, and a peptidomimetic oligomer;
  each $R^3$ is independently selected from hydrogen, $C_1$-$C_8$ alkyl, —$(OCH_2CH_2)_{1-3}$, optionally substituted alicyclyl, and optionally substituted heteroalicyclyl;
  each $R^8$ is independently $C_1$-$C_8$ alkyl;
  u is an integer from 1 to about 500; and,
  k is 0 or an integer from 1 to about 20.

In yet in another aspect, the invention is generally relates to a single MW compound having a linear, branched or macrocyclic multimer sugar alcohol comprising three or more monomeric sugar alcohol unit $B^1$; and
  each monomeric sugar alcohol unit is bound to one or more other monomeric units through a linking group W formed by a reaction between the X, Y or Z portion of one monomeric unit with the X, Y or Z of another monomeric unit;
wherein
each $B^1$ has the chemical structural Formula XV:

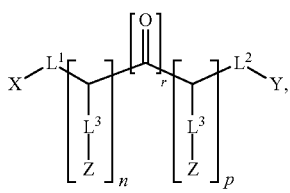

(XV)

wherein for each $B^1$, independently:
  each of n and p is independently selected from 0 and an integer selected from 1 to about 12; and n+p is between 1 and 12;
  r is 0 or 1;
  each of X, Y and Z is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-Mesyl, —O-Tosyl, —NH—C(=O)—$CH_2$—O-Mesyl, —NH—C(=O)—$CH_2$—O-Tosyl, —SH, —S—S-tBuyl, —SR7, —$SR^5$, —S—S—$R^8$, —S(=O)$_2$-J, —$NH_2$, —$NHR^5$, —N($R^5$)$R^5$, —$NHR^7$, —NH-Fmoc, —NH-Boc, —C(=O)H, —C(=O)—$R^5$, —C(=O)OH, —N=C=S, —N=C=O, —C≡C—$R^5$, —N=N$^+$=N$^-$, —O—$NH_2$, —O—NH-Fmoc, —O—NH-Boc, —O—N-(Boc)$_2$, —O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=NH$^2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group,;
  each $R^5$ is independently selected from hydrogen, $C_1$-$C_8$ alkyl, alicyclyl, heteroalicyclyl, benzyl or aryl, wherein any ring in $R^5$ is optionally substituted;
  each $R^6$ is independently selected from benzoyl, acetyl, benzyl, $C_1$-$C_8$ alkyl silyl, tetrahydropyranyl, tetrahydrofuranyl, and tetrahydrothiofuranyl;
  each $R^7$ is independently selected from trityl, MMT, and DMT;
  each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
  each J is independently selected from Cl, Br and I
  each of $L^1$, $L^2$, and $L^3$ is independently a $R^2$ or —$R^9$—V—$R^2$—*, wherein:
    "*" represents a portion of $L^1$, $L^2$, and $L^3$ bound to X, Y, S, $M_1$ or $M_2$, or a Z, respectively;
  each V and W are independently selected from the group consisting of Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S(O)$_2$—, —S(O)$_2$—$(CH_2)_2$—S—, —S(O)$_2$—N($R^3$)—, —N($R^3$)—S(O)$_2$—, —C(O)—NH—NH—$CH_2$—, —C(O)—NH—N=CH—, —CH=N—NH—C(O)—, —$CH_2$—NH—NH—C(O)—, —N($R^3$)—S(O)$_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)(O$^-$)—NH—, —NH—P(=O)(O$^-$)—O—, —$CH_2$—CH($NH_2$)—$CH_2$—S—, —S—$CH_2$—CH($NH_2$)—$CH_2$—, —O—P(=O)(O$^-$)—O—, —O—P(=O)(S$^-$)—O—, and —O—P(=S)(S$^-$)—O—,

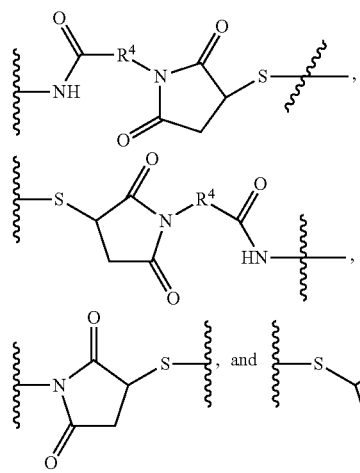

wherein:
  each $G^1$ is independently selected from NH, O, and S;
  each $G^2$ is independently O or S;

each $G^3$ is independently selected from S, O, $NR^3$, and $SO_2$;

each $G^4$ is independently O or $NR^3$;

each $R^2$ is independently selected from a bond, $C_1$-$C_{12}$ alkyl, —$(CH_2CH_2O)_{1-10}$—, —$(CH_2CH_2O)_{1-10}$—$CH_2$13, optionally substituted alicyclyl, heteroalicyclyl, aryl, a peptide, and a peptidomimetic oligomer;

each $R^3$ is independently selected from hydrogen, $C_1$-$C_8$ alkyl, —$(OCH_2CH_2)_{1-3}$, optionally substituted alicyclyl, and optionally substituted heteroalicyclyl;

each $R^8$ is independently $C_1$-$C_8$ alkyl;

each $R^9$ is a bond or —$CH_2$—;

and at least in one of the $B^1$ unit each -$L^3$-Z portion is —$OR^1$; wherein each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

at least in one of the $B^1$ unit, n+p+r is greater than 1.

In yet another aspect, the invention is generally relates to a monomeric sugar alcohol having the chemical structural Formula XXVI:

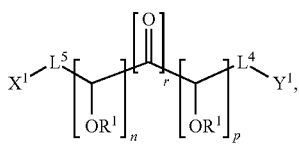

(XXVI)

each of n and p is independently selected from 0 and an integer selected from 1 to about 12; and n+p is between 2 and 12;

r is 0 or 1;

each of $X^1$ is independently selected from —OH, -J, —C(=O)—$CH_2$-J, —$OR^5$, —S—S—$R^8$, —NH—C(=O)—$CH_2CH_2$—S—S—$R^8$, —S—C(=O)—$CH_3$, —C(=O)H, —C(=O)—$R^5$, —C(=O)OH, —C≡C—$R^5$, —N=$N^+$=$N^-$, —O—$NH_2$, —O—NH-Fmoc, —O—NH-Boc, —O—N-$(Boc)_2$, —O—N(-phthalimidyl), —C(=O)—NH—$NH_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, a imidoester, a maleimide, a phosphoramidite;

each of $Y^4$ is independently selected from —S—S-tButyl, —$SR^7$, —S—S—$R^8$, —NH—C(=O)—$CH_2CH_2$—S—$SR^8$, —$NHR^7$, —NH-Fmoc, —NH-Boc, —O—$NH_2$, —O—NH-Fmoc, —O—NH-Boc, —O—N-$(Boc)_2$, —O—N(-phthalimidyl), an optionally substituted trifluoromethylphenyldiazirine, an optionally substituted N-hydroxysuccinimide ester, a imidoester, a maleimide;

each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from Cl, Br, and I $L^4$ and $L^5$ is independently selected from a bond, —$CH_2$—*, —C(=O)—NH—$C_{1-8\ alkyl}$—*, —$CH_2$—NH—C(=O)—$C_{1-8\ alkyl}$—*, —$CH_2$—C(=O)—NH—$C_{1-8\ alkyl}$—*;

"*" represents a portion of $L^4$ and $L^5$ bound $X^1$ or $Y^1$;

In yet another aspect, the invention is generally relates to a dimeric sugar alcohol having the chemical structural Formula XVIII:

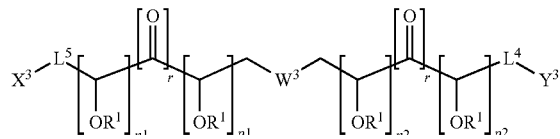

(XXVIII)

each of n1, n2, p1, and p2 is independently selected from 0 and an integer selected from 1 to about 12; and n1+p2 is between 1 and 12, n2+p2 is between 2 and 12;

r is 0 or 1;

wherein $W^3$ is selected from —S—, —O—, —NH—, —$NC_1$-$C_6$alkyl-, —C(=O)NH—, —NHC(=O)—, —S(=O)—, —$S(=O)_2$, —$P(=S)_2O$—, and —P(=S)(=O)O—.

each of $X^3$ is independently selected from —OH, -J, —C(=O)—$CH_2$-J, —$OR^5$, —S—S—$R^8$, —NH—C(=O)—$CH_2CH_2$—S—S—$R^8$, —S—C(=O)—$CH_3$, —C(=O)H, —C(=O)—$R^5$, —C(=O)OH, —C≡C—$R^5$, —N=$N^+$=$N^-$, —O—$NH_2$, —O—NH-Fmoc, —O—NH-Boc, —O—N-$(Boc)_2$, —O—N(-phthalimidyl), —C(=O)—NH—$NH_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, a imidoester, a maleimide, a phosphoramidite;

each of $Y^3$ is independently selected from —S—S-tButyl, —$SR^7$, —S—S—$R^8$, —NH—C(=O)—$CH_2CH_2$—S—S—$R^8$, —$NHR^7$, —NH-Fmoc, —NH-Boc, —O—$NH_2$, —O—NH-Fmoc, —O—NH-Boc, —O—N-$(Boc)_2$, —O—N(-phthalimidyl), an optionally substituted trifluoromethylphenyldiazirine, an optionally substituted N-hydroxysuccinimide ester, a imidoester, a maleimide;

each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

each $R^5$ is independently selected from hydrogen, $C_1$-$C_8$ alkyl, alicyclyl, heteroalicyclyl, benzyl or aryl, wherein any ring in $R^5$ is optionally substituted;

each R⁶ is independently selected from benzoyl, acetyl, benzyl, $C_1$-$C_8$ alkyl silyl, tetrahydropyranyl, tetrahydrofuranyl, and tetrahydrothiofuranyl;

each R⁷ is independently selected from trityl, MMT, and DMT;

each R⁸ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from Cl, Br, and I

L⁴ and L⁵ is independently selected from a bond, —CH₂—*, —C(=O)—NH—$C_{1-8\ alkyl}$—*, —CH₂—NH—C(=O)—$C_{1-8\ alkyl}$—*, —CH₂—C(=O)—NH—$C_{1-8\ alkyl}$*, "*" represents a portion of L⁴ and L⁵ bound X³ or Y³

In another aspect, the invention is generally relates to a compound having the structure

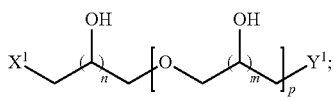

wherein n is an integer from 2 to about 8;

m is an integer from 1 to about 8;

p is an integer from about 1 to about 2000;

each of X¹ is selected from the group consisting of:

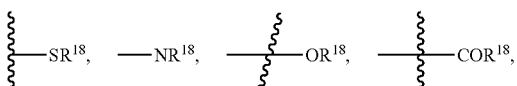

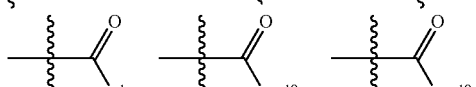

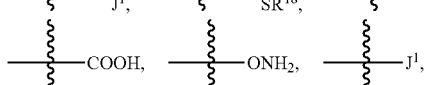

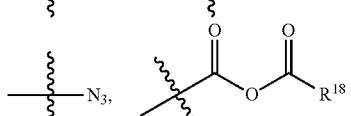

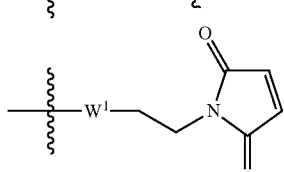

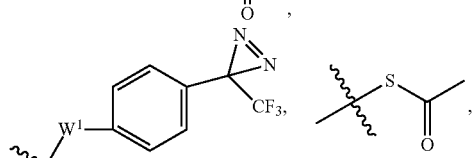

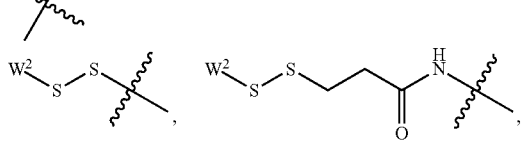

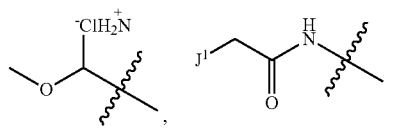

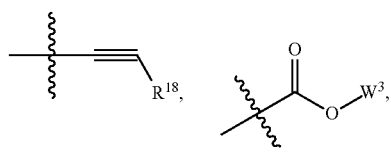

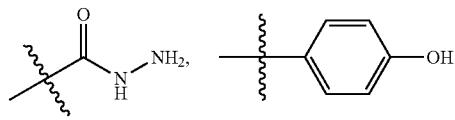

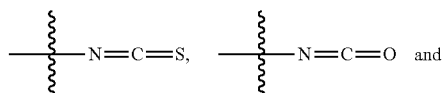

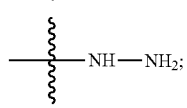

each Y¹ is selected from the group consisting of:

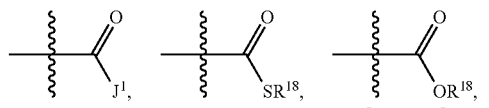

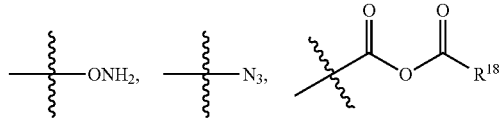

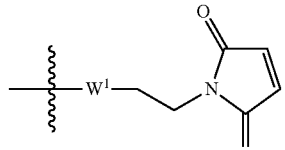

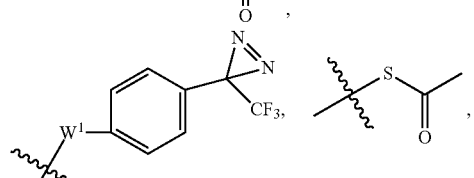

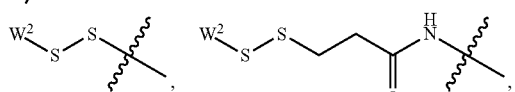

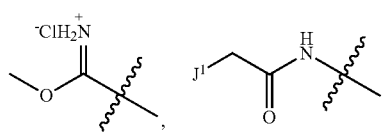

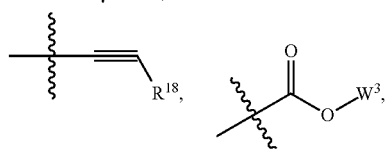

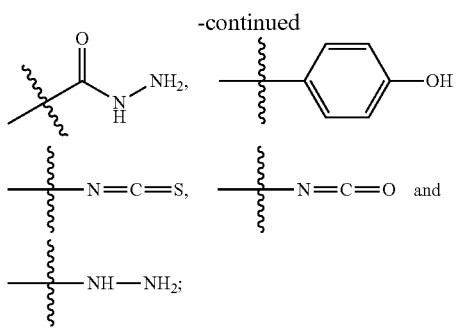

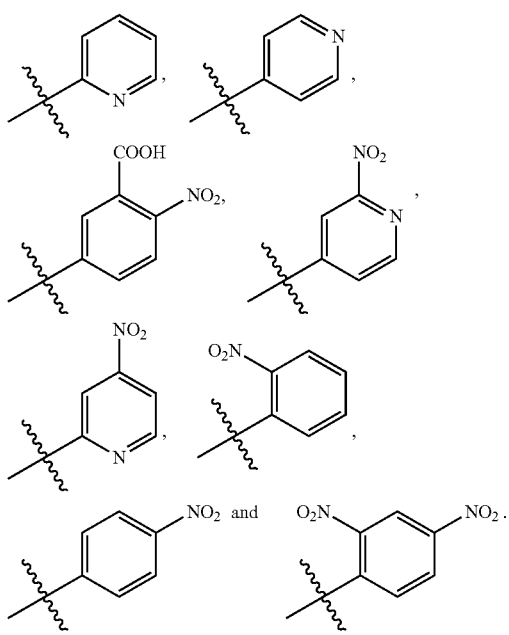

Each of $W^3$ is independently selected from the group consisting of

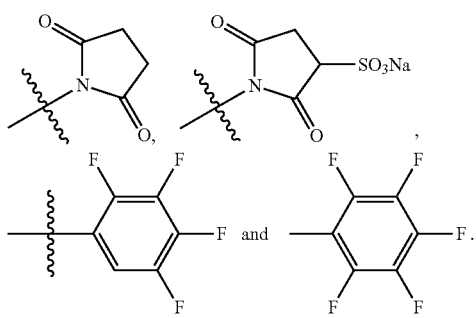

each of $W^1$ is selected from the group consisting of —C(=O)—NH—, —NH—C(=O)—,
each of $J^1$ is selected from the group consisting of Cl, Br and I;
$R^{18}$ is selected from the group consisting of hydrogen, $C_{1-8\ alkyl}$; alicyclyl, heteroalicyclyl, benzyl or aryl, wherein any ring in $R^{18}$ is optionally substituted
each of $W^2$ is independently selected from the group consisting of In one aspect, the invention is generally relates to a sugar alcohol-derived compound having the structure.

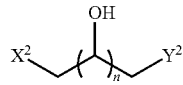

wherein n is an integer selected from about 2 to about 8;

$X^2$ is a chemical- or photocrosslinking group selected from the groups consisting of:

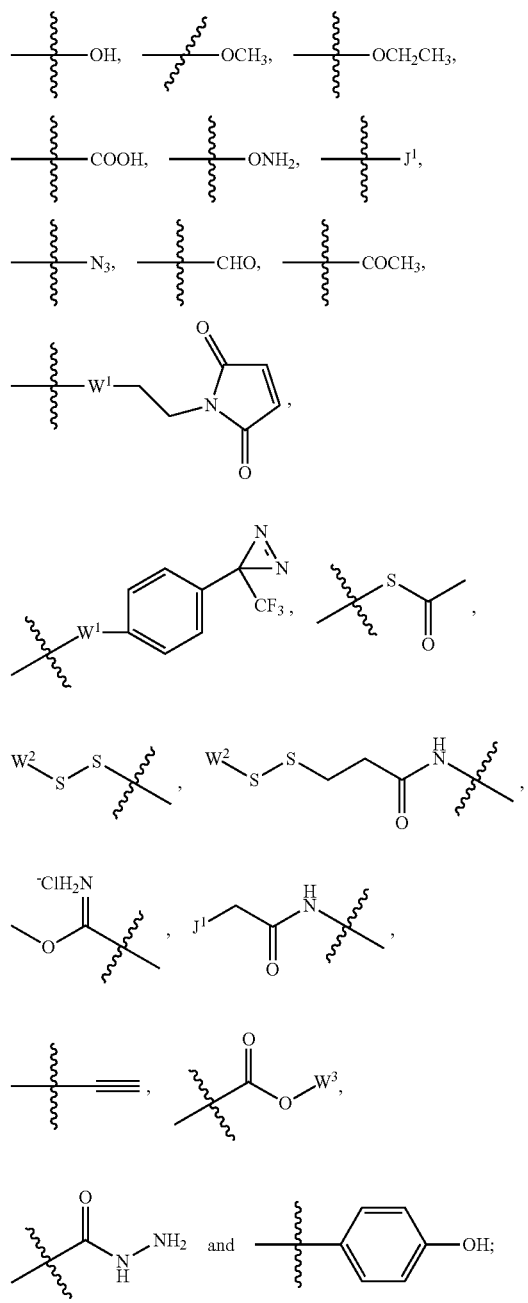

$Y^2$ is a chemical- or photocrosslinking group selected from the group consisting of:

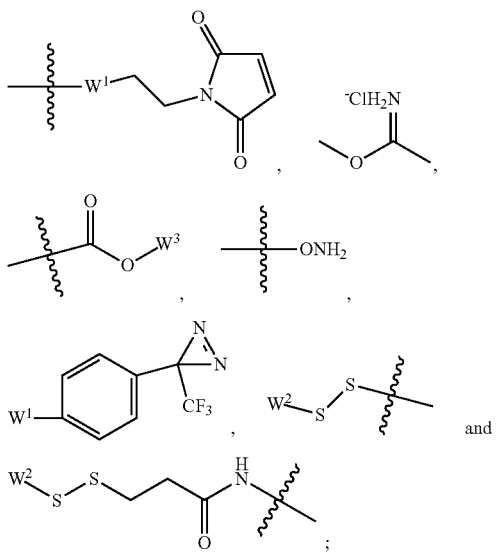

$W^1$ is an independent linker selected from the group consisting of —C(=O)—NH—, and, —NH—C(=O)—;

Each of $J^1$ is independently selected from Cl, Br and I;

Each of $W^2$ is independently selected from the group consisting of

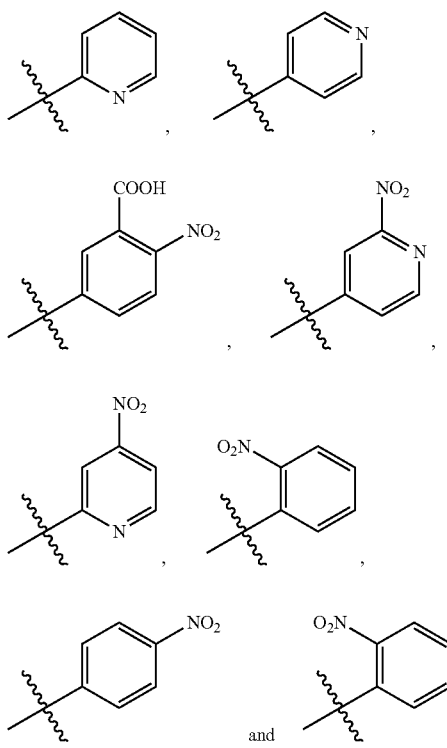

Each of $W^3$ is independently selected from the group consisting of

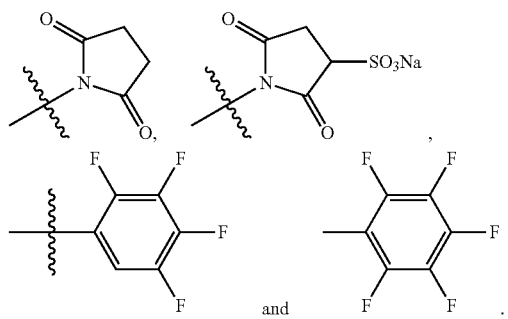

In yet another aspect, the invention is generally relates to a compound having the structure.

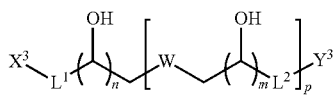

wherein n is an integer selected from 2 to about 8;
m is an integer selected from 1 to about 8;
p is an integer selected from 2 to about 2000;
wherein each W is independently selected from —S—, —NH—, —O—, —NC$_1$-C$_6$alkyl-, —C(=O)NH—, —NHC(=O)—, —S(=O)—, —S(=O)$_2$—, —P(=O)$_2$O—, —P(=S)$_2$O—, —C(=O)O— and —P(=S)(=O)O—.

each of $X^3$ and $Y^3$ is independently a chemical- or photocrosslinking group selected from the group consisting of

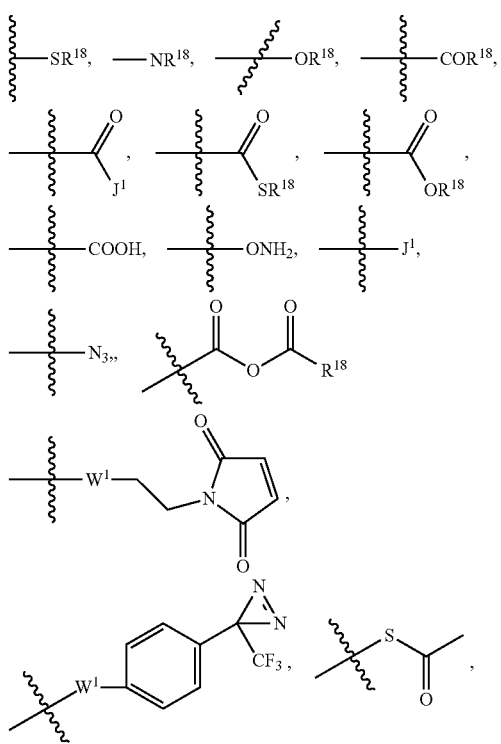

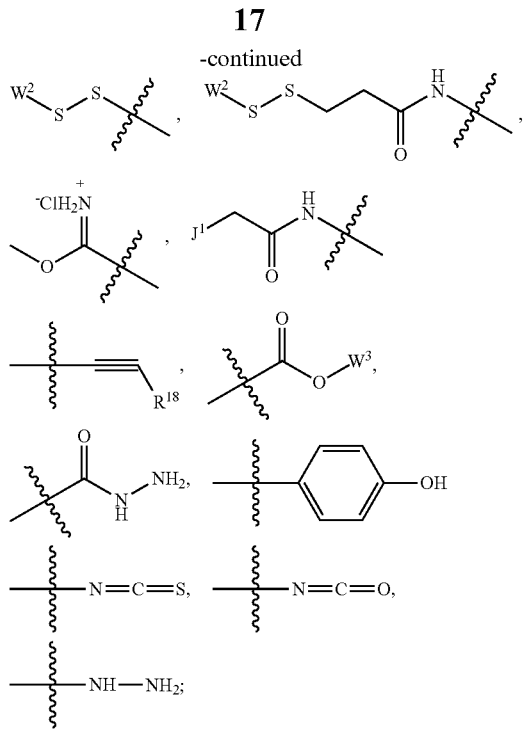

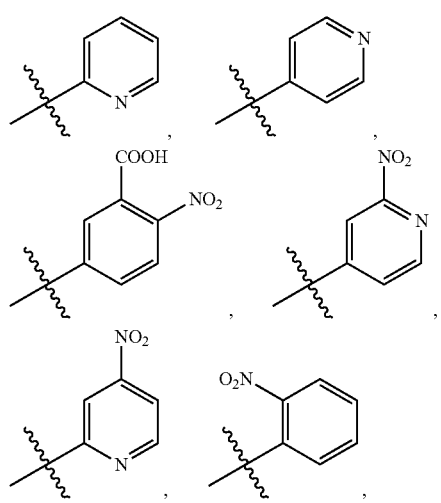

a diene, a dienophil, a 1,3-dipole, a dipolarophile, an alkene, a ketene, an olefin, an alkene with allylic hydrogen, a benzophenone, an aryl diazonium, a vinylsulfone and an allyl sulfone;

$L^1$ and $L^2$ is independently selected from a bond, —$CH_2$—*,

"*" represents a portion of $L^1$ and $L^2$ bound $X^3$ or $Y^3$;

$R^{18}$ is hydrogen, $C_{1-8\ alkyl}$; alicyclyl, heteroalicyclyl, benzyl or aryl, wherein any ring in $R^{18}$ is optionally substituted.

each of $W^1$ is an independent linker selected from the group consisting of —C(=O)—NH—, —NH—C(=O)—, each of $J^1$ is independently selected from Cl, Br and I;

each of $W^2$ is independently selected from the group consisting of

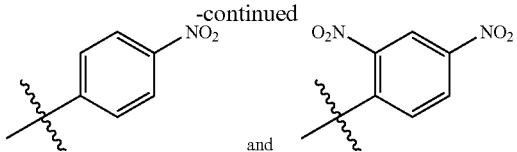

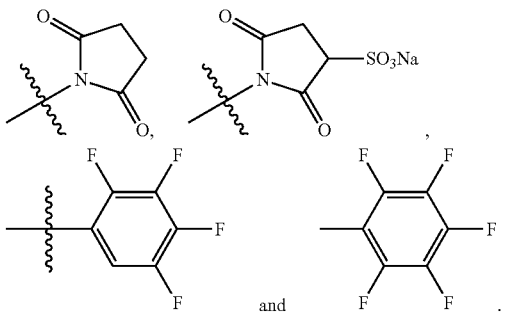

each of $W^3$ is independently selected from the group consisting of

Additionally, the present invention provides methods for synthesizing SA crosslinking reagents and SA macromolecules.

The foregoing aspects and embodiments of the invention may be more fully understood by referencing the following figures, detailed description, and claims.

BRIEF DESCRIPTION OF THE FIGURES

FIG. 1 illustrates the chemical structures, MWs, and Log P values of sugar alcohol-based linkers and polyethylene glycol-based linkers.

FIG. 2 illustrates the general methods for synthesizing monofunctional, homobifunctional, and heterobifunctional SA crosslinking reagents.

FIG. 3 illustrates the general methods for synthesizing monofunctional, homobifunctional, and heterobifunctional SA crosslinking reagents with extra linkers.

FIG. 4 illustrates examples of useful crosslinking reagents.

FIG. 5 illustrates examples of useful SA reagents for solid phase peptide and oligo synthesis.

FIG. 6 illustrates methods of synthesizing di-, tetra-, and higher MW SA molecules.

FIG. 7 illustrates the MW of linear SA macromolecules based on D-mannitol.

FIG. 8 illustrates the general methods for incorporating crosslinking groups at the side chain of SA macromolecules.

FIG. 9 illustrates examples of two linear SA macromolecules synthesized by solid phase.

FIG. 10 illustrates examples of a few different configurations of hyper branched SA macromolecules.

FIG. 11 illustrates examples of SA macromolecules based on D-mannitol.

FIG. 12 illustrates a general method of synthesizing branched SA macromolecules.

DEFINITIONS

The term "conjugation" or "bioconjugation", as used herein, refers to a chemical process that links two or more molecules together to create new molecules. One of the molecules is preferably a biomolecule. Thus, "bioconjugation" or "conjugation" refers to any chemical process that involves changing a molecule's properties through covalent modification, labeling, conjugation, or immobilization. Conjugation reactions include, for example, amide bond formation through pre-activated carboxylate, such as NHS ester formation with amine; thioether formation through the reaction of sulfhydryl with maleimide or alkyl halide; hydrazone formation through the reaction of hydrazine with ketone or aldehyde; oxime formation through the reaction of aminooxy with ketone or aldehyde; semicarbazone formation through the reaction of semicarbazide with ketone or aldehyde; and reductive amination to conjugate aldehydes and amines. Other less common conjugation reactions include click chemistry (Cu(I)-promoted azide-alkyne [3+2] cycloaddition), the Diels-Alder reaction, and photochemical reactions involving azide.

The term "conjugate", as used herein, refers to a product produced by a "conjugation" reaction of two or more molecules. Examples of molecules that can be conjugated include small molecules, antibodies and their fragments, proteins (soluble and membrane proteins), enzymes, nucleic acids and their analogs, peptides and peptidomimetics, fluorescent compounds, chemiluminescent compounds, radioactive compounds, isotopic containing compounds, biotin and avidin/streptavidin, toxins, drugs, solid support media, and other biologically active molecules. Examples of conjugates include antibody-drug conjugates, protein-drug conjugates, peptide-drug conjugates, oligo-drug conjugates, peptide-oligo conjugates, protein-oligo conjugates, antibody-enzyme conjugates, antibody-protein conjugates, protein-protein conjugates, protein-peptide conjugates, protein-oligo conjugates, fluorescent compounds, immobilized proteins, immobilized peptides, immobilized enzymes, and immobilized oligos.

The term "sugar alcohol" (SA) or "sugar alcohols" (SAs), as used herein, refers to a sugar alcohol or keto sugar that has a general formula of OH—$CH_2$—$(CHOH)_n$—$(C(O))_r$—$(CHOH)_p$—$CH_2$—OH, wherein r is 0 or 1, n and p ranges from 0 to approximately 12 with the combined value of n and p being greater than 1. When n is O, SA refers to the hydrogenated form of carbohydrate whose carbonyl group (aldehyde or ketone) has been reduced to a primary or secondary OH group. In some cases, SA refers to polyol, polyhydric alcohol, or polyalcohol. A sugar alcohol has the general formula HO—$CH_2$—$(CHOH)_n$—$CH_2$—OH. Examples of natural sugar alcohols are glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), and iditol (6-carbon). Sugar alcohols can also be synthetic. When r is 1, sugar alcohol refers to a keto sugar or ketose. Examples of natural ketoses are dihydroxyacetone (3-carbon), erythrulose (4-carbon), ribulose (5-carbon), xylulose (5-carbon), fructose (6-carbon), psicose (6-carbon), sorbose (6-carbon), tagatose (6-carbon), sedoheptulose (7-carbon).

The term "sugar alcohol unit" (SA unit) or "sugar alcohol units" (SA units), as used herein, refers to an "unmodified" or "modified" mono sugar alcohol. An "unmodified" SA unit has the general formula —$CH_2$—$(CHOH)_n$—$(C(O))_r$—$(CHOH)_p$—$CH_2$— wherein r is 0 or 1, n and p ranges from 0 to approximately 12 with the combined value of n and p being greater than 1. A "modified" SA unit refers to a SA unit in which one or more of its OH groups has been chemically modified by substitution with another functional group. A "modified" SA unit also refers to a SA unit in which one or both of its —$CH_2OH$ groups has been oxidized and then further modified with other functional groups. A "modified" SA unit also refers to a SA unit wherein the hydrogen atom at one or more of the OH groups has been replaced by a chemical protecting group, leaving group, or other functional group. Examples of OH protecting groups include $C_1$-$C_8$ alkyl, benzoyl, acetyl, benzyl, $C_1$-$C_6$ alkyl silyl, tetrahydropyranyl, tetrahydrofuranyl, and tetrahydrothiofuranyl.

The term "monomer" refers to a molecule that can bind chemically to other molecules to form a polymer. The term "monomeric" as used herein refers to an "unmodified" or "modified" mono sugar alcohol.

The term "dimeric", as used herein, refers to a chemical entity consisting of two monomeric sugar alcohols chemically binding to each other.

The term "trimeric", as used herein, refers to a chemical entity consisting of three of the monomeric sugar alcohols.

The term "tertrameric", as used herein, refers to a chemical entity consisting of four of the monomeric sugar alcohols.

The term "biocompatible", as used herein, refers to the possession of a property by a compound that makes it biologically compatible, e.g., by not producing a toxic, injurious, or immunological response in living cells, tissues, or a living system. The term "biocompatibility" as used herein refers to the ability of a biomaterial to initiate an appropriate host response in a specific application. In another sense, the term "biocompatibility" means the quality of not having toxic or injurious effects on biological systems. In the case of a medical therapy, "biocompatibility" refers to the ability of a biomaterial to perform its desired function without eliciting any undesired local or systemic effects in the recipient or beneficiary of that therapy, as it generates the most appropriate beneficial cellular or tissue response in that specific situation and optimizes the clinically relevant performance of that therapy.

The term "biodegradable", as used herein, refers to the possession of a property by a compound that allows it to decompose through one or more in vivo biological processes, such as via a metabolic pathway. As used herein, "biodegradable" compounds are those that, when taken up by cells, can be broken down by the lysosome pathway or other biochemical machinery or by hydrolysis into components that the cells can either reuse or dispose of without significant toxic effects on the cells.

The terms "crosslink", "crosslinking", "crosslinked", and grammatical derivatives thereof, refer to the covalent bonding or bonds between molecules or between molecules and solid supports.

The terms "crosslinking group", "functional group", "activated group", and "chemically reactive group", as used herein, refer to distinct, definable portions or units of a molecule that react readily with electrophilic or nucleophilic groups on other molecules to form a new molecule through covalent bonding. Crosslinking groups include, for example, OH, protected OH, carboxylic acid, protected carboxylic groups, amines, protected amines, thiols, protected thiols, disulfides, alkyl groups, benzophenones, anthraquinones, diazo groups, azido groups, acyl azides, alkynes, diazonium groups, diazirenes, dienes, dienophils, 1,3-dipoles, dipolarophiles, alkenes, ketenes, olefins, alkenes with allylic hydrogen, dicarbonyl groups, epoxides, oxiranes, organosilanes, isothiocyanate, isocyanate, phosphonium groups, tosylates, mesylates, acyl azides, esters (e.g., N-hydroxysuccinimidyl ester and 1-benzotriazolyl esters), sulfonyl chlorides, anhydrides, tetrahydropyranyl groups, tetrahydrofuranyl groups, tetrahydrothiofuranyl groups, carbonate groups (e.g., N-hydroxysuccinimidyl carbonates and 1-benzotriazolyl carbonates), aldehydes, ketones, aryl ketones, glyoxals, imidoesters, anhydrides, fluorophenyl esters, hydroxymethyl phosphine derivatives, haloacetyl groups, ethyl vinyls, aryl halides, trityl halides, alkyl halides, acyl halides, silyl halides, maleimides, vinylsulfones, thioesters, cisplatin derivatives, fluorobenzene derivatives, aziridines, acryloyl groups, aminooxy, protected aminooxy, semicarbazide, thiosemicarbazide, hydrazine, guanidinyl, phosphoramidites, and sugar groups. An extensive description of such groups of typical art can be found in the following reference: Greg T. Hermanson "Bioconjugate Techniques", 2008 Elsevier, Inc.

The term "crosslinking reagent", as used herein, refers to a molecule that includes a crosslinking group and is capable of crosslinking with another molecule.

The term "leaving group", as used herein, refers to a chemical moiety that can be substituted with another chemical moiety. Examples of leaving groups include halides (e.g., chloride, bromide, iodide), methanesulfonyl (mesyl), p-toluenesulfonyl (tosyl), trifluoromethyl sulfonyl (triflate), and trifluoromethylsulfonate. An extensive description of leaving groups of typical art can be found in: Jerry March, Advanced Organic Chemistry: Reactions, Mechanisms, and Structure, 4$^{th}$ Ed., John Wiley and Sons, New York, 1992, 352-357.

The term "protecting group" (PG), as used herein, refers to a molecular group or chemical moiety that blocks a functional group from reacting during other chemical operations/transformations. A protecting group is inert to these chemical operations/transformations but can be removed or cleaved by specific chemical, enzymatic, or photochemical means in such a way that it liberates the original functional group for further reaction. A wide variety of protecting groups are available and known in the art. An extensive description of protecting groups of typical art can be found in: Theodora W. Green and Peter G. M. Wuts, Protective Groups in Organic Synthesis, 2$^{nd}$ ed., Wiley-Interscience, New York, 1991.

The term "OH protecting group", as used herein, refers to a molecular group or chemical moiety that blocks an OH group from reacting during other chemical operations/transformations. Examples of chemical moieties include, but are not limited to, alkyl, aryl, benzoyl, acetyl, benzyl, alkyl silyl, tetrahydropyranyl, tetrahydrofuranyl, and tetrahydrothiofuranyl.

The terms "linker" or "linkage" or "linking group", as used herein, refer to groups or bonds that are normally formed as the result of a chemical reaction and typically with covalent bond(s). A linker may contain an extra spacer(s), such as ethylene glycol, methylene, a peptide, or a peptidomimetic oligomer. Linkers include, for example, substituted or un-substituted heteroalicyclyl $C_1$-$C_{12}$ alkyl, —(CH$_2$CH$_2$O)$_{1-10}$—, —(CH$_2$CH$_2$O)$_{1-10}$—CH$_2$—, substituted or un-substituted alicyclyl, heteroalicyclyl, aryl, peptides, and peptidomimetic oligomers. The linkers may include linking groups, such as acyl-based linking groups (e.g., —C(O)—NH— and —OC(O)NH—). Exemplary linking groups include, but are not limited to, each V and W independently selected from a Diels-Alder adduct, a 1,3-dipolar dduct, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH (CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2$$^+$)—NH—, —NH—C(=NH$_2$$^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

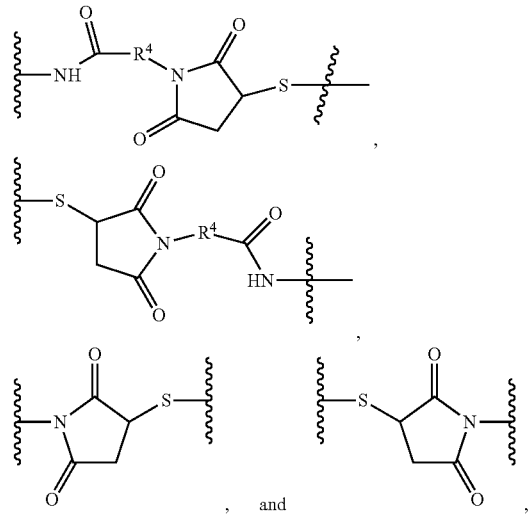

, and , wherein each G$^1$ is independently selected from NR$^3$, O, and S; each G$^2$ is independently O or S; each G$^3$ is independently selected from S, O, NR$^3$, and SO$_2$; each G$^4$ is independently O or NR$^3$; each R$^3$ is independently selected from hydrogen, C$_1$-C$_8$ alkyl, —(OCH$_2$CH$_2$)$_{1-3}$, optionally substituted alicyclyl, and optionally substituted heteroalicyclyl; each R$^8$ is independently C$_1$-C$_8$ alkyl;

The term "alkyl", as used herein, refers to a branched, unbranched, or cyclic hydrocarbon having, for example, from 1 to 20 carbon atoms, and often 1 to about 12, 1 to 6, or 1 to 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups.

The term "SA molecule", as used herein, refers to a molecule that includes an SA unit. SA molecule refers to any of the SA crosslinking reagents, SA macromolecules, linear SA macromolecules, branched SA macromolecules, and hyperbranched SA macromolecules.

The term "SA macromolecule" as used herein refers to a high molecular weight compound derivatized from the sugar alcohol. Typically, an SA macromolecule is at least two SA units long. The preferred size of an SA macromolecule ranges from approximately 1000 Da to approximately 120,000 Da.

The term "branching", as used herein, refers to the replacement of a substituent, for example a hydrogen atom on a sugar alcohol, by another covalently bonded chain of a sugar alcohol, or by a chain of another type.

The terms "macrocycle" or "macrocyclic", as used herein, refer to a cyclic macromolecule or a macromolecular cyclic portion of a molecule. Typically, a macrocycle includes a 7- or greater membered ring.

The terms "peptide" or "polypeptide", as used herein, refer to a polymer of amino acid residues linked together by a peptide bond. Typically, a peptide is at least two amino acids long. A peptide bond is commonly known in biochemistry as an amide linkage between the carboxyl group of one amino acid and the amino group of another amino acid. The preferred size of peptides ranges from about 2 to about 40 amino acids. The term peptide may also apply to amino acid polymers in which one or more amino acid residues are artificial chemical analogs of a corresponding naturally occurring amino acid. An amino acid polymer in which one or more amino acid residues is an "unnatural" amino acid not corresponding to any naturally occurring amino acid is also encompassed by the term "peptide".

The term "protein", as used herein, refers to a polymer of amino acid residues linked together by a peptide bond. The term is meant to include proteins and polypeptides of any size, structure, or function. However, a protein is typically at least 10 amino acids long. A protein may be naturally occurring, recombinant, synthetic, or any combination of these. A protein may also be a fragment of a naturally occurring protein. A protein may be a single molecule or it may be a multi-molecular complex. The term protein may also apply to amino acid polymers in which one or more amino acid residues are artificial chemical analogs of a corresponding naturally occurring amino acid. An amino acid polymer in which one or more amino acid residues is an "unnatural" amino acid not corresponding to any naturally occurring amino acid is also encompassed by the use of the term "protein".

The term "protein fragment", as used herein, refers to a peptide that is a portion of another protein. For example, protein fragments may be polypeptides obtained by digesting a full-length protein. A protein fragment typically comprises at least two amino acids.

The term "therapeutic agent", as used herein, refers to a compound, or a molecule that is useful in the treatment of a disease. Therapeutic agents include, for example, antibody fragments, drugs, toxins, nucleases, hormones, immunomodulators, pro-apoptotic agents, anti-angiogenic agents, boron compounds, photoactive agents, dyes and radioisotopes, proteins, and constructs that include proteins, oligonucleotides, oligonucleotide analogs, polysaccharides, metabolites, enzymes, polypeptides, and toxins. Therapeutic agents include prodrugs of bioactive agents and constructs.

The term "therapeutic moiety", as used herein, refers to a functional moiety that is derived from a "therapeutic agent".

The term "diagnostic agent", as used herein, refers to a compound, or a molecule that alone or in combination with another agent is able to be used for revealing, pinpointing, and defining the localization of a pathological process. Diagnostic agents include, for example, radioactive substances, fluorescent dyes, chemiluminescent compounds, mass tags, chromophores, biotin, toxins, proteins, enzymes, antibodies, antibody fragments, polypeptides, avidin, streptavidin, oligonucleotides, oligonucleotide analogs, polysaccharides, metabolites, drugs, chemotherapeutic agents, cytotoxic agents, immunosuppressive agents, and radioligands.

The term "diagnostic moiety", as used herein, refers to a functional moiety that is derived from a "diagnostic agent".

The term "a biologically functional moiety", as used herein, refers to a moiety that can elicit some kind of biological function or interact with biological systems to elicit some kind of biological function. "Biologically functional moiety" also refers to a moiety that can aid in detecting or diagnosing some biological function. Examples of biologically functional moieties include therapeutic moieties and diagnostic moieties.

The term "antibody", as used herein, refers to a full-length immunoglobulin molecule or an immunologically active portion of an immunoglobulin molecule, such as an antibody fragment. "Antibody" is used in the broadest sense and includes monoclonal antibodies, polyclonal antibodies, multispecific antibodies (e.g., bispecific antibodies), and antibody fragments. The immunoglobulin disclosed herein can be of any type, for example, IgM, IgD, IgG, IgE, IgA, or any subclass of immunoglobulin, such as IgG1, IgG2a, IgG2b, IgG3, IgA1, and IgA2. Antibodies may be murine, human, humanized, chimeric, rabbit, chicken, or derived from other species.

The term "antibody fragment", as used herein, refers to a portion of an antibody, such as F(ab')2, Fab', Fab, Fv, sFv, diabodies, linear antibodies, fragments produced by a Fab expression library, anti-idiotypic (anti-Id) antibodies, the complementarity determining region (CDR), the extracellular domain (EDC), and epitope-binding fragments of any of the above that immunospecifically bind to cancer cell antigens, viral antigens or microbial antigens, single-chain antibody molecules, and multispecific antibodies formed from antibody fragments. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker (scFv proteins).

The terms "nucleic acid", "oligonucleotide", "oligo", or "polynucleotide", as used herein, refer to a polymer of nucleotides. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), or a threose nucleic acid (TNA).

The term "small interfering RNA" or "siRNA", as used herein, refers to small inhibitory double-stranded RNA molecules that induce the RNA interference (RNAi) pathway. siRNA generally have from about 18 to about 30 base pairs and exhibit varying degrees of complementarity to their target mRNA in the antisense strand. Some, but not all, siRNA have unpaired overhanging bases on the 5' or 3' end of the sense strand and/or antisense strand. The term "siRNA" includes duplexes of two separate strands, as well as single strands that can form hairpin structures comprising a duplex region.

The term "polyglycerol", as used herein, refers to a polymerized glycerol. Glycerol has the structure OH—CH$_2$—CH(OH)—CH$_2$—OH. A polyglycerol contains two or more glycerol units. Polyglycerol is prepared by general polymerization of glycerol at a higher temperature or under basic conditions.

The term "hydrophobic moiety", as used herein, refers to a nonpolar molecule or group that has little affinity for water. A hydrophobic molecule or portion of a molecule is one that has a tendency to cluster together with other hydrophobic groups in an aqueous environment because they are unable to disrupt the network of strong hydrogen bonds in the water around them. Examples of hydrophobic moieties include alkanes, aromatic groups, cholesterol, lipids, phospholipids, and fatty acids.

The term "aliphatic group", as used herein, refers to acyclic or cyclic, non-aromatic compounds. Examples of aliphatic groups include, but are not limited to, linear or branched alkyl chains, fatty acid chains (e.g., oleic acid), and long chain alkyl thiols (e.g., hexanethiol).

The term "solid support", as used herein, refers to a support that is conventionally used in organic chemistry, for example in oligo and peptide synthesis. The term "solid support", as used herein, also refers to a support that has been used in biochemistry and biology, for example, for biopolymer immobilization and purification. Examples of a solid support includes polystyrene supports, polyamide supports, polyethylene glycol supports, polyacrylic supports, composite supports and polymers thereof, such as polyacrylic/beta-alanine copolymer supports, polyacrylamide/polystyrene copolymer supports, polyacrylamide/polyethylene glycol copolymer supports, polyethyleneglyco/polystyrene copolymer supports, controlled pore glass, agarose, dextran gel, and polysaccharide based polymers. In some cases, the term "solid support" also refers to a particle that has been used in biological assays, for example, or a polymeric microsphere. Examples of such support include a latex microsphere, a polymeric particle consisting of polystyrene or copolymers of styrene, poly(methyl methacrylate), polyvinyltoluene, polu(2-hydroxyethyl methacrylate) and the copolymer, poly(ethylene glycol dimethacrylate/2-hydroxyethylmetacrlate), and poly(lactic-co-polycolic acid). "Solid support" can also include inorganic constructs, metals and semiconductors, super paramagnetic composites, biodegradable constructs, and synthetic dendrimers and dendrons, such as a quantum dot, a dye-coded particle, and a magnetic-coded particle.

The term "MW", as used herein refers to molecular weight.

The term "small molecule", as used herein refers to a low molecular weight organic compound that is below 800 Da. Examples of the small molecules such as biotin, fluorescent labeling compound, sugar, sugar alcohol, metabolites, drugs, pesticides, amino acids, nucleotide, chemilluminent compound, crosslinking reagent.

The term "single MW" or "monodisperse", as used herein refers to one or a collection of compounds having the same size and molecular weight. Natural polymers, such as proteins, peptides, and DNA, are typically monodisperse. SA macromolecules are synthesized and purified from pure chiral starting materials as single MW compounds via standard organic synthesis techniques. SA macromolecules may contain mixtures of compounds that have the same MW but are the stereo or regional isomers of each other. These isomers are generated during synthesis and can be minimized by choosing the right conditions or purification method.

The term "polydisperse" or "polydispersity", as used herein refer to a collection of polymer compounds that have different sizes, shapes, or molecular weights. For example, a polymer usually has a distribution of molecular mass over a certain range. The polydispersity index (PDI), or heterogeneity index, measures the distribution of molecular mass in a given polymer. The index is calculated based on the following formula: $PDI=M_w/M_n$, wherein $M_w$ is the weight average molecular weight and $M_n$ is the number average molecular weight. Depending on the synthetic method used, most of the synthetic polymers except peptides and oligos are polydisperse. Peptides and oligos are synthesized based on standard organic synthesis techniques using pure starting materials and are generally purified to obtain monodispersity.

DETAILED DESCRIPTION OF THE INVENTION

Crosslinking reagents and conjugation chemistry are two key parts of bioconjugation technologies. Several factors need to be considered when choosing a crosslinking reagent for bioconjugation reactions: (i) reactive groups at the termini of the linker; (ii) the length of the spacer; and (iii) the physical properties of the spacer, such as whether it is hydrophobic or hydrophilic, and cleavable or biodegradable after conjugation.

Typical reactive groups at the termini of the linkers are pre-activated carboxylate, such as N-hydroxysuccinimide (NHS) ester; thiol-reacting groups, such as maleimide/alkyl halide; and ketone or aldehyde-reacting groups, such as hydrazine/semicarbazide/aminooxy. Other termini groups are azide/alkyne and diene/dienophile. Biomolecules, such as antibodies and proteins, usually have several same or similar functional groups that can interact with the terminal group of the crosslinking reagents. The position and degree of biomolecule labeling usually varies after conjugation. Heterogeneity of the conjugates is a major concern in drug R&D. Using a single and pure heterobifunctional crosslinking reagent and site-specific labeling can decrease the complexity. For example, sulfhydryl is a popular functional group due to its reaction specificity and easy introduction through in vitro cysteine mutagenesis. Sulfhydryl also plays special roles in specific antibody modification and conjugation. Other functional groups that can be targeted include post-introduced aldehyde, hydrazine, and azide functional groups.

Previous technologies for conjugating biomolecules rely on classical spacers, such as hydrophobic alkyl chains, peptides, and ethylene glycol. Many important conjugation reactions involve linking a very hydrophobic compound, such as a hydrophobic drug, toxin, biotin, or fluorescent compound, to a water soluble biomolecule, such as an antibody, protein, or enzyme. In most cases the reaction is performed in an aqueous buffer. The presence of a hydrophilic linker favors the conjugation reaction and preserves the stability of the final products.

Hydrophilic linkers have been adapted by biochemists to modulate the properties of various molecules. Such linkers, which are available in different motifs, have been used as agents of drug delivery, aqueous solubility enhancers for hydrophobic molecules, tethers or spacers in conjugation, encapsulating molecules in nanotechnology, and in cosmetic formulations. Polyethylene glycol (PEG) is one of the most commonly used hydrophilic linkers and commercially available. Lower MW heterobifunctional PEG compounds are the most frequently used compounds for linking hydrophobic compounds.

High MW polymers have been used to conjugate proteins, peptides, oligonucleotides, siRNA, and other therapeutic biopolymers. Conjugating high MW polymers to therapeutic biopolymers may stabilize the substances being conjugated in circulation, reduce their immunogenicity, decrease antibody recognition, and increase body residence time. Other benefits of polymer conjugation include the possibility of modifying organ disposition, drug penetration by endocytosis, and new drug targeting (F. M. Veronese, M. Morpurgo "Bioconjugation in pharmaceutical chemistry" IL Farmaco 1999, 54, 497-516). In the case of conjugating proteins and peptides, modification also protects the protein and peptide from proteolytic degradation in vivo.

High MW polydisperse PEG linkers have been used to modify therapeutic proteins, antibodies, and small toxins due to their hydrophilicity and biocompatibility (Veronese M. F. "PEGylated protein in drugs: basic science and clinical applications." 2009, Birkhäuser Verlag). Examples of PEGylated proteins or oligonucleotides approved by the FDA are pegadamase (Adagen®), pegfilgrastim (Neulasta®), pegaspargase (Oncaspar®), and PEG-EO (Mirera®).

However, PEG-based linkers have several drawbacks. (i) The polydispersity of high MW ($M_w$) PEG molecules due to the nature of polymerization chemistry. The $M_w/M_n$ (number-average) value is approximately 1.01 for polymers with $M_w$ ranging from 2 to 10 KDa, but reaches values up to 1.2 for higher MW polymers. The use of polydisperse PEG molecules to label biomolecules generates polydisperse conjugates with subtle differences in biological properties. This result also complicates analysis of the conjugates. A monodisperse, high $M_w$ molecule is desirable, but current technologies for synthesizing and purifying PEG are too difficult and expensive for a commercial monodisperse PEG product. Efforts have been made by scientists from Quanta Biodesign Limited Company to develop a better process for making single pure PEG (US 2010/0009902 A1, 2010). Thus far, the highest single MW commercially available PEG is in the range of 1600~1700 Da (36 ethylene glycol monomer). This process is not likely to result in a single pure MW PEG larger than 2000 Da due to the small MW increments of the monomer (one repeat unit: 44 Da). (ii) PEG is not biodegradable. The use of high $M_w$ PEG and chronic administration of any $M_w$ PEG may have long-term effects on human beings with questionable safety. (iii) Limited functional groups are available for conjugating small MW drugs, resulting in low drug loading. Only one or two OH groups are available for drug attachment per linear PEG. Thus, no PEGylated small MW drugs are commercially available at this point. Branched PEG and a dendrimeric structure bearing a few more OH groups have been introduced. (iv) Despite the hydrophilicity of the PEG linker, certain conjugates through the PEG linker still lack sufficient solubility for biological applications. Better hydrophilic linkers need to be developed.

Sugar molecules are probably the most hydrophilic natural compounds to date due to their hydrogen bonding capability (donor and acceptor). Polysaccharides have been linked to proteins of therapeutic interest, leading to an increased retention time in the blood, decreased immunogenicity, and the desired minimal loss of biological activity (Imperiali, B, O'Connor S E, *Curr. Opin. Chem. Biol.* 1999, 3, 643-649; Sinclair A M, Elliott S. *J. Pharm. Sci.* 2005, 94, 1626-1635; Fernandes A I, Gregoriadis G. *Int. J. Pharm.* 2001, 217, 215-224). Polysaccharide derivatives, such as hydroxyethyl starch (M. Orlando, *Justus-Liebig Universitat Giesssen*, 2003, p 191) and poly(sialic acid), have been used for protein conjugation (Constantinou, A. et al. *Bioconjugate Chem.* 2008, 19, 643-650; Gregoriadis G. *Int. J. Pharm.* 2005, 300, 125-130). Due to the complexity and difficulties of sugar chemistry, the polysaccharides used in such studies tend to be polydisperse, as in the case of PEG, and variable in structure. In addition, polysaccharides with rigid structures may result in a great propensity for immunogenicity.

Sugar alcohol, also known as polyol, is a hydrogenated form of carbohydrate in which the carbonyl group (aldehyde or ketone) has been reduced to a primary or secondary OH group. Sugar alcohols occur naturally in foods and come from plant products, such as fruits and berries. Sugar alcohols are often used as ingredients in sweeteners, for making polymers such as hydrogel.

Some structures of simple functionalized low MW monomeric sugar alcohols have been reported. Table 1 lists most of the functionalized monomeric sugar alcohols that may be used for the conjugation published in the literature (if the compound has more CAS numbers or references, only one is listed here). The data were obtained by extensively searching for the formula X—$CH_2$—$(CH_2OR)_n$—$CH_2$—Y, where n is 2 to 12, R can be H, Me, or any other protecting group, and X and Y can be anything. Compounds containing only $NH_2$, COOH, SH, OH, Br, or $NO_2$ were excluded from the table because these compounds require further activation before they can be used for conjugation. A total of approximately 60 compounds containing any kind of functional group were found for monomeric sugar alcohol. The purpose of synthesizing such compounds falls mainly into the following categories: 1) as an initiator or starting material for polymerization, such as making polyhydroxylated nylon 6 or other polymers containing hydroxyl groups; 2) as starting material for a small molecule drug, in most cases becoming a part of the drug with little resemblance to the sugar alcohol; or 3) as pure, synthetic method development for functional group conversion. In rare cases the functional group is used as a purification handle (item 20, hydrazide). In a more common case, a functionalized isotopic coded mannitol (item 14) is used for protein footprinting. In another case, a D-mannitol is used as a spacer to link 2-aminopyridyl to a sugar molecule (Galb1-4Fuc) for fluorescent assay purposes (Nishiyama K. et al. *Chem. Pharm. Bull.* 2010, 58, 495-500). To the best of our knowledge, none of these small molecule functionalized SA compounds have been used as a spacer for linking two or more therapeutic drugs together, such as a toxin, protein, antibody, siRNA, etc. The reported SA compounds have limited utility due to the fact that all of these compounds are very simple and not very efficient; in particular, no efficient heterobifunctional crosslinkers have been reported in the literature.

TABLE 1

Published functionalized monomeric sugar alcohol compounds
(Chemical formula: X—$CH_2$—$(CHOH)_n$—$CH_2$—Y).

| Item # | n | X | Y | CAS # | Reference |
|---|---|---|---|---|---|
| 1 | 2 | —OH | —$N_3$ | 87691-84-7 | Ger. Offen.1983, DE 3150917 A1 19830630. |
| 2 | 2 | —OH | —C≡C—Et | 129549-24-2 | Tetrahedron Letters, 1990, 31(12), 1783-4. |
| 3 | 2 | —OH | —C≡CH | 460348-22-5 | Compt. rend. 1961, 252, 751-3. |
| 4 | 2 | —SH | —S—S-pyridyl | 106005-81-6 | Eur. Pat. Appl., 1986, EP 184361 A2 19860611. |
| 5 | 2 | —SH | —$ONH_2$ | 103528-14-9 | Bioorganicheskaya Khimiya, 1986, 12(6), 845-7. |
| 6 | 2 | —$N_3$ | —$N_3$ | 1221568-11-1 | J. Am. Chem. Soc., 2010, V132(31), P10642-10644 |
| 7 | 2 | —C≡C—CH3 | —C≡C—CH3 | 103722-73-2 | Tetrahedron, 1985, V41(17), P3497-509 |
| 8 | 2 | —C≡CH | —C≡CH | 28227-44-3 | Bulletin de la Societe Chimique de France1963, 10, 2105-13 |
| 9 | 2 | —$CONHNH_2$ | —$CONHNH_2$ | 4461-85-2 | Canadian Journal of Chemistry1956, 34, 1440-3. |
| 10 | 3 | —OH | —$N_3$ | 178757-82-9 | Tetrahedron Letters, 1996, 37(21), 3683-3686. |
| 11 | 3 | —$N_3$ | —$N_3$ | 178757-79-4 | Journal of Carbohydrate Chemistry, 2004, V23(2 & 3), P95-110 |
| 12 | 3 | —OH | —C≡CH | 524035-70-9 | Tetrahedron 2003, 59(2), 155-164. |
| 13 | 3 | —Br | —CO—NH—$NH_2$ | 95103-66-5 | Acta Chemica Scandinavica, Series B: Organic Chemistry and Biochemistry 1984, B38(7), 555-61. |
| 14 | 3 | —OH | —CO—NH—$NH_2$ | 95103-68-7 | Acta Chemica Scandinavica, Series B: Organic Chemistry and Biochemistry 1984, B38(7), 555-61. |
| 15 | 4 | —OH | —NH—$NH_2$ | 151069-61-3 | Eur. Pat. Appl., 1993, EP 545195 A1 19930609. |
| 16 | 4 | —OH | —$N_3$ | 138245-74-6 | Tetrahedron: Asymmetry, 2006, V17(9), P1349-1354 |
| 17 | 4 | —OH | —NH—C(O)—$CH_2$Br | 1313868-84-6 | J. Mol. Bio 2011, 409(4), 483-495. |
| 18 | 4 | —OH | —NH—C(O)—$NH_2$ | 885024-84-0 | Fr. Demande, 2006, FR 2877221 A1 20060505. |
| 19 | 4 | —$N_3$ | —$N_3$ | 52868-75-4 | Journal of Carbohydrate Chemistry, 2004, V23(2 & 3), P95-110 |
| 20 | 5 | —OH | —C(O)$NHNH_2$ | 130538-63-5 | J. Am. Chem. Soc. 1946, V68, P1509-10 |

Synthetic high MW SA molecules are rare in the literature. A mannitol dimer has been synthesized for use as liquid crystal (Akiyama, H. et al. *Journals of Materials Chemistry*, 2009, 19, 5956-5963). New derivatives of disorbityl-amine have been reported (Pol. 2010, PL 206420 B1 20100831). However, none of these possess any useful crosslinker groups. On the other hand, nature produces some of the SA polymers. For example, the bacterial cell wall-associated teichoic acids predominantly contain D-ribitol residues interconnected by phosphodiester linkages. Because of their location, Fekete, Aniko et al. synthesized octa- and dodecamers of D-ribit1-1-phosphate for the purpose of developing a new vaccine (*Carbohydrate Research*, 2006, V341(12), P2037-2048). The polymer is coupled to a vaccine carrier, bovine serum albumin, through a keto handle and will be used as a single-component experimental vaccine. Nothing in the literature has suggested that such oligomers can be used to modulate the pharmacokinetic and pharmacodynamic properties of other therapeutic drugs or as carriers for drug delivery in vivo.

Other less relevant sugar alcohol structures, most of which are polymers, can also be found in WO2010014678, PL206420, WO2010/134476, WO2010134476, JP2009249500, FR2906245, WO2009053596, FR2906245, WO2004025297, WO2001005224, FR2701949, WO9421595, EP536939, U.S. Pat. No. 4,172,094, EP675101A1, polyglycerol U.S. Pat. No. 2,520,670, polyhydroxy compound U.S. Pat. No. 2,520,671, and polyhydric alcohol U.S. Pat. No. 2,532,036.

Thus, a critical need exists for hydrophilic crosslinking reagents, single high MW compounds, and high loading carriers in the biotechnology and pharmaceutical fields. The idea of using a hydrophilic sugar alcohol as a backbone to build up crosslinking reagents for linking different class of drugs, a single MW SA macromolecule to site-specifically label therapeutic proteins, and enable such practice can revolutionize the whole pharmaceutical industry.

The present invention provides for a conjugate having a structural formula selected from the group consisting of $M_1$-(L-B)$_u$      Formula (I), and B-(L-$M_1$)$_u$      Formula (II)

wherein, each $M_1$ is independently selected from the group consisting of a protein, an enzyme, an antibody, an antibody fragment, a polypeptide, an oligonucleotide, an oligonucleotide analog, and a polysaccharide;

each B is a single MW modified sugar alcohol polymer, comprising from 2 to about 2000 sugar alcohol monomer(s);

each monomer has from 3 to about 14 —$OR^1$ groups;

each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

each L is independently selected from the group consisting of a $R^2$ and, a structure of —$V_1$—$R^2$—$V_2$—, each $V_1$ and $V_2$ are independently selected from the group consisting of a Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S(=O)$_2$—, —S(=O)$_2$—$(CH_2)_2$—S—, —S(=O)$_2$—N($R^3$)—, —N($R^3$)—S(=O)$_2$—, —C(=O)—NH—NH—$CH_2$—, —C(=O)—NH—N=CH—, —CH=N—NH—C(=O)—, —$CH_2$—NH—NH—C(O=)—, —N($R^3$)—S(=O)$_2$—N($R^3$)—, —C(=O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH^{2+}$)—NH—, —NH—C(=$NH^{2+}$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

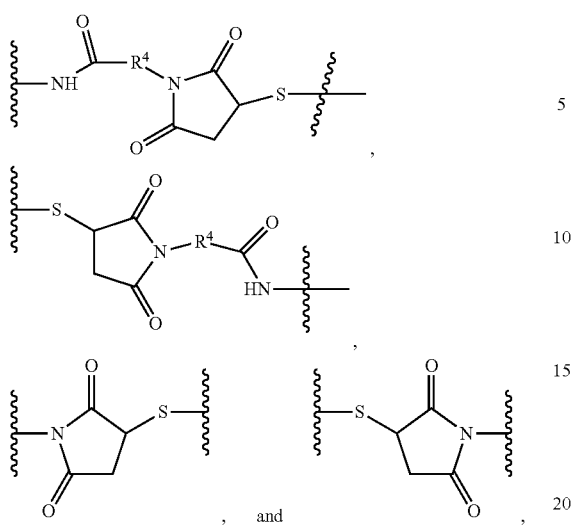

, and , each G¹ is independently selected from the group consisting of NR³, O, and S;
each G² is independently selected from the group consisting of O and S;
each G³ is independently selected from the group consisting of S, O, NR³, and SO₂;
each G⁴ is independently selected from the group consisting of O and NR³;
each R² is independently selected from the group consisting of a bond, $C_1$-$C_{12}$ alkyl, —(CH₂CH₂O)$_{1-10}$—, —(CH₂CH₂O)$_{1-10}$—CH₂—, optionally substituted alicyclyl, heteroalicyclyl, aryl, a peptide, and a peptidomimetic oligomer;
each R³ is independently selected from the group consisting of hydrogen, $C_1$-$C_8$ alkyl, —(OCH₂CH₂)$_{1-3}$, alicyclyl, and heteroalicyclyl, wherein any ring in R³ is optionally substituted.
each R⁴ is independently $C_1$-$C_8$ alkyl; and,
u is an integer from 1 to about 20.

The present invention also provides for a conjugate having a structural formula:

$(M_2\text{-L})_q\text{-B}$    Formula (III)

wherein,
each M₂ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, and a small molecule,
each B is a single MW modified sugar alcohol polymer, comprising from 2 to about 2000 sugar alcohol monomer(s);
each monomer has from 3 to about 14 —OR¹ groups;
each R¹ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of a R² and, a structure of —V₁—R²—V₂—,
each V₁ and V₂ are independently selected from the group consisting of a Diels-Alder adduct, a 1,3-dipolar adduct, —C(=G²)-G¹-, -G¹-C(=G²)-, -G³-, -G¹-C(=G²)-G¹-, —S—S—, —S—(CH₂)₂—S(=O)₂—,
—S(=O)₂—(CH₂)₂—S—, —S(=O)₂—N(R³)—, —N(R³)—S(=O)₂—, —C(=O)—NH—NH—CH₂—, —C(=O)—NH—N=CH—, —CH=N—NH—C(=O)—, —CH₂—NH—NH—C(=O)—, —N(R³)—S(=O)₂—N(R³)—, —C(=O)—NH—CH(CH₂SH)—, —N=CH—, —NH—CH₂—, —NH—C(=O)—CH₂—C(=O)—NH—, —CH=N-G⁴-, —CH₂—NH-G⁴-, -G⁴-NH—CH₂—, -G⁴-N=CH—, —C(=NH₂₊)—NH—, —NH—C(=NH₂₊)—, —O—P(=O)(O⁻)—NH—, —NH—P(=O)(O⁻)—O—, —CH₂—CH(NH₂)—CH₂—S—, —S—CH₂—CH(NH₂)—CH₂—, —O—P(=O)(O⁻)—O—, —O—P(=O)(S⁻)—O—, —O—P(=S)(S⁻)—O—,

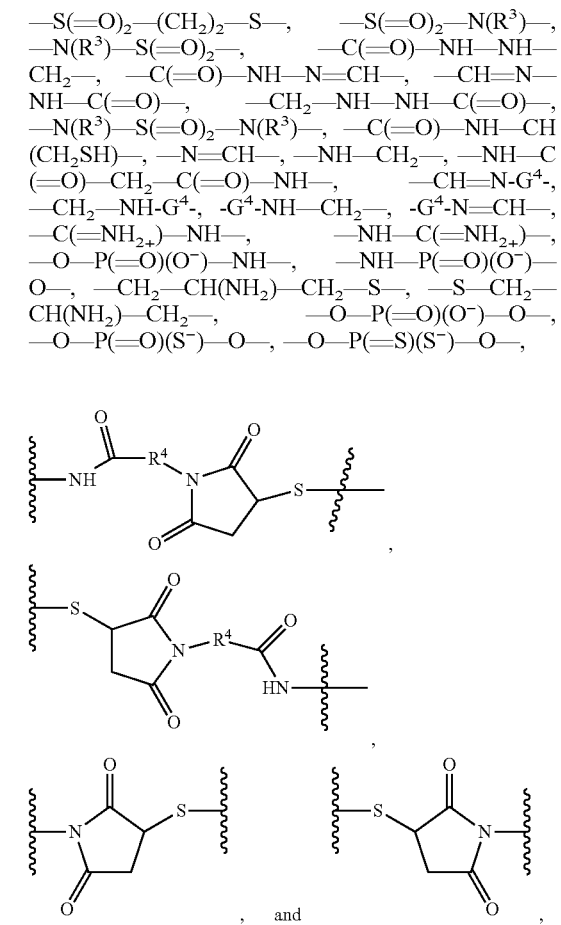

, and , each G¹ is independently selected from the group consisting of NR³, O, and S;
each G² is independently selected from the group consisting of O or S;
each G³ is independently selected from the group consisting of S, O, NR³, and SO₂;
each G⁴ is independently selected from the group consisting of O or NR³;
each R² is independently selected from the group consisting of a bond, $C_1$-$C_{12}$ alkyl, —(CH₂CH₂O)$_{1-10}$—, —CH₂CH₂O)$_{1-10}$—CH₂—, optionally substituted alicyclyl, heteroalicyclyl, aryl, a peptide, and a peptidomimetic oligomer;
each R³ is independently selected from the group consisting of hydrogen, $C_1$-$C_8$ alkyl, —(OCH₂CH₂)$_{1-3}$, alicyclyl, and heteroalicyclyl, wherein any ring in R³ is optionally substituted.
each R⁴ is independently $C_1$-$C_8$ alkyl;
q is an integer from 1 to about 100.

The present invention also provides for a conjugate having a structural formula selected from the group consisting of $(M_1)_q\text{-L-(B-(L-}M_2)_k)_u$    Formula (IV)

$(M_1\text{-L})_q\text{-(B-(L-}M_2)_k)_u$    Formula (V) and $M_1\text{-(L-B-(L-}M_2)_k)_u$    Formula (VI)

wherein,
each M₁ is independently selected from the group consisting of a protein, an enzyme, an antibody, an antibody fragment, a polypeptide, avidin, streptavidin, an oligonucleotide, an oligonucleotide analog, and a polysaccharide;

each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, and a small molecule;

each B is a single MW modified sugar alcohol polymer, comprising from 2 to about 2000 sugar alcohol monomer(s);

each monomer has from 3 to about 14 —$OR^1$ groups;

each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;

each L is independently selected from the group consisting of a $R^2$ and, a structure of —$V_1$—$R^2$—$V_2$—, each $V_1$ and $V_2$ are independently selected from the group consisting of Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(=O)$_2$—, —S(=O)$_2$—(CH$_2$)$_2$—S—, —S(=O)$_2$—N($R^3$)—, —N($R^3$)—S(=O)$_2$—, —C(=O)—NH—NH—CH$_2$—, —C(=O)—NH—N=CH—, —CH=N—NH—C(=O)—, —CH$_2$—NH—NH—C(=O)—, —N($R^3$)—S(=O)$_2$—N($R^3$)—, —C(=O)—NH—CH(CH$_2$SH)—, —N=CH—, —NH—CH$_2$—, —NH—C(=O)—CH$_2$—C(=O)—NH—, —CH=N-$G^4$-, —CH$_2$—NH-$G^4$-, -$G^4$-NH—CH$_2$—, -$G^4$-N=CH—, —C(=NH$_{2+}$)—NH—, —NH—C(=NH$_{2+}$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

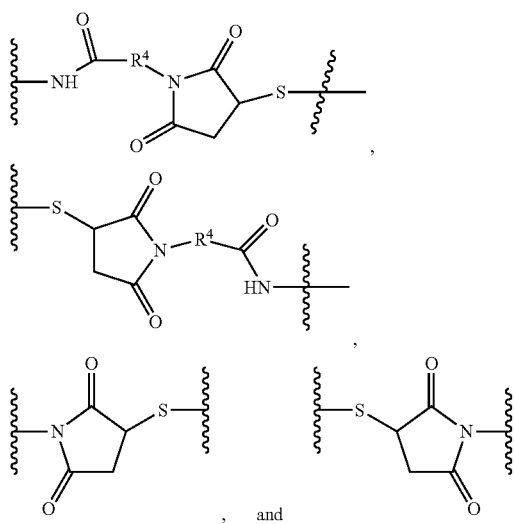

, and each $G^1$ is independently selected from the group consisting of $NR^3$, O, and S;
each $G^2$ is independently selected from the group consisting of O and S;
each $G^3$ is independently selected from the group consisting of S, O, $NR^3$, and SO$_2$;

each $G^4$ is independently selected from the group consisting of O and $NR^3$;
each $R^2$ is independently selected from the group consisting of a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each $R^3$ is independently selected from the group consisting of hydrogen, $C_1$-$C_8$ alkyl, —(OCH$_2$CH$_2$)$_{1-3}$, alicyclyl, and heteroalicyclyl, wherein any ring in $R^3$ is optionally substituted.
each $R^4$ is independently a $C_1$-$C_8$ alkyl;
u is an integer from 1 to about 100
q is an integer from 1 to about 100 and
k is 0 or an integer from 1 to about 20.

Preferably, B comprises from 4 to about 2000 sugar alcohol monomers.

Preferably, u is an integer from 1 to about 10.

Optionally, $M_1$ is selected from the group consisting of an antibody and an antibody fragment, and $M_2$ is a chemotherapeutic drug, q is 1, u is an integer from 1 to about 20; and, k is an integer from 1 to about 10. More preferably, in this embodiment k is 1, and u is an integer selected from 1 to about 8.

The sugar alcohol monomers may be linked together by an ether linkage.

In one aspect, $M_2$ may a chemotherapeutic agent. In this aspect, $M_2$ is a chemotherapeutic agent used in anticancer therapy. Most preferably, $M_2$ maybe selected from the group consisting of adrenocortical suppressants, antimetabolites, alkylating agents, alkyl sulfonates, antibiotics, antimitotics, anthracyclines, anti-angiogenic agents, camptothecins, COX-2 inhibitors, CPT-11, doxorubicin, doxorubicin analogs, enzyme inhibitors, endostatin, epipodophyllotoxins, ethylenimine derivatives, folic acid analogs, gemcitabine, HDAC inhibitors, heat shock protein (HSP)90 inhibitors, hormone antagonists, methotrexate, methyl hydrazine derivatives, mTOR inhibitors, nitrosoureas, nitrogen mustards, pyrimidine analogs, purine analogs, platinum coordination complexes, substituted ureas, SN-38, taxols, triazenes, taxanes, tyrosine kinase inhibitors, proteosome inhibitors, pro-apoptotic agents, vinca alkaloids, paclitaxel, maytansine, calicheamicin, and dolastatins.

$M_1$ may be an antibody. More preferably, $M_1$ is a fully human antibody.

Optionally, $M_1$ may be an antibody specific for an antigen selected from the group consisting of tumor-associated antigens, antigens associated with pancreatic cancer, antigens associated with malignant disease, antigens associated with autoimmune disease, antigens associated with immune dysfunction disease, antigens associated with leukemia, antigens associated with neurological disease, antigens against transmembrane activator, and an antigen against CAML-interactor.

$M_1$ may also be an antibody specific for an antigen selected from the group consisting of CA125, CA 15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, CEA, gp100, MART1, IL-2 receptor, CD4, CD5, CD8, CD14, CD15, CD19, CD20, CD21, CD22, CD23, CD25, CD33, CD37, CD38, CD40, CD40L, CD46, CD52, CD54, CD66a-d, CD67, CD74, CD79a, CD80, CD126, CD138, CD154, B7, MUC1, LALI, HM1.24, HLA-DR, tenascin, VEGF, P1GF, ED-B fibronectin, oncogenes, oncogene products, necrosis antigens, T101, TAG, IL-6, MIF, TRAIL-R1 (DR4), TRAIL-R2 (DR5), human chorionic gonadotropin, mucin, P21, MPG, and Neu oncogene product.

At least one $M_2$ may comprise a radioactive isotope.

At least one $M_1$ may be a therapeutic protein or polypeptide. Preferably, the amino acid sequence of the therapeutic protein contains at least 80% sequence homology to the wild-type therapeutic proteins selected from the group consisting of granulocyte macrophage colony stimulating factor, interferon, interferon alpha-2a, interferon alpha-2b, interleukin, interleukin-2, erythropoietin, growth hormone, human growth hormone, apomyoglobin, asparaginase, leptin, serum proteins, human chorionic gonadotropin, insulin, follicle stimulating hormone, luteinizing hormone, urate oxidase, adenosine deaminase, antibody fusion proteins, and factor VII. More preferably, the amino acid sequence of the therapeutic protein contains at least 90% sequence homology to the wild-type therapeutic proteins selected from the group consisting of granulocyte macrophage colony stimulating factor, interferon, interferon alpha-2a, interferon alpha-2b, interleukin, interleukin-2, erythropoietin, growth hormone, human growth hormone, apomyoglobin, asparaginase, leptin, serum proteins, human chorionic gonadotropin, insulin, follicle stimulating hormone, luteinizing hormone, urate oxidase, adenosine deaminase, antibody fusion proteins, and factor VII.

At least one $M_1$ may be selected from the group consisting of an oligonucleotide and siRNA.

The present invention also provides for a conjugate having a structural formula selected from the group consisting of S-(L-B-(L-M$_1$)$_k$)$_u$      Formula (VII), S-(L-B-L-(M$_1$)$_k$)$_u$      Formula (VIII), S-(L-B-(L-M$_2$)$_k$)$_u$      Formula (IX), and S-(L-B-L-(M$_2$)$_k$)$_u$      Formula (X)

wherein,
S comprises a solid support;
each $M_1$ is independently selected from the group consisting of a protein, an enzyme, an antibody, an antibody fragment, a polypeptide, avidin, streptavidin, an oligonucleotide, an oligonucleotide analog, a polysaccharide;
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a small molecule;
each B is a single MW modified sugar alcohol polymer, comprising from 2 to about 2000 sugar alcohol monomer(s);
each monomer has from 3 to about 14 —OR$^1$ groups;
each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of a $R^2$ and, a structure of —V$_1$—R$^2$—V$_2$—,
each V$_1$ and V$_2$ are independently selected from the group consisting of a Diels-Alder adduct, a 1,3-dipolar adduct, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(=O)$_2$—,

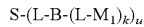
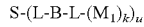
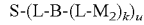
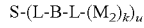

—S(=O)$_2$—(CH$_2$)$_2$—S—, —S(=O)$_2$—N(R$^3$)—, —N(R$^3$)—S(=O)$_2$—, —C(=O)—NH—NH—CH$_2$—, —C(=O)—NH—N=CH—, —CH=N—NH—C(=O)—, —CH$_2$—NH—NH—C(=O)—, —N(R$^3$)—S(=O)$_2$—N(R$^3$)—, —C(=O)—NH—CH(CH$_2$SH)—, —N=CH—, —NH—CH$_2$—, —NH—C(=O)—CH$_2$—C(=O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

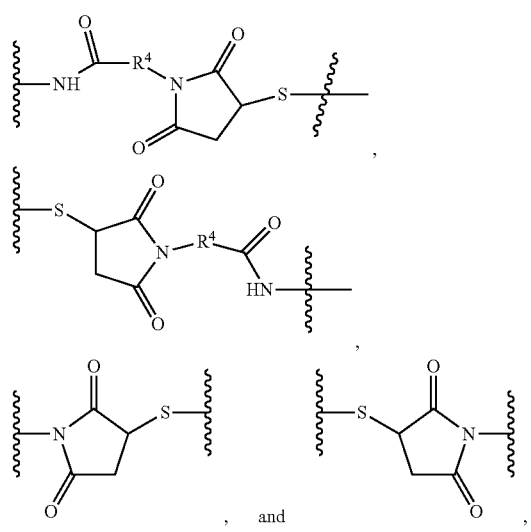

, and , each G$^1$ is independently selected from the group consisting of NR$^3$, O, and S;
each G$^2$ is independently selected from the group consisting of O and S;
each G$^3$ is independently selected from the group consisting of S, O, NR$^3$, and SO$_2$;
each G$^4$ is independently selected from the group consisting of O and NR$^3$;
each R$^2$ is independently selected from the group consisting of a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each R$^3$ is independently selected from the group consisting of hydrogen, $C_1$-$C_8$ alkyl, —(OCH$_2$CH$_2$)$_{1-3}$, alicyclyl, and heteroalicyclyl, wherein any ring in R$^3$ is optionally substituted.
each R$^4$ is independently a $C_1$-$C_8$ alkyl;
u is an integer from 1 to about 500; and,
k is 0 or an integer from 1 to about 20.

In this embodiment, B may be from 3 to about 1000 sugar alcohol units.

In this embodiment, S may be selected from the group consisting of polystyrene supports, polyamide supports, polyethylene glycol supports, polyacrylic supports, polyacrylic/beta-alanine copolymer supports, polyacrylamide/polystyrene copolymer supports, polyacrylamide/polyethylene glycol copolymer supports, polyethyleneglyco/polystyrene copolymer supports, controlled pore glass, agarose, dextran gel, polysaccharide based polymer. a polymeric microsphere, a latex microsphere, a polymeric particle consist of polystyrene, a polymeric particle consist of copolymers of styrene, poly(methyl methacrylate), polyvinyltoluene, poly(2-hydroxyethyl methacrylate), the copolymer of poly(2-hydroxyethyl methacrylate), poly(ethylene glycol dimethacrylate/2-hydroxyethylmetacrlate), poly(lactic-co-polycolic acid), inorganic constructs, metals, semiconductors, super paramagnetic composites, biodegradable constructs, synthetic dendrimers, dendrons, a quantum dot, a dye coated particle, and a magnetic coated particle. Optionally, S is an agarose bead. Alternatively, S may be a magnetic coated particle.

In all of the above mentioned embodiments, B may be a modified sugar alcohol polymer, comprising from 2 to about 2000 sugar alcohol monomer(s) $B^1$, and each sugar alcohol monomer being bound to one or more sugar alcohol monomers through a linking group W formed by a reaction between the X, Y or Z portion of one monomeric unit with the X, Y or Z of another monomeric unit;

wherein, for each $B^1$, independently, has the chemical structural of Formula XI

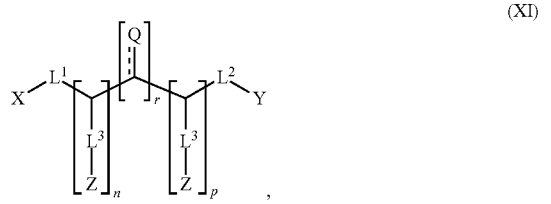

(XI)

each of n and p is independently selected from 0 and an integer selected from 1 to about 12, and n+p is between 3 and 12;

r is 0 or 1;

each bond represented by ------- is a single or a double bond;

Q is selected from the group consisting of =O, =N—O-L-$M_1$, =N—O-L-$M_2$, =N—O-L-S, —NH—O-L-S, —NH—O-L-$M_1$, and —NH—O-L-$M_2$;

each of X, Y and Z, when bound to $M_1$, $M_2$ or S, is a linker V, each of X, Y and Z, when not bound to S or $M_1$, $M_2$, is a functional group independently selected from the group consisting of —OH, -J, —$R^5$J, —C(=O)-J, —C(=O)—$CH_2$-J, —NH—C(=O)—$CH_2$-J, —$OR^5$, —$OR^6$, —$OR^7$, —O-Mesyl, —O-Tosyl, —NH—C(=O)—$CH_2$—O-Mesyl, —NH—C(=O)—$CH_2$—O-Tosyl, —SH, —S—S-tBuyl, —SR7, —$SR^5$, —S—S—$R^8$, —S(=O)$_2$-J, —$NH_2$, —$NHR^5$, —N($R^5$)$R^5$, —$NHR^7$, —NH-Fmoc, —NH-Boc, —C(=O)H, —C(=O)—$R^5$, —C(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_{2+}$)—$NH_2$, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$NH^2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;

each $R^5$ is independently selected from the group consisting of hydrogen, $C_1$-$C_8$ alkyl, alicyclyl, heteroalicyclyl, benzyl or aryl, wherein any ring in $R^5$ is optionally substituted;

each $R^6$ is independently selected benzoyl, acetyl, benzyl, $C_1$-$C_8$ alkyl silyl, cyclic ortho ester, actinide, acetate, tetrahydropyranyl, tetrahydrofuranyl, and tetrahydrothiofuranyl;

each $R^7$ is independently selected from the group consisting of trityl, MMT, and DMT;

each $R^8$ is independently selected from the group consisting of 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from the group consisting of Cl, Br and I each of $L^1$, $L^2$, and $L^3$ is independently a $R^2$ or —$R^9$—V—$R^2$—*, wherein:

"*" represents a portion of $L^1$, $L^2$, and $L^3$ bound to X, Y, S, $M_1$ or $M_2$, or a Z, respectively;

each W and V are independently selected from the group consisting of a Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—($CH_2$)$_2$—S(=O)$_2$—, —S(=O)$_2$—($CH_2$)$_2$—S—, —S(=O)$_2$—N($R^3$)—, —N($R^3$)—S(=O)$_2$—, —C(=O)—NH—NH—$CH_2$—, —C(=O)—NH—N=CH—, —CH=N—NH—C(=O)—, —$CH_2$—NH—NH—C(=O)—, —N($R^3$)—S(=O)$_2$—N($R^3$)—, —C(=O)—NH—CH($CH_2$SH)—, —N=CH—, —NH—$CH_2$—, —NH—C(=O)—$CH_2$—C(=O)—NH—, —CH=N-$G^4$-, —$CH_2$—NH-$G^4$-, -$G^4$-NH—$CH_2$—, -$G^4$-N=CH—, —C(=$NH_{2+}$)—NH—, —NH—C(=$NH_{2+}$)—, —O—P(=O)(O$^-$)—NH—, —NH—P(=O)(O$^-$)—O—, —$CH_2$—CH($NH_2$)—$CH_2$—S—, —S—$CH_2$—CH($NH_2$)—$CH_2$—, —O—P(=O)(O$^-$)—O—, —O—P(=O)(S$^-$)—O—, and —O—P(=S)(S$^-$)—O—,

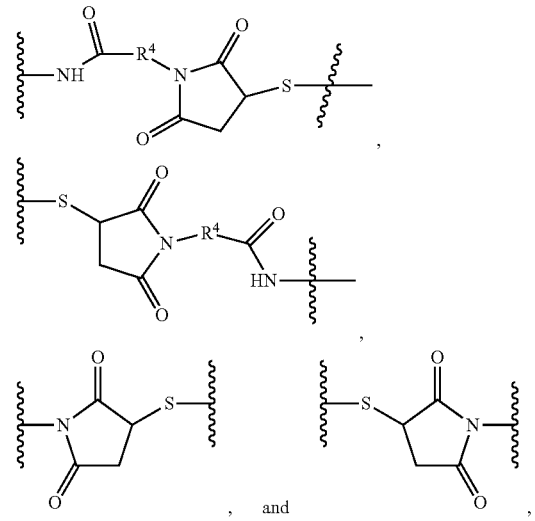

, and

, wherein:
each $G^1$ is independently selected from $NR^3$, O, and S;
each $G^2$ is independently O or S;

each G³ is independently selected from S, O, NR³, and SO₂;
each G⁴ is independently O or NR³;
each R² is independently selected from a bond, C₁-C₁₂ alkyl, —(CH₂CH₂O)₁₋₁₀—, —(CH₂CH₂O)₁₋₁₀—CH₂—, optionally substituted alicyclyl, heteroalicyclyl, aryl, a peptide, and a peptidomimetic oligomer;
each R³ is independently selected from hydrogen, C₁-C₈ alkyl, —(OCH₂CH₂)₁₋₃, optionally substituted alicyclyl, and optionally substituted heteroalicyclyl;
each R⁴ is independently C₁-C₈ alkyl;
each R⁹ is a bond or —CH₂—;
and
at least in one of the B¹ unit each -L³-Z portion is —OR¹;
wherein each R¹ is independently selected from the group consisting of hydrogen, C₁-C₈ alkyl, benzoyl, acetyl, benzyl, C₁-C₈ alkyl silyl, cyclic ortho ester, actinide, acetate, tetrahydropyranyl, tetrahydrofuranyl, and tetrahydrothiofurany.

Optionally, B has the chemical structural of Formula XII:

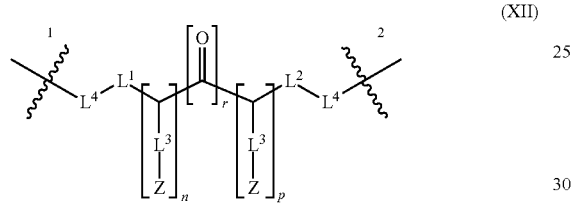

(XII)

wherein,

represents a bond to M₁, M₂ or S;
each of L⁴, when bound to M₁, M₂ or S, is a linker V when k is 0,

represents Y, when k is an integer selected from 1 to about 20,

represents a bond to M₁, M₂ or S.

Alternatively, B may have the chemical structural Formula XIII:

(XIII)

wherein:
"*1" represents a portion of the L⁴ bound to S, M1 or M2;
each of L⁴, when bound to M1 or M2, is a linker V s is 0 or an integer independently selected from 1 to about 500;
when k is 0, L4-*2 represents Y; and
when k is an integer selected from 1 to about 20, "*2" represents a portion of the L⁴ bound to M1, M2, or S and
each B1, independently, has the chemical structural Formula XIV:

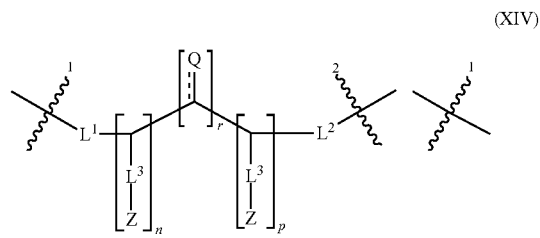

(XIV)

represents a bond to L¹; and

represents a bond to L².

In another aspect, present invention also provides for a single MW compound having a linear, branched or macrocyclic multimer sugar alcohol comprising three or more monomeric sugar alcohol units B'; and
each monomeric sugar alcohol unit is bound to one or more other monomeric units through a linking group W formed by a reaction between the X, Y or Z portion of one monomeric unit with the X, Y or Z of another monomeric unit;
wherein
each B¹ has the chemical structural Formula XV:

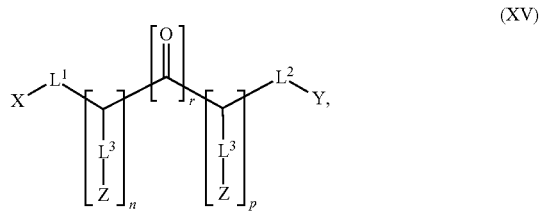

(XV)

wherein for each B', independently:
each of n and p is independently selected from 0 and an integer selected from 1 to about 12; and
n+p is between 1 and 12;
r is 0 or 1;
each of X, Y and Z is independently selected from —OH, -J, —R⁵J, —C(=O)-J, —C(=O)—CH₂-J, —NH—C(=O)—CH₂-J, —OR⁵, —OR⁶, —OR⁷, —O-Mesyl, —O-Tosyl, —NH—C(=O)—CH₂—O-Mesyl, —NH—C(=O)—CH₂—O-Tosyl, —SH, —S—S-tButyl, —SR7, —SR⁵, —S—S—R⁸, —S(=O)₂-J, —NH₂, —NHR⁵, —N(R⁵)R⁵, —NHR⁷, —NH-Fmoc, —NH-Boc, —C(=O)H, —C(=O)—R⁵, —C(=O)OH, —N=C=S, —N=C=O, —C≡C—R⁵, —N=N⁺=N⁻, —O—NH₂, —O—NH-Fmoc, —O—NH-Boc, —O—N-(Boc)$_2$, —O—N(-phthalimidyl), —NH—NH$_2$, —C(=O)—NH—NH$_2$, —NH—C(=O)—NH—NH$_2$, —NH—C(=S)—NH—NH$_2$, -toluenesulfonylhydrazide, —R$^5$—NH—C(=NH$_2^+$)—NH$_2$, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=NH$^2$)—O—R$^5$, a hydroxymethyl phosphine derivative, an ethyl vinyl, a maleimide, a vinylsulfone, an allyl sulfone, a thioester, a cisplatin derivative, an aziridine, an acryloyl group;

each R$^5$ is independently selected from hydrogen, C$_1$-C$_8$ alkyl, alicyclyl, heteroalicyclyl, benzyl or aryl, wherein any ring in R$^5$ is optionally substituted;

each R$^6$ is independently selected from benzoyl, acetyl, benzyl, C$_1$-C$_8$ alkyl silyl, cyclic ortho ester, actinide, acetate, tetrahydropyranyl, tetrahydrofuranyl, and tetrahydrothiofuranyl;

each R$^7$ is independently selected from trityl, MMT, and DMT;

each R$^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from Cl, Br and I each of L$^1$, L$^2$, and L$^3$ is independently a R$^2$ or —R$^9$—V—R$^2$—*, wherein:

"*" represents a portion of L$^1$, L$^2$, and L$^3$ bound to X, Y, or a Z, respectively;

each V and W is independently selected from the group consisting of a Diels-Alder adduct, a 1,3-dipolar adduct, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(=O)$_2$—, —S(=O)$_2$—(CH$_2$)$_2$—S—, —S(=O)$_2$—N(R$^3$)—, —N(R$^3$)—S(=O)$_2$—, —C(=O)—NH—NH—CH$_2$—, —C(=O)—NH—N=CH—, —CH=N—NH—C(=O)—, —CH$_2$—NH—NH—C(=O)—, —N(R$^3$)—S(=O)$_2$—N(R$^3$)—, —C(=O)—NH—CH(CH$_2$SH)—, —N=CH—, —NH—CH$_2$—, —NH—C(=O)—CH$_2$—C(=O)—NH—, —CH=N-G$^4$-, —CH$_2$—NH-G$^4$-, -G$^4$-NH—CH$_2$—, -G$^4$-N=CH—, —C(=NH$_{2+}$)—NH—, —NH—C(=NH$_{2+}$)—, —O—P(=O)(O$^-$)—NH—, —NH—P(=O)(O)—O—, —CH$_2$—CH(NH$_2$)—CH$_2$—S—, —S—CH$_2$—CH(NH$_2$)—CH$_2$—, —O—P(=O)(O)—O—, —O—P(=O)(S$^-$)—O—, and —O—P(=S)(S$^-$)—O—,

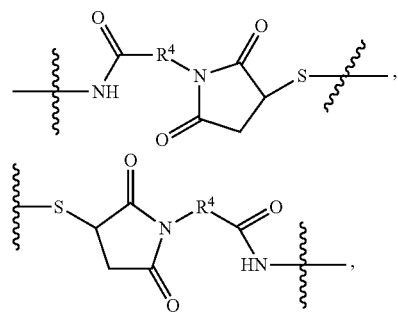

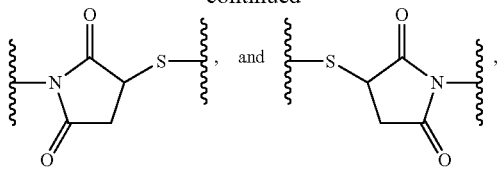

wherein:
each G$^1$ is independently selected from NH, O, and S;
each G$^2$ is independently O or S;
each G$^3$ is independently selected from S, O, NR$^3$, and SO$_2$;
each G$^4$ is independently O or NR$^3$;
each R$^2$ is independently selected from a bond, C$_1$-C$_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each R$^3$ is independently selected from hydrogen, C$_1$-C$_8$ alkyl, —(OCH$_2$CH$_2$)$_{1-3}$, alicyclyl, heteroalicyclyl, wherein any ring in R$^3$ is optionally substituted;
each R$^4$ is independently C$_1$-C$_8$ alkyl;
each R$^9$ is a bond or —CH$_2$—; and,
at least in one of the B$^1$ unit each -L$^3$-Z portion is —OR$^1$; wherein each R$^1$ is independently selected from the group consisting of hydrogen, C$_1$-C$_8$ alkyl, benzoyl, acetyl, benzyl, C$_1$-C$_8$ alkyl silyl, cyclic ortho ester, actinide, acetate, tetrahydropyranyl, tetrahydrofuranyl, and tetrahydrothiofurany; at least in one of the B$^1$ unit, n+p+r is greater than 1.

Preferably, the compound has a molecular weight from about 5 kDa to about 500 kDa. More, preferably, the compound has a the molecular weight of the compound is from about 10 kDa to about 100 kDa. Most preferably, the compound has a molecular weight is from about 10 kDa to about 60 kDa.

Preferably, the compound has a purity of greater 90%. More preferably, the compound has a purity of greater than 95%.

Most preferably, the compound has a molecular weight from about 10 kDa to about 60 kDa and the compound has a purity of greater 95%.

The compound may have a W selected from the group consisting of —S—, —O—, —NH—, —C(=O)NH—, —NHC(=O)—, —S(=O)—, —S(=O)$_2$—, —P(=S)$_2$O—, and —P(=S)(=O)O—.

Optionally the compound has a W selected from the group consisting of —S—, —O—, —S(=O)—, —S(=O)$_2$—, —P(=S)$_2$O—, and —P(=S)(=O)O—. More preferably, W is —O—.

Preferably, at least one of X, Y, or Z of the compound may be selected from —O—NH$_2$, —N=C=S, —N=C=O, —C≡C—R$^5$, —N=N$^+$=N—, —SR$^5$, —S—S—R$^8$, —C(=O)—CH$_2$-J, a diene, a dienophil, a ketone, an aldehyde, a 1,3-dipole, a dipolarophile, an alkene, a ketene, an olefin, an alkene with allylic hydrogen, trifluoromethyl phenyldiazirine, N-hydroxysuccimidyl ester, and maleimide;

each R$^5$ may be independently selected from hydrogen, C$_1$-C$_8$ alkyl, alicyclyl, heteroalicyclyl, benzyl and aryl, wherein any ring in R$^5$ is optionally substituted;

each R$^8$ may be independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl; and each J is independently selected from Cl, Br, and I.

Optionally, for the compound, each of $L^1$, $L^2$ may be —$CH_2$—, each $L^3$ may be a bond, and each Z may be —$OR^1$, wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany Optionally, for the compound, each X may be —O—($C_1$-$C_8$ alkyl); at least one Y may be —N=$N^+$=$N^-$, —O—$NH_2$, alkyl, —NH—C(=O)—$CH_2CH_2$-maleimide, —S—S—$R^8$, —NH—(C=O)—$CH_2$—Br, —NH—C(=O)—$CH_2$—$CH_2$—S—S—$R^8$, —SH, —S—C(=O)—$CH_3$,

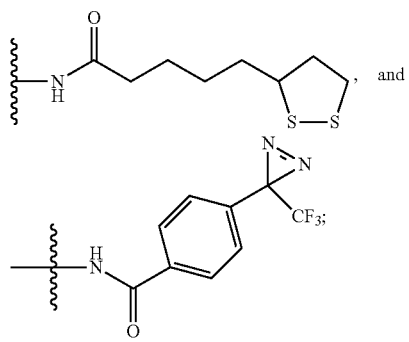

and each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

Optionally, each -$L^3$-Z portion of the compound may be —$OR^1$ wherein $R^1$ may be independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany.

Optionally, for the compound, each $L^1$ and $L^2$ may be —$CH_2$—.

For the compound, each r may be 0.

The compound may have at least one X and at least one Y that are the same and may be selected from N-hydroxysuccimidyl, —NH—C(=O)—$CH_2CH_2$-maleimide, —N=$N^+$=$N^-$, —O—$NH_2$, —C≡C—$C_1$-$C_4$ alkyl,

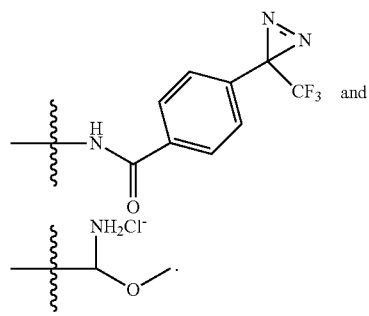

The compound may also have each -$L^3$-Z be —OH.

The compound may also have each $L^1$ and $L^2$ be a —$CH_2$—.

The compound may also have each r be 0.

The compound may have at least one X, and at least one Y independently selected from —OH, —$OC_1$-$C_8$ alkyl, —S—S—$R^8$, —O—$NH_2$, —C(=O)—OH, N-hydroxysuccimide, —NH—C(=O)—$CH_2CH_2$-maleimide, —NH—C(=O)—$CH_2$—Br,

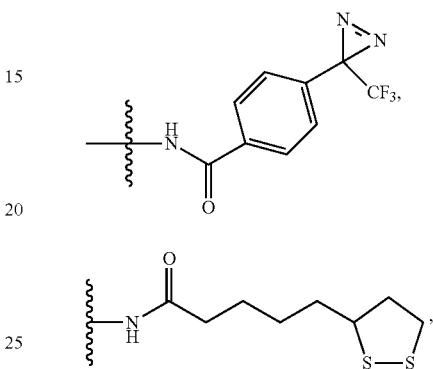

and —S—C(=O)—$CH_3$; and wherein X and Y are different. Preferably, each -$L^3$-Z is —OH. More preferably each -$L^3$-Z may be —OH and each $L^1$, $L^2$ may be —$CH_2$—. Most preferably, each -$L^3$-Z is —OH, each $L^1$, $L^2$ may be —$CH_2$— and each r is 0.

The compound may have at least one X, Y, or Z may be a vinylsulfone group or has the formula:

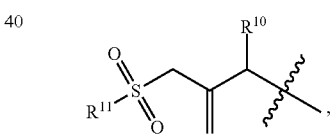

wherein $R^{10}$ is an electron withdrawing group; and $R^{11}$ is an optionally substituted aryl.

Optionally, the multimer of the compound may be linear and have the following structure XVI

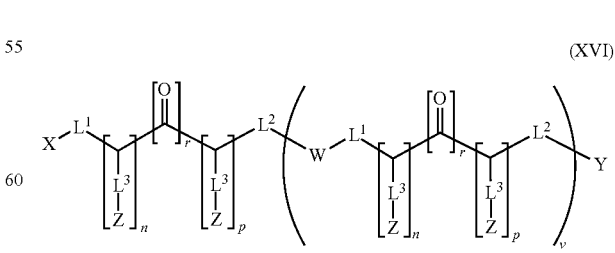

(XVI)

wherein v is an integer from 2 to about 2000. More preferably, each -$L^3$-Z portion of the compound is —$OR^1$ and has the following structure XXI

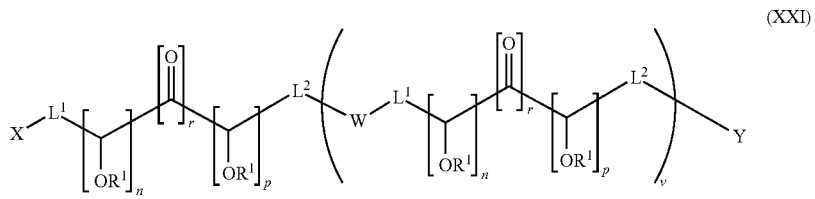
(XXI)

wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany. Even more preferably, each r is 0 and the multimer has the following structure XVII

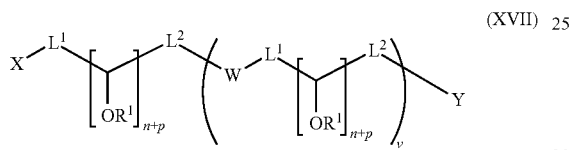
(XVII)

wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany. Even more preferably, the compound has the following structure XVIII

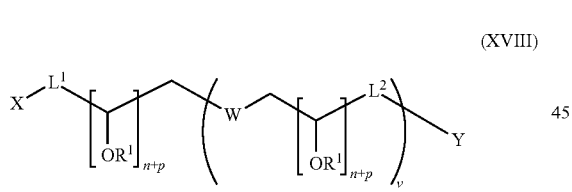
(XVIII)

wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany. Even more preferably, the compound wherein W is selected from the group consisting of —S—, —O—, —NH—, —C(═O)NH—, —NHC(═O)—, —S(═O)—, —S(═O)$_2$—, —P(═S)$_2$O—, and —P(═S)(═O)O—.

Optionally W may be selected from the group consisting of —S—, —O—, —S(═O)—, —S(═O)$_2$—, —P(═S)$_2$O—, and —P(═S)(═O)O—. Preferably, W is —O—. Optionally, X and Y is not the same.

Optionally, the compound may be a multimer which is cyclic having the structural formula XIX

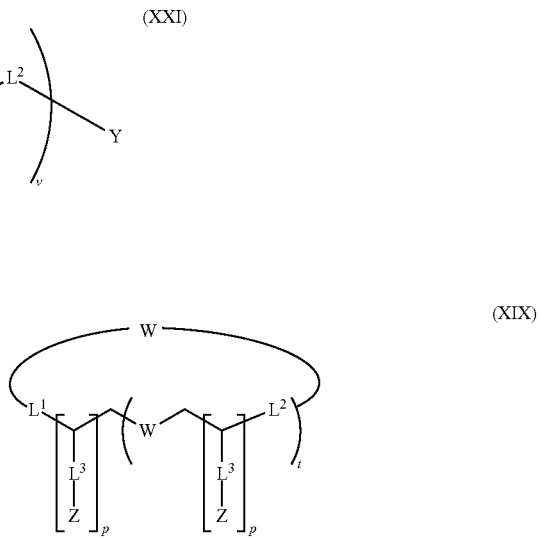
(XIX)

wherein t is an integer from 3 to about 2000, each p may be independently selected from 1 to about 12.

Optionally, the compound may be a multimer which is a branched macro sugar alcohol compound having the structural formula XX:

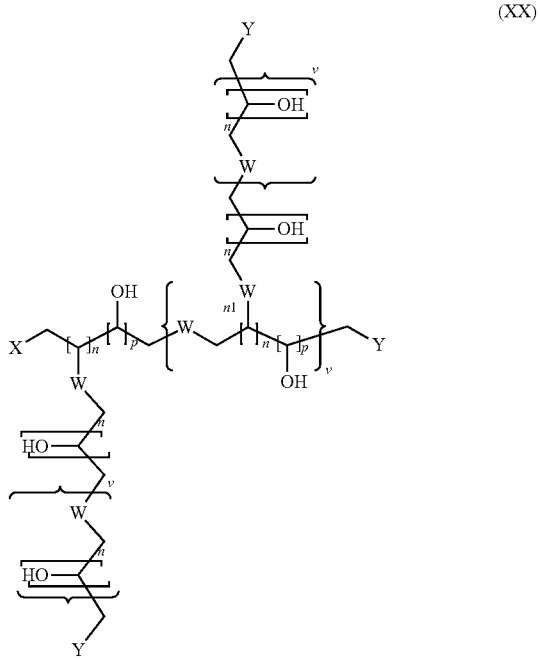
(XX)

wherein each n and p is an integer independently selected from 0 to 12, and n+p is between 2 and 12 each n is an integer independently selected from 1 to 12;

each v is an integer independently selected from 0 to 2000.

The present invention also provides, a monomeric sugar alcohol having the chemical structural Formula XXVI:

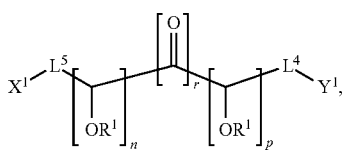

(XXVI)

each of n and p may be independently selected from 0 and an integer selected from 1 to about 12; and n+p is between 2 and 12;

r is 0 or 1;

each of $X^1$ may be independently selected from —OH, -J, —C(=O)—CH$_2$-J, —OR$^5$, —S—S—R$^8$, —NH—C(=O)—CH$_2$CH$_2$—S—S—R$^8$, —S—C(=O)—CH$_3$, —C(=O)H, —C(=O)—R$^5$, —C(=O)OH, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —C(=O)—NH—NH$_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, a imidoester, a maleimide;

each of $Y^1$ may be independently selected from —S—S-tButyl, —SR$^7$, —S—S—R$^8$, —NH—C(=O)—CH$_2$CH$_2$—S—SR$^8$, —NHR$^7$, —NH-Fmoc, —NH-Boc, —O—NH$_2$, —O—NH-Fmoc, —O—NH-Boc, —O—N-(Boc)$_2$, —O—N(-phthalimidyl), an optionally substituted trifluoromethylphenyldiazirine, an optionally substituted N-hydroxysuccinimide ester, a imidoester, a maleimide;

each $R^1$ may be independently selected from the group consisting of hydrogen, C$_1$-C$_8$ alkyl, benzoyl, acetyl, benzyl, C$_1$-C$_8$ alkyl silyl, cyclic ortho ester, actinide, acetate, tetrahydropyranyl, tetrahydrofuranyl, and tetrahydrothiofurany;

each $R^5$ may be independently selected from hydrogen, C$_1$-C$_8$ alkyl, alicyclyl, heteroalicyclyl, benzyl or aryl, wherein any ring in $R^5$ is optionally substituted.

each $R^7$ may be independently selected from trityl, MMT, and DMT;

each $R^8$ may be independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J may be independently selected from Cl, Br, and I $L^4$ and $L^5$ may be independently selected from a bond, —CH$_2$—*, —C(=O)—NH—C$_{1-8\ alkyl}$—*, —CH$_2$—NH—C(=O)—C$_{1-8\ alkyl}$—*, —CH$_2$—C(=O)—NH—C$_{1-8\ alkyl}$—*;

"*" represents a portion of $L^4$ and $L^5$ bound $X^1$ or $Y^1$.

Optionally, the monomeric sugar alcohol may have $X^1$ be —C(=O)—OH; r is 0, and $Y^1$ be independently selected from —NH—R$^7$, —NH-Fmoc, —NH-Boc, —S—S—R$^8$, —S—S—R$^7$, —S—S-tButyl, —O—NH-Fmoc, —O—N-(Boc)$_2$, and —O—N(-phthalimidyl); wherein;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^7$ is independently selected from trityl, MMT, and DMT; and when r is 1, then $Y^1$ is OR$^1$ wherein;

each $R^1$ is independently selected from the group consisting of hydrogen, C$_1$-C$_8$ alkyl, benzoyl, acetyl, benzyl, C$_1$-C$_8$ alkyl silyl, cyclic ortho ester, actinide, acetate, tetrahydropyranyl, tetrahydrofuranyl, and tetrahydrothiofurany.

Optionally, the monomeric sugar alcohol may have $X^1$ be a phosphoramidite;

when r is 0, $Y^1$ be independently selected from —S—S—(C$_1$-C$_4$ alkyl)-OR$^7$, S—S—R$^8$, —NH-TFA, —NH—R$^7$, wherein each $R^7$ is independently selected from trityl, MMT, and DMT each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

The monomeric sugar alcohol may have $X^1$ and $Y^1$ not be the same. More preferably, at least one of $X^1$ and $Y^1$ is selected from the group consisting of —O—NH$_2$, —S—S—R$^8$, —NH—C(=O)—CH$_2$CH$_2$—S—S—R$^8$, an optionally substituted N-hydroxysuccimide ester group, a optionally substituted trifluoromethylphenyldiazirine, a maleimide group; wherein each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl The monomeric sugar alcohol may have a chemical formula of

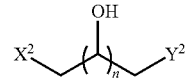

wherein, n is an integer selected from about 2 to about 8;

$X^2$ is a chemical- or photocrosslinking group selected from the group consisting of

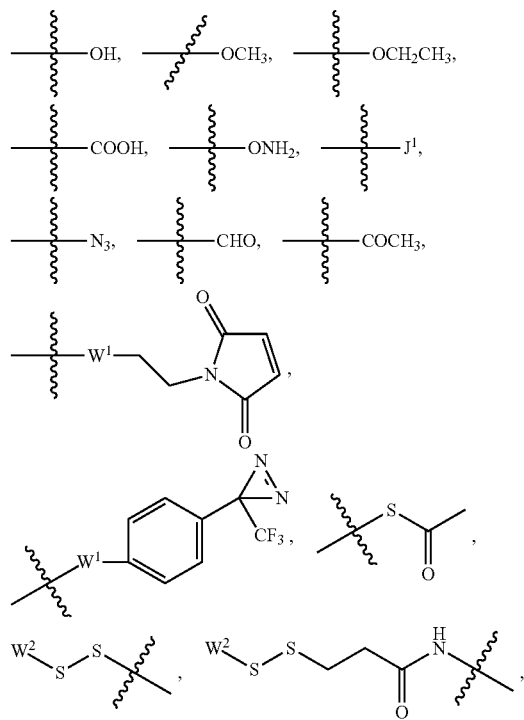

-continued

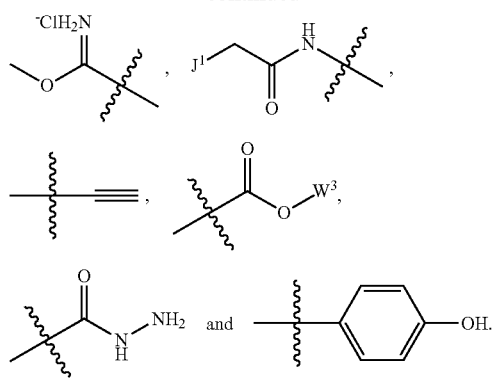

$Y^2$ is a chemical- or photocrosslinking group selected from the group consisting of:

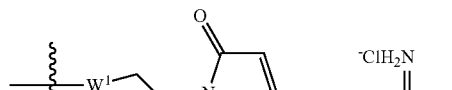, 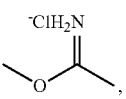,

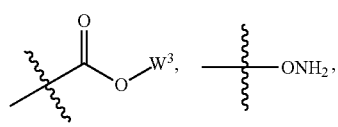

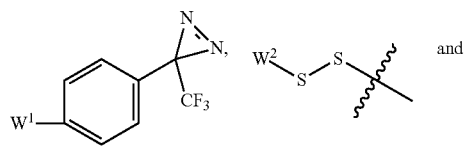

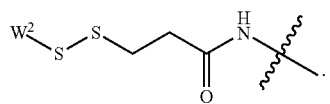

$W^1$ is an independent linker selected from the group consisting of —C(=O)—NH—, and, —NH—C(=O)—;

each of $J^1$ is independently selected from Cl, Br and I;

each of $W^2$ is independently selected from the group consisting of

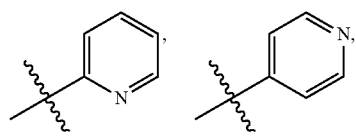

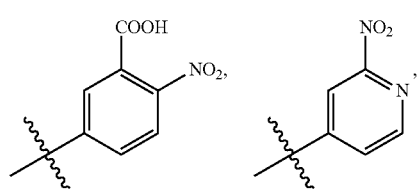

-continued

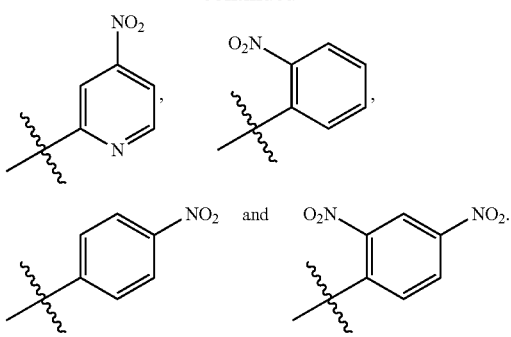

each of $W^3$ is independently selected from the group consisting of

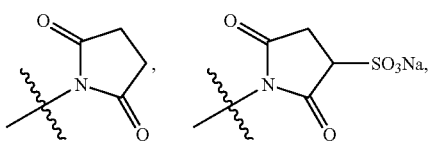

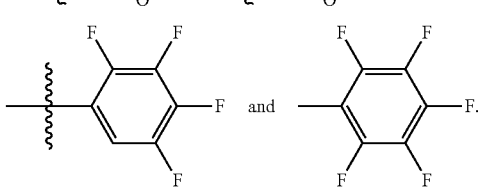

Preferably, the monomeric sugar alcohol may has the structure of a chemical formula selected from the group consisting of

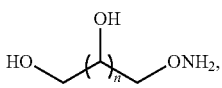

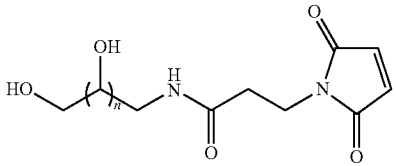

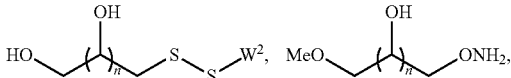

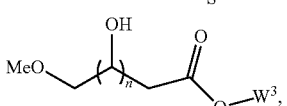

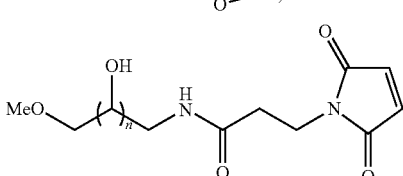

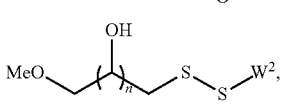

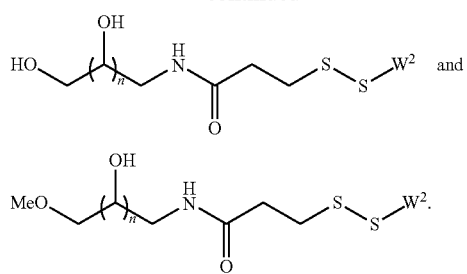

More preferably, the monomeric sugar alcohol has the structure of a chemical formula selected from the group consisting of

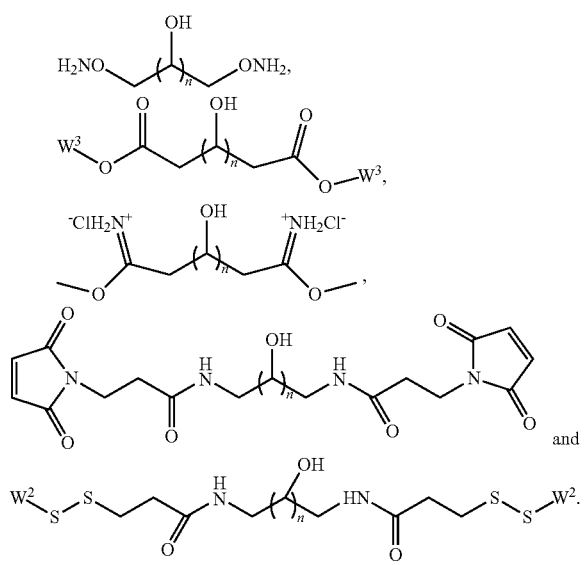

Alternatively, the monomeric sugar alcohol has chemical formula selected from the group consisting of

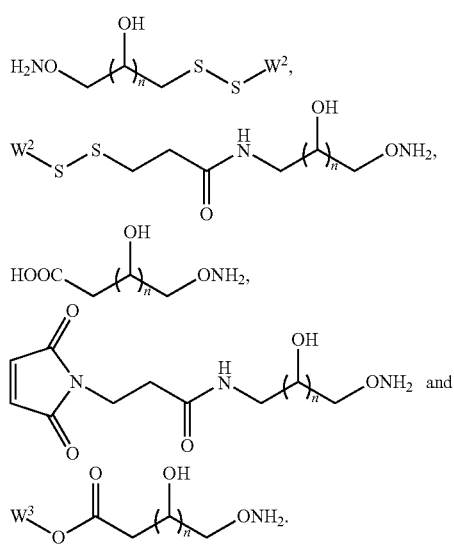

Alternatively, the monomeric sugar alcohol has chemical formula selected from the group consisting of

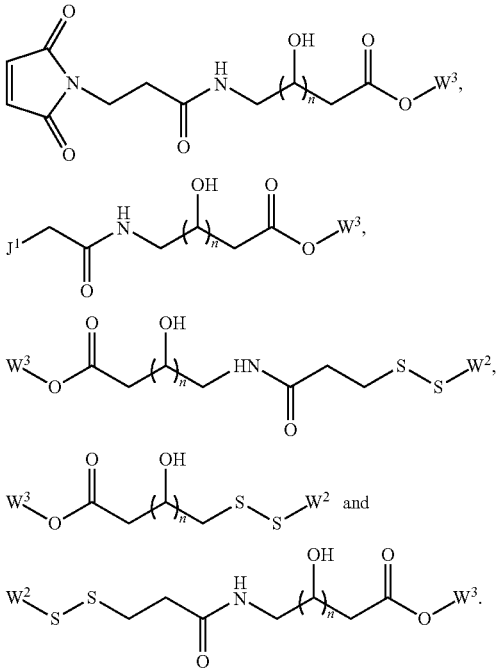

Most preferably, the monomeric sugar alcohol has chemical formula selected from the group consisting of

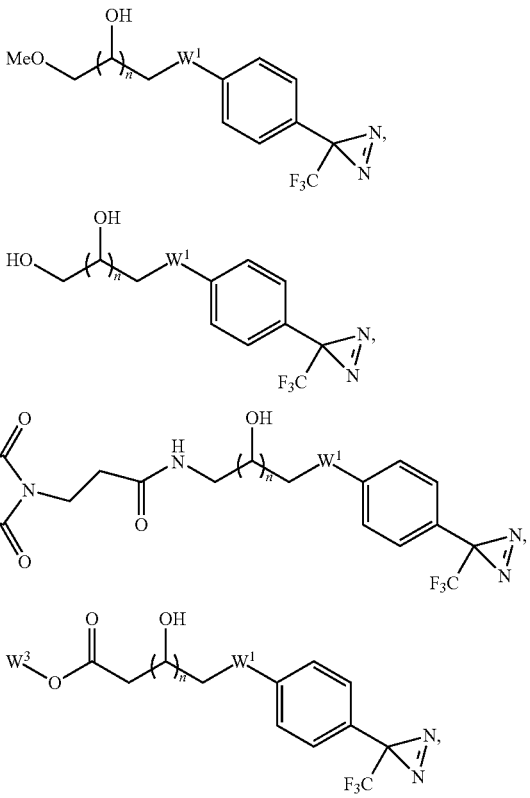

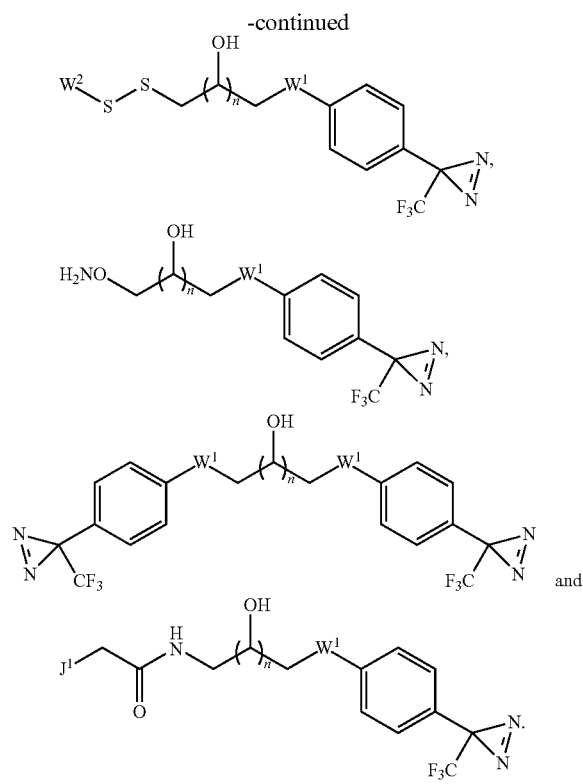

Most preferably, the monomeric sugar alcohol has chemical formula selected from the group consisting of

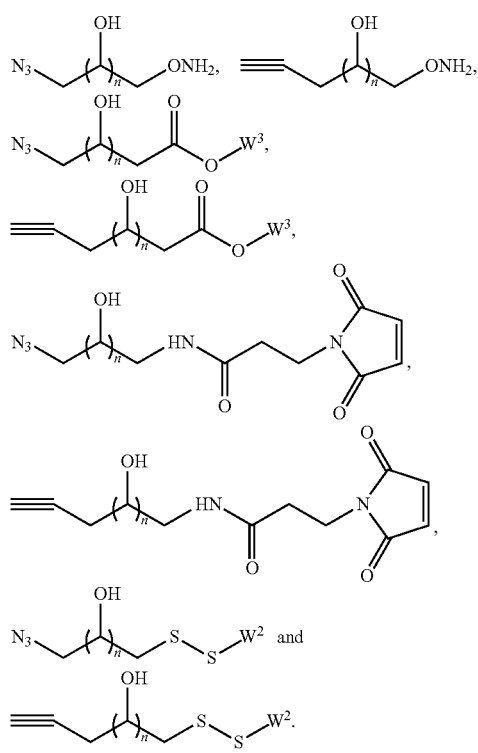

The present invention also provides for a dimeric sugar alcohol having the chemical structural Formula XVIII:

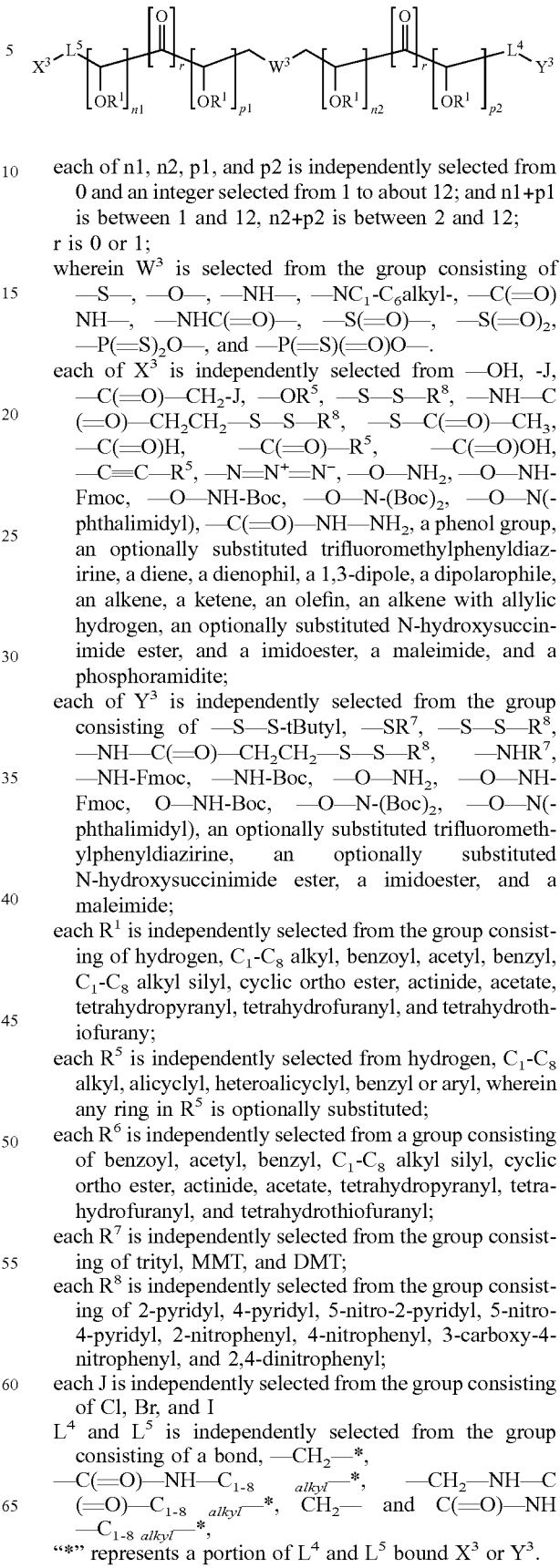

each of n1, n2, p1, and p2 is independently selected from 0 and an integer selected from 1 to about 12; and n1+p1 is between 1 and 12, n2+p2 is between 2 and 12;

r is 0 or 1;

wherein $W^3$ is selected from the group consisting of —S—, —O—, —NH—, —NC$_1$-C$_6$alkyl-, —C(=O)NH—, —NHC(=O)—, —S(=O)—, —S(=O)$_2$, —P(=S)$_2$O—, and —P(=S)(=O)O—.

each of $X^3$ is independently selected from —OH, -J, —C(=O)—CH$_2$-J, —OR$^5$, —S—S—R$^8$, —NH—C(=O)—CH$_2$CH$_2$—S—S—R$^8$, —S—C(=O)—CH$_3$, —C(=O)H, —C(=O)—R$^5$, —C(=O)OH, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —C(=O)—NH—NH$_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, and a imidoester, a maleimide, and a phosphoramidite;

each of $Y^3$ is independently selected from the group consisting of —S—S-tButyl, —SR$^7$, —S—S—R$^8$, —NH—C(=O)—CH$_2$CH$_2$—S—S—R$^8$, —NHR$^7$, —NH-Fmoc, —NH-Boc, —O—NH$_2$, —O—NH-Fmoc, O—NH-Boc, —O—N-(Boc)$_2$, —O—N(-phthalimidyl), an optionally substituted trifluoromethylphenyldiazirine, an optionally substituted N-hydroxysuccinimide ester, a imidoester, and a maleimide;

each $R^1$ is independently selected from the group consisting of hydrogen, C$_1$-C$_8$ alkyl, benzoyl, acetyl, benzyl, C$_1$-C$_8$ alkyl silyl, cyclic ortho ester, actinide, acetate, tetrahydropyranyl, tetrahydrofuranyl, and tetrahydrothiofurany;

each $R^5$ is independently selected from hydrogen, C$_1$-C$_8$ alkyl, alicyclyl, heteroalicyclyl, benzyl or aryl, wherein any ring in $R^5$ is optionally substituted;

each $R^6$ is independently selected from a group consisting of benzoyl, acetyl, benzyl, C$_1$-C$_8$ alkyl silyl, cyclic ortho ester, actinide, acetate, tetrahydropyranyl, tetrahydrofuranyl, and tetrahydrothiofuranyl;

each $R^7$ is independently selected from the group consisting of trityl, MMT, and DMT;

each $R^8$ is independently selected from the group consisting of 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from the group consisting of Cl, Br, and I $L^4$ and $L^5$ is independently selected from the group consisting of a bond, —CH$_2$—*, —C(=O)—NH—C$_{1-8}$ $_{alkyl}$—*, —CH$_2$—NH—C(=O)—C$_{1-8}$ $_{alkyl}$—*, CH$_2$— and C(=O)—NH—C$_{1-8}$ $_{alkyl}$—*, "*" represents a portion of $L^4$ and $L^5$ bound $X^3$ or $Y^3$.

Preferably, the dimeric sugar alcohol compound has a $W^3$ selected from the group consisting of —S—, —O—, —S(=O)—, —S(=O)$_2$—, —P(=S)$_2$O—, and —P(=S)(=O)O—.

The dimeric sugar alcohol compound may have a $W^3$ which is —O— The dimeric sugar alcohol compound may have $X^3$ is —C(=O)—OH, r is 0, and $Y^3$ is independently selected from the group consisting of —NH—$R^7$, —NH-Fmoc, —NH-Boc, —S—S—$R^8$, —S—S—$R^7$, —S—S-tButyl, —O—NH-Fmoc, —O—N-(Boc)$_2$, and —O—N(-phthalimidyl); wherein, each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^7$ is independently selected from the group consisting of trityl, MMT, and DMT; and
when r is 1, then Y is $OR^1$ wherein;
$R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany.

The dimeric sugar alcohol compound may have $X^3$ be a phosphoramidite when r is 0, $Y^3$ is independently selected from the group consisting of —S—S—($C_1$-$C_4$ alkyl)-$OR^7$, S—S—$R^8$, —NH-TFA, —NH—$R^7$, wherein
each $R^7$ is independently selected from trityl, MMT, and DMT
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

The dimeric sugar alcohol compound may have $X^3$ and $Y^3$ not be the same.

The dimeric sugar alcohol compound may have $X^3$ and $Y^3$ be independently selected from the group consisting of —O—NH$_2$, —S—S—$R^8$, —NH—C(=O)—CH$_2$CH$_2$—S—S—$R^8$, an optionally substituted N-hydroxysuccimide ester group, a optionally substituted trifluoromethylphenyl-diazirine, and a maleimide group; wherein,
each $R^8$ is independently selected from the group consisting of 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

The dimeric sugar alcohol compound may have $X^3$ be an aminooxy group, $Y^3$ be selected from the group consisting of a maleimide group, a sulfhydryl group, a disulfide group, a haloacetyl group, an azide group, and an alkyne group.

The dimeric sugar alcohol compound may have $X^3$ be an optionally substituted N-hydroxysuccinimide ester, $Y^3$ be selected from the group consisting of a maleimide group, a sulfhydryl group, a disulfide group, a haloacetyl group, an azide group, and an alkyne group.

The present invention also provides an embodiment of a first sugar alcohol-derived compound that has a chemical formula

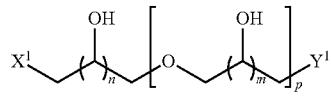

wherein,
n is an integer from 2 to about 8;
m is an integer from 1 to about 8;
p is an integer from 1 to about 2000;

each of $X^1$ is selected from the group consisting of:

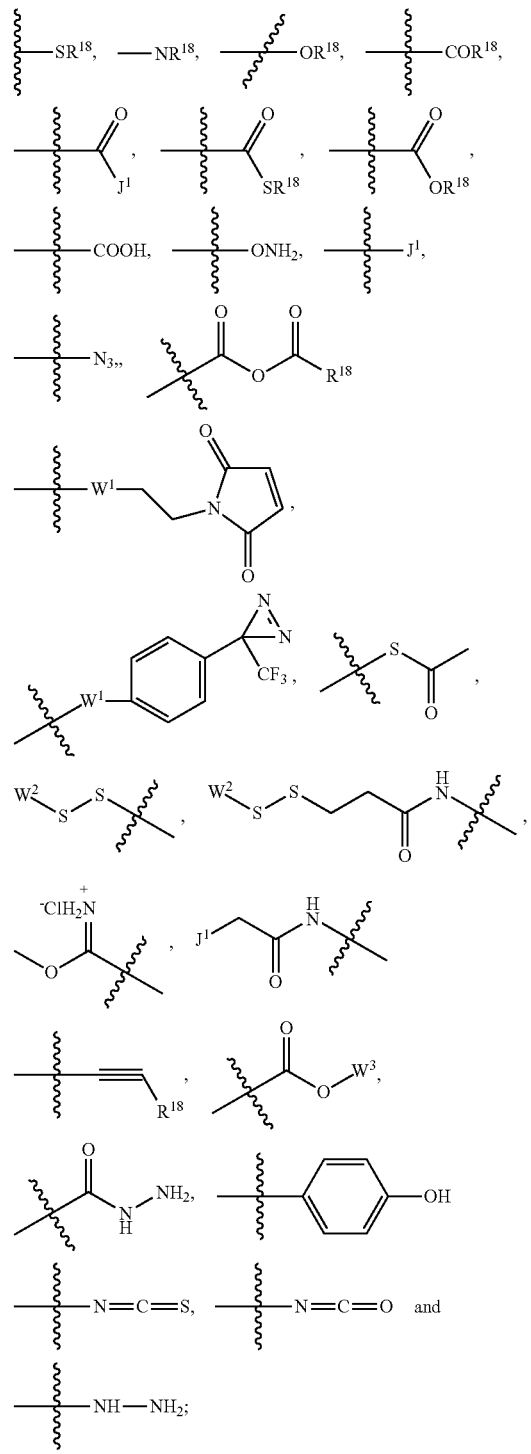

each $Y^1$ is selected from the group consisting of

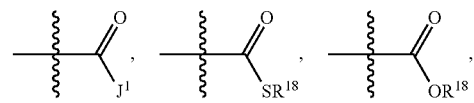

-continued

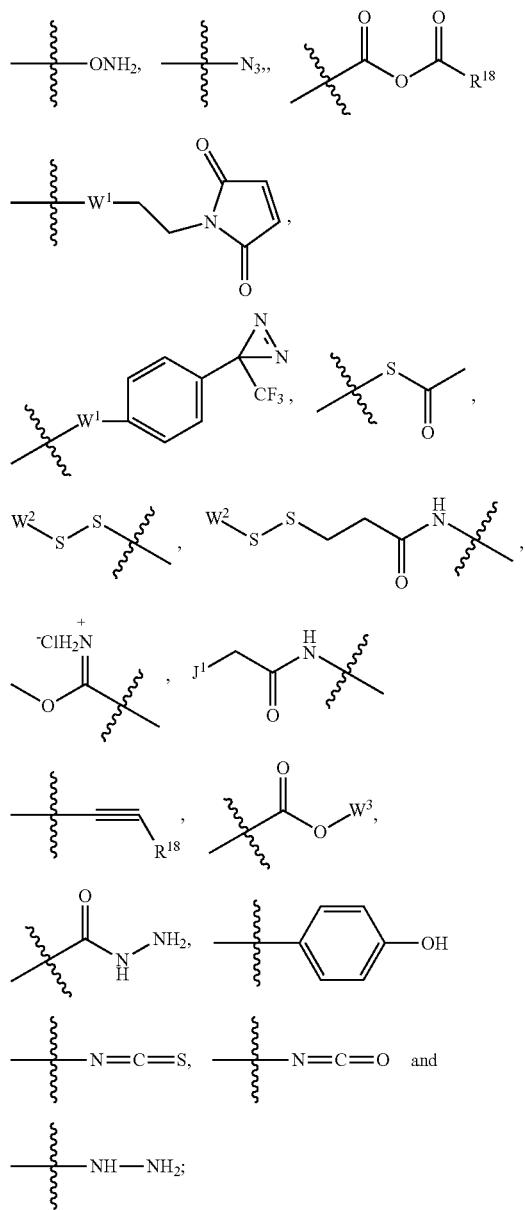

each W¹ is selected from the group consisting of —C(=O)—NH— and —NH—C(=O)—;
each J¹ is selected from the group consisting of Cl, Br or I;
R¹⁸ is selected from the group consisting of hydrogen, $C_{1-8}$ alkyl, alicyclyl, heteroalicyclyl, benzyl and aryl, wherein any ring in R¹⁸ is optionally substituted
each W² is independently selected from the group consisting of

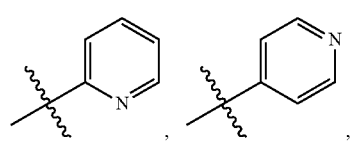

-continued

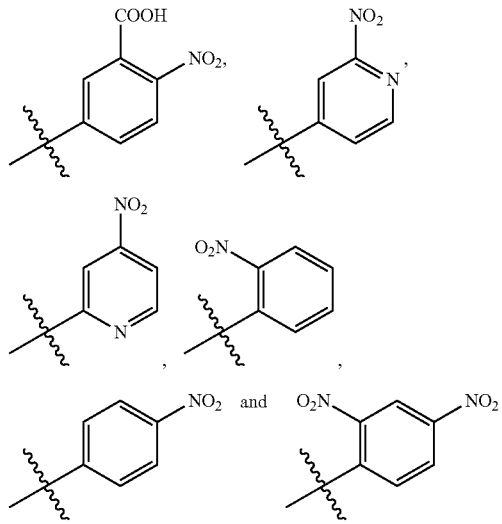

and,
each of W³ is independently selected from the group consisting of

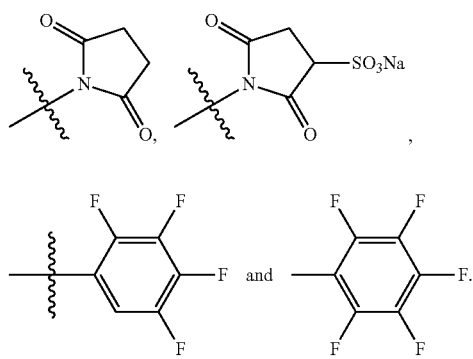

Preferably, the first sugar alcohol-derived compound has a chemical formula selected from the group consisting of:

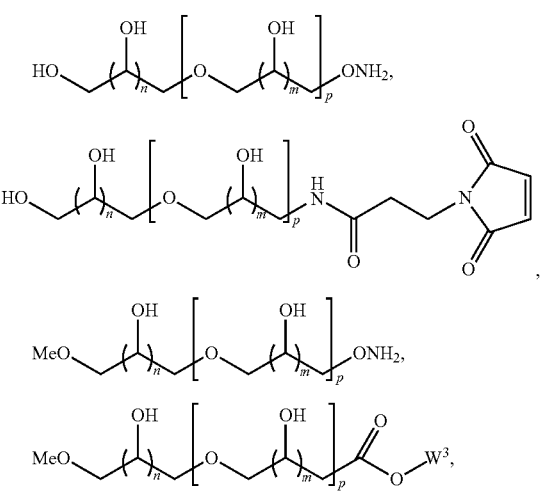

-continued

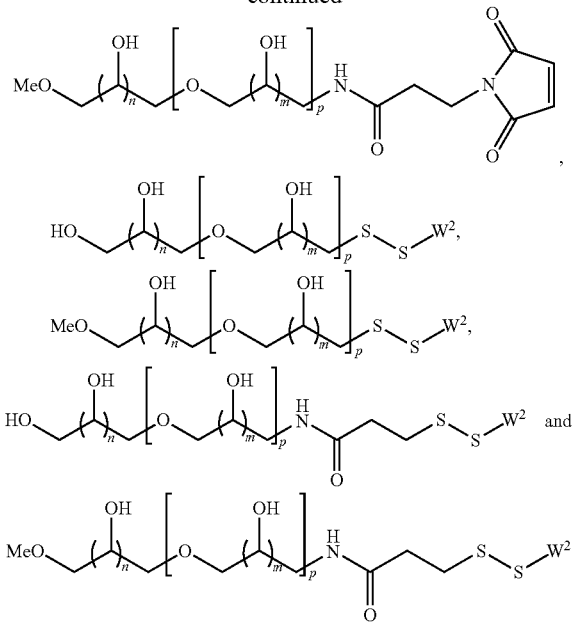

More preferably, the first sugar alcohol-derived compound has a chemical formula selected from the group consisting of:

-continued

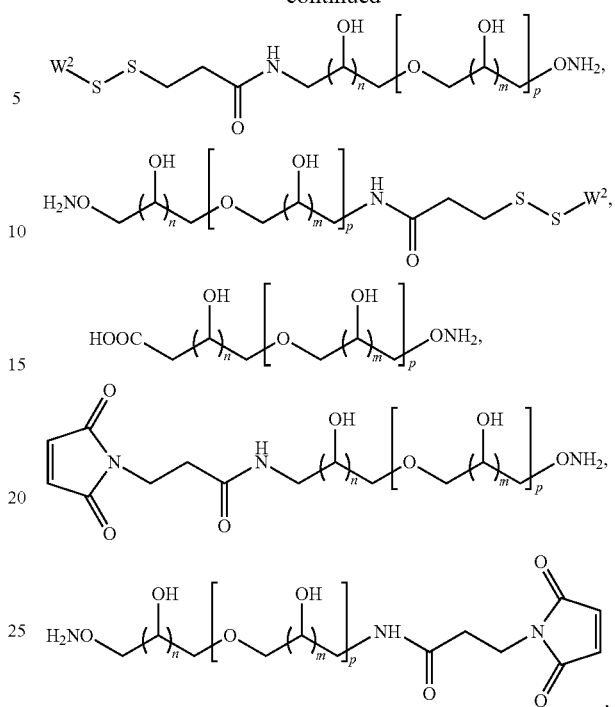

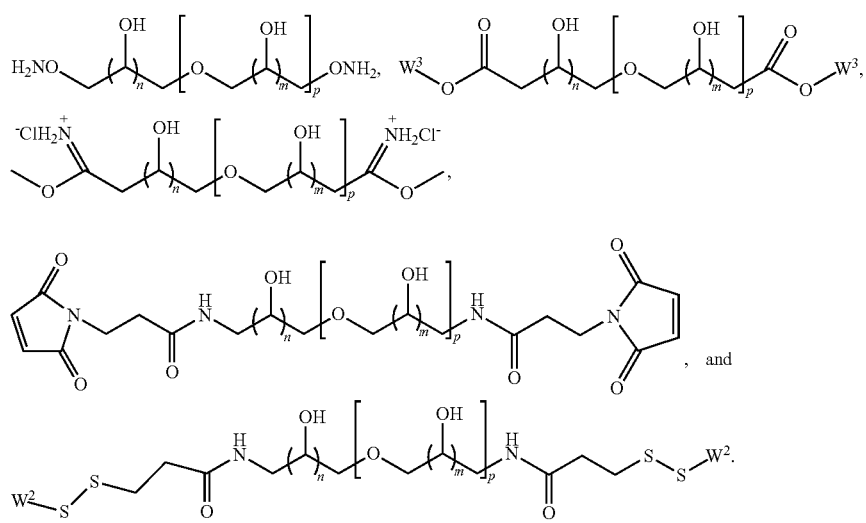

Most preferably, the first sugar alcohol-derived compound has a chemical formula selected from the group consisting of:

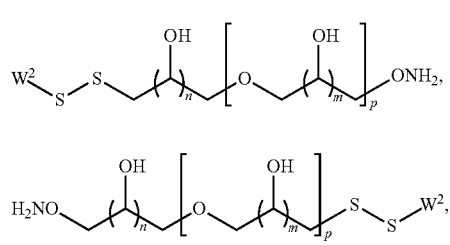

-continued

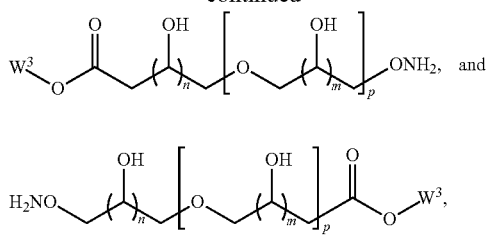

Alternatively, the first sugar alcohol-derived compound has a chemical formula has a chemical formula selected from the group consisting of:

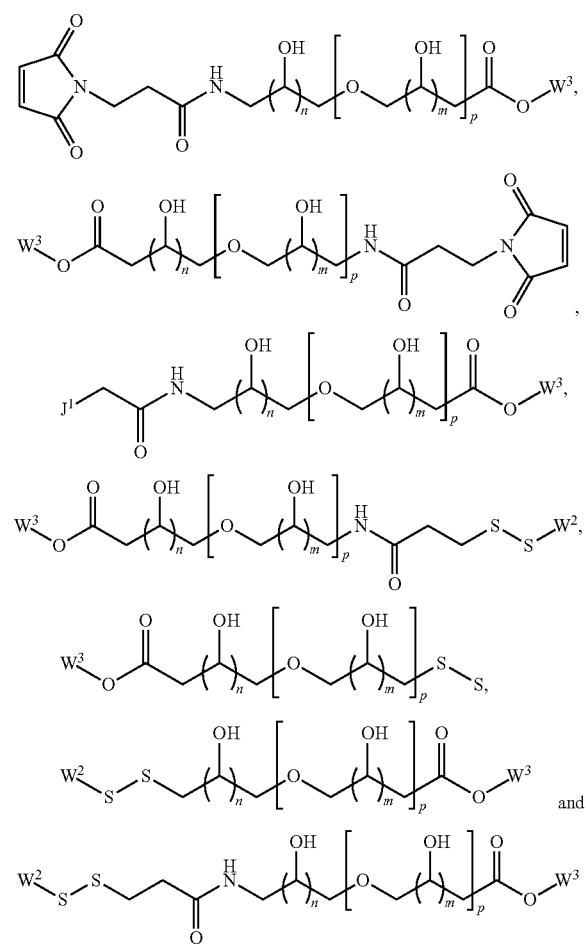
Alternatively, the first sugar alcohol-derived compound has a chemical formula selected from the group consisting of:
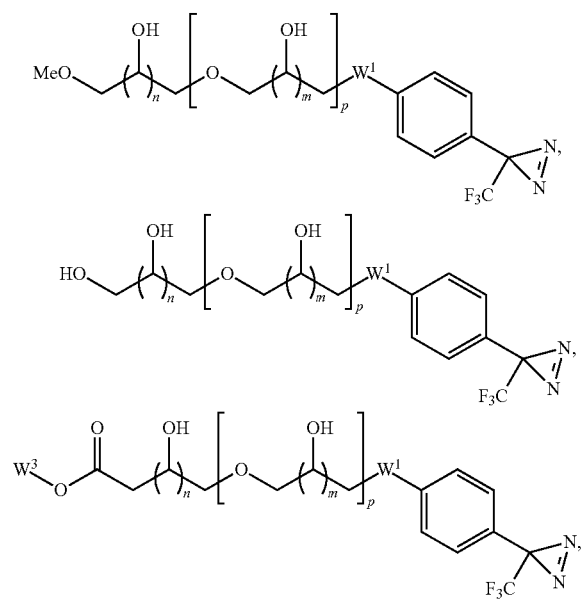
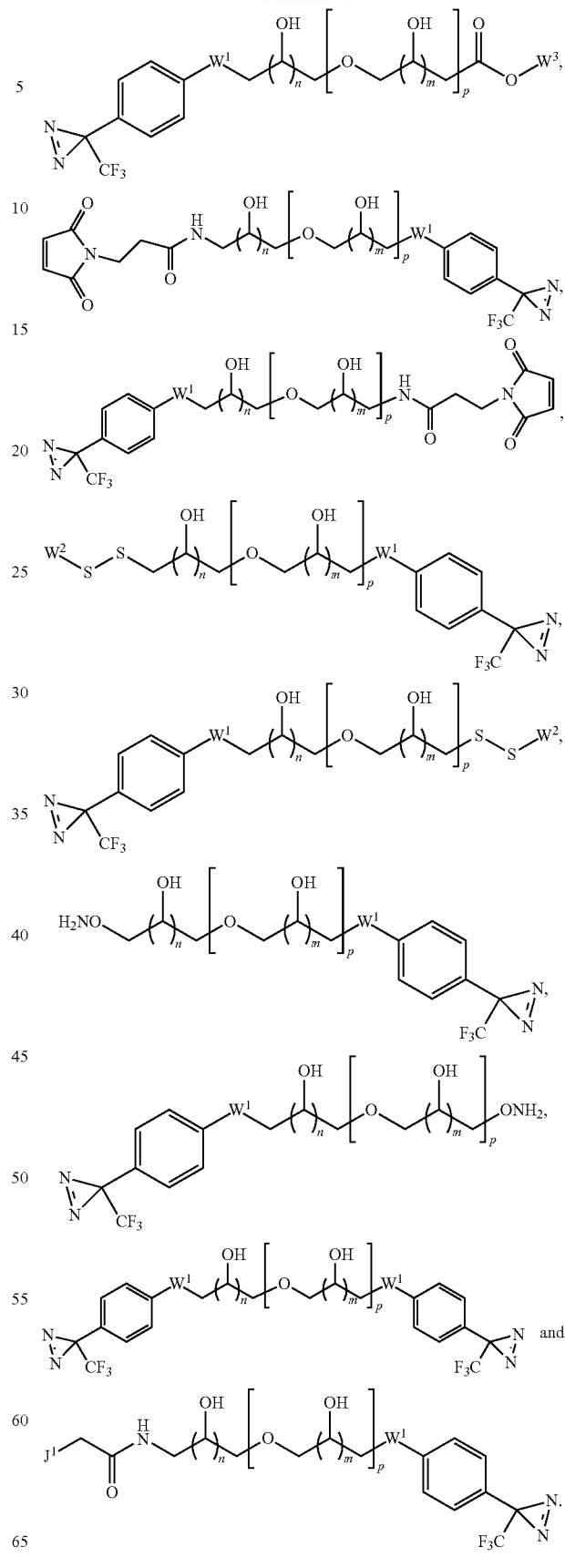

Alternatively, the first sugar alcohol-derived compound has a chemical formula selected from the group consisting of:

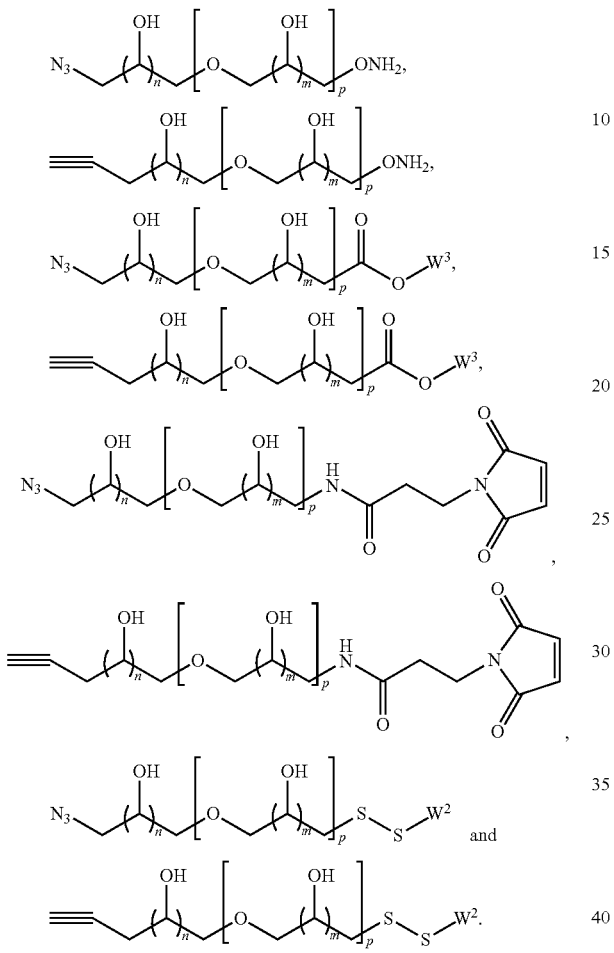

Preferably, the first sugar alcohol-derived compound has a p which is an integer from 1 to about 1000.

Preferably, compound embodiment may be a sugar alcohol derived compound wherein p is an integer from 1 to about 500.

Optionally, the molecular weight of the first sugar alcohol-derived compound may be about 5 KDa to about 500 KDa. Preferably, the molecular weight of the compound is about 10 KDa to about 100 KDa. More preferably, the molecular weight of the compound is about 10 KDa to about 60 KDa.

Optionally, the first sugar alcohol-derived compound is about 90% pure. Preferably, the compound is about 95% pure. More preferably, the compound is about 97% pure.

The molecular weight of the first sugar alcohol-derived compound may be about 5 KDa to about 500 KDa and the compound may be about 90% pure. More preferably the molecular weight of compound may be about 10 KDa to about 100 KDa and the compound may be about 90% pure. Most preferably, the molecular weight of the compound may be about 10 KDa to about 60 KDa and the compound may be about 90% pure.

The present invention also provides a second sugar alcohol-derived compound having the chemical formula.

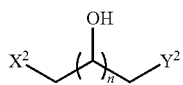

wherein,
n is an integer from 2 to about 8;
$X^2$ is a chemical- or photocrosslinking group selected from the group consisting of

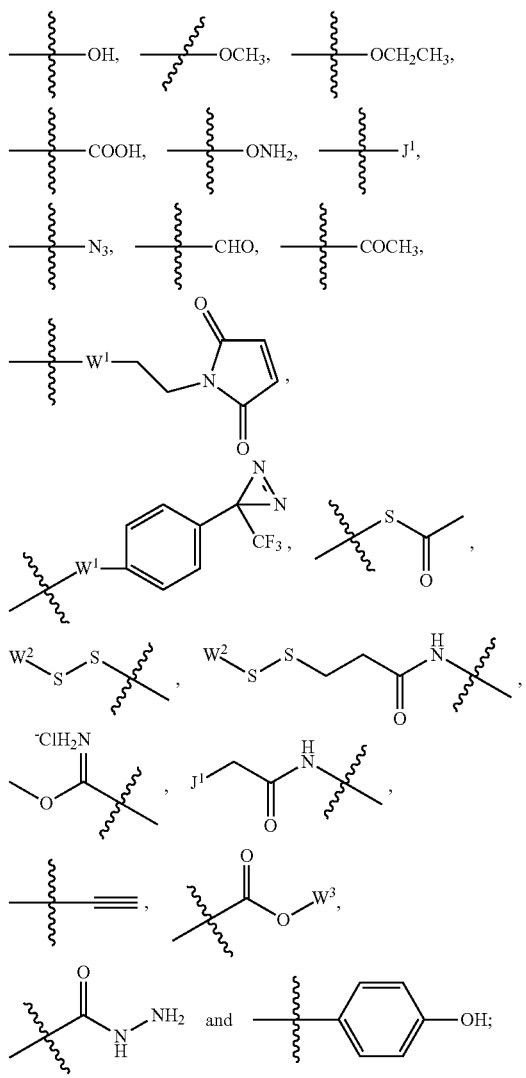

$Y^2$ is a chemical- or photocrosslinking group selected from the group consisting of

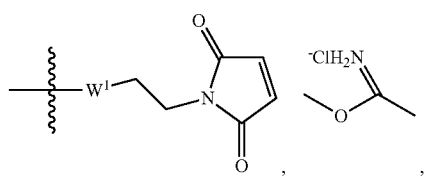

-continued

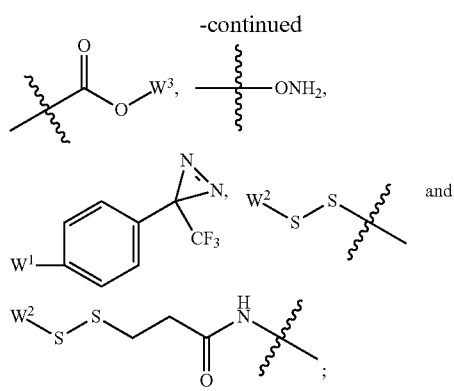

W[1] is an independent linker selected from the group consisting of —C(=O)—NH—, and, —NH—C(=O)—;
each J[1] is independently selected from Cl, Br and I;
each W[2] is independently selected from the group consisting of

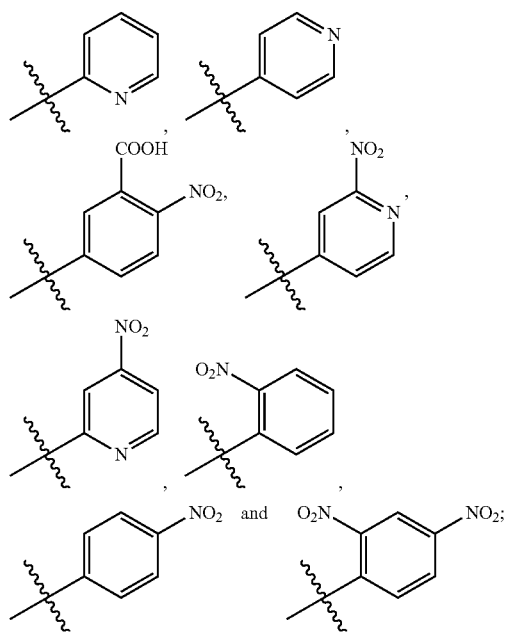

each W[3] is independently selected from the group consisting of

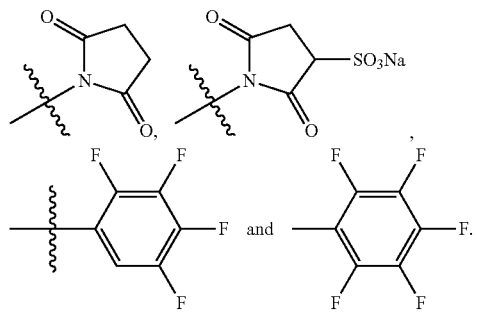

Preferably the second sugar alcohol-derived compound has a chemical formula selected from the group consisting of

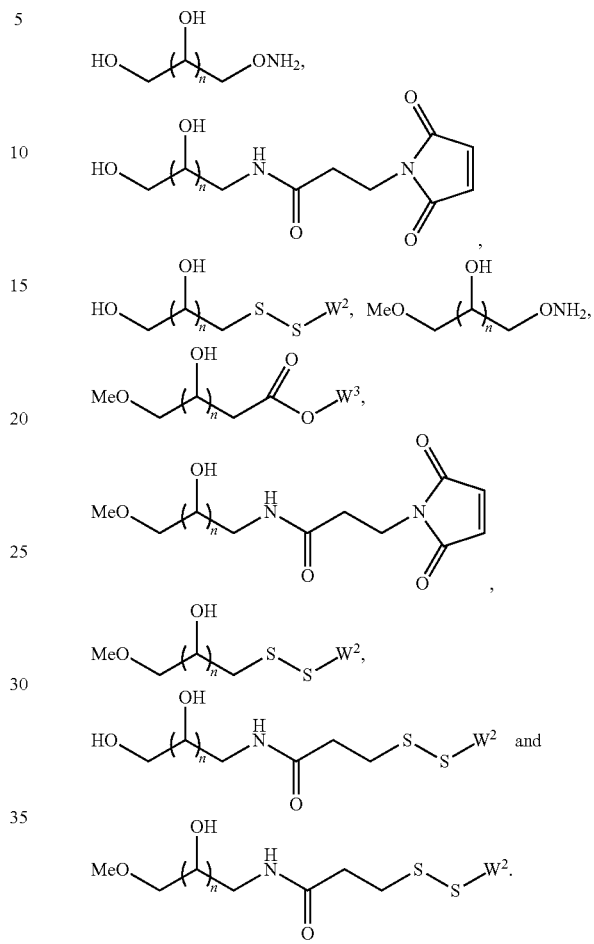

Preferably the second sugar alcohol-derived compound has a chemical formula selected from the group consisting of

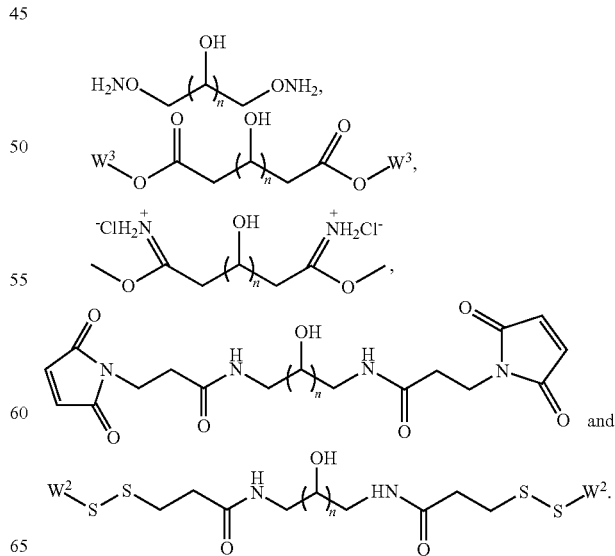

Preferably the second sugar alcohol-derived compound has a chemical formula selected from the group consisting of

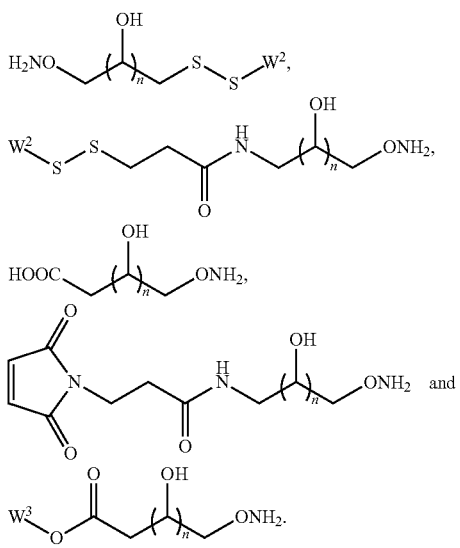

Preferably the second sugar alcohol-derived compound has a chemical formula selected from the group consisting of

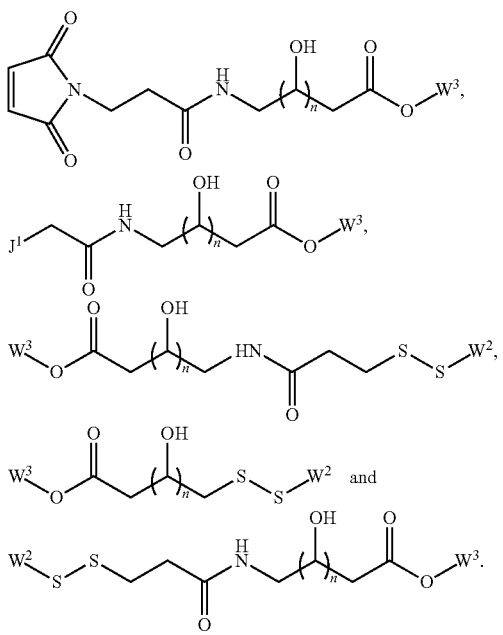

Preferably the second sugar alcohol-derived compound has a chemical formula selected from the group consisting of

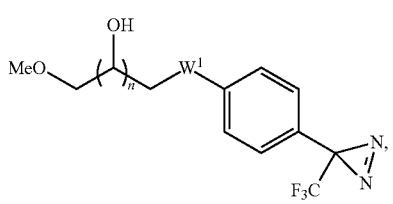

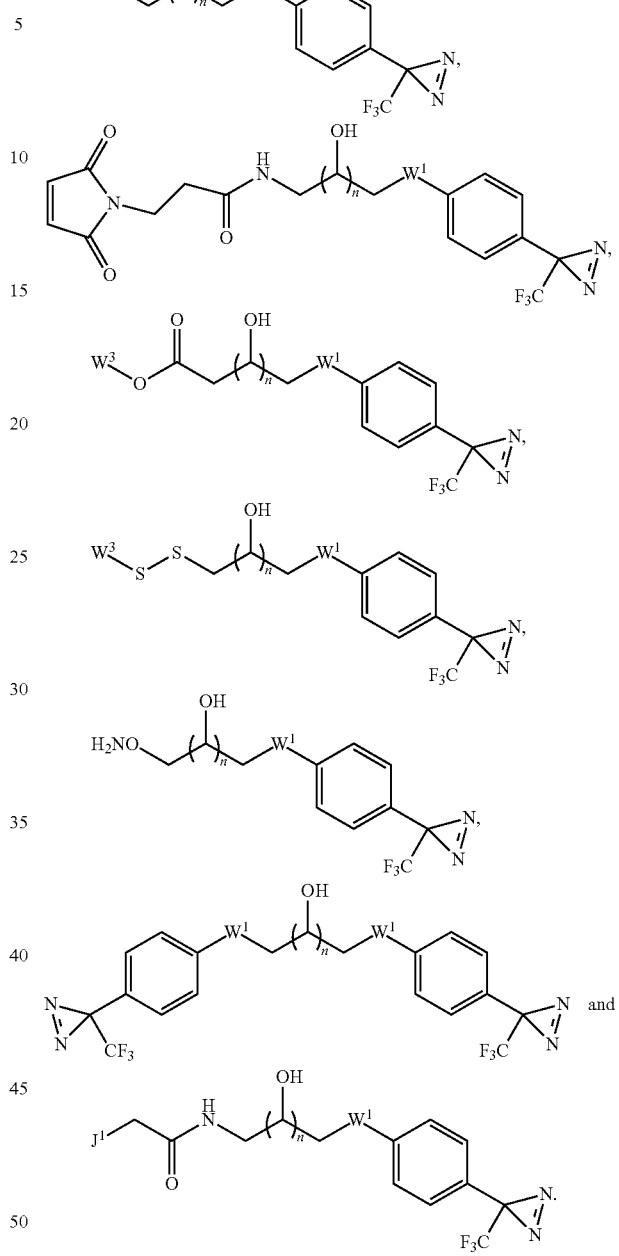

Preferably the second sugar alcohol-derived compound has a chemical formula selected from the group consisting of

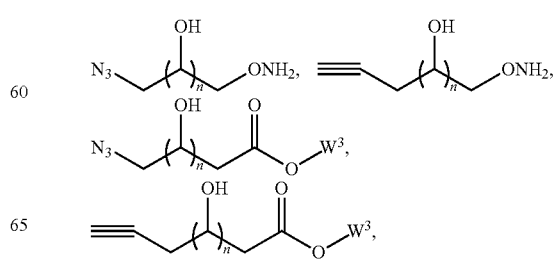

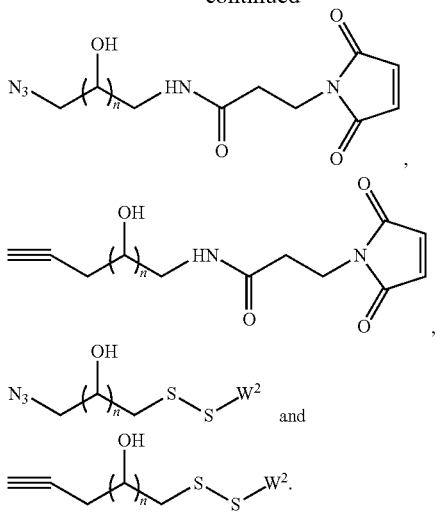

Optionally, the molecular weight of the second sugar alcohol-derived compound may be about 5 KDa to about 500 KDa. Preferably, the molecular weight of the compound is about 10 KDa to about 100 KDa. More preferably, the molecular weight of the compound is about 10 KDa to about 60 KDa.

Optionally, the second sugar alcohol-derived compound is about 90% pure. Preferably, the compound is about 95% pure. More preferably, the compound is about 97% pure.

Preferably, the molecular weight of the second sugar alcohol-derived compound may be about 5 KDa to about 500 KDa and the compound may be about 90% pure. More preferably the molecular weight of the compound may be about 10 KDa to about 100 KDa and the compound may be about 90% pure. Most preferably, the molecular weight of the compound may be about 10 KDa to about 60 KDa and the compound is about 90% pure.

The present invention also provides a third sugar alcohol derived compound having a chemical formula

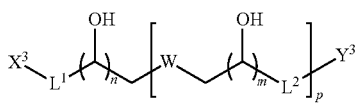

wherein
n is an integer selected from 2 to about 8;
m is an integer selected from 1 to about 8;
p is an integer selected from 2 to about 2000;
wherein each W is independently selected from —S—, —NH—, —O—, —NC$_1$-C$_6$alkyl-, —C(=O)NH—, —NHC(=O)—, —S(=O)—, —S(=O)$_2$—, —P(=O)$_2$O—, —P(=S)$_2$O—, —C(=O)O— and —P(=S)(=O)O—.
each of X$^3$ and Y$^3$ is independently a chemical- or photocrosslinking group selected from the group consisting of

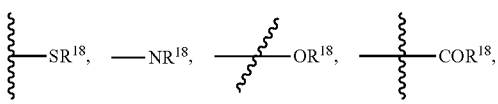

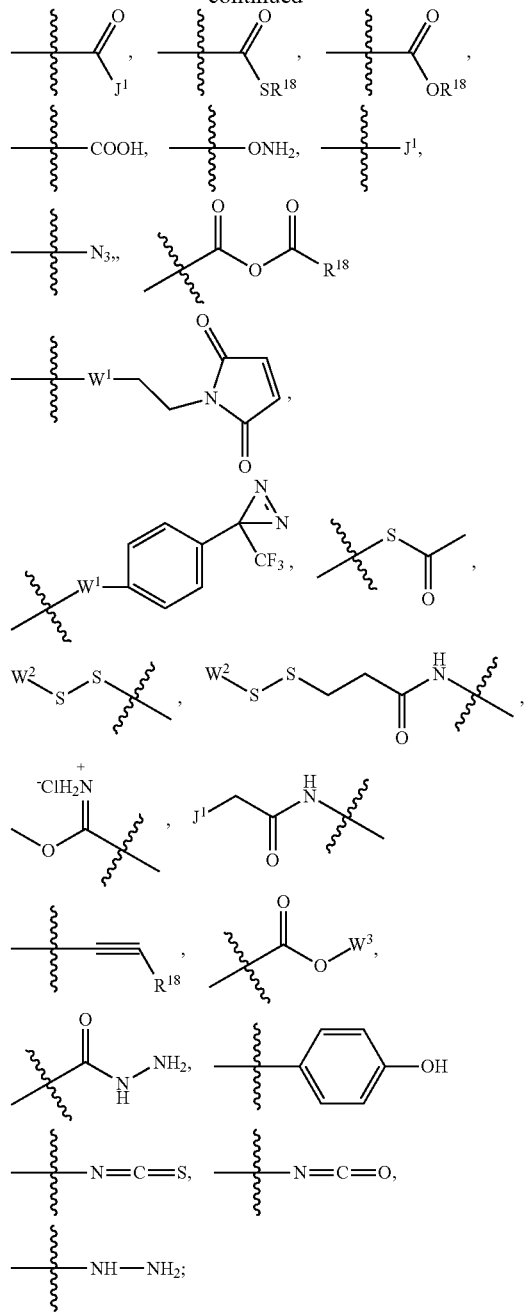

a diene, a dienophil, a 1,3-dipole, a dipolarophile, an alkene, a ketene, an olefin, an alkene with allylic hydrogen, a benzophenone, an aryl diazonium, a vinylsulfone and an allyl sulfone;

L$^1$ and L$^2$ is independently selected from a bond, —CH$_2$—*,

"*" represents a portion of L$^1$ and L$^2$ bound X$^3$ or Y$^3$;

R$^{18}$ is hydrogen, C$_{1-8\ alkyl}$; alicyclyl, heteroalicyclyl, benzyl or aryl, wherein any ring in R$^{18}$ is optionally substituted.

each of W$^1$ is an independent linker selected from the group consisting of —C(=O)—NH—, —NH—C(=O)—, each of $J^1$ is independently selected from Cl, Br and I;
each of $W^2$ is independently selected from the group consisting of

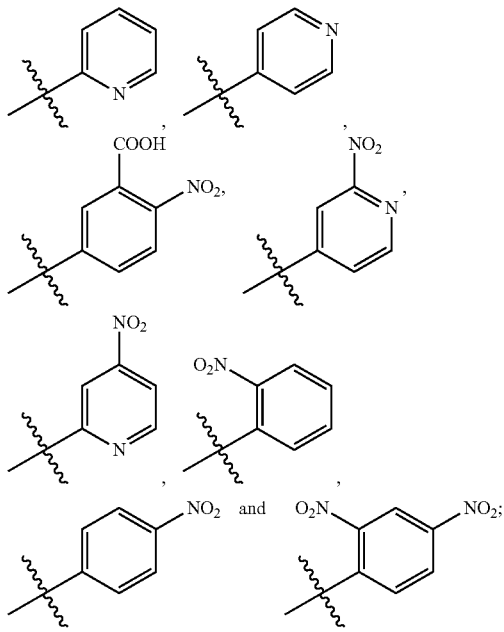

each of $W^3$ is independently selected from the group consisting of

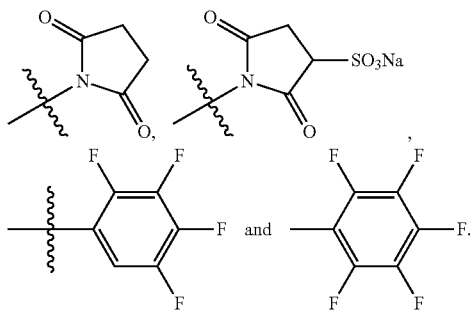

Preferably, the third sugar alcohol derived compound embodiment has a p which is an integer selected from about 2 to about 1000. More preferably, p is an integer selected from 1 to about 1000. Most preferably p is an integer selected from 1 to about 500.

Preferably, the third sugar alcohol derived compound has a molecular weight from about 5 KDa to about 500 KDa. More preferably, the molecular weight of the compound is from about 10 KDa to about 100 KDa. Most preferably, the molecular weight of the compound is from about 10 KDa to about 60 KDa.

Preferably, the third sugar alcohol derived compound is about 90% pure. More preferably, the compound is about 95% pure. Most preferably, the compound is about 97% pure.

Preferably, the molecular weight of the third sugar alcohol-derived compound may be about 5 KDa to about 500 KDa and the compound may be about 90% pure. More preferably the molecular weight of compound may be about 10 KDa to about 100 KDa and the compound may be about 90% pure. Most preferably, the molecular weight of the compound may be about 10 KDa to about 60 KDa and the compound may be about 90% pure.

The present invention provides methods and compositions, wherein a sugar alcohol (SA) molecule is used as a backbone for building a series of novel chemical entities, including SA crosslinking reagents and SA macromolecules, that are suitable for labeling and conjugating biomolecules and for drug delivery. The new molecules have significant advantages over the existing system. (i) Super hydrophilicity in which hydrophilicity is conferred from the hydrogen bonds. The SA has hydrogen bond donors and acceptors available throughout the molecule, making the molecule more similar to a network of water. As shown in FIG. 1, SA is much more hydrophilic (lower Log P value, Log P=−3.995) than the comparable PEG linker (Log P=−2.117). (ii) Single and pure high MW SA macromolecules can be synthesized easily. For the same atom length, SA has a higher MW compared to the PEG linker (FIG. 1). The MW of a similar length SA macromolecule is approximately 45% higher. The molecular and synthetic economy or efficiency can be advantageous when making high MW biological conjugates as a single compound. (iii) Multiple accessible functional groups in SA macromolecules. In the drug delivery field, a polymer with variable MW compounds is usually used, such as poly(lactic-co-glycolic acid) (PLGA), which has been widely used in a host of FDA approved therapeutic devices. However, when PLGA is used for labeling or conjugating biomolecules, the functional groups are only limited to the termini, resulting in very low loading of the molecules. This is also true for PEG. SA macromolecules have functional groups throughout the molecules and are easily accessible. Depending on the architecture of the SA macromolecules, a high-density 3D network of drug can be achieved. (iv) Biodegradability and biocompatibility. SA macromolecules are based on natural sugar alcohols and can easily be degraded in vivo. Where labeling is via an OH group using the ester linkage, it can be degraded (hydrolyzed) in the presence of water. This property makes SA crosslinking reagents and SA macromolecules great candidates for the delivery of small molecule drugs, as well as big molecule pharmaceuticals (e.g., biologics).

The present invention provides a collection of novel SA crosslinking reagents with various functional groups that can be used for labeling, conjugating, and immobilizing molecules of interest. In one aspect, the invention generally relates to a monomeric, linear, branched, or macrocyclic multimer sugar alcohol moiety comprising one or more of monomeric sugar alcohol unit $B^1$ (a modified SA unit). When the precursor compound comprises two or more monomeric sugar alcohol units, each monomeric sugar alcohol unit is bound to one or another monomeric sugar alcohol unit through a linking group W, wherein W is formed by a reaction between the X and Y portion of one monomeric unit with the X and Y of any other monomeric unit. Each $B^1$ has the chemical structure Formula XV:

(XV)

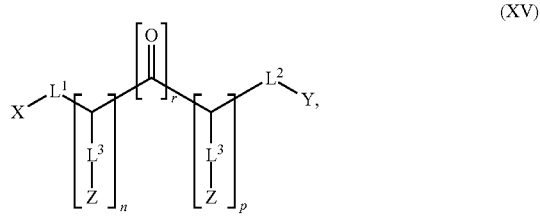

wherein for each B¹, independently:
  each of n and p is independently selected from 0 and an integer selected from about 1 to about 12; and n+p is between 1 and 12;
  r is 0 or 1;
  each X, Y, and Z is independently selected from —OH, -J, —R⁵J, —C(═O)-J, —C(═O)—CH₂-J, —NH—C(═O)—CH₂-J, —OR⁵, —OR⁶, —OR⁷, —O-Mesyl, —O-Tosyl, —NH—C(═O)—CH₂—O-Mesyl, —NH—C(═O)—CH₂—O-Tosyl, —SH, —S—S-tButyl, —SR7, —SR⁵, —S—S—R⁸, —S(═O)₂-J, —NH₂, —NHR⁵, —N(R⁵)R⁵, —NHR⁷, —NH-Fmoc, —NH-Boc, —C(═O)H, —C(═O)—R⁵, —C(═O)OH, —N═C═S, —N═C═O, —C≡C—R⁵, —N═N⁺═N⁻, —O—NH₂, —O—NH-Fmoc, —O—NH-Boc, —O—N-(Boc)₂, —O—N(-phthalimidyl), —NH—NH₂, —C(═O)—NH—NH₂, —NH—C(═O)—NH—NH₂, —NH—C(═S)—NH—NH₂,-toluenesulfonylhydrazide, —R⁵—NH—C(═NH₂⁺)—NH₂, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(═NH²)—O—R⁵, a hydroxymethyl phosphine derivative, an ethyl vinyl, a maleimide, a vinylsulfone, an allyl sulfone, a thioester, a cisplatin derivative, an aziridine, an acryloyl group. each R⁵ is independently selected from hydrogen, C₁-C₈ alkyl, alicyclyl, heteroalicyclyl, benzyl or aryl, wherein any ring in R5 is optionally substituted;
  each R⁶ is independently selected from benzoyl, acetyl, benzyl, C₁-C₈ alkyl silyl, tetrahydropyranyl, tetrahydrofuranyl, and tetrahydrothiofuranyl;
  each R⁷ is independently selected from trityl, MMT, and DMT;
  each R⁸ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
  each J is independently selected from Cl, Br and I.
  each of L¹, L², and L³ is independently a R² or —R⁹—V—R²—*

In some embodiments the linker is —R⁹—V—R²—*, wherein "*" represents a portion of the linker bound to X, Y, or Z, and V is a linking group.

In some embodiments each V and W is independently selected from a Diels-Alder adduct, a 1,3-dipolar adduct, —C(═G²)-G¹-, -G¹-C(═G²)-, -G³-, -G¹-C(═G²)-G¹-, —S—S—, —S—(CH₂)₂—S(O)₂—, —S(O)₂—(CH₂)₂—S—, —S(O)₂—N(R³)—, —N(R³)—S(O)₂—, —C(O)—NH—NH—CH₂—, —C(O)—NH—N═CH—, —CH═N—NH—C(O)—, —CH₂—NH—NH—C(O)—, —N(R³)—S(O)₂—N(R³)—, —C(O)—NH—CH(CH₂SH)—, —N═CH—, —NH—CH₂—, —NH—C(O)—CH₂—C(O)—NH—, —CH═N-G⁴-, —CH₂—NH-G⁴-, -G⁴-NH—CH₂—, -G⁴-N═CH—, —C(═NH₂⁺)—NH—, —NH—C(═NH₂⁺)—, —O—P(═O)(O⁻)—NH—, —NH—P(═O)(O⁻)—O—, —CH₂—CH(NH₂)—CH₂—S—, —S—CH₂—CH(NH₂)—CH₂—, —O—P(═O)(O⁻)—O—, —O—P(═O)(S⁻)—O—, and —O—P(═S)(S⁻)—O—,

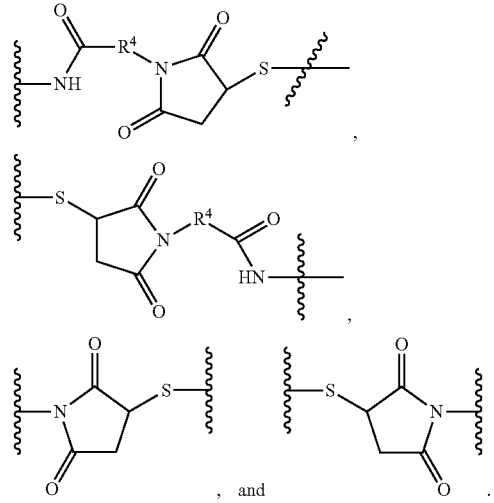

, and

Each G¹ is independently selected from NR⁷, O, or S; each G² is independently O or S; each G³ is independently selected from S, O, NR³, or SO₂; each G⁴ is independently O or NR³; each R³ is independently selected from a bond, C₁-C₁₂ alkyl, —(CH₂CH₂O)₁₋₁₀—, —(CH₂CH₂O)₁₋₁₀—CH₂—, optionally substituted alicyclyl, heteroalicyclyl, aryl, a peptide, and a peptidomimetic oligomer; each R⁹ is a bond or —CH₂—; each R³ is independently selected from hydrogen, C₁-C₈ alkyl, —(OCH₂CH₂)₁₋₃, optionally substituted alicyclyl, and optionally substituted heteroalicyclyl; and each R⁸ is independently C₁-C₈ alkyl.

In some preferred embodiments, linking group W is selected from —S—, —O—, —NH—, —NC₁-C₆ alkyl-, —C(═O)NH—, —NHC(═O)—, —S(═O)—, —S(═O)₂—, —P(═S)₂O—, or —P(═S)(═O)O—.

In certain more preferred embodiments, W is selected from —S—, —O—, —S(═O)—, —S(═O)₂—, —P(═S)₂O—, or —P(═S)(═O)O—. In certain even more preferred embodiments, W is —O—.

In some embodiments a "modified" SA unit refers to a SA unit in which one or more of its OH groups have been chemically modified by substitution with another functional group. In this case, L¹ connecting to an OH substituted X is —CH₂—; L² connecting to an OH substituted Y is —CH₂—; and any L³ connecting to an OH substituted Z is a bond. In some embodiments, a "modified" SA unit refers to a SA unit in which one or both of its —CH₂OH groups has been oxidized, usually to an aldehyde or carboxylic acid, and then further modified with other functional groups. In this case, L¹ and L² are bonds. In some embodiments, a "modified" SA unit also refers to a SA unit in which the hydrogen atom at one or more of the OH groups has been replaced by a chemical protecting group, leaving group, or other functional group. In this case, each of L¹ and L² is —CH₂— and L³ is a bond. Preferably, each -L³-Z is —OR¹ wherein each R¹ is independently selected from the group consisting of hydrogen, C₁-C₈ alkyl, benzoyl, acetyl, benzyl, C₁-C₈ alkyl silyl, cyclic ortho ester, actinide, acetate, tetrahydropyranyl, tetrahydrofuranyl, and tetrahydrothiofurany. The following is a list of various simplified structures of an SA B¹ unit.

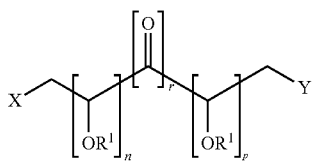
(XXXI)

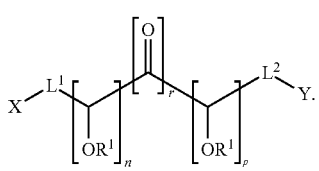
(XXXII)

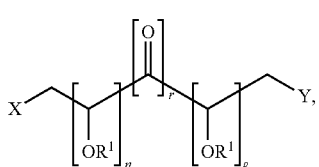
(XXXIII)

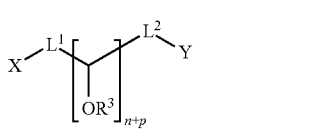
(XXXIV)

In certain embodiments, the functional groups X, Y, and Z are amine reactive groups. The primary coupling reaction for amine is through acylation or alkylation. The preferred amine active groups include, for example, carboxylic acid, ketenes, isothiocyanate, isocyanate, acyl azides, acyl halides, N-hydroxysuccinimide (NHS) ester, sulfonyl chloride, carbonyl groups such as aldehydes, ketones, and glyoxals, epoxides or oxiranes, carbonate groups, aryl halides such as fluorobenzene derivatives, alkyl halides, imidoester, or imidate functional groups, anhydrides, fluorophenyl ester, and hydroxymethyl phosphine derivatives. In a particular example, X or Y is an arginine-reactive group. The guanidinyl group on the arginine side chain can be specifically targeted using 1,2-dicarbonyl reagents, such as the diketone group of glyoxal.

In certain embodiments the functional groups X, Y, and Z are thiol reactive groups. The primary coupling reaction for thiol is through alkylation or disulfide exchange. The preferred thiol reactive groups include, for example, thiol, haloacetyl and alkyl halides, maleimide, aziridines, acryloyl derivatives, arylating agents such as benzene derivatives that possess either halogen or sulfonate groups on the ring, thiol-disulfide exchange reagents such as pyridyl dithiol and thiolnitrobenzoic acid, vinylsulfone, cysteine derivatives, thioesters, and cisplatin derivatives.

In certain embodiments the functional groups X, Y, and Z are carboxylic acid reactive groups. The preferred carboxylic acid reactive groups include, for example, OH, amines, thiols, diazomethane and diazoacetate derivatives, and acylimidazole leaving groups.

In certain embodiments the functional groups X, Y, and Z are OH reactive groups. The preferred hydroxyl reactive groups include, for example, epoxides or oxiranes, alkyl halogens, carboxylic acid and its active esters, isocyanate, isothiocyanate, phosphonium intermediates, tosylate or mesylate, sulfonyl chlorides, anhydrides, acyl azides, tetrahydropyranyl, tetrahydrofuranyl, tetrahydro thiofuranyl, ethyl vinyl, trityl halides, fluorobenzene derivatives, silylhalides, and ketenes.

In some preferred embodiments the functional groups X, Y, and Z are aminooxy groups capable of reacting with aldehyde or ketone groups to form the oxime bond. In another embodiment, the functional groups X, Y, and Z are hydrazines capable of reacting with aldehyde or ketone groups to form the hydrazine linkage. In another embodiment, the functional groups X, Y, and Z are semi or thiosemicarbazides capable of reacting with aldehyde or ketone groups to form the semi or thiosemicarbazone linkage. In another embodiment, X or Y can be amine functional groups. Amine groups can react with aldehydes through Schiff base formation and the formed carbon amine double bond can be further reduced to a stable secondary or tertiary amine bond. Amine groups can also react with an active hydrogen-containing compound in the presence of formaldehyde (Mannich reaction).

In some embodiments the functional groups X, Y, and Z are able to react with certain reactive (or replaceable) hydrogens that exist in certain biomolecules. For example, X, Y, or Z may be a diazonium group that reacts with active hydrogen sites on aromatic rings to produce covalent diazo bonds.

In some preferred embodiments the functional groups X, Y, and Z are photoreactive groups that can be induced to couple with molecules of interest by exposure to UV light. The preferred photoreactive groups include, for example, diazirine groups. More preferable than a diazirine group is 3-trifluoromethyl-3-aryaldiazirine. Other preferred photoreactive groups are aryl azides, halogenated aryl azides, benzophenones, anthraquinones, diazos such as diazotrifluoropropionates and diazopyruvate, and psoralen derivatives.

In some preferred embodiments the functional groups X, Y, and Z are dienes, dienophile groups, or alkenes that are capable of linking molecules through the Diels-Alder reaction. Preferably, X, Y, or Z may be an azido functional group or alkyne that is capable of linking molecules through [3+2] cycloaddition. In another embodiment X, Y, or Z may be an alkene with an allylic hydrogen (the ene) or a multiple bond (the enophile). In another embodiment X, Y, or Z may be 1,3-dipole or a dipolarophile (substitute alkenes).

In some preferred embodiments X is a protected amine and Y is an acid wherein each -$L^3$-Z is an —$OR^1$. SA crosslinking reagents can be incorporated into any molecule (e.g., peptide and nucleic acid oligomers) through the solid phase synthesis strategy. For example, X can be a fluorenymethyloxycarbonyl (Fmoc) protected amine. In another example, X can be a tert-butyloxycarbonyl (Boc) protected amine. In another example, X can be a triphenylmethyl chloride (trityl), dimethoxytrityl (DMT), or monomethoxytrityl (MMT) protected amine, so SA crosslinking reagents can be incorporated into an oligomer through solid phase synthesis.

In some preferred embodiments X is a protected thiol (e.g., trityl or t-butyl thiol protected) and Y is an acid wherein each -$L^3$-Z is an —$OR^3$, wherein $R^3$ is independently selected from hydrogen, $C_1$-$C_8$ alkyl, —$(OCH_2CH_2)_{1-3}$, optionally substituted alicyclyl, and optionally substituted heteroalicyclyl.

In some preferred embodiments X is a protected amine (e.g., trityl, DMT, or MMT protected) and Y is a phosphoramidite wherein each -$L^3$-Z is an —$OR^3$.

In some embodiments the X and Y groups are the same, wherein each -$L^3$-Z is an —$OR^1$ and as such a homobifunctional SA functional reagent. Examples of homobifunctional SA functional reagents include homobifunctional NHS ester, homobifunctional imidoester, homobifunctional dithiopyridyl group containing crosslinking reagent, homobifunctional maleimide group containing crosslinking reagent, homobifunctional alkyl halide containing crosslinking reagent, homobifunctional photoreactive crosslinking reagent, homobifunctional aldehyde or ketone, homobifunctional epoxide, homobifunctional hydrazide, homobifunctional aminooxy, and homobifunctional diazonium.

In some embodiments the X and Y groups are different wherein each $-L^3-Z$ is an $-OR^1$ and as such a heterobifunctional SA crosslinking reagent. In certain preferred embodiments X is an amine-reactive group and Y is a sulfhydryl-reactive group. In certain preferred embodiments X is a carbonyl-reactive (aldehyde/keto), such as aminooxy, hydrazine, semicarbazide, or thiosemicarbazide, and Y is a sulfhydryl-reactive group. In certain preferred embodiments X is an amine-reactive group and Y is a photoreactive group. In certain preferred embodiments X is a sulfhydryl-reactive group and Y is a photoreactive group. In certain preferred embodiments X is a carbonyl-reactive group and Y is a photoreactive group. In certain embodiments X is a carboxylate-reactive group and Y is a photoreactive group. In certain embodiments X is a ketone or aldehyde and Y is a photoreactive group.

In addition, SA crosslinking reagents may incorporate the cleavable linkage that allows systematic drug release for a conjugate in vivo. For example, aminooxy functional groups may be introduced at the termini of the crosslinking reagent, and a cleavable oxime linker may be used to release the molecules being crosslinked. In another example, disulfide bonds may be incorporated, allowing the release of the molecules in a reductive environment. Moreover, SA crosslinking reagents can link two or more SAs through another bond that may be enzymatically cleaved in vivo.

Furthermore, SA crosslinking reagents having two or more OH groups (secondary OH groups) in the backbone may themselves be cleavable linkages. For instance, an SA backbone with two or more OH groups may be cleaved by periodate oxidation to generate a new aldehyde functional group.

Furthermore, SA crosslinking reagents may incorporate a reducing sugar unit in the backbone. In at least one of $SA_1$ or $SA_2$, r is 1. For example, if one of the reducing sugar units is the reduced form of fructose, an SA crosslinking reagent containing trifunctional group X, Y, and ketone can be envisioned. In some embodiments X may be a protected amine and Y an acid. This configuration is useful for introducing a ketone functional group into a peptide or oligo through solid phase synthesis. This ketone handle can be used conveniently for the conjugation of other molecules.

Monomeric SA and linear SA crosslinking reagents

In one aspect, the present invention provides a monofunctional, homobifunctional, and heterobifunctional crosslinking reagent comprising one SA unit. The compound has the chemical structure Formula XXVI:

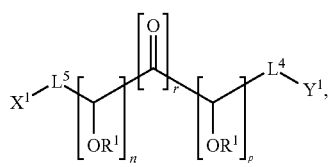

(XXXVI)

each of n and p is independently selected from 0 and an integer selected from 1 to about 12; and n+p is between 2 and 12; r is 0 or 1; $L^3$ and $L^4$ is independently selected from a bond, $-CH_2-*$, $-C(=O)-NH-C_{1-8\ alkyl}-*$, $-CH_2-NH-C(=O)-C_{1-8\ alkyl}-*$, $-CH_2-C(=O)-NH-C_{1-8\ alkyl}-*$, "*" represents a portion of $L^3$ and $L^4$ bound $X^1$ or $Y^4$. Each $R^1$ is independently selected from the group consisting of hydrogen, $C_1-C_8$ alkyl, benzoyl, acetyl, benzyl, $C_1-C_8$ alkyl silyl, cyclic ortho ester, actinide, acetate, tetrahydropyranyl, tetrahydrofuranyl, and tetrahydrothiofurany.

In certain embodiments each of $X^1$ is independently selected from $-OH$, -J, $-C(=O)-CH_2-J$, $-OR^5$, $-S-S-R^8$, $-NH-C(=O)-CH_2CH_2-S-S-R^8$, $-S-C(=O)-CH_3$, $-C(=O)H$, $-C(=O)-R^5$, $-C(=O)OH$, $-C\equiv C-R^5$, $-N=R^+=N^-$, $-O-NH_2$, $-O-NH-Fmoc$, $-O-NH-Boc$, $-O-N-(Boc)_2$, $-O-N(-phthalimidyl)$, $-C(=O)-NH-NH_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, a imidoester, a maleimide, a phosphoramidite; each $R^5$ is independently selected from hydrogen, $C_1-C_8$ alkyl, alicyclyl, heteroalicyclyl, benzyl or aryl, wherein any ring in R5 is optionally substituted; each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, or 2,4-dinitrophenyl; and each J is independently selected from Cl, Br, or I.

In some preferred embodiments $X^1$ is $-C(=O)-OH$, r is 0, and $Y^1$ is independently selected from $-NH-R^7$, $-NH-Fmoc$, $-NH-Boc$, $-S-S-R^8$, $-S-S-R^7$, $-S-S-tButyl$, $-O-NH-Fmoc$, $-O-N-(Boc)_2$, and $-O-N(-phthalimidyl)$; wherein; each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl; each $R^7$ is independently selected from trityl, MMT, and DMT; and when r is 1, then $Y^1$ is $OR^1$, wherein; each $R^1$ is independently selected from the group consisting of hydrogen, $C_1-C_8$ alkyl, benzoyl, acetyl, benzyl, $C_1-C_8$ alkyl silyl, cyclic ortho ester, actinide, acetate, tetrahydropyranyl, tetrahydrofuranyl, and tetrahydrothiofurany.

In some preferred embodiments $X^1$ is a phosphoramidite; when r is 0, $Y^1$ is independently selected from $-S-S-(C_1-C_4\ alkyl)-OR^7$, $S-S-R^8$, $-NH-TFA$, or $-NH-R^7$, wherein each $R^7$ is independently selected from trityl, MMT, or DMT and each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, or 2,4-dinitrophenyl.

In some preferred embodiments $X^1$ and $Y^1$ are not the same.

In some preferred embodiments one of each $X^1$ and $Y^4$ is $-O-NH_2$, $-S-S-R^8$, $-NH-C(=O)-CH_2CH_2-S-S-R^8$, an optionally substituted N-hydroxysuccimide ester group, a optionally substituted trifluoromethylphenyldiazirine, or a maleimide group, wherein each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, or 2,4-dinitrophenyl.

In some more preferred embodiments the monomeric sugar alcohol has the following structure:

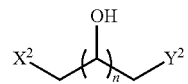

Wherein n is an integer selected from about 2 to about 8;
each of $X^2$ is a chemical- or photocrosslinking group selected from the groups consisting of:

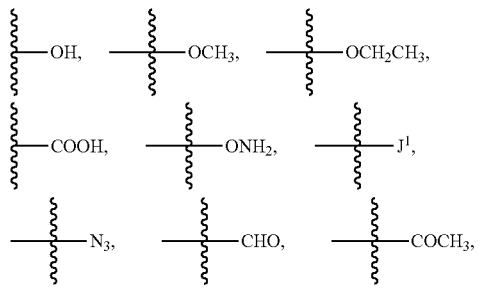

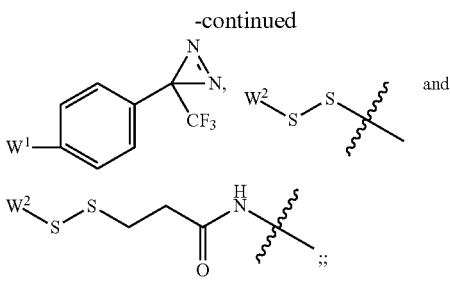

-continued each of $W^1$ is an independent linker selected from the group consisting of —C(=O)—NH— and —NH—C(=O)—;

each of $J^1$ is independently selected from Cl, Br or I;

each of $W^2$ is independently selected from the group consisting of

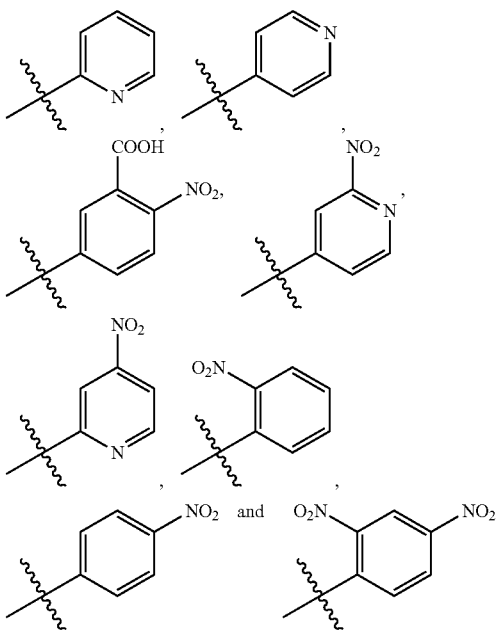

each of $Y^2$ is a chemical- or photocrosslinking group selected from the group consisting of:

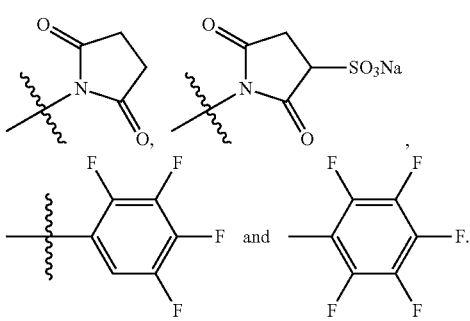

each of $W^3$ is independently selected from the group consisting of

In some preferred embodiments the monomeric sugar alcohol compound is a monofunctionalized sugar alcohol crosslinking reagent with the following chemical structures:

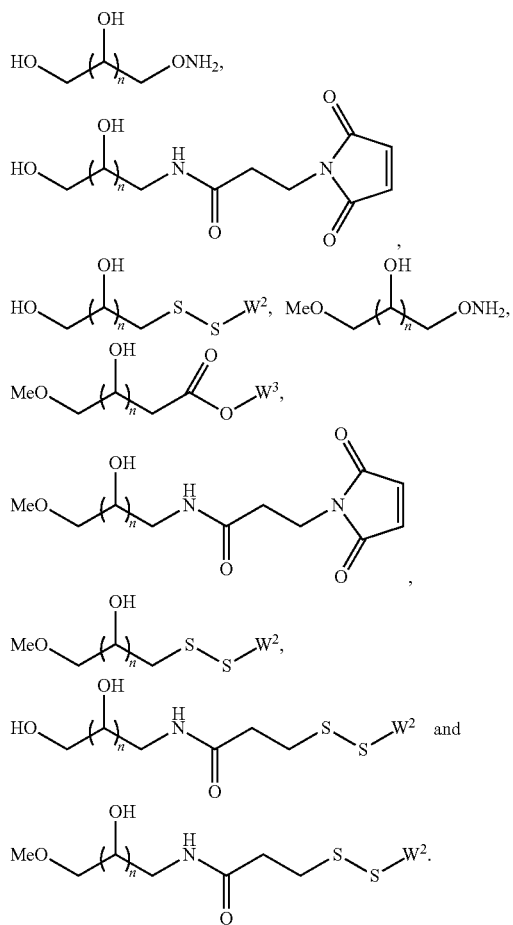

In some preferred embodiments the monomeric sugar alcohol compound is a homobifunctional crosslinking reagent with the following chemical structures

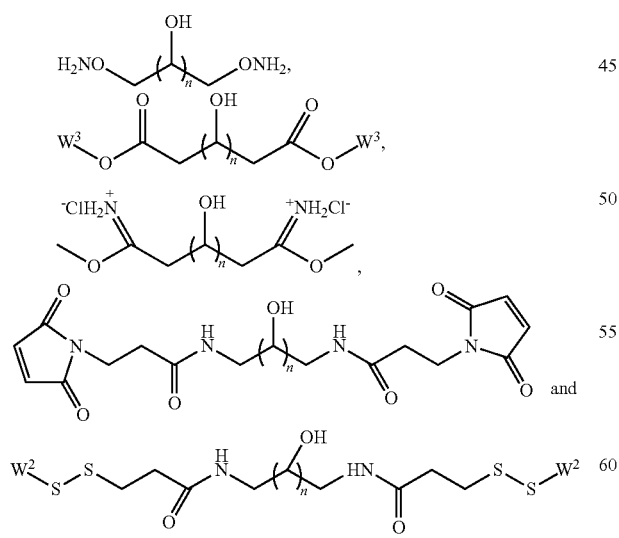

In some preferred embodiments the monomeric sugar alcohol compound is a heterobifunctional aminooxy crosslinking reagent with the following chemical structures:

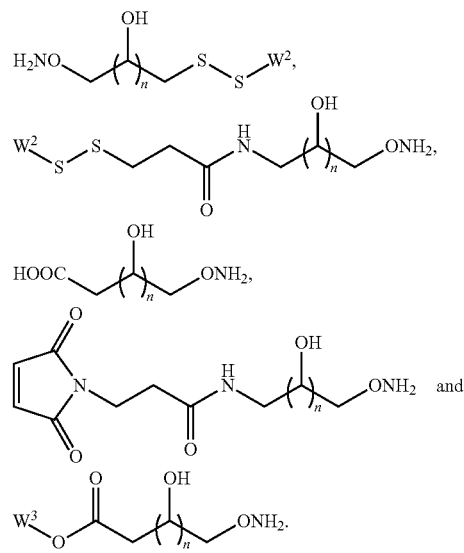

In some preferred embodiments the monomeric sugar alcohol compound is a heterobifunctional N-hydroxysuccimide ester crosslinking reagent with the following chemical structures

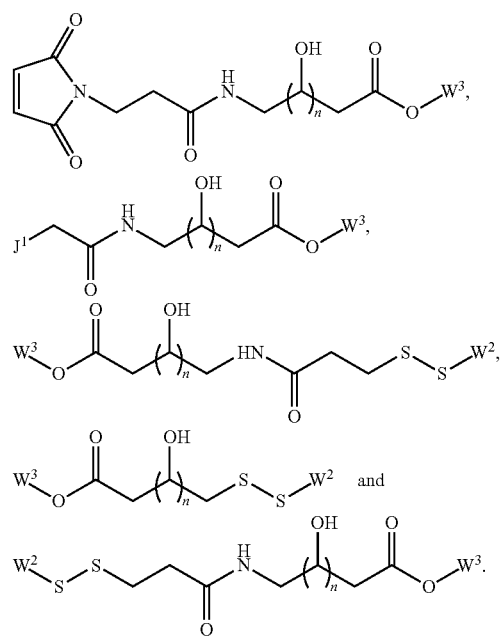

In some preferred embodiments the monomeric sugar alcohol compound is a photocrosslinker reagent with the following chemical structures

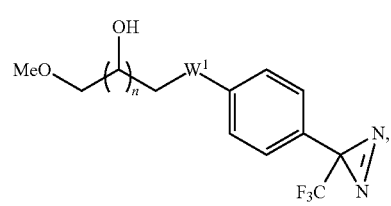

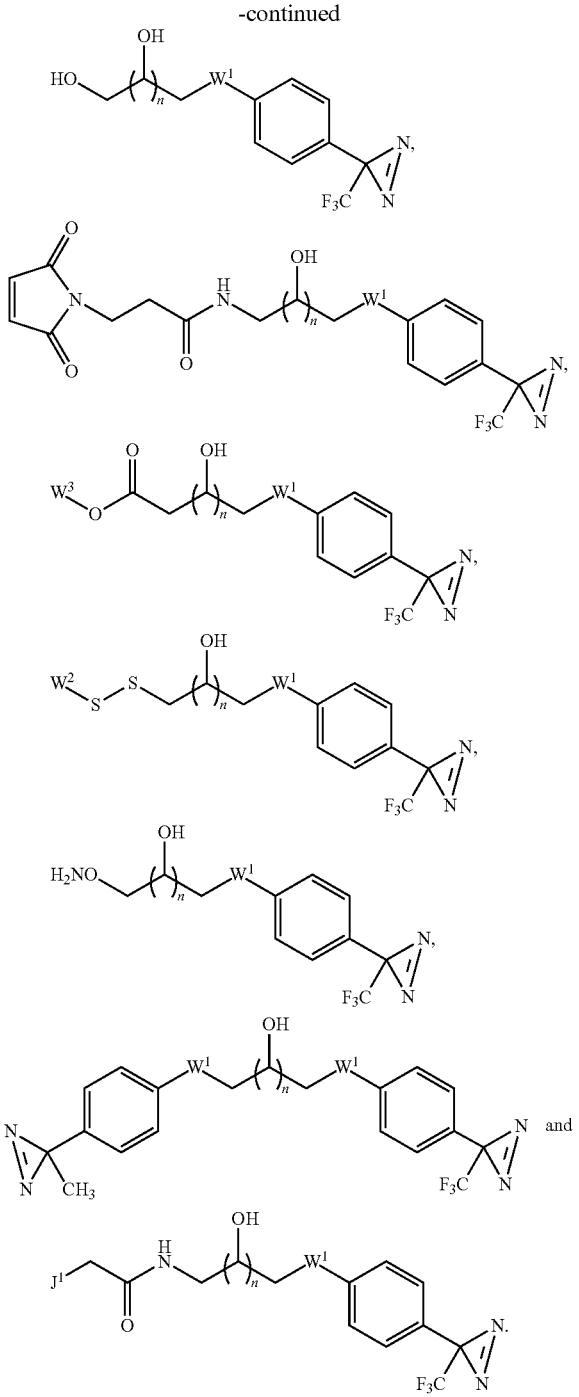

In some preferred embodiments the monomeric sugar alcohol compound is a heterobifunctional crosslinking reagent with the following chemical structures

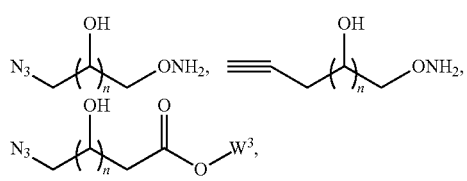

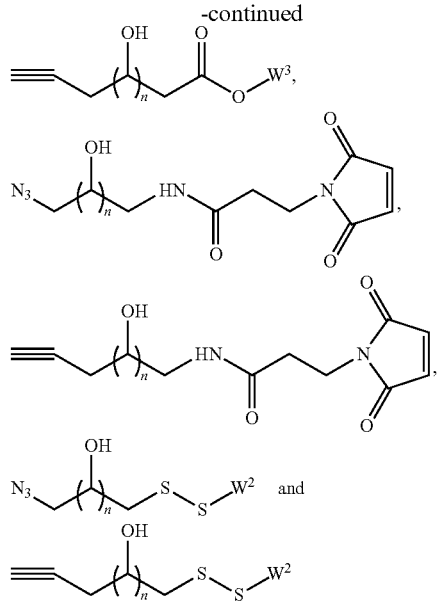

In one aspect, the present invention provides a dimeric sugar alcohol with the chemical structure Formula XVIII:

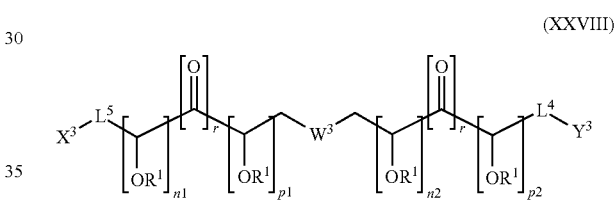

(XXVIII)

each of n1, n2, p1, and p2 is independently selected from 0 and an integer selected from 1 to about 12; and n1+p2 is between 1 and 12, n2+p2 is between 2 and 12;

r is 0 or 1;

wherein $W^3$ is selected from —S—, —O—, —NH—, —NC$_1$-C$_6$alkyl-, —C(═O)NH—, —NHC(═O)—, —S(═O)—, —S(═O)$_2$—, —P(═S)$_2$O—, or —P(═S)(═O)O—.

each of $X^3$ is independently selected from —OH, -J, —C(═O)—CH$_2$-J, —OR$^5$, —S—S—R$^8$, —NH—C(═O)—CH$_2$CH$_2$—S—S—R$^8$, —S—C(═O)—CH$_3$, —C(═O)H, —C(═O)—R$^5$, —C(═O)OH, —C≡C—R$^5$, —N═N$^+$═N$^-$, —O—NH$_2$, —O—NH-Fmoc, —O—NH-Boc, —O—N-(Boc)$_2$, —O—N(-phthalimidyl), —C(═O)—NH—NH$_2$, a phenol group, an optionally substituted trifluoromethylphenyldiazirine, a diene, a dienophil, a 1,3-dipole, a dipolarophile, an alkene, a ketene, an olefin, an alkene with allylic hydrogen, an optionally substituted N-hydroxysuccinimide ester, a imidoester, a maleimide, a phosphoramidite;

each of $Y^3$ is independently selected from —S—S-tButyl, —SR$^7$, —S—S—R$^8$, —NH—C(═O)—CH$_2$CH$_2$—S—S—R$^8$, —NHR$^7$, —NH-Fmoc, —NH-Boc, —O—NH$_2$, —O—NH-Fmoc, —O—NH-Boc, —O—N-(Boc)$_2$, —O—N(-phthalimidyl), an optionally substituted trifluoromethylphenyldiazirine, an optionally substituted N-hydroxysuccinimide ester, a imidoester, a maleimide;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from Cl, Br, and I $L^4$ and $L^5$ is independently selected from a bond, —$CH_2$—*, —C(=O)—NH—$C_{1-8\ alkyl}$—*, —$CH_2$—NH—C(=O)—$C_{1-8\ alkyl}$—*, —$CH_2$—C(=O)—NH—$C_{1-8\ alkyl}$—*, "*" represents a portion of $L^4$ and $L^5$ bound $X^3$ or $Y^3$ In some embodiments W is selected from the group consisting of —S—, —O—, —S(=O)—, —S(=O)$_2$—, —P(=S)$_2$O—, or —P(=S)(=O)O—. More preferably, W is —O—.

In some embodiments, when $X^3$ is —C(=O)—OH; r is 0, and $Y^3$ is independently selected from —NH—$R^7$, —NH-Fmoc, —NH-Boc, —S—S—$R^8$, —S—S—$R^7$, —S—S-tButyl, —O—NH-Fmoc, —O—N-(Boc)$_2$, and —O—N(-phthalimidyl); wherein; each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl; each $R^7$ is independently selected from trityl, MMT, and DMT; and when r is 1, then Y is $OR^1$, wherein; $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany In some embodiments, when $X^3$ is a phosphoramidite; When r is 0, $Y^3$ is independently selected from —S—S—($C_1$-$C_4$ alkyl)-$OR^7$, S—S—$R^8$, —NH-TFA, —NH—$R^7$, wherein each $R^7$ is independently selected from trityl, MMT, and DMT; each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

In some preferred embodiments, at least one of each $X^3$ and $Y^3$ is —O—$NH_2$, —S—S—$R^8$, —NH—C(=O)—$CH_2CH_2$—S—S—$R^8$, an optionally substituted N-hydroxysuccimide ester group, an optionally substituted trifluoromethylphenyldiazirine, or a maleimide group; wherein each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl.

In some more preferred embodiments $X^3$ is an aminooxy group and $Y^3$ is selected from the group consisting of a maleimide group, a sulfhydryl group, a disulfide group, a haloacetyl group, an azide group, and an alkyne group. In some embodiments $X^3$ is an optionally substituted N-hydroxysuccinimide ester, $Y^3$ is selected from the group consisting of a maleimide group, a sulfhydryl group, a disulfide group, a haloacetyl group, an azide group, and an alkyne group.

In another aspect, the sugar alcohol is a linear trimer or a higher oligomer having the following structure

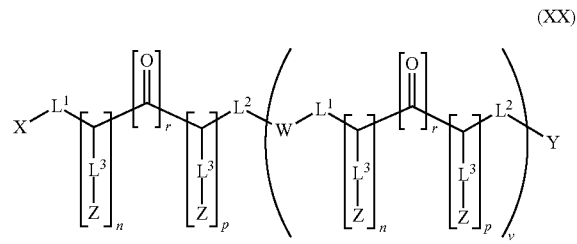

(XX)

wherein v is an integer selected from 2 to 2000.

In some preferred embodiments -$L^3$-Z is —$OR^1$ and has the following structure XXI

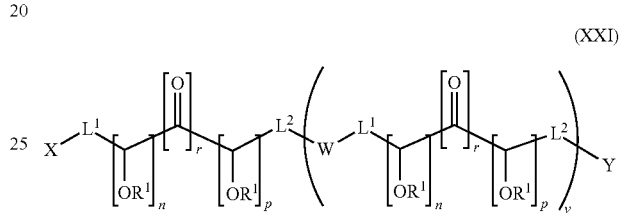

(XXI)

wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany.

In some more preferred embodiments wherein each r is 0 and has the following structures:

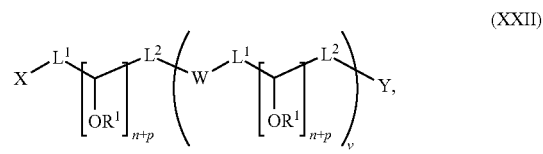

(XXII)

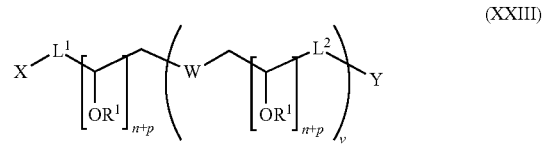

(XXIII)

In another aspect, the sugar alcohol-derived compound has the structure

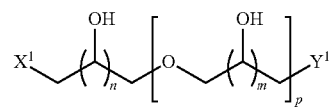

Wherein:

n is an integer selected from 2 to about 8;

m is an integer selected from 1 to about 8;

p is an integer selected from about 1 to about 2000;

each of $X^1$ is a chemical- or photocrosslinking group selected from the group consisting of:

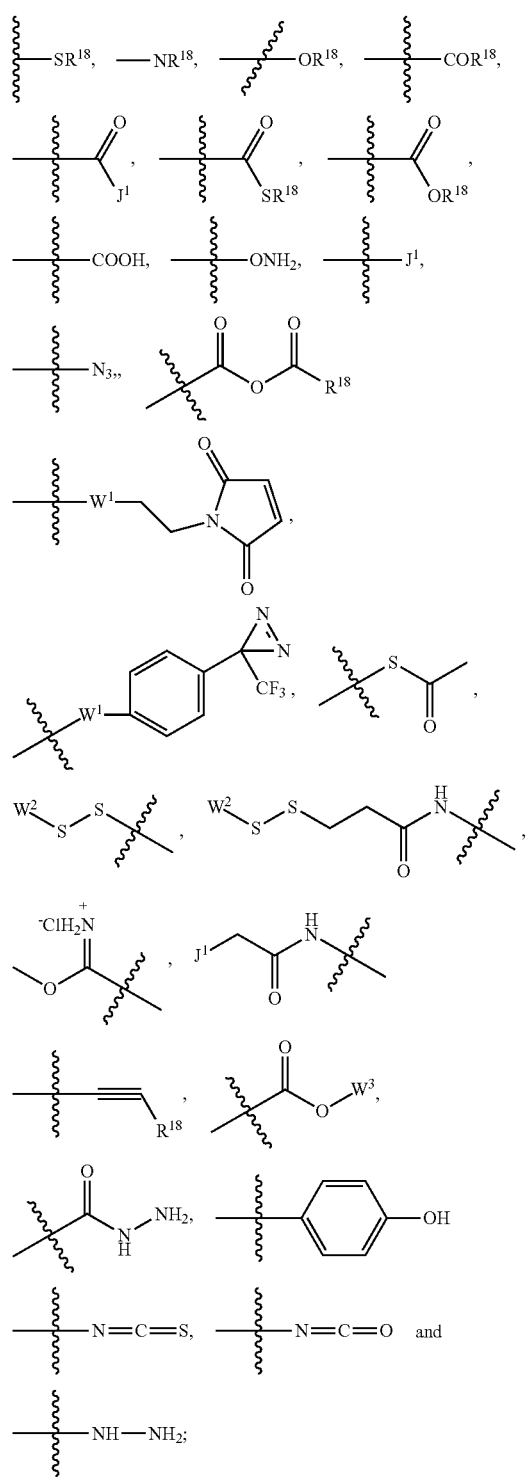

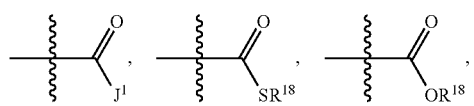

each Y[1] is a chemical- or photocrosslinking group selected from the group consisting of:

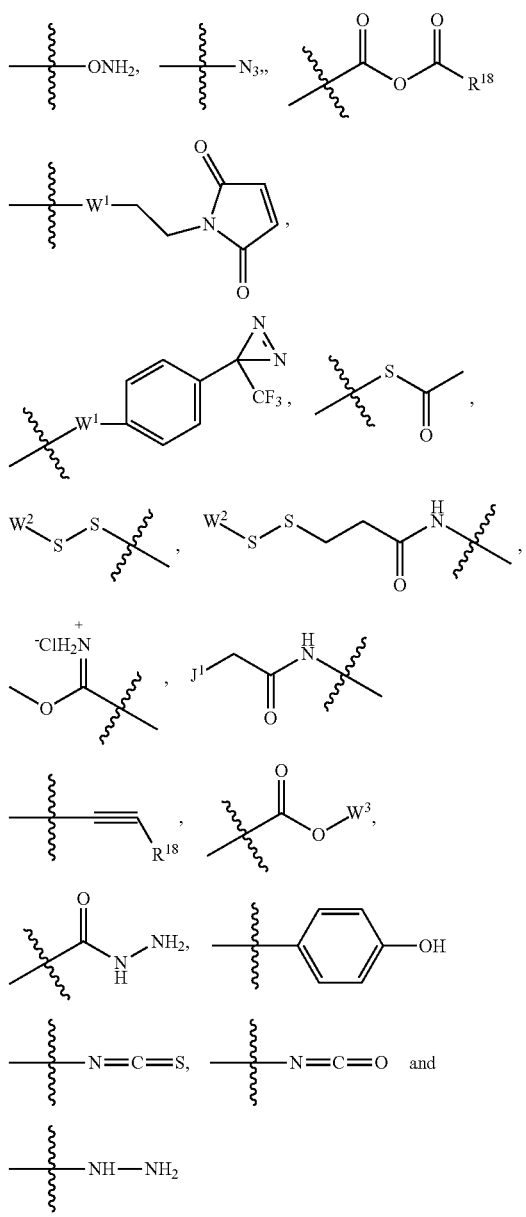

each of W[1] is an independent linker selected from the group consisting of —C(=O)—NH— and —NH—C(=O)—;

each of J[1] is independently selected from Cl, Br or I;

R[18] is hydrogen, $C_{1-8\ alkyl}$, alicyclyl, heteroalicyclyl, benzyl, or aryl, wherein any ring in R[18] is optionally substituted;

each of W[2] is independently selected from the group consisting of

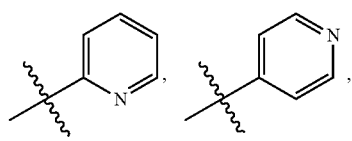

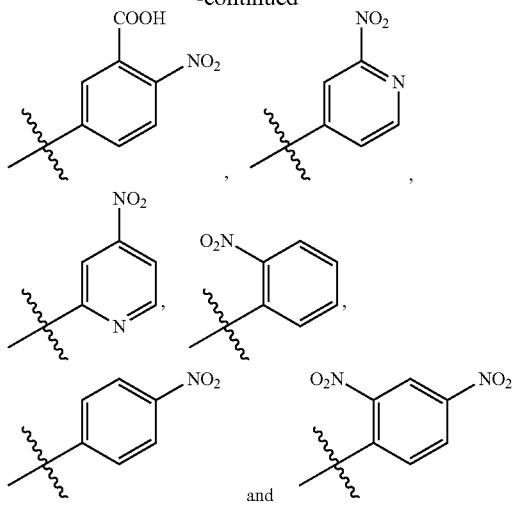

each of W³ is independently selected from the group consisting of

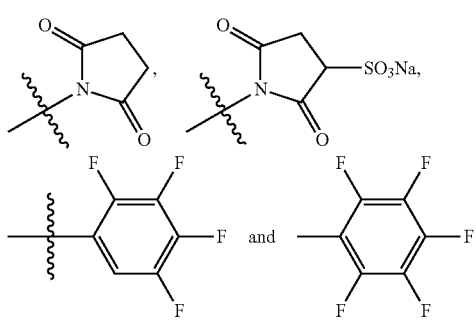

In some embodiments only one of the OH groups is modified with a crosslinking group and the linear sugar alcohol-derived compound has the following chemical structures:

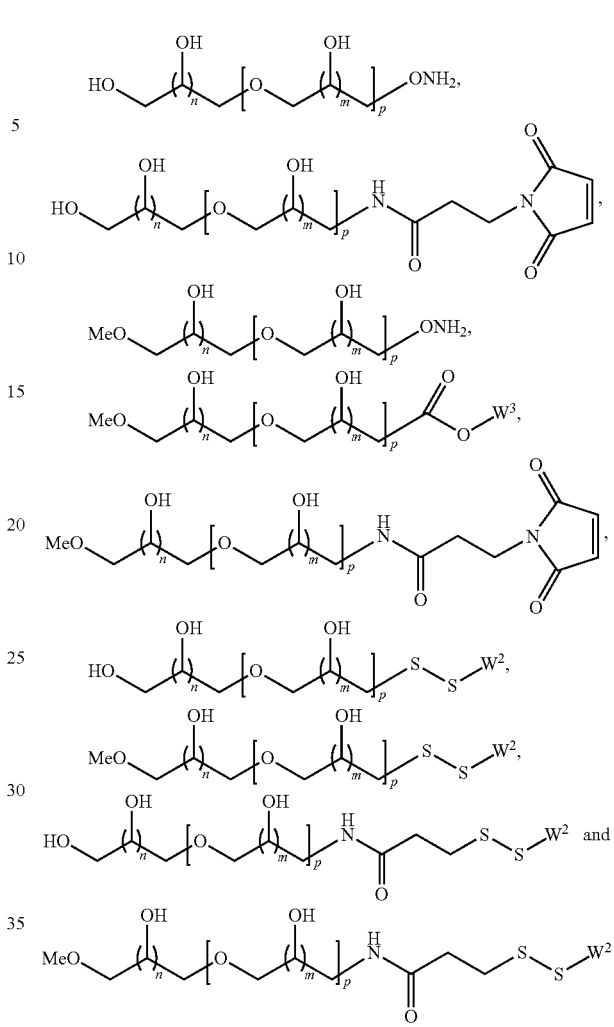

In some embodiments two of the primary OH groups are modified with the same crosslinking groups, a homobifunctional crosslinker with the following chemical structures:

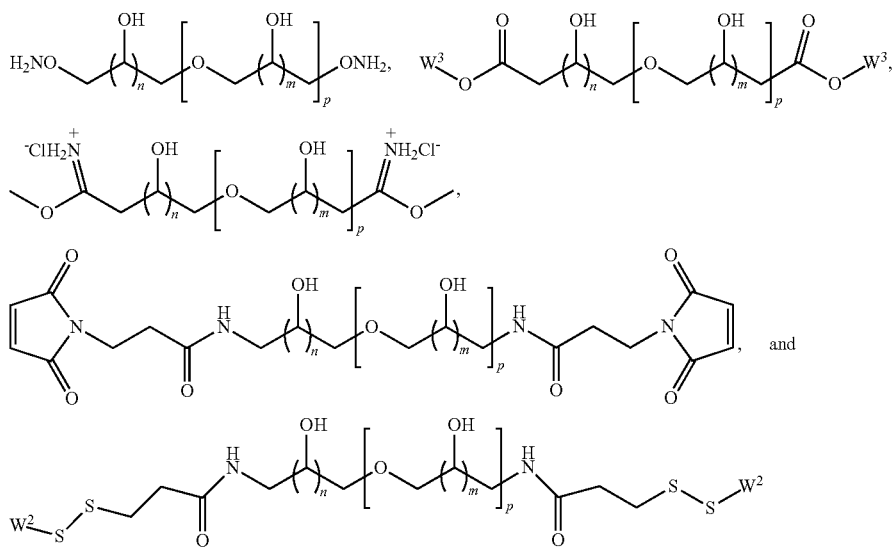

In some embodiments two of the primary OH groups are modified with different crosslinking groups, an aminooxy heterobifunctional crosslinker with the following chemical structures:

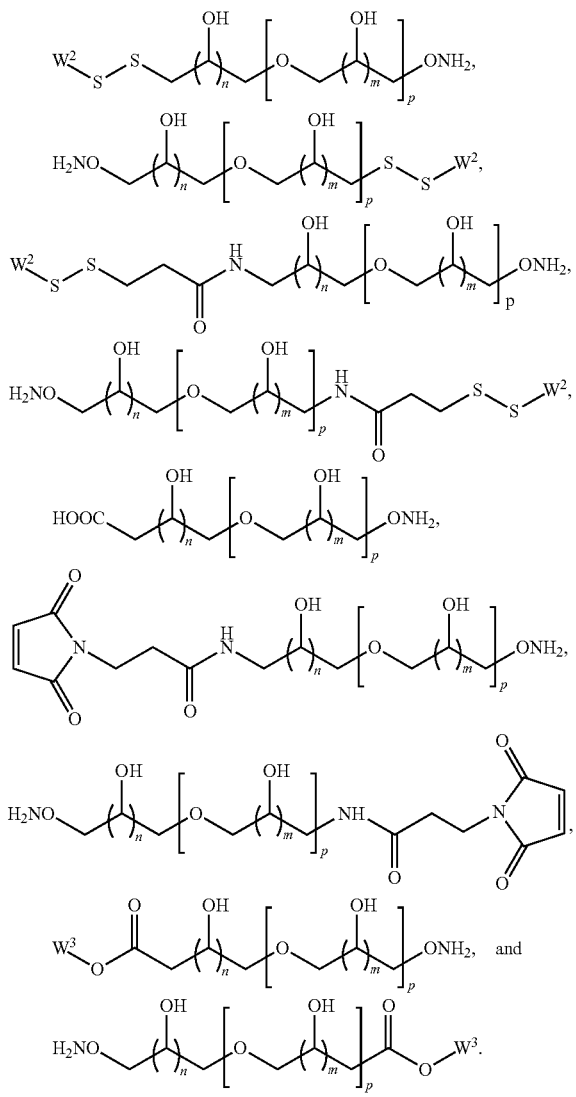

In some embodiments two of the primary OH groups are modified with different crosslinking groups, an active ester heterobifunctional crosslinker with the following chemical structures:

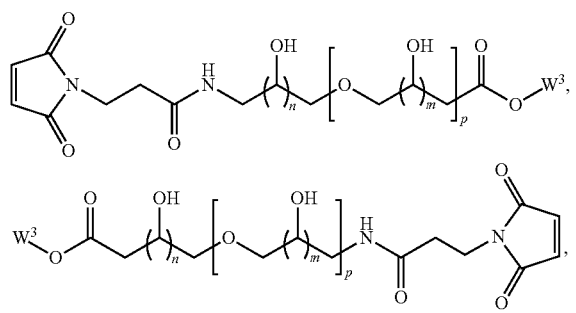

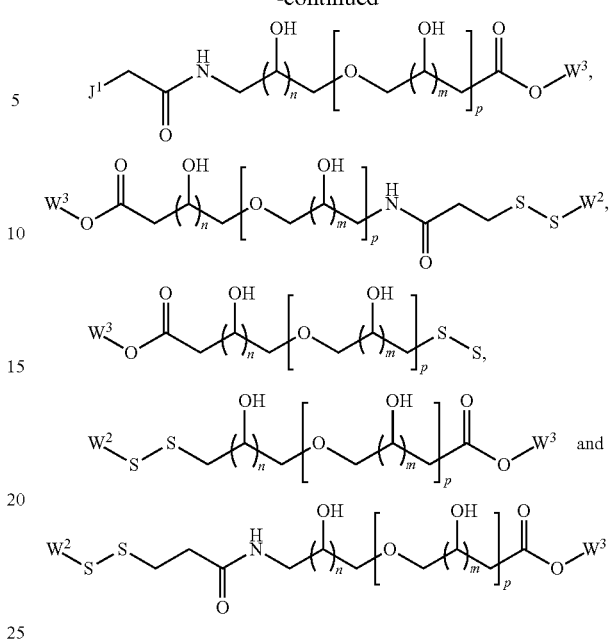

In some embodiments the linear SA molecule is a photocrosslinking reagent with the following chemical structures:

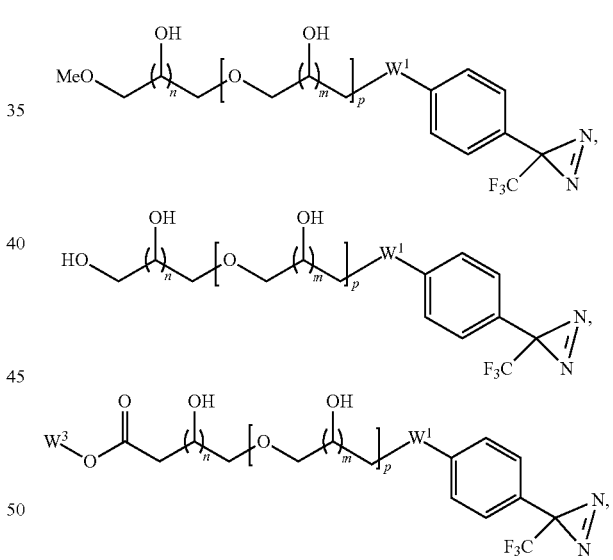

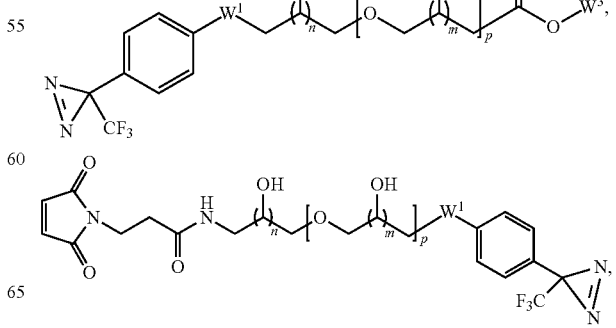

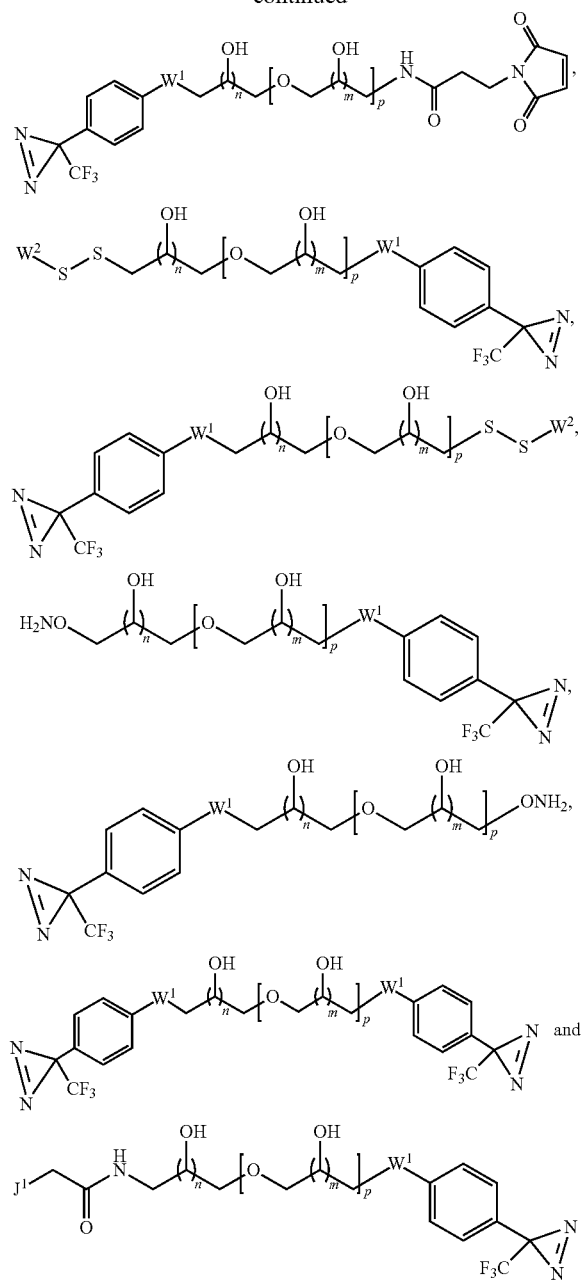

In some embodiments the linear SA molecule has the following chemical structures:

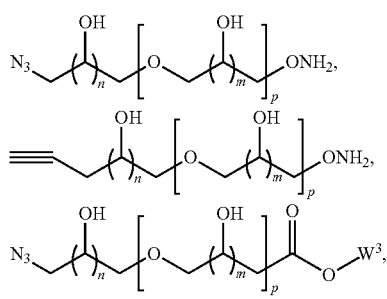

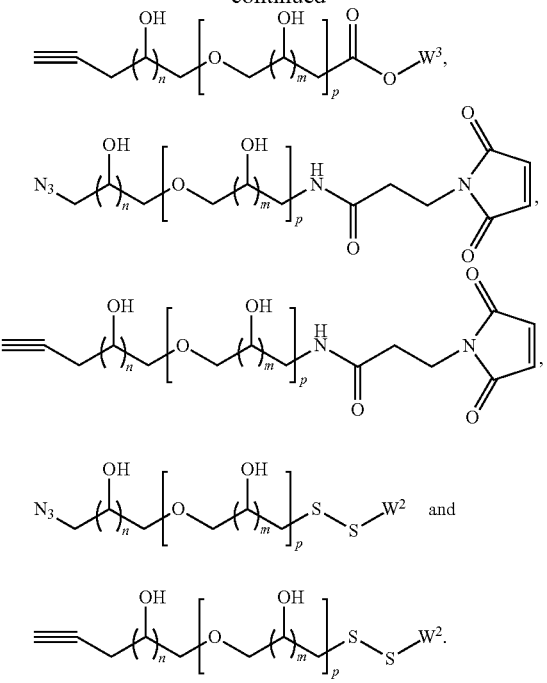

Methods of synthesizing linear SA crosslinking reagents

The present invention provides methods for synthesizing SA crosslinking reagents, for example, a method for synthesizing monodisperse, pre-determined high MW SA macromolecules. FIG. 2 illustrates an embodiment of a general approach for synthesizing monofunctional, homobifunctional, and heterobifunctional SA crosslinking reagents. The method consists of: (i) providing a sugar alcohol; (ii) combining the SA with reagents that can selectively protect the two terminal primary OH groups to form an intermediate (I1); (iii) combining the SA with reagents that react with the secondary OH to form an intermediate (I2); (iv) combining the SA with reagents that selectively deprotect one of the primary OH groups to generate an intermediate (I3); and (v) reacting with reagents that introduce different functional groups X other than OH groups (I4).

In one approach, I4 can be fully deprotected to obtain a monosubstituted SA crosslinking reagent (P3). Further alkylation of the monosubstituted SA crosslinking reagent P3 generates an SA crosslinking reagent with a single active functional group (P4), an alkylated monosubstituted SA crosslinking reagent. Alkylation can also be achieved in the beginning by blocking the secondary OH groups with alkyl groups.

In one approach, I4 can be combined with reagents that selectively deprotect the primary OH group to generate I5, which can further react with reagents that introduce non-hydroxyl functional group Y. Deprotection of the secondary OH groups of I6 generates a heterobifunctional SA crosslinking reagent, P1. Alkylation of the secondary OH groups results in P2, an alkylated heterobifunctional SA crosslinking reagent. Alkylation can also be achieved in the beginning by blocking the secondary OH groups with alkyl groups. In another approach, direct alkylation of the primary OH group, followed by the deprotection of secondary OH groups generates a monoalkylated monofunctional SA crosslinking reagent (P5).

In one approach, I2 can be combined with reagents that deprotect both primary OH groups to generate I8, which can further react with reagents to introduce functional groups at both termini. Deprotection of the secondary OH groups of I9 generates a homobifunctional SA crosslinking reagent (P6). Alkylation of the secondary OH groups results in P7, an alkylated homobifunctional SA crosslinking reagent. Alkylation can also be achieved in the beginning by blocking the secondary OH groups with alkyl groups.

In some embodiments X or Y functional groups can be attached to the SA backbone through extra linkers ($L^1$ and $L^2$). FIG. 3 illustrates an embodiment of a general approach for synthesizing monofunctional, homobifunctional, and heterobifunctional SA crosslinking reagents with extra linkers. The method consists of: (i) providing a sugar alcohol intermediate (I4) with functional group X at one termini and protected primary OH group at the other termini and (ii) combining the SA with reagents that react with X to form an intermediate (I10) with an extra linker ($L^2$). In some embodiments the linker is a stable linker. In some embodiments the linker is a cleavable linker. In some embodiments the linker is a reversible linker.

In one approach, I10 can be fully deprotected to obtain a monohydroxyl SA crosslinking reagent with an extra linker (P8). Further alkylation provides an SA crosslinking reagent containing a single active functional group (P9). Alkylation can also be achieved in the beginning by blocking the secondary OH groups with alkyl groups.

In one approach, I10 can be combined with reagents that selectively deprotect the primary OH group to generate I11, which can further react with reagents that introduce another functional group X that is not an OH group. Deprotection of the secondary OH groups of I12 generates a heterobifunctional SA crosslinking reagent with an extra linker (P13). Alkylation of the secondary OH groups results in P14, an alkylated heterobifunctional SA crosslinking reagent with an extra linker. Alkylation can also be achieved in the beginning by blocking the secondary OH groups with alkyl groups. In another case, direct alkylation of the primary OH group, followed by deprotection of the secondary OH groups, generates a monoalkylated monosubstituted SA crosslinking reagent with an extra linker (P10).

In another approach, I12 can further react with reagents to generate a second linker with a functional group (I14). Deprotection of the secondary OH groups generates a heterobifunctional SA crosslinking reagent with two extra linkers (P11). Alkylation of the secondary OH groups results in P12, an alkylated heterobifunctional SA crosslinking reagent with two extra linkers. Alkylation can also be achieved in the beginning by blocking the secondary OH groups with alkyl groups.

In one approach, homobifunctional SA crosslinking reagent I9 can react with reagents that generate linkers at both termini (I15). Deprotecting the secondary OH groups of I15 generates a homobifunctional SA crosslinking reagent with two extra linkers (P15). Alkylation of the secondary OH groups results in P16, an alkylated homobifunctional SA crosslinking reagent with two extra linkers. Alkylation can also be achieved in the beginning by blocking the secondary OH groups with alkyl groups.

The methods described herein utilize the general protection and deprotection mechanism for OH groups. The orthogonal OH protecting groups (PG1, PG2, PG3) can be selected from the varieties of protecting groups (for example, as disclosed in Greene, T W; Wuts, PGM Protective groups in organic synthesis, third edition, John Wiley & Sons, Inc. 1999). The techniques and experiments involved in the actual reduction in practice involve all classical organic synthesis methods and can be easily implemented by a skilled artisan in view of the disclosure herein. FIGS. 4 and 5 provide numerous examples of the SA crosslinking reagents that can be made using the methods and representative examples disclosed herein.

To enable such strategies in FIGS. 2 and 3 the right protection groups must be selected for the primary OH and secondary OH groups. The protecting groups (PG1 and PG2) need to be orthogonal in the deprotection conditions. Synthesizing a monofunctional and homobifunctional crosslinking reagent is often easier than synthesizing a heterobifunctional crosslinking reagent. For heterobifunctional crosslinkers, PG1 has to be able to be selectively cleaved, as only one of the OH groups can be replaced with a crosslinking group at a time.

Different protecting groups have been explored as examples for obtaining a single OH-reactive SA molecule. 1) Tert-butyldimethylsilyl (TBDMS) ether protection of the primary OH groups is easy to form and can one of the primary OH groups can be selectively deprotected using dilute iodine solution. To selectively protect the primary OH, a more hindered silylation reagent, t-butyl-diphenylsilyl chloride (TBDPSCl), was also explored. The reaction was much cleaner than TBDMS protection. Unlike TBDMS, no indication was seen that three protection groups were added. 2) Benzoate ester is base sensitive and orthogonal to the TBDMS removing conditions. 3) Benzyl ether is stable to acid and base, and hydrogenation is used to remove it. 4) THP ether protection: 3,4-dihydro-2H-pyran is known as a useful strategy for protecting the primary and secondary OH groups to obtain tetrahydropyranyl ethers. THP ether is stable in basic media and under oxidation and reduction conditions, but can easily be removed by acid hydrolysis. THP protection can be achieved by using any of the following catalysts: zinc tetrafuloroborate (Ranu, B. C. et al. *Tetrahedron Letters*, 1999, 40, 1985-1988), pyridinium p-toleuensulphonate (Miyashita, M. et al *J. Org. Chem.*, 1977, 42, 3772-3774), bis(trimethylsilyl) sulfate (Morizawa, Y. et al *Synthesis* 1981, 899-901), or amberlyst H-15 (Bongini, A. et al. *Synthesis* 1979, 618-620).

The general schemes and methods for introducing crosslinking groups from the OH group are as follows. Multiple crosslinking groups can be introduced sequentially by releasing other OH groups one by one. Homobifunctional crosslinkers are synthesized when both PG1 groups are deprotected.

Scheme 1: Converting an OH group to —ONH$_2$.

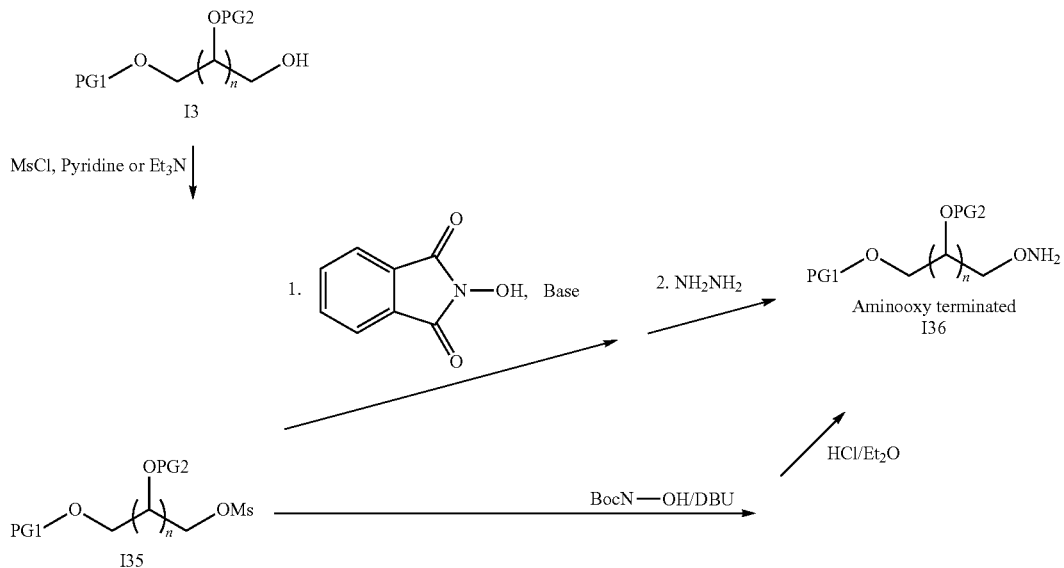

The single free OH group of the SA can first react with methanesulfonyl chloride and convert to mesylated OH (OMs). The alcohol mesylate group (OMes) is a very good leaving good, and various nucleophiles (such as N3 and CN) can easily attack and replace it. O-alkylation of tert-butyl N-hydroxycarbamate (BocN-OH) with alcohol mesylate, followed by acidic N-deprotection, results in the corresponding aminooxy terminated SA (Albrecht, S. et al. *Synthesis* 2006, 10, 1635-1638.). Alternatively, the SA alcohol mesylate can react with N-hydroxyphthalimide-protected hydroxyamic acid to create a compound that is deprotected under basic conditions (hydrazine).

Scheme 2: Converting an OH group to an azide and amine.

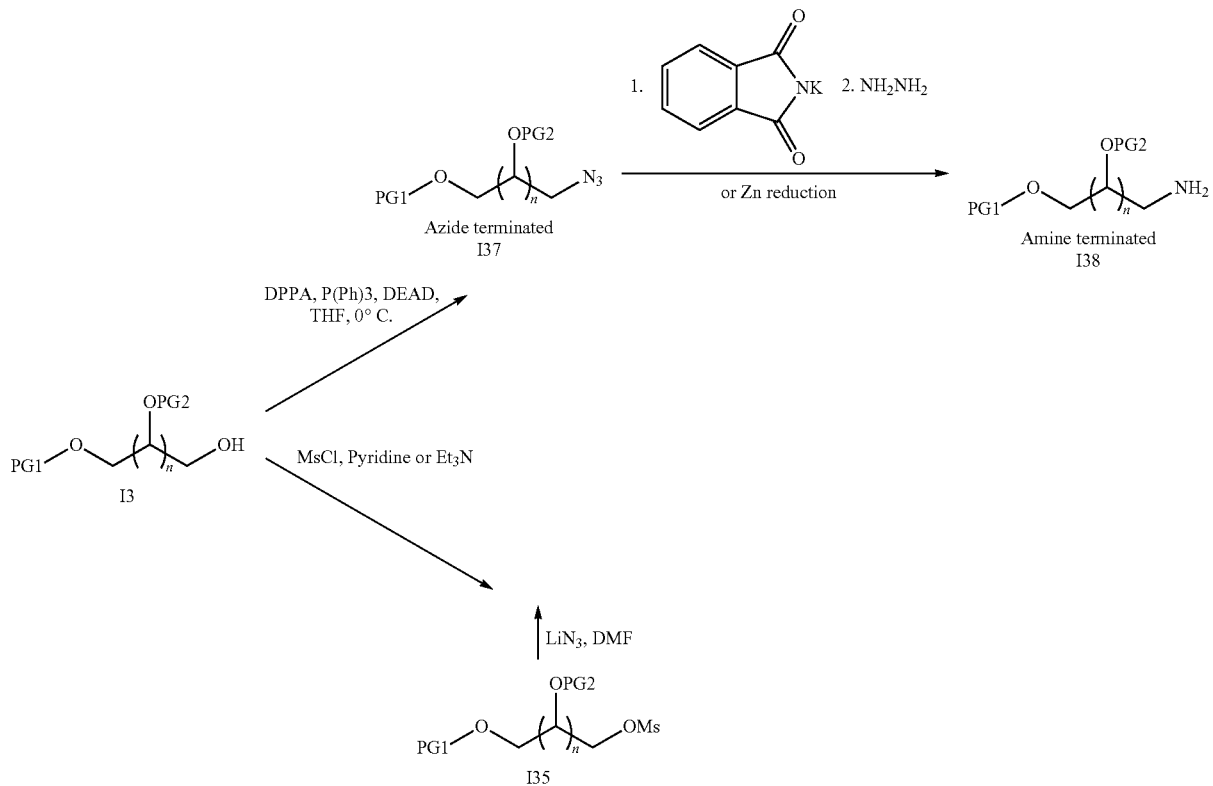

Azide can be prepared in high yields via nucleophilic displacement of the corresponding mesylate or modified Mitsunobu conditions (triphenyl phosphine, diethylazodicarboxylate: DEAD; diphenylphosphoryl azide: DPPA) (Jackson, M. D. et al. *J. Org. Chem.* 2002, 67, 2934-2941). The azide can be further reduced to an amine using different reducing reagents, such as Zn.

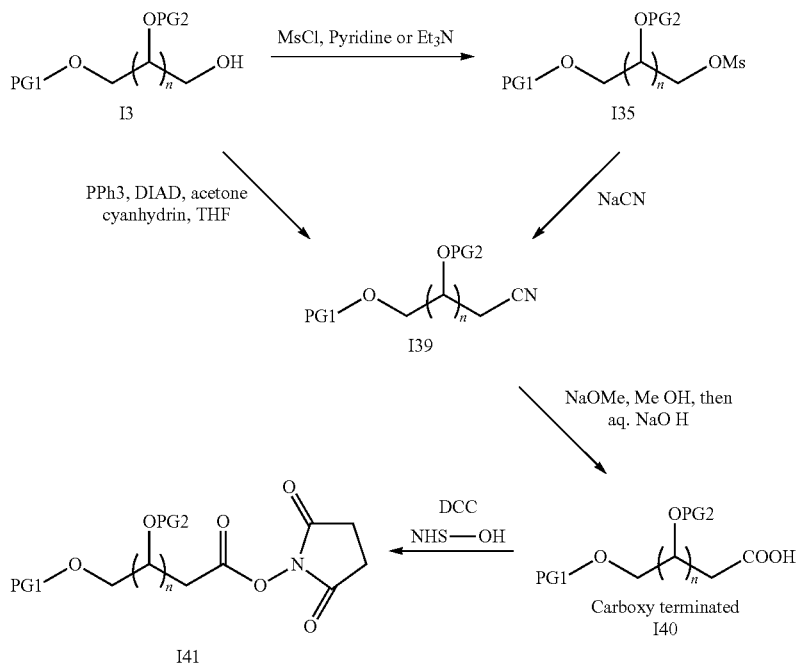

Scheme 3: Converting an OH group to CN, COOH, or N-hydroxysuccinimide (NHS) ester.

OH can be directly converted to a CN group following a procedure from the literature (Gollner, A.; Mulzer, J. *Organic Letters,* 2008, 10, 4701-4704) or via the mesylated alcohol intermediate. After hydrolysis of the CN group by acid or base (Bernardes, G. J. L. et al *ChemBioChem* 2011, 12, 1383-1386), a carboxylic acid can easily be obtained. The carboxylic acid can be activated further using dicyclohexylcarbodiimide (DCC) and N-hydroxysuccinimide to form an NHS ester.

Scheme 4: Converting a carboxylic acid to a hydrazide.

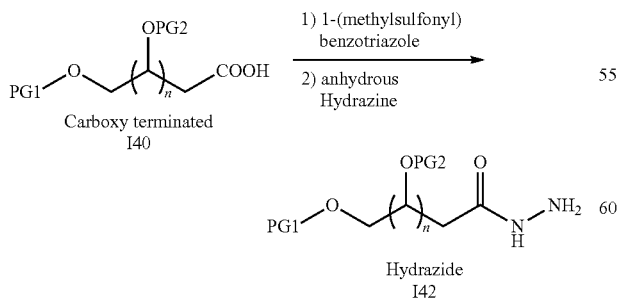

A carboxylic acid group can be conveniently converted to a hydrazide in one pot via hydrazinolysis of the intermediate N-acylbenzotriazole (Katritzky, A. R. *ARKIVOC* 2001 (ix) 19-23, issue in honor of academician Michael G. Voronkov).

Scheme 5: Converting a CN group to an imidoester

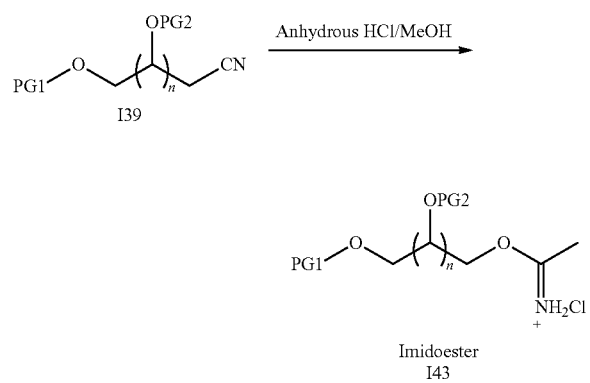

Imidoesters are highly specific reagents for amino groups in biopolymers. Imidoester can easily be prepared from a nitrile following procedures in the literature (McElvain, S. M.; Schroeder, J. P. *J. Amer. Chem. Sco.* 1949, 71, 40; Davies, G. E.; Stark, G. R. *Proceed of the National Academy of Sciences,* 1970, 66, 651-656).

101
Scheme 6: Converting an OH group to an alkyne.
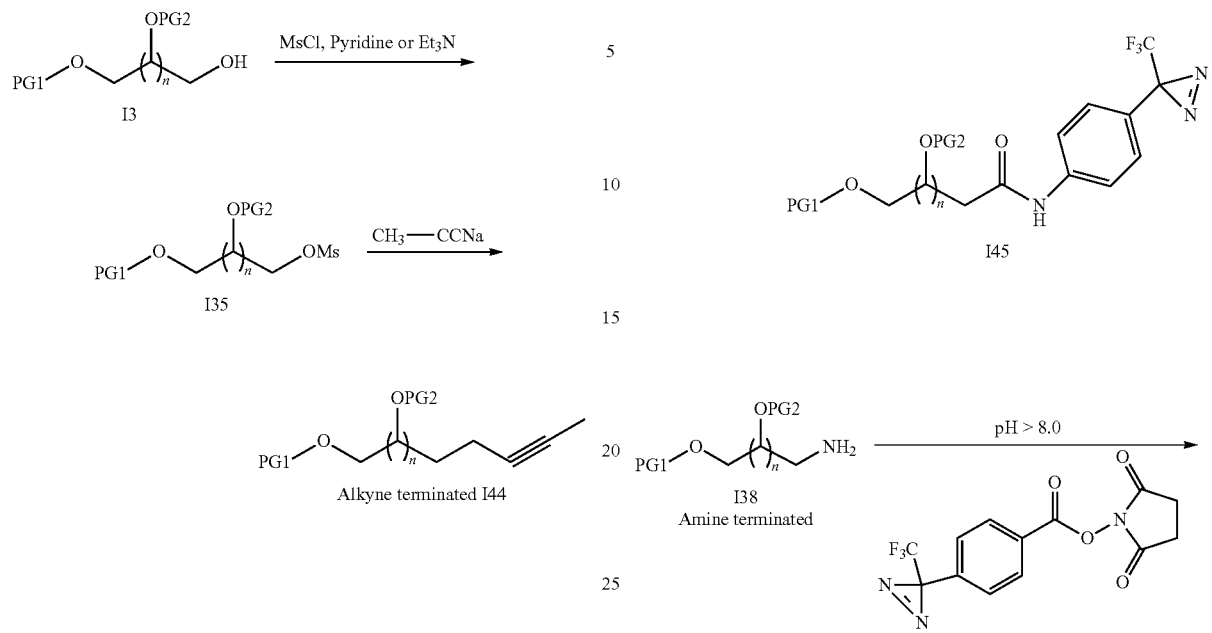
102
-continued
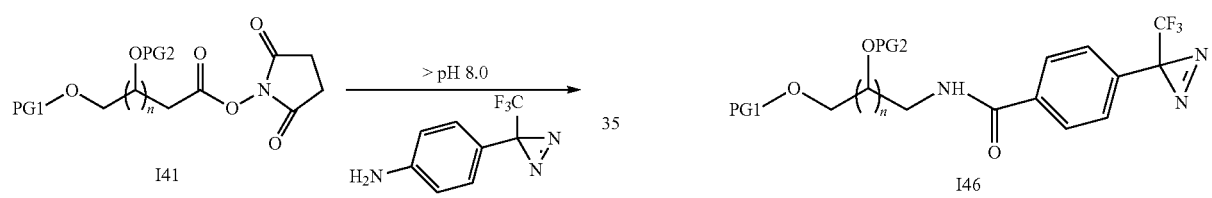
Scheme 7: Introducing a trifluoromethylphenyldiazirine via a carboxylic acid group or amine group.
Scheme 8: Converting an OH group to a free SH and protected thiol.
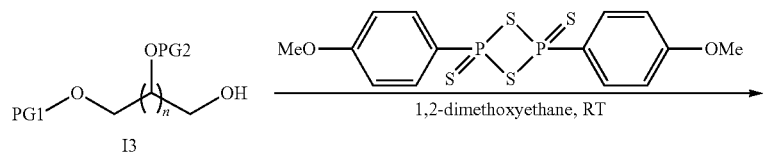
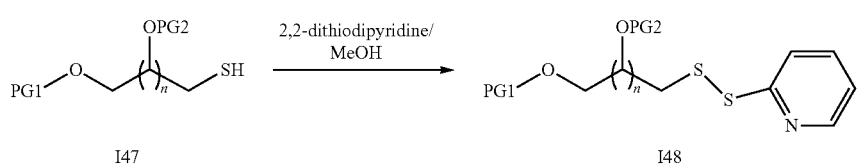

OH can be converted to a free thiol in one pot using 2,4-bis(4-methoxyphenyl)-1,3,2,4-dithiadiphosphetane 2,4-disulfide (Lawesson's reagent, LR) (Nishio, T. *J. Chem. Soc. Perkin Trans* 1993, 1113-1117). The free thiol can react further with 2,2'-dithio dipyridine in MeOH to give the disulfide-protected product (Jones, L. R. et al *J. Am. Chem. Soc.* 2006, 128, 6526-6527). Other disulfide reagents, such as Ellman's reagent (5,5'-dithiobis-(2-nitrobenzoic) acid, or DTNB) can be introduced in a similar fashion.

Scheme 9: Introducing a maleimide group via a carboxylic acid group or an amine group.

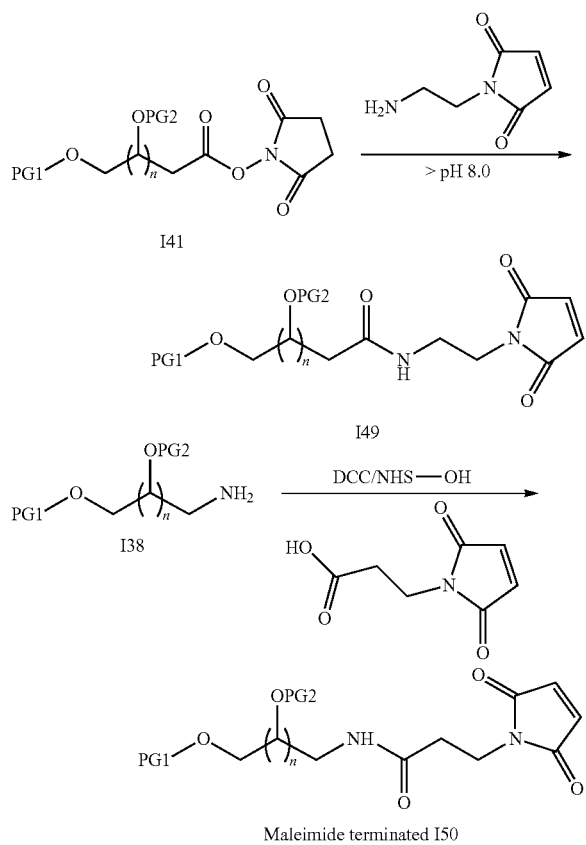

Maleimide terminated I50

SA Macromolecules

In one aspect, the present invention provides a collective of novel SA macromolecules that can be used for the modification of biomolecules, formulation of biologics, and drug delivery. In addition, sophisticated three-dimensional architecture can be readily built into the system to make single pure SA macromolecules, such as linear, circular, branched, and dendrimer SA macromolecules, depending on the requirement of the tethered molecules. These features enable modulation of the formulation and the physical properties of the final conjugates. Furthermore, this system may be used to transport potent antitumor drugs to tumor tissue, reducing undesirable side effects and frequency of dosing.

SA macromolecules can be made from the SA backbone by (i) linking SAs linearly through the OH group of the backbone, (ii) cyclizing the SA unit at the termini, (iii) asymmetrically branching the SA unit together, (iv) symmetrically branching the SA, or (v) repetitively branching SAs to build sophisticated three-dimensional structures. In all cases, a high MW (>1000 Da) crosslinking reagent or carrier molecule can be made.

Linear SA Macromolecule
Methods of Synthesizing Linear SA Macromolecules

FIG. 6 illustrates an embodiment of a general approach for synthesizing SA building blocks containing multiple SA units. The method consists of: (i) providing the first SA unit with a free primary OH, (ii) substituting the primary OH group with a good leaving group, (iii) providing the second SA unit with a free primary OH with the protective group of the other primary OH (PG3) orthogonal to the protecting groups of the primary OH of the first SA unit (PG1), (iv) combining the first SA unit with the second SA unit under conditions that permit the condensation of these two units, and (v) deprotecting one of the primary OH groups to provide a di-SA building block (two SA units) that can be utilized to build a higher MW SA molecule. Higher orders of SA building blocks (higher number of SA units) can be built following repetitive steps (i) to (v) using r-SA building blocks, where r represents the number of SA units in one molecule.

Higher MW linear SA molecules can be built by stepwise or convergent, or stepwise plus convergent, methods depending on the heterogeneity of the secondary alcohol groups in the SA molecules. For example, tetra-SA building blocks containing different numbers and different kinds (different stereochemistry) of secondary OH groups on each SA unit can be built by coupling four different mono-SA units stepwise. Tetra-SA building blocks with different numbers and different kinds of secondary OH groups on each SA unit can also be built by coupling two units stepwise first, and then converging two of the di-SA building blocks together. Tetra-SA units with the same number and same kinds of secondary OH groups on each SA unit can be built by coupling two di-SA building blocks (e.g., I20 plus I19). In most cases, the low MW SA building blocks are usually built stepwise and the high MW SAs are assembled by convergence. An embodiment of a general method for the convergent synthesis of tetra-SA building blocks is shown in FIG. 6.

FIG. 7 shows the calculated MW of linear SA macromolecules that can be synthesized by iterative coupling using tetra-D-mannitol as the building block. After the fifth iteration, single and pure SA macromolecules over 20 KDa can be readily synthesized from inexpensive starting materials.

In one approach, SA macromolecules containing crosslinking groups X and Y at the termini can be synthesized in a similar fashion as SA crosslinking reagents (method shown in FIG. 2 and FIG. 3). For example, tetra-SA molecules I22 and I23 can first react with a reagent that introduces functional group X. Then, after deprotecting the second primary OH group, a second functional group, Y, can be introduced. Deprotection of the secondary OH groups produces tetra-SA crosslinking reagents.

Functional groups X and Y may be incorporated into either the primary OH groups at the termini or secondary OH groups at the side chains. FIG. 8 illustrates an embodiment of a general approach for incorporating X and Y groups into the SA macromolecules. A mono SA building block with the X or Y group already in place at the secondary OH groups is coupled to a SA macromolecule (I27). If n equals 1 and the mono SA building block is coupled only once, then one X group is introduced. If n is greater than 1 or the mono SA building block of one X group is coupled several times, multiple X groups can be introduced. The number of X and Y groups and the position of the X and Y groups can easily be adjusted based on the mono SA building block and sequence of coupling.

Table 2 lists the molecular weight distribution of examples of single MW SA macromolecules that can be synthesized based on the above methods. By using only four types of sugar alcohol monomer (where n is 2, 3, 4, or 5), after nine iterations of the same sugar alcohol monomer, the MWs of the obtained compounds range from 400 to 400,000 Da. One can also fine tune the MW range by mixing and reacting with other monomers, dimers, trimers, tetramers, or higher SA molecules. For example, when a tetramer of threitol (n=2) is mixed with a tetramer of mannitol (n=4), a MW of 1109 is obtained. When a tetramer of xylitol (n=3) is mixed with a tetramer of mannitol (n=4), a MW of 1230 is obtained. All of these molecules are made with chemically pure starting materials bearing a single reactive site; only one coupling product can be obtained. This is the key to obtaining single pure SA molecules.

TABLE 2

MW distribution of single MW SA macromolecules that can be synthesized by chemical methods.

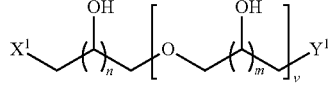

| Item # | MW (Da) | n | m | v | X$^1$ | Y$^1$ | Iteration # | SA unit # |
|---|---|---|---|---|---|---|---|---|
| 1 | 449 | 2 | 2 | 3 | OH | —ONH$_2$ | 0 | 4 |
| 2 | 570 | 3 | 3 | 3 | OH | —ONH$_2$ | 0 | 4 |
| 3 | 690 | 4 | 4 | 3 | OH | —ONH$_2$ | 0 | 4 |
| 4 | 810 | 5 | 5 | 3 | OH | —ONH$_2$ | 0 | 4 |
| 5 | 866 | 2 | 2 | 7 | OH | —ONH$_2$ | 1 | 8 |
| 6 | 1,106 | 3 | 3 | 7 | OH | —ONH$_2$ | 1 | 8 |
| 7 | 1,346 | 4 | 4 | 7 | OH | —ONH$_2$ | 1 | 8 |
| 8 | 1,586 | 5 | 5 | 7 | OH | —ONH$_2$ | 1 | 8 |
| 9 | 1,699 | 2 | 2 | 15 | OH | —ONH$_2$ | 2 | 16 |
| 10 | 2,179 | 3 | 3 | 15 | OH | —ONH$_2$ | 2 | 16 |
| 11 | 2,660 | 4 | 4 | 15 | OH | —ONH$_2$ | 2 | 16 |
| 12 | 3,140 | 5 | 5 | 15 | OH | —ONH$_2$ | 2 | 16 |
| 13 | 3,364 | 2 | 2 | 31 | OH | —ONH$_2$ | 3 | 32 |
| 14 | 4,325 | 3 | 3 | 31 | OH | —ONH$_2$ | 3 | 32 |
| 15 | 5,286 | 4 | 4 | 31 | OH | —ONH$_2$ | 3 | 32 |
| 16 | 6,247 | 5 | 5 | 31 | OH | —ONH$_2$ | 3 | 32 |
| 17 | 6,696 | 2 | 2 | 63 | OH | —ONH$_2$ | 4 | 64 |
| 18 | 8,617 | 3 | 3 | 63 | OH | —ONH$_2$ | 4 | 64 |
| 19 | 10,539 | 4 | 4 | 63 | OH | —ONH$_2$ | 4 | 64 |
| 20 | 12,461 | 5 | 5 | 63 | OH | —ONH$_2$ | 4 | 64 |
| 21 | 13,358 | 2 | 2 | 127 | OH | —ONH$_2$ | 5 | 128 |
| 22 | 17,202 | 3 | 3 | 127 | OH | —ONH$_2$ | 5 | 128 |
| 23 | 21,045 | 4 | 4 | 127 | OH | —ONH$_2$ | 5 | 128 |
| 24 | 24,888 | 5 | 5 | 127 | OH | —ONH$_2$ | 5 | 128 |
| 25 | 26,684 | 2 | 2 | 255 | OH | —ONH$_2$ | 6 | 256 |
| 26 | 34,370 | 3 | 3 | 255 | OH | —ONH$_2$ | 6 | 256 |
| 27 | 42,057 | 4 | 4 | 255 | OH | —ONH$_2$ | 6 | 256 |
| 28 | 49,744 | 5 | 5 | 255 | OH | —ONH$_2$ | 6 | 256 |
| 29 | 53,335 | 2 | 2 | 511 | OH | —ONH$_2$ | 7 | 512 |
| 30 | 68,708 | 3 | 3 | 511 | OH | —ONH$_2$ | 7 | 512 |
| 31 | 84,081 | 4 | 4 | 511 | OH | —ONH$_2$ | 7 | 512 |
| 32 | 99,454 | 5 | 5 | 511 | OH | —ONH$_2$ | 7 | 512 |
| 33 | 106,636 | 2 | 2 | 1023 | OH | —ONH$_2$ | 8 | 1024 |
| 34 | 137,383 | 3 | 3 | 1023 | OH | —ONH$_2$ | 8 | 1024 |
| 35 | 168,129 | 4 | 4 | 1023 | OH | —ONH$_2$ | 8 | 1024 |
| 36 | 198,876 | 5 | 5 | 1023 | OH | —ONH$_2$ | 8 | 1024 |
| 37 | 213,239 | 2 | 2 | 2047 | OH | —ONH$_2$ | 9 | 2048 |
| 38 | 274,732 | 3 | 3 | 2047 | OH | —ONH$_2$ | 9 | 2048 |
| 39 | 336,225 | 4 | 4 | 2047 | OH | —ONH$_2$ | 9 | 2048 |
| 40 | 397,719 | 5 | 5 | 2047 | OH | —ONH$_2$ | 9 | 2048 |

Scheme 10:

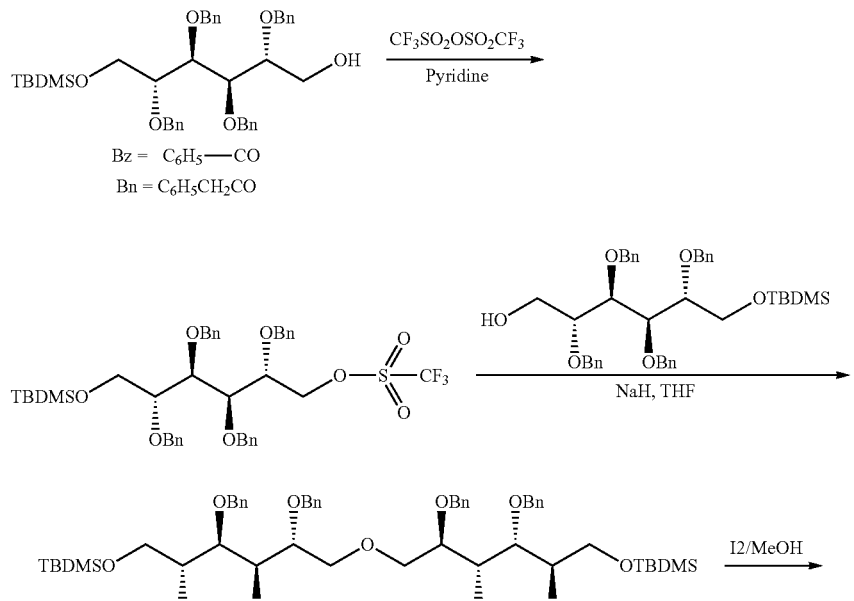

Bz = C$_6$H$_5$—CO
Bn = C$_6$H$_5$CH$_2$CO

15 Atom spacer: Di-mannitol

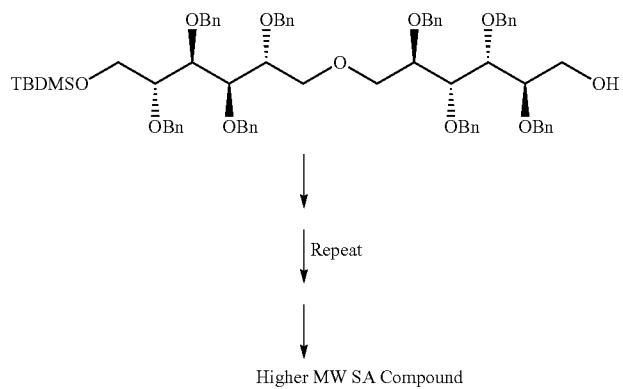

Scheme 10 shows a general strategy for synthesizing a higher MW sugar alcohol. One of the primary OH groups of the mannitol is protected as a TBDMS ether and the secondary OH group as benzyl ether. The remaining OH group is activated by reacting with trifluoromethanesulfonic acid anhydride in pyridine. Another mild leaving strategy can also be used, such as O-mesylation. This pre-activated mannitol carrying a good leaving group can couple to another mannitol carrying a single free OH group in the presence of a base, such as NaH, LiHMDS, or potassium tert-butoxide. The initial strategy of using benzoate ester as the starting material (compound I3-a) for the dimerization was unsuccessful under similar conditions. Apparently, the benzoate ester of I3-a underwent intramolecular isomerization during the reaction with little or no dimer formation. I3-a has an $R_f$ value of 0.43 (TLC, 25:75 EtOAc:hexanes; HPLC, 11.014 minutes using Method B), whereas the isomerized product has an $R_f$ value of 0.55 (HPLC: 11.182 min) (m/z expected for [M+H]=713.3, observed m/z=713.6; m/z expected for [M+Na]=735.3, observed m/z=735.6; m/z expected for [2M+Na]=1447.6, observed m/z=1448.2). In contrast, the benzyl ether protection was very stable under the dimerization reaction conditions during a separate run using threitol as an example and was easily removed during hydrogenation. The above strategy uses benzyl ether protection instead of benzoate ester protection. The only drawback of the above strategy is that the yield for selective iodine deprotection of the TBDMS is not very high (~50%) based on previous experiments, which will affect the overall efficiency of multiple synthesis.

Scheme 11:

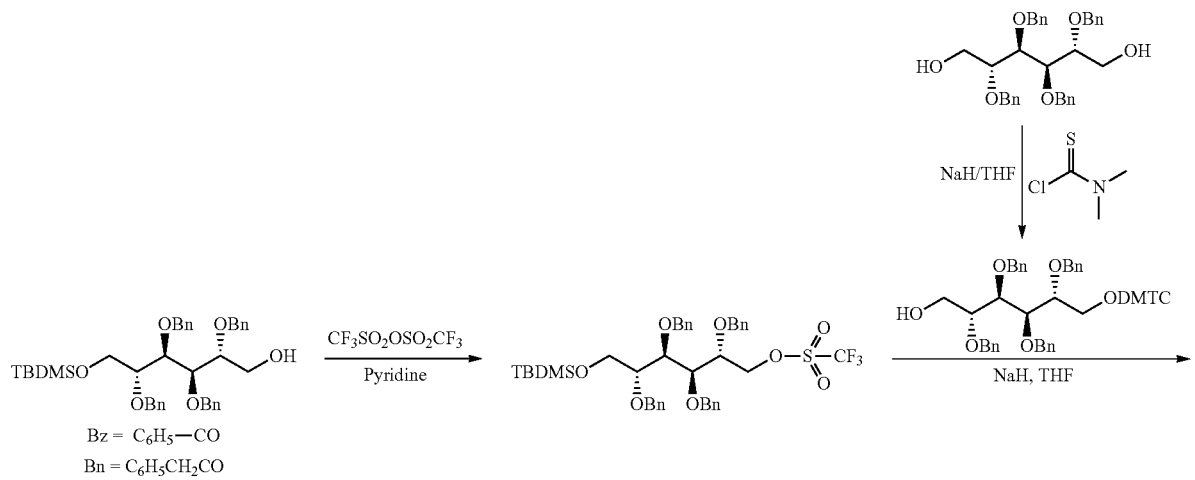

Bz = C₆H₅—CO
Bn = C₆H₅CH₂CO

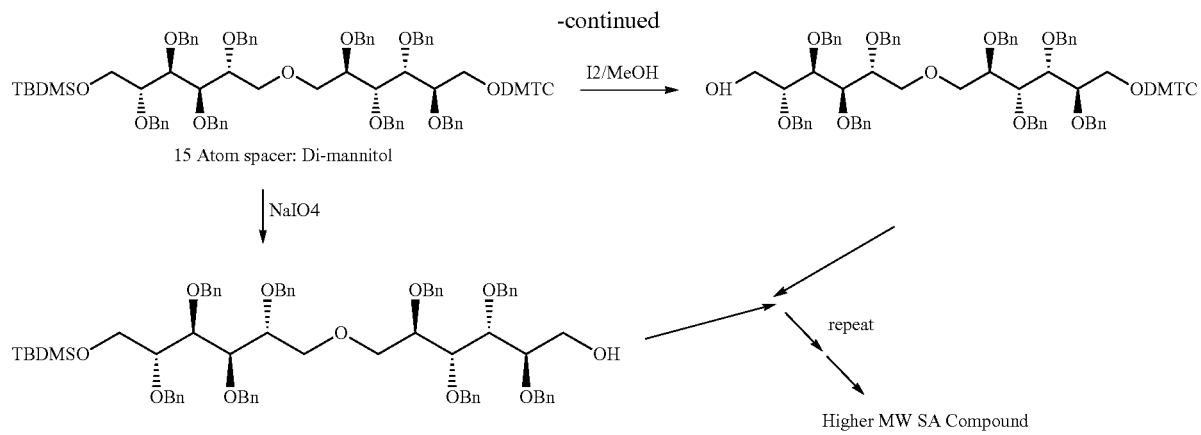

Scheme 11 outlines another strategy in which a third protecting group, such as DMTC (dimethylthiocarbamate), is used. DMTC is stable with a wide range of reagents and conditions, including metal hydrides, acid, base, and heat. It is easily removed by $NaIO_4$ or $H_2O_2$ and the other common alcohol protecting groups (Barma, D. K. et al. *Organic Letters*, 2003, 5, 4755-4757). This property will greatly increase the efficiency of the synthesis.

Linear SA macromolecules can also be synthesized using the solid phase approach by coupling mono SA units or r-SA units (multiple SA units) one by one. For example, an SA unit containing an Fmoc-protected amine at one terminus and a carboxylic acid at another terminus may be synthesized first, then the linear SA macromolecule can easily be synthesized following the Fmoc solid phase strategy similar to peptide synthesis. In another example, an SA unit containing a DMT-protected amine at one terminus and a phosphoramidite at another terminus can be synthesized first, then the linear SA macromolecule can be assembled following the standard oligonucleotide synthesis strategy. FIG. 9 provides two examples of such linear SA macromolecules synthesized by the solid phase strategy.

Cyclic, Branched, Hyperbranched Macro SA Molecules

In another aspect, the invention generally relates to a precursor compound that is a macrocyclic SA molecule comprising three or more monomeric SA units, $B^1$ (formula III), with each monomeric SA unit connected linearly through the X and Y portion of the SA unit one by one and then cyclized through the reaction of the X group of the first SA unit to the Y group of the last SA unit. In certain embodiments the SA units of the macrocyclic SA molecule are cyclized through the reaction of the X group of the first SA unit to the Z group of the last SA unit. In certain embodiments the SA units of the macrocyclic SA molecule are connected through the Z group of any SA in any order but in a cyclized form.

The precursor compound may be a branched SA macromolecule comprising three or more monomeric sugar alcohol units, $B^1$, with each monomeric sugar alcohol unit bound to one or another monomeric sugar alcohol unit through a linking group, W, wherein at least one of the linking groups is formed by a reaction between the X, Y, or Z portion of one monomeric unit with the Z of another monomeric unit.

The precursor compound may be a three-dimensional hyperbranched SA macromolecule comprising six or more monomeric sugar alcohol units, $B^1$, in which the core is an SA unit and several SA units branch out from the core structure. The hyperbranched SA macromolecule is largely a monodispersed, three-dimensional molecule with a well-defined MW. The characteristic hyperbranched SA macromolecule is a multiple branching molecule in three dimensions. When the size of the hyperbranched SA macromolecule approaches nano or micro scales, or microsphere may be obtained.

In certain embodiments the OH groups in an SA macromolecule (cyclic, branched, and hyperbranched) are unmodified and can be used directly to link molecules of interest through the OH groups. In some embodiments one or more of the OH groups may be replaced with X, Y, or Z crosslinking groups. Molecules of interest can be conjugated by reacting with X, Y, or Z crosslinking groups.

FIG. 10 lists a few configurations of hyperbranched SA macromolecules. In some embodiments hyperbranched SA macromolecules have a tree-like configuration wherein the core is an SA unit and other multiple SA (mSA) building blocks are attached to all of the OH groups at the core SA unit. In some embodiments hyperbranched SA macromolecules have a dendrimer-like configuration wherein the SA macromolecules continue to grow through the branches of the tree-like SA macromolecules. In another embodiment, hyperbranched SA macromolecules have a pyramid-like configuration wherein the core is a glycerol unit. Branching can also occur to the side chain of the cyclic SA macromolecule as shown in the few configurations in FIG. 10. FIG. 11 shows examples of some actual branched molecules (e.g., symmetrical, asymmetrical, linear, and cyclic) based on D-mannitol.

Hyperbranched molecules, such as dendrimers, have been found to have the characteristics of an ideal drug delivery vehicle and have been widely investigated as potential carriers of drugs, genes, and vaccines (Patri, A. K. et al. *Curr. Opin. Chem. Biol.* 2002, 6, 466-471.; Qivand, L. Y. and Bae, Y. H. *Pharm. Res.* 2006, 23, 1-30; Al-Jamal. K. T. et al. *J. Pharm. Sci.* 2005, 94, 102-113). The synthesis of a dendrimer was first reported in 1985 (Tomolia, D. A. et al. *Polym. J.* (Tokyo), 1985, 17, 117-132; Newkome, G. R. et al. *J. Org. Chem.* 1985, 50, 2003-2004). The details of dendrimer synthesis have been reviewed extensively (Bai, S. et al. *Crit. Rev. Ther. Drug Carrier Syst.* 2006, 23, 437-495).

Methods of Synthesizing Branched SA Macromolecules

Branched SA macromolecules can be synthesized by incorporating linear SA macromolecules at the side chain of the monomeric SA unit (secondary OH groups). FIG. 12 illustrates embodiments of a general approach for synthesizing a branched SA macromolecule. The method consists of: (i) providing the first SA unit with a free secondary OH group while the primary OH groups are protected with PG1, (ii) substituting the secondary OH groups with a good leaving group, (iii) providing the second linear SA macromolecule building block with a free primary OH while the secondary OH groups are protected with PG2 and the other primary OH is protected with PG3, which is orthogonal to the protecting group (PG1) of the primary OH of the first SA unit, (iv) combining the first SA unit with the second linear SA macromolecule under conditions that permit the condensation of these two units, and (v) deprotecting one or two of the primary OH groups to provide sites for further branching. The macromolecule is usually non-symmetrical (e.g., P19). When a glycol is used as the core SA unit, the macromolecule is symmetric (e.g., P20).

Small MW SA homobifunctional and heterobifunctional crosslinking reagents may be used to crosslink different organic molecules or biomolecules together. Similar conjugates created with other crosslinking reagents have found many uses as research tools in biomedical research, as diagnostic reagents, and as new pharmaceutical drugs. High MW SA crosslinking reagents can be used to modify therapeutic agents and as carriers for drug delivery. For example, high MW SA macromolecules can be used to conjugate proteins of pharmaceutical interest that have a MW of less than 30 KDa, such as enzymes, cytokines, hormones, and monoclonal antibody fragments. In addition, SA macromolecules may be used to conjugate peptides, nucleic acids and their analogs, and siRNAs. The benefit of conjugating such high MW SA macromolecules to these molecules include (i) an increased hydrodynamic volume of the conjugate molecules, reducing their kidney excretion and prolonging the in vivo half-life of proteins to stabilize the protein, (ii) protecting amino acids of peptides from degradation, (iii) masking the critical sites sensitive to enzymatic degradation, (iv) reducing aggregation, and (v) increasing bioavailability.

In addition, SA macromolecules can be metabolized in vivo, which may generate a new mechanism for drug release.

Furthermore, SA macromolecules may be used to load drugs or small molecules, not only at the termini, but throughout the SA macromolecule. For example, molecules containing acid groups can be coupled to the OH group of the backbone, increasing the amount of small molecules delivered to the tissue.

Site-Specific Labeling Through SA Crosslinking Reagents and SA Macromolecules

Site-specific labeling may be achieved through various strategies: (i) terminal amino acid in the protein of interest, (ii) insertion of a non-paired cysteine as a labeling site, (iii) structure-based approach by predicting the most reactive group in the surface, such as amine, phenolic hydroxyl, and thiol, (iv) oxidation or enzymatic reaction of a glycosylated moiety on the protein followed by tethering, (v) insertion of unnatural amino acids into the protein sequence to enable labeling at that specific site, and (vii) cysteine mutagenesis to introduce single reactive Cys groups.

SA crosslinking reagents may be used for the site-specific labeling of molecules of interest. For example, an SA molecule can label only the N-termini of proteins, antibodies, and enzymes through reductive amination. In some embodiments, the X or Y groups are aldehyde functional groups. For example, this strategy was used for site-specific PEGylation (Lee, D. et al. *J. Interferon Cytokine Res.* 2008, 28, 101-112). An example of a conjugate made by this chemistry is Neulasta® (PEG-filgrastim) (Kinstler O B. *Pharm. Res.* 1996, 13, 996-1002.).

In some embodiments, thiol-specific SA crosslinking reagents or SA macromolecules are used for site-specific labeling of Cys in the protein, with which single reactive Cys can be obtained by Cys mutagenesis. SA crosslinking reagents or SA macromolecules can undergo thiol exchange reactions or alkylation reactions through ether substitution (such as iodoacetiamide derivatives) or an addition reaction (such as a vinyl sulfone, vinyl pyridine, or maleimide end-group).

In some embodiments X or Y is a conjugation moiety with the formula

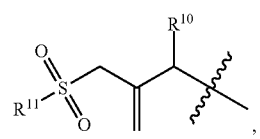

wherein $R^{11}$ is an optionally substituted aryl and $R^{10}$ is an electron withdrawing group (e.g., carbonyl), an $\alpha,\beta$-unsaturated double bond, or an $\alpha,\beta$ sulfonyl group prone to elimination as sulfonic acid. This compound can be used to label any protein or antibody with a disulfide bond in a site-specific manner through two steps: (i) mild disulfide reduction to release the free thiols and (ii) conjugation of both thiols by sequential interactive bis-alkylation to yield a three-carbon bridge to which the SA molecule is covalently attached (Shaunak S. et al. *Nat. Chem. Bio.* 2006, 312-313; Balan S. et al., *Bioconjugate Chem.* 2007, 18, 61-76.; Brocchini, S. et al. *Nat. Protocols.* 2006, 1, 2241-2252).

In some embodiments various enzymatic methods can be used to label molecules of therapeutic interest in a site-specific manner using SA macromolecules. The enzymes recognize and specifically modify only a select single or few amino acid residues, such as glycosyl-transferases and transglutaminases.

In some embodiments X or Y is a sialic acid group linked either directly to the SA macromolecules or through other spacers. Site-specific labeling can be achieved through enzymatic GalNAc glycosylation at serine and threonine residues in the protein, followed by the enzymatic transfer of SA-linked sialic acid to the previously introduced GalNAc residues. GlycoPEGylation has been applied successfully to the modification of granulocyte colony stimulating factor (G-CSF) (Defrees, S. US Patent Publication No. 20070254836A1), granulocyte macrophage colony stimulating factor (GM-CSF) (DeFrees, S. et al. *Glycobiology,* 2006, 16, 833-843), interferon alpha-2b (IFNα-2b) (DeFrees, S. et al. *Glycobiology,* 2006, 16, 833-843), follicle stimulating hormone (DeFrees, S. et al. US patent application 20080015142), erythropoietin (DeFrees, S. et al. US Patent Publication No. 20060287224A1), and factor VII (Klausen N K et al. US Patent Publication No. 20080039373A1).

In some embodiments X or Y is an amine functional group linked either directly to the SA macromolecules or through another spacer/linker. The conjugation reaction of a single amine SA macromolecule is achieved through transglutaminase, where the amino group of the SA macromolecule serves as a donor and glutamine in the protein or peptide serves as an acceptor. This process has been used to conjugate PEG to granulocyte-colony stimulating factor (BK0026) (Tonon G. 2008, WO 2008/017603), interleukin-2 (Sato H. *Adv. Drug. Deliv. Rev.* 2002, 54, 487-504), growth hormone (Zundel M. 2006, WO2006/084888), and erythropoietin (Pool C T, 2004, WO 2004/108667).

SA Crosslinked Conjugates

The SA macromolecules herein may be used to conjugate and link one molecule to another to produce new homogeneous or heterogeneous chemical entities. Here, any of the X, Y, Z, or ketone groups can react with one or a few crosslinking groups of the other molecule of interest to form a conjugate.

In one aspect, the invention generally relates to a conjugate having a chemical structure selected from the group consisting of:

$$M_1\text{-}(L\text{-}B)_u \quad \text{Formula (I), and}$$

$$B\text{-}(L\text{-}M_1)_u \quad \text{Formula (II)}$$

wherein
each $M_1$ is independently selected from the group consisting of a protein, an enzyme, an antibody, an antibody fragment, a polypeptide, an oligonucleotide, an oligonucleotide analog, a polysaccharide;
each B is a single MW modified sugar alcohol polymer, comprising:
  from 2 to about 2000 sugar alcohol monomer(s);
    wherein each monomer has from 3 to about 14 —$OR^1$ groups;
      wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of:
a $R^2$ and, a structure of —$V_1$—$R^2$—$V_2$—, wherein:
  $V_1$ and $V_2$ are independently selected from the group consisting of:
    Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

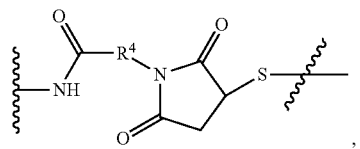
,
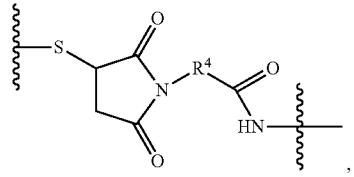
,

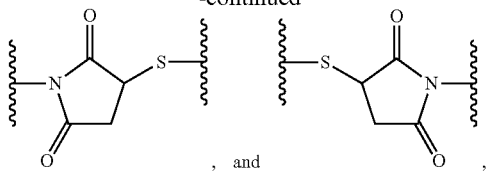
, and
, wherein:
  each $G^1$ is independently selected from NR$^3$, O, and S;
  each $G^2$ is independently O or S;
  each $G^3$ is independently selected from S, O, NR$^3$, and SO$_2$;
  each $G^4$ is independently O or NR$^3$;
  each $R^2$ is independently selected from a bond, $C_1$-$C_{12}$ alkyl, —(CH$_2$CH$_2$O)$_{1\text{-}10}$—, —(CH$_2$CH$_2$O)$_{1\text{-}10}$—CH$_2$—, optionally substituted alicyclyl, heteroalicyclyl, aryl, a peptide, and a peptidomimetic oligomer;
  each $R^3$ is independently selected from hydrogen, $C_1$-$C_8$ alkyl, —(OCH$_2$CH$_2$)$_{1\text{-}3}$, optionally substituted alicyclyl, and optionally substituted heteroalicyclyl;
  each $R^4$ is independently $C_1$-$C_8$ alkyl;
  u is an integer from 1 to about 20; and, In another aspect, the invention is generally relates to a conjugate having chemical structural Formula (III):

$$(M_2\text{-}L)_q\text{-}B \quad (III)$$

wherein
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, and a small molecule,
each B is a single MW modified sugar alcohol polymer, comprising:
  from 2 to about 2000 sugar alcohol monomer(s);
    wherein each monomer has from 3 to about 14 —$OR^1$ groups;
      wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of:
a $R^2$ and, a structure of —$V_1$—$R^2$—$V_{1\text{-}5}$ wherein:
  $V_1$ and $V_2$ are independently selected from the group consisting of:
    Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —C H=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-CH$_2$—NH-G$^{4\text{-}5}$-G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—

$CH_2$—, —O—P(=O)(O$^-$)—O—, —O—P(=O)(S$^-$)—O—, —O—P(=S)(S$^-$)—O—,

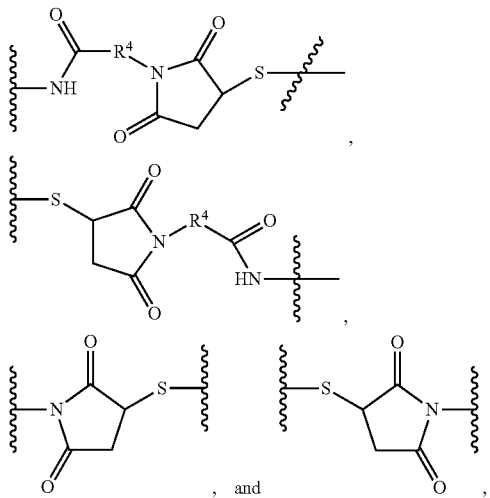
, and , wherein:
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;
each $R^4$ is independently $C_1$-$C_8$ alkyl;

In another aspect, the invention is generally relates to a conjugate having a chemical structure selected from the group consisting of:

$(M_1)_q$-L-(B-(L-$M_2$)$_k$)$_u$ (IV) and $(M_1$-L)$_q$-(B-(L-$M_2$)$_k$)$_u$ (V) and $M_1$-(L-B-(L-$M_2$)$_k$)$_u$ (VI)

wherein
each $M_1$ is independently selected from the group consisting of a protein, an enzyme, an antibody, an antibody fragment, a polypeptide, avidin, streptavidin, an oligonucleotide, an oligonucleotide analog, a polysaccharide;
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a small molecule, and another biologically active molecule;
each B is a single MW modified sugar alcohol polymer, comprising:
from 2 to about 2000 sugar alcohol monomer(s);
wherein each monomer has from 3 to about 14 —OR$^1$ groups;

wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany;
each L is independently selected from the group consisting of:
a $R^2$ and, a structure of —V$_1$—R$^2$—V$_2$—, wherein:
$V_1$ and $V_2$ are independently selected from the group consisting of:
Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

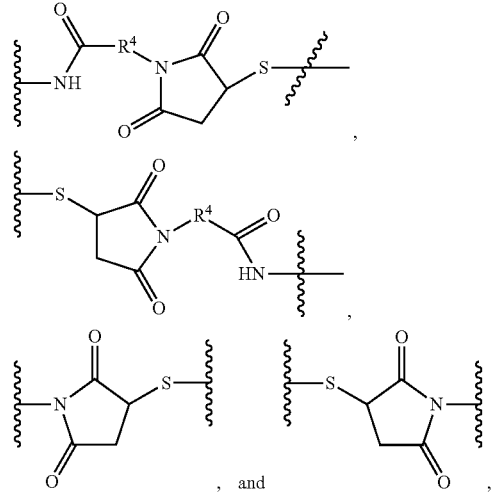
, and , wherein:
each $G^1$ is independently selected from NH, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;

each $R^4$ is independently $C_1$-$C_8$ alkyl;
u is an integer from 1 to about 100;
q is an integer from 1 to about 100; and,
k is 0 or an integer from 1 to about 20.

In some embodiments, q is an integer from 1 to about 10 and B comprises from 3 to about 2000 sugar alcohol monomers. In some embodiments, u is an integer from 1 to about 10 and B comprises: from 3 to about 2000 sugar alcohol monomers.

In some embodiments, $M_1$ is selected from the group consisting of an antibody and an antibody fragment; and $M_2$ is a chemotherapeutic drug, q is 1; u is an integer from 1 to about 20; and q is an integer from 1 to about 10.

In another aspect, the invention is relates to a conjugate having chemical selected from the group consisting of:

S-(L-B-(L-$M_1$)$_k$)$_u$ (VII)

S-(L-B-L-($M_1$)$_k$)$_u$ (VIII)

S-(L-B-(L-$M_2$)$_k$)$_u$ (IX)

S-(L-B-L-($M_2$)$_k$)$_u$ (X)

wherein
S comprises a solid support;
each $M_1$ is independently selected from the group consisting of a protein, an enzyme, an antibody, an antibody fragment, a polypeptide, avidin, streptavidin, an oligonucleotide, an oligonucleotide analog, a polysaccharide;
each $M_2$ is independently selected from the group consisting of a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a small molecule, and another biologically active molecule;
each B is a modified sugar alcohol polymer, comprising:
from 2 to about 2000 sugar alcohol monomer(s);
wherein each sugar alcohol monomer has from 3 to about 14 —OR' groups;
wherein $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofuranyl;
wherein each L is independently selected from the group consisting of a $R^2$ and —$V_1$—$R^2$—$V_2$—,
wherein:
$V_1$ and $V_2$ are independently selected from the group consisting of:
Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—,
—CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

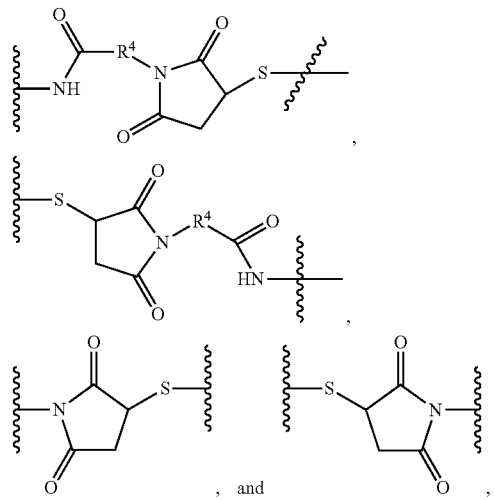

, and wherein:
each $G^1$ is independently selected from NH, O, and S;
each $G^2$ is independently O or S;
each $G^3$ is independently selected from S, O, N$R^3$, and SO$_2$;
each $G^4$ is independently O or N$R^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, optionally substituted alicyclyl, heteroalicyclyl, aryl, a peptide, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;
each $R^4$ is independently $C_1$-$C_8$ alkyl;
u is an integer from 1 to about 500; and,
k is 0 or an integer from 1 to about 20.

Solid support includes, for example, agarose beads, dextran, silica gel-based polymer, polystyrene, PLGA, PMMA, and colloidal gold. S may be a microparticle. The chemical composition of the particles may be polymers or copolymers, inorganic constructs, metals and semiconductors, superparamagnetic composites, biodegradable constructs, or synthetic dendrimers and dendrons. S may be buckyballs, fullerenes, or carbon nanotubes. S may also be a quantum dot, dye-coded particle, or magnetic-coded particle.

In some embodiments, each B is a single MW modified sugar alcohol polymer, comprising from 2 to about 2000 sugar alcohol monomer(s) and each sugar alcohol monomer is bound to one or more sugar alcohol monomers through a linking group W formed by a reaction between the X, Y or Z portion of one monomeric unit with the X, Y or Z of another monomeric unit;

wherein
for each $B^1$, independently, has the chemical structural Formula XI:

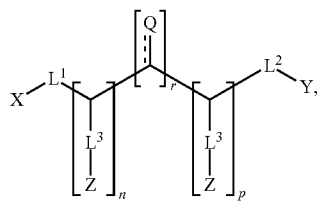

(XI)

each of n and p is independently selected from 0 and an integer selected from 1 to about 12, and n+p is between 1 and 12;

r is 0 or 1;

each bond represented by ---------- is a single or a double bond;

Q is selected from =O, =N—O-L-$M_1$, =N—O-L-$M_2$, =N—O-L-S, —NH—O-L-S, —NH—O-L-$M_1$, and —NH—O-L-$M_2$;

each of X, Y and Z, when bound to $M_1$, $M_2$ or S, is a linker V, each of X, Y and Z, when not bound to S or $M_1$, $M_2$, is a functional group that independently selected from —OH, -J, —$R^5$J, —C(=O)-J, —C(=O)—$CH_2$-J, —NH—C(=O)—$CH_2$-J, —$OR^5$, —$OR^6$, —$OR^1$, —O-Mesyl, —O-Tosyl, —NH—C(=O)—$CH_2$—O-Mesyl, —NH—C(=O)—$CH_2$—O-Tosyl, —SH, —S—S-tBuytl, —SR7, —$SR^5$, —S—S—$R^8$, —S(=O)$_2$-J, —$NH_2$, —$NHR^5$, —N($R^5$)$R^5$, —$NHR^7$, —NH-Fmoc, —NH-Boc, —C(=O)H, —C(=O)—$R^5$, —C(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$NH^2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;

each $R^5$ is independently selected from hydrogen, $C_1$-$C_8$ alkyl, alicyclyl, heteroalicyclyl, benzyl or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each J is independently selected from Cl, Br and I each of $L^1$, $L^2$, and $L^3$ is independently a $R^2$ or —$R^9$—V—$R^2$—*, wherein:

"*" represents a portion of $L^1$, $L^2$, and $L^3$ bound to X, Y, S, $M_1$ or $M_2$, or a Z, respectively;

each W and V are independently selected from the group consisting of Diels-Alder adduct, a 1,3-dipolar adduct, —C(=$G^2$)-$G^1$-, -$G^1$-C(=$G^2$)-, -$G^3$-, -$G^1$-C(=$G^2$)-$G^1$-, —S—S—, —S—($CH_2$)$_2$—S(O)$_2$—, —S(O)$_2$—($CH_2$)$_2$—S—, —S(O)$_2$—N($R^3$)—, —N($R^3$)—S(O)$_2$—, —C(O)—NH—NH—$CH_2$—, —C(O)—NH—N=CH—, —CH=N—NH—C(O)—, —$CH_2$—NH—NH—C(O)—, —N($R^3$)—S(O)$_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, and —O—P(=S)($S^-$)—O—,

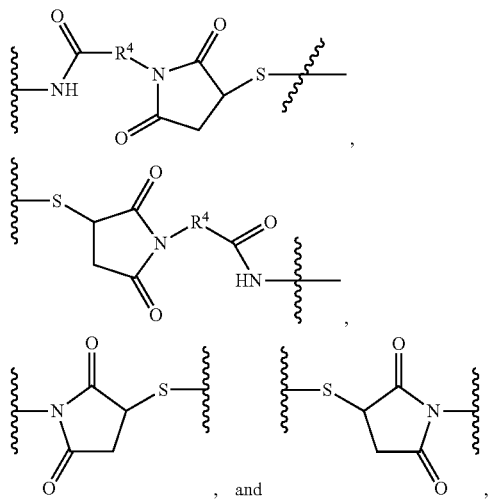

, and , wherein:
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —($CH_2CH_2O$)$_{1-10}$—, —($CH_2CH_2O$)$_{1-10}$—$CH_2$—, optionally substituted alicyclyl, heteroalicyclyl, aryl, a peptide, and a peptidomimetic oligomer;
each $R^3$ is independently selected from hydrogen, $C_1$-$C_8$ alkyl, —($OCH_2CH_2$)$_{1-3}$, optionally substituted alicyclyl, and optionally substituted heteroalicyclyl;
each $R^4$ is independently $C_1$-$C_8$ alkyl;
each $R^9$ is a bond or —$CH_2$—;
and at least in one of the $B^1$ unit each -$L^3$-Z portion is —OR';
wherein each $R^1$ is independently selected from the group consisting of hydrogen, $C_1$-$C_8$ alkyl, benzoyl, acetyl, benzyl, $C_1$-$C_8$ alkyl silyl, cyclic ortho ester, actinide, acetate, tetrahydropyranyl, tetrahydrofuranyl, and tetrahydrothiofurany.

In some preferred embodiments B has the chemical B has the chemical structural Formula XII:

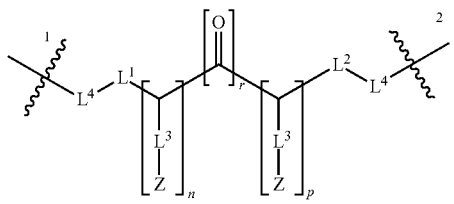
(XII)

wherein

represents a bond to $M_1$, $M_2$ or S.

each of $L^4$, when bound to $M_1$, $M_2$ or S, is a linker V when k is 0,

represents Y. when k is an integer selected from 1 to about 20,

represents a bond to $M_1$, $M_2$ or S.

In another preferred embodiment B has the chemical structural Formula XIII:

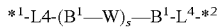
(XIII)

wherein:

"*¹" represents a portion of the $L^4$ bound to S, $M_1$ or $M_2$;

each of $L^4$, when bound to $M_1$, $M_2$ or S, is a linker V s is 0 or an integer independently selected from 1 to about 500;

when k is 0, $L^4$-*² represents Y; and when k is an integer selected from 1 to about 20, "*²" represents a portion of the $L^4$ bound to $M_1$, $M_2$, or S and.

each $B^1$, independently, has the chemical structural Formula XIV:

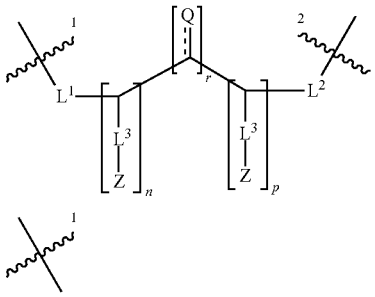
(XIV)

represents a bond to $L^1$; and

represents a bond to $L^2$.

In some embodiments, when each of q and k is 1, and u is larger than 1, the conjugate has the formula $M_1$-L-(B-L-$M_2$)$_u$ or. $M_1$-(L-B-L-$M_2$)$_u$. In some preferred embodiments B is a sugar alcohol modifier with a MW<1000, for example, an antibody linked to several cytotoxic drugs through sugar alcohol moiety B, or a fluorescence-labeled protein or enzyme through sugar alcohol crosslinking reagent.

In some embodiments, when k is 0 and q is 1, the conjugate has the formula $M_1$-L-$B_u$. $M_1$ is simply labeled with different numbers of modifier B, which can further react with other molecules of interest to form a conjugate, $M_1$-(L-B-L-$M_2$)$_u$. In certain preferred embodiments B is a sugar alcohol modifier with a MW<1000.

In some embodiments, when k is 0, u is 1, and q is larger than 1, the conjugate has the formula $(M_1)_q$-L-B, B-(L-$M_1$)$_u$ or $(M_2$-L)$_q$-B. In some preferred embodiments B is an SA macromolecule with MW>1000 Da (e.g., a drug carrier). Polymeric microspheres, polymer micelles, soluble polymers, and PEGylation have been shown to be effective in enhancing drug stability and target specificity and decreasing toxicity. SA macromolecules can be used to pharmaceutically load useful groups or entities, then deliver the drug in vivo.

In some embodiments, when k is 0, u is 1, and q is 1, the conjugate has the formula $M_1$-B or $M_2$-B. In a preferred embodiment B is an SA macromolecule with MW >10000 Da, wherein B can carry various large MW biomolecules, such as proteins, siRNAs, oligos, peptides, and polypeptides.

In certain embodiments $M_2$ is a biomolecule, a metabolite, a fluorescent compound, biotin, a toxin, a drug, a chemotherapeutic agent, a diagnostic agent, or other biologically active molecule.

In certain embodiments $M_1$ or $M_2$ may include one or more radioactive isotopes or isotopic elements.

In certain embodiments $M_2$ is a metabolite. Metabolites are the intermediates and products of metabolism. Examples of metabolites include alkaloids, glycosides, lipids, flavonoids, nonribosomal peptides, phenazines, phenols, polyketides, terpenes, and tetrapyrroles. Metabolites may also be fragments of drugs or drugs modified by living organisms through specialized enzymatic systems.

In certain embodiments the conjugate is an antibody-drug conjugate. $M_1$ is an antibody or antibody fragment and $M_2$ is a chemotherapeutic drug. From 1 to 8 drug molecules may be connected to a single antibody.

In some preferred embodiments $M_1$ and $M_2$ is a therapeutic agent, such as a drug, toxin, cytokine, hormone, hormone antagonist, enzyme, enzyme inhibitor, inhibitory oligonucleotide (e.g., RNAi, siRNA), immunomodulator (e.g., cytokine, lymphokine, chemokine, growth factor, or tumor necrosis factor), radionuclide, anti-angiogenic agent, pro-apoptotic agent, antibody, radiolabeled antibody, or photoactive therapeutic agent.

In certain embodiments the therapeutic agent is a chemotherapeutic drug. Examples of chemotherapeutic drugs include adrenocortical suppressants, antimetabolites, alkylating agents, alkyl sulfonates, antibiotics, antimitotics, anthracyclines, anti-angiogenic agents, camptothecins, COX-2 inhibitors, CPT-11, doxorubicin, doxorubicin analogs, enzyme inhibitors, endostatin, epipodophyllotoxins, ethylenimine derivatives, folic acid analogs, gemcitabine, HDAC inhibitors, heat shock protein $(HSP)_{9-0}$ inhibitors, hormone antagonists, methotrexate, methyl hydrazine derivatives, mTOR inhibitors, nitrosoureas, nitrogen mustards, pyrimidine analogs, purine analogs, platinum coordination complexes, substituted ureas, SN-38, taxols, triazenes, taxanes, tyrosine kinase inhibitors, proteosome inhibitors, pro-apoptotic agents, and vinca alkaloids. Suitable chemotherapeutic agents are described in the literature (Remington's Pharmaceutical Sciences, 19$^{th}$ Ed. Mack Publishing Co. 1995; Goodman and Gilman's the Pharmacological Basis of Therapeutics, 7$^{th}$ Ed. McMillan Publishing Co. 1985).

In certain embodiments the therapeutic agent is a cytotoxic or immunosuppressive agent, such as an antitubulin agent, auristatin, DNA minor groove binder, DNA replication inhibitor, alkylating agent, anthracycline, antibiotic, antifolate, antimetabolite, chemotherapy sensitizer, cyclooxygenase inhibitor, duocarmycin, etoposide, fluorinated pyrimidine, ionophore, lexitropsin, lipoxygenase inhibitor, nitrosourea, platinol, pre-forming compound, purine antimetabolite, puromycin, radiation sensitizer, steroid, taxane, topoisomerase inhibitor, vinca alkaloid, and the like.

Individual cytotoxic agents include, for example, auristatin (e.g., MMAE, MMAF), azathioprine, bleomycin, bortezomib, busulfan, calicheamicin, capecitabine, carboplatin, carmustine, chlorambucil, cisplatin, cladribine, colaspase, cyclophosphamide, cytarabine, dacarbazine, dactinomycin, dauorubicin, docetaxel, doxorubicin, duocarmycin, epirubicin, etoposide, etoposide phosphate, fludarabine, fluorouracil, fotemustine, ganiclovir, gemcitabine, hydroxyurea, idarubicin, ifosfamide, irinotecan, lomustine, melphalan, mercaptopurine, methotrexate, mitomycin, mitozantrone, oxaliplatin, paclitaxel, premetrexed, procarbazine, raltitrexed, temozolomide, temiposide, thioguanine, thiotepa, topotecan, valganciclovir, vinblastine, vincristine, vinorebine, and maytansine (e.g., DM1, DM4). Drugs that have been conjugated to the antibody and are currently in clinical trials are auristatin, maytansine, calicheamicin, and duocarmycin (Alley, S C, et al. *Current opinion in chemical biology* 2010, 14, 529-537).

In certain embodiments the cytotoxic agent is dolastatin (e.g., auristatin E, AFP, MMAF, MMAE) or derivatives thereof. In certain embodiments the cytotoxic agent is a conventional chemotherapeutic, such as doxorubicin, paclitaxel, melphalan, vinca alkaloids, methotrexate, mitomycin C, or etoposide. In addition, potent agents include CC-1065 analogs, calicheamicin, maytansine (or DM-1), analogues of dolastatin 10, rhizoxin, and palytoxin.

In certain embodiments the immunosuppressive agent may be, for example, arylcarboxylic derivatives, azathioprine, cyclosporine, cyclooxygenase inhibitors, cyclophosphamide, etanercept, gancyclovir, glucocorticoids or glucocorticoid analogs, leukotriene receptor antagonists, 5-lipoxygenase inhibitors, mycophenolate mofetil or methotrexate, nicotinic acid derivatives, oxicam derivatives, pyrazole-containing derivatives, rapamycin, or tacrolimus.

In some preferred embodiments the therapeutic agent is a toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

In some preferred embodiments the therapeutic agent is an immunomodulator selected from the group consisting of cytokines, stem cell growth factors, lymphotoxins, hematopoietic factors, colony stimulating factor (CSF), interferons (IFNs), erythropoietin, thrombopoietin, and a combination thereof.

M may be any antibody or fragment that is capable of binding specifically to a target antigen associated with a disease state or condition. Antibody sequences or antibody-secreting hybridomas against almost any disease-associated antigen may be obtained from ATCC (American Type Culture Collection), NCBI, and USPTO databases. Useful polyclonal antibodies are heterogeneous populations of antibody molecules derived from the sera of immunized animals. Useful monoclonal antibodies are homogeneous populations of antibodies to a particular antigenic determinant of a target antigen. A polyclonal and monoclonal antibody to a target antigen may be prepared by using any technique known in the art.

Suitable antibodies include monoclonal antibodies, such as chimeric, humanized, or human antibodies, or an antigen-binding fragment thereof. In one embodiment the antibody fragment is, for example, AC10, BR96, 1F6 or 2F2, or growth inhibitory antibody.

Individual therapeutic antibodies include, for example, alemtuzumab (Campath; Leukosite, MA), Allomune (BioTransplant), bevacizumab (Avastin; Genetech, Inc., CA), CEAcide (Immunomedics, NJ), cetuximab (Erbitux; Imclone Systems Inc., NY), epratuzamab (Immunomedics, Inc., NJ and Amgen, CA), LymphoCide (Immunomedics, Inc., NJ), Oncolym (Techniclone, Inc., CA), OVARE (AltaRex Corporation, MA), Panorex (Glaxo Wellcome, NC), rituximab (Rituxan; Genetech), Smart MI95 (Protein Design Labs, Inc., CA), Smart ID10 (Protein Design Labs, Inc., CA), trastuzumab (Herceptin; Genetech), and Vitaxin (MedImmune, Inc., MD).

In certain embodiments the antibodies include, for example, antibodies against the following antigens: tumor-associated antigens; antigens associated with pancreatic cancer, malignant disease, autoimmune disease, immune dysfunction disease, leukemia, or neurological disease; and antigens against transmembrane activator and CAML-interactor (TACI, Yu et al. *Nat. Immunol.* 2000, 1, 252-256). Examples of antigens include: CA125, CA 15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, CEA, gp100, MART1, IL-2 receptor, CD4, CD5, CD8, CD14, CD15, CD19, CD20, CD21, CD22, CD23, CD25, CD33, CD37, CD38, CD40, CD40L, CD46, CD52, CD54, CD66a-d, CD67, CD74, CD79a, CD80, CD126, CD138, CD154, B7, MUC1, LAL1, HM1.24, HLA-DR, tenascin, VEGF, P1GF, ED-B fibronectin, oncogenes, oncogene products, necrosis antigens, T101, TAG, IL-6, MIF, TRAIL-R1 (DR8), TRAIL-R2 (DR5), human chorionic gonadotropin, mucin, P21, MPG, and Neu oncogene product.

The antibody can also be a multispecific antibody, such as a bispecific antibody. Methods for making bispecific antibodies are known in the art. In some embodiments the antibody fragment is an Fv, Fab, Fab', or F(ab')$_2$. Other useful antibodies are heavy chain and light chain dimers of antibodies, single chain antibodies, a minibody, a diabody, a triabody, a tetrabody, dsFv, sc-Fv-Fc, (sFv)$_2$, a fragment produced by a Fab expression library, an anti-idiotypic (anti-Id) antibody, or multispecific antibodies from antibody fragments.

In certain embodiments the antibody and proteins may comprise one or more radioactive isotopes useful for treating diseased tissue. Suitable therapeutic radionuclides include, but are not limited, iodine-131, iodine-125, bismuth-212, bimuth-213, lutetium-177, yttrium-90, yttrium-88, technetium-99m, copper-62, copper-67, rhenium-188, rhenium-186, galium-66, galium-67, indium-111, indium-114m, indium-115, boron-10, astatine-211, phosphorus-32, phosphorus-33, scandium-47, silver-111, praseodyminum-142, samarium-153, terbium-161, dysprosium-166, holmium-166, rhenium-186, rhenium-188, rhenium-189, lead-212, lead-211, radium-223, actinium-225, iron-59, selenium-75, arsenic-77, strontium-89, molybdenum-99, rhodium-105, palladium-109, praseodymium-143, promethium-149, erbium-169, iridium-194, gold-198, and gold-199.

Additional potential therapeutic radioisotopes include carbon-11, nitrogen-13, oxygen-15, bromine-75, bromine-76, gold-198, actinium-224, iodine-126, iodine-133, bromine-77, indium-113, ruthenium-95, ruthenium-97, ruthenium-103, ruthenium-105, mercury-107, mercury-203, tellurium-121m, tellurium-122m, tellurium-125m, tellurium-165, tellurium-167, tellurium-168, platinum-197, palladium-109, rhodium-105, praseodymium-142, praseodymium-143, terbium-161, holminum-166, gold-199, cobalt-57, cobalt-58, chromium-51, iron-59, selenium-75, thallium-201, actinium-225, ytterbium-169, and the like.

Therapeutic reagents may be attached to the antibody through partial reduction of the SH group or surface amines. Therapeutic reagents may also be attached to carbohydrate side chains if available.

In certain embodiments the therapeutic agents may include one or more copies of the same therapeutic agent or combinations of different therapeutic agents.

In certain embodiments M$_2$ is a diagnostic agent. Examples of diagnostic agents include fluorescent probes, chemiluminescent compounds, radio ligands, mass spectrometric tags, chromophores, and UV-active compounds.

In certain embodiments M$_2$ is a fluorescent compound. Examples of fluorescent compounds include fluorescein, rhodamine, coumarin, green fluorescent protein, BODIPY, Texas Red, Cascade Blue, Lucifer yellow derivatives, phycobiliprotein cyanine dye, lanthanide chelate, and quantum dot. Various fluorescent compounds are commercially available (e.g., from Molecular Probes and Invitrogen).

The position at which M$_1$ or M$_2$ attaches to B can be a single site or multiple sites. M$_1$ or M$_2$ can be attached to B through an ester linkage or other crosslinking group.

In a preferred embodiment M$_1$ is a therapeutic protein or polypeptide. SA macromolecules may conjugate the protein or peptide at a single specific site or multiple sites. The therapeutic proteins may be cytokines, hormones, hemapoietic proteins, blood proteins, enzymes, or peptides.

In certain embodiments M$_1$ is G-CSF, its fragments, or modified derivatives. G-CSF is a 174-amino-acid glycosylated cytokine that stimulates the proliferation, survival, and differentiation of neutrophil granulocyte progenitor cells and mature neutrophils (Hill C P, et al. *Proc. Natl. Acad. Sci.* 1993, 90, 5167-5171). G-CSF is rapidly eliminated from the blood. Modification of G-CSF using a single SA macromolecule may help stabilize the substance. PEGylated G-CSF has been marketed under the trade name Neulasta (Kinstler O. B. et al. *Pharm Res* 1996, 13, 996-1002).

In certain embodiments the therapeutic proteins are GM-CSF, IFNα-2a, IFNα-2b, IL-2 (Waldmann T A, *Nature Rev. Immuol.* 2006, 6, 595-601), erythropoietin (EPO, Macdougall I C, *Curr Hematol Rep* 2005, 4, 436-440), growth hormone (GH; Zundel M, Peschke B, 2006, WO 2006/084888), human growth hormone (hGH; Li C H, *Mol Cell Biochem* 1982, 46, 31-41), or apomyoglobin (apoMb; Evans S V et al *J. Mol. Biol.* 1990, 213, 885-897). Other examples of therapeutic proteins and peptides include asparaginase, interferons (e.g., IFN-α, -β, -γ), interleukins, leptin, serum proteins (e.g., factor VII, factor VIIa, factor VIII, factor IX, and factor X), human chorionic gonadotropin (HCG), insulin, follicle stimulating hormone (FSH), luteinizing hormone (LH), urate oxidase (uricase), adenosine deaminase (ADA), and antibody fusion proteins (e.g., tumor necrosis factor receptor (TNFR)/Fc domain fusion protein).

Other useful proteins include proteins that selectively localize in a particular tissue or region of the body. Examples of such proteins include transferrin, HS-glycoprotein, coagulation factors, serum proteins, O-glycoprotein, G-CSF, GM-CSF, M-CSF, EPO, and the like.

In some preferred embodiments M$_1$ is a derivative of a therapeutic protein or peptide. For example, fragments of the proteins and chemically modified proteins (e.g., glycosylation, acylation, amino acid substitution). In some preferred embodiments M is a recombinant protein.

In certain embodiments M$_1$ is an oligonucleotide, oligonucleotide analog, or small interference RNA (siRNA). Examples of oligonucleotide analogs include peptide nucleic acids (PNAs), locked nucleic acids (LNAs), threose nucleic acid (TNA), and alpha PNAs.

In certain embodiments the therapeutic agent may include one or more copies of the same therapeutic agent or combinations of different therapeutic agents.

EXAMPLES

The following examples contain important additional information, exemplification, and guidance that can be adapted to the practice of this invention in its various embodiments and equivalents thereof. Practice of the invention will be more fully understood from the following examples, which are presented here for illustrative purposes only and should not be construed as limiting in anyway.

Instrumentation: $^1$H-NMR spectra were recorded at 500 MHz (Brukar) and are reported in parts per million (ppm) on the δ scale relative to residual CHCl$_3$ (δ 7.25) and DMSO-d$_6$ (δ 2.49). All NMR experiments were performed at room temperature (RT) unless otherwise stated. HPLC was performed in an Agilent 1100 HPLC system with automatic sample injector and diode array detector. Analytical HPLC was performed on an XTerra™ C18 column (Waters, 2.5 μm, 3.0×30 mm). The HPLC method used (method A) was a linear gradient of AB solvent (5% B to 95% B in 10 minutes) at a flow rate of 0.6 mL/min. In the case of very hydrophobic compounds, a Nova-Pack C18 column (Waters, 5 μm, 3.9×150 mm) was used with a linear AB gradient (10% B to 95% B in 10 minutes, then held at 95% B for another 5 minutes) at a flow rate of 1.0 mL/min (method B). Solvent A was 0.1% aqueous TFA and solvent B was 0.1% TFA in acetonitrile. The UV detector was set at 210 nm and 254 nm. Most mass spectra were collected on a Quadrupole MDS Sciex Q-TRAP. In a typical experiment, crude or purified samples were dissolved or diluted in methanol containing 0.1% formic acid and infused directly into the electrospray inlet. For some large molecular weight compounds, mass spectra were collected on a 4700 Proteomic Analyzer with TOF/TOF optics (AB Sciex, Framingham). In a typical experiment, 5 μL of sample solution was mixed with 5 μL of 1 mg/mL dihydroxy benzoic acid solution in water, then 1 μL of the mixture was spotted onto the MALDI plate and air dried. The sample either co-crystallized or formed a dried droplet with a matrix. Upon laser excitation, the matrix absorbs the laser energy and transfers the energy to the sample, facilitating its ionization and vaporization.

Solvents and Reagents: All moisture-sensitive reactions were performed in an inert, dry atmosphere of nitrogen. Reagent grade solvents were used for chromatography and extraction. D-glucamine, D-glucosamic acid, N-hydroxyphthalimide, and pyridinium p-toluenesulfonate were purchased from TCI America. Acetone cyanohydrin, 10% palladium on carbon, 3,4-dihydro-2H-pyran, acetic anhydride, formic acid, anhydrous dichloromethane, and anhydrous N,N-dimethylformamide were purchased from Sigma-Aldrich. N-(9-fluorenylmethoxycarbonyloxy)succinimide ("Fmoc-OSu") was purchased from Chem-Impex International; triethylamine was purchased from Mallinckrodt; pyridine was purchased from EMD; and ACS grade solvents were purchased from EMD, BDH, Macron, or Mallinckrodt. All other chemicals and reagents were purchased from Alfa Aesar and used as received.

Chromatography: Thin-layer chromatography (TLC) analysis was performed using EMD TLC silica gel 60 $F_{254}$ (0.25 mm thickness). The plates were visualized first with UV illumination, followed by charring with chemical solutions. Different charring solutions were used: 1) PMA (3% phosphomolybdic acid in ethanol w/v); 2) CAM (ceric ammonium molybdate, 2.5% ammonium molybdate, 1% cerium sulfate in 10% aqueous sulfuric acid); 3) 5% ninhydrin in ethanol; and 4) 2% $KMnO_4$ in water. Flash chromatography was performed on an ISCO companion using pre-packed columns. The solvent compositions were on a volume/volume (v/v) basis.

Example 1-6

Selective Protection and Deprotection Strategies for the Primary and Secondary Alcohol Groups in a Sugar Alcohol Example 1

Synthesis of a Single Free OH SA Molecule Using a Benzoate Ester and TBDMS Protecting Strategy

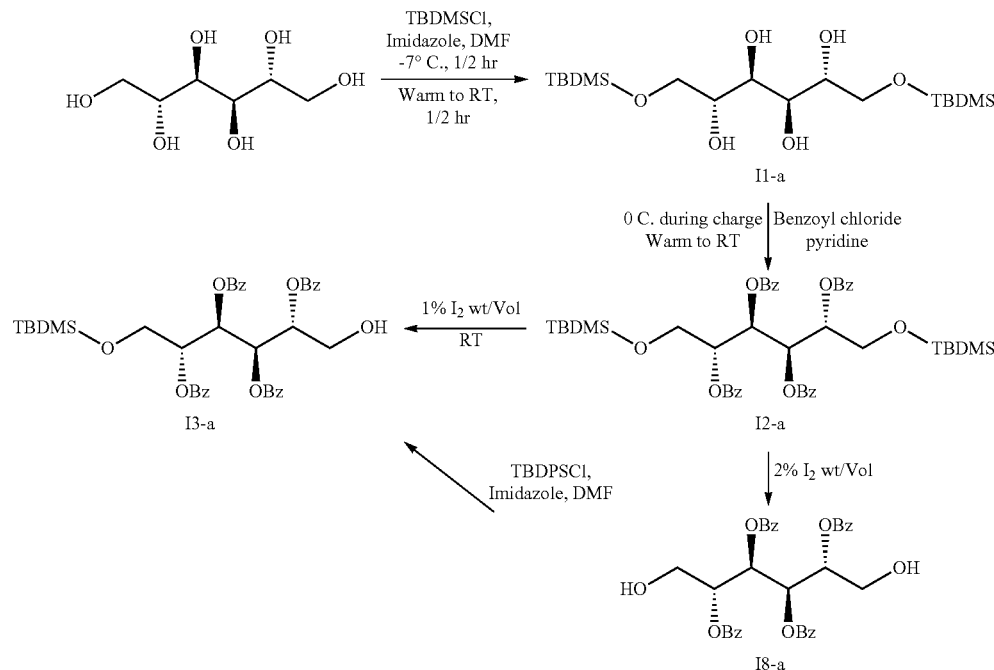

Compound I1-a: Compound I1-a was synthesized based on a similar procedure from the literature (*Chem. Pharm. Bull.* 2010, 58, 495). 4.55 g (25.0 mmol, 1 eq.) of D-mannitol and 5.56 g (81.6 mmol, 3.3 eq.) of imidazole were partially dissolved in 20 mL of DMF and cooled to −7° C. In a separate flask, 7.52 g (50.2 mmol, 2 eq.) of t-butyldimethylsilyl chloride was dissolved in 10 mL of DMF. This solution was then added slowly to the D-mannitol suspension over a period of 20 minutes at −7° C. and the reaction allowed to warm to RT. The DMF was removed under reduced pressure to provide an oil that was then dissolved in 90 mL of ethyl acetate. A gummy solid formed. The ethyl acetate was decanted away from the solid, which was completely dissolved in 12 mL of water. This aqueous phase was extracted with 25 mL of ethyl acetate and the ethyl acetate extracts combined. The extracts were then washed three times with 10 mL of water, followed by a wash with 15 mL of brine. The organic phase was dried over anhydrous $Na_2SO_4$, filtered, and concentrated under reduced pressure. The resulting material was purified by silica gel column chromatography to obtain 2.10 g of desired product ($R_f$=0.20, EtOAc:hexanes=25:75, charring by 2% $KMnO_4$). MALDI: exact mass 410.25, obtained 433.44 [M+Na]$^+$. $^1$H-NMR (500 MHz, DMSO-d$_6$): δ 4.32 (d, J=5.7 Hz, 2H), 4.02 (d, J=7.1 Hz, 2H), 3.76 (dd, J=10.4, 3.0 Hz, 2H), 3.57-3.48 (m, 4H), 3.43 (dtd, J=8.7, 5.9, 3.0 Hz, 2H), 0.83 (s, 18H), 0.00 (s, 12H). Higher substituted byproducts were also present (confirmed by mass spec): 5.05 g of tri-TBDMS protection (39% yield) ($R_f$=0.53) and tetra-TBDMS substitution ($R_f$=0.71).

Compound I2-a: 0.9746 g (2.374 mmol, 1 eq.) of I1-a were dissolved in 4.6 mL (57 mmol) of pyridine and cooled to 0° C. Next, 1.50 mL (12.2 mmol, 5.1 eq.) of benzoyl chloride was added drop wise. The reaction was allowed to warm to RT and stir overnight. The majority of the pyridine was removed by evaporation under reduced pressure, and the resulting residue was dissolved in 15 mL of ethyl acetate. The ethyl acetate was then washed with 5 mL of 1 N HCl (aq.), followed by 5 mL of saturated $NaHCO_3$ (aq.). The ethyl acetate was dried over anhydrous $Na_2SO_4$, filtered and concentrated under reduced pressure, and purified by silica gel column chromatography to obtain 1.59 g of the desired product (80% yield). Mass spec analysis (electrospray): exact mass 826.36, obtained 827.7 [M+H]$^+$; 849.7 [M+Na]$^+$.

Compound I3-a: 0.1060 g of elemental iodine was dissolved in 10 mL of methanol to create an approximately 1% by weight solution. Next, 0.800 g (0.967 mmol, 1 eq.) of I2-a was dissolved in 7.5 mL of the $I_2$/MeOH solution at RT. An additional 1.0 mL of THF was added to obtain a homogeneous solution. The reaction was monitored by TLC. After 9 hours, the reaction was quenched by the drop wise addition of 3% $Na_2S_2O_3$ (aq.) until all of the iodine color was consumed. MeOH and THF were removed under reduced pressure and the residue dissolved in 6 mL of ethyl acetate and 2 mL of water. The phases were separated and the organic phase washed twice with 2 mL of water, followed by 2 mL of brine. Ethyl acetate was removed by evaporation under reduced pressure. The resulting material was purified by silica gel column chromatography to obtain 0.2338 g of the desired product (0.328 mmol, 34% yield, $R_f$=0.57, 25:75 EtOAc:hexanes). Mass spec analysis (electrospray): exact mass 712.27, obtained 713.6 [M+H]$^+$; 735.3 [M+Na]$^+$. A total of 0.2681 g (0.324 mmol, 34% yield) of starting material was recovered. A total of 0.1045 g (0.175 mmol, 18%) of the tetra-benzoyl diol (I8-a) was obtained ($R_f$=0.20, confirmed by mass spec). Mass spec analysis (electrospray): exact mass 598.18, obtained 599.5[M+H]$^+$.

Compound I8-a: A solution of 2% iodine in methanol (30 mL) was added to a solution of the crude 12-a (5.50 g, 6.7 mmol) in 15 mL of THF. The reaction mixture was stirred at RT overnight. The reaction was quenched with the addition of 3% aqueous sodium thiosulfate until the brown color disappeared. The suspension was concentrated in vacuo. The residue was taken up in water (~60 mL) and extracted three times with 60 mL of dichloromethane. The combined organic layers were dried over sodium sulfate and purified by silica gel column chromatography to obtain 3.84 g of the desired product (96%). TLC (EtOAc:hexanes=1:1, Rf=0.5).

Mass spec analysis (electrospray): exact mass 598.2, obtained 621 [M+Na]$^+$ and 1219 [2M+Na]$^+$.

Compound I3-a (Converting from I8-a to I3-a): A solution of t-butyldimethylsilyl chloride (256 mg, 1.0 equiv.) in anhydrous dichloromethane (5 mL) was added dropwise via syringe pump at a rate of 2.5 mL/h to a stirred solution of compound k (1.0 g, 1.7 mmol) and imidazole (116 mg, 1 equiv.) in anhydrous DMF (10 mL) under nitrogen at RT. The reaction was then stirred for an additional hour. Next, the reaction was placed in an ice bath and quenched with 70 mL of water added in small portions. The mixture was extracted three times with 40 mL of dichloromethane. The combined organic layers were washed three times with 20 mL of water, followed by two washes with 20 mL of brine. The organic layer was dried over sodium sulfate overnight, filtered, and concentrated in vacuo at 40° C. The residue was purified by silica gel column chromatography to obtain the desired product (584 mg, 48%). TLC (EtOAc:hexanes=2:3, 254 nm UV): Rf=0.83. Mass spec analysis (electrospray): exact mass 712.27, obtained 592 [M−OBz]$^+$, 713 [M+H]$^+$. $^1$H-NMR (500 MHz, chloroform-d): δ 8.07-7.99 (m, 4H), 8.00 (dd, J=8.2, 1.4 Hz, 2H), 7.92 (dd, J=8.4, 1.3 Hz, 2H), 7.64-7.32 (m, 12H), 6.16 (dd, J=6.9, 2.5 Hz, 1H), 6.08 (dd, J=8.2, 2.6 Hz, 1H), 5.56 (dt, J=7.0, 4.6 Hz, 1H), 5.35 (dt, J=8.1, 3.3 Hz, 1H), 4.04-3.94 (m, 2H), 3.89 (dd, J=11.3, 4.8 Hz, 1H), 3.79 (dd, J=13.3, 3.8 Hz, 1H), 2.50 (s, 1H), 0.81 (s, 9H), −0.02 (s, 3H), −0.06 (s, 3H).

Example 2

Synthesis of a Single Free OH SA Molecule Using the Acetate Ester and TBDMS Protecting Strategy Scheme 13:

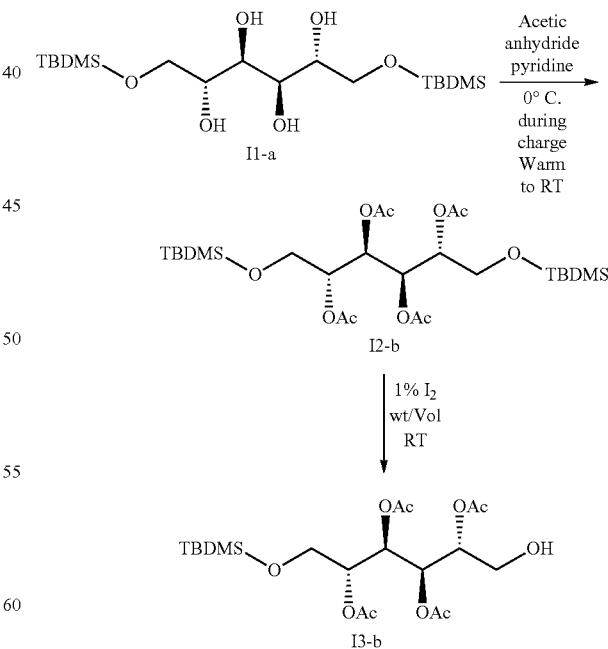

Compound I2-b: Acetic anhydride (7 mL, 5.1 equiv.) was added dropwise via syringe to a stirred solution of compound I1-a (4.3 g, 10.5 mmol) in pyridine (10 mL) at 0° C. The reaction was allowed to warm to RT overnight. The reaction was quenched by the addition of water in small portions (~20 mL total) to produce a biphasic liquid, which was extracted three times with 40 mL of ethyl acetate. The combined organic layers were washed three times with 15 mL of 0.1 N HCl, followed by 20 mL of brine, and then dried over sodium sulfate overnight. The dried organic layer was filtered and concentrated in vacuo until no UV absorption was observed at 254 nm on the TLC plate, suggesting the removal of residual pyridine, to yield the product (5.9 g, 97%), which was used without further purification. TLC (EtOAc:hexanes=1:3, charring by 2% $KMnO_4$): Rf=0.65.

Compound I3-b: Compound I2-b (4.9 g, 8.7 mmol) was suspended in methanol (18 mL) by sonication for 5 minutes. A solution of 2% (w/v) iodine in methanol (17 mL) was added, and the reaction was stirred at RT overnight. The reaction was quenched by the addition of 3% aqueous sodium thiosulfate in small portions until no brown color remained (~15 mL total). The suspension was concentrated in vacuo to remove most of the MeOH, diluted by the addition of 15 mL water, then extracted three times with 30 mL of dichloromethane. The combined organic layers were washed with 20 mL of brine, dried over sodium sulfate, and purified by silica gel column chromatography to obtain the desired product (720 mg, 18%). TLC (EtOAc:hexanes=1:1, charring by 2% $KMnO_4$): Rf=0.57. Mass spec analysis (electrospray): exact mass 464.21, obtained 333 [M−OTB-DMS]$^+$; 405 [M−OAc]$^+$, 465 [M+H]$^+$, 483 [M+H$_3$O]$^+$, 951 [2M+Na]$^+$.

Example 3

THP (Tetrahydropyranyl) and TBDMS Protecting Strategy

Scheme 14:

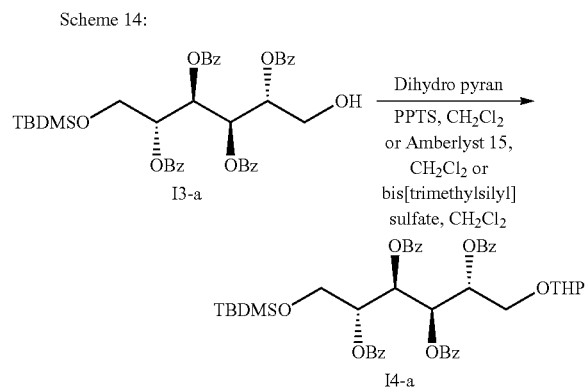

I4-a

Compound I4-a: Three different methods were explored for THP protection of the primary hydroxyl group using I3-a as the starting material. Method A: 29.2 mg of I3-a (41 µmol) were dissolved in 100 µL of $CH_2Cl_2$ in an HPLC vial, followed by the addition of 4.17 µL of 3,4-dihydro-2H-pyran and 20 µL of 0.1 mg/µL beads in $CH_2Cl_2$. The mixtures were stirred at RT for 2 hrs. TLC indicated that some starting material remained (Rf=0.28 for starting material), and a new spot with Rf=0.59 was observed. Additional starting material (4.17 µL) was added. After 30 minutes the reaction was complete with a single spot detected by UV, which is presumably the product. The mixture was filtered through glass wool to obtain the crude product. Method B: 14.7 mg of I3-a (20 µmol) was dissolved in 100 µL of $CH_2Cl_2$ in an HPLC vial, followed by the addition of 1.92 µL of 3,4-dihydro-2H-pyran and 1.1 µL of 50 mM bis(trimethylsilyl) sulfate in $CH_2Cl_2$. The mixtures were stirred at 0° C. for 2 hrs. TLC indicated that some starting material remained (Rf=0.28), and a new spot with Rf=0.59 was observed. Additional starting material (1.92 µL) was added. After 30 minutes, approximately 50% of the starting material remained in the solution. Method C, 21.4 mg of I3-a (30 µmol) was dissolved in 100 µL of $CH_2Cl_2$ in an HPLC vial, followed by the addition of 3.82 µL of 3,4-dihydro-2H-pyran (1.5 equiv.) and 10 µL of 76 mg/mL pyridinium p-tolenesulfonate (PPTS) in $CH_2Cl_2$. The mixtures were stirred at RT for 2 hrs. TLC indicated that some starting material remained (Rf=0.28), and a new spot with Rf=0.59 was observed. Additional starting material (3.82 µL) was added. After 30 minutes the reaction was complete. 150 µL of ethyl ether (PPTS forms white precipitate) was added to the vial plus 100 µL of 4M NaCl. The mixture was extracted twice with $CH_2Cl_2$. The organic layers were combined to obtain the crude product. Mass spec analysis (electrospray): exact mass for I4-a 796.33 and observed 797.8 [M+H]$^+$.

Example 4

Selective Protection of a Single Primary Alcohol of SA Using the TBDPSCl Strategy Scheme 15:

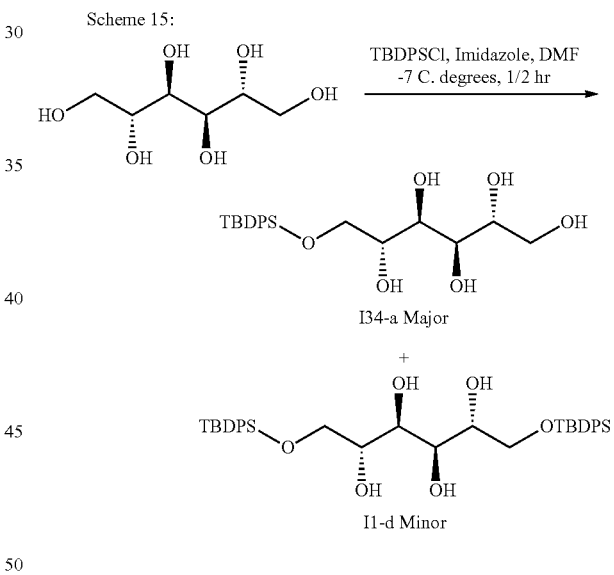

Compound I34-a: 0.53 g (6.4 mmol) of D-mannitol and 0.54 g (7.9 mmol) of imidazole were dissolved by heating in 16 mL of DMF, then cooled to −7° C. In a second flask, 1.65 mL (6.4 mmol) of t-butyl-diphenylsilyl chloride was dissolved in 10 mL of DMF. This solution was then added to the mannitol solution over a period of 20 minutes at −7° C. and stirred for an additional 5 minutes. The DMF was removed under reduced pressure to provide an oil that was then dissolved in 50 mL of ethyl acetate. A white solid (imidazole hydrochloride) precipitated and was removed by filtration. The ethyl acetate extract was washed twice with 10 mL of water, followed by a wash with 10 mL of brine. The organic phase was concentrated under reduced pressure, providing 2.4 g of oil. Analysis by TLC indicated that the majority of the product was mono-protected (I34-a). Mass spec analysis (MALDI): exact mass 420.20, observed 443.39 [M+Na]$^+$ ($R_f$=0.21, 25:75 EtOAc:hexanes) and a minor spot corresponding to the di-protected substance ($R_f$=0.93). Mass spec analysis (MALDI): exact mass 658.31, observed 680.7 [M+Na]$^+$.

Example 5

Benzyl Protection of OH

Scheme 16:

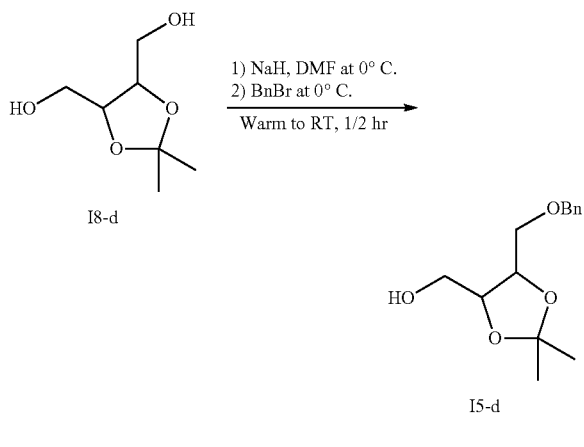

Compound I5-d: A solution of 1.0607 g (6.54 mmol, 1.0 eq.) 2,3-O-isopropylidine-D-threitol (TCI America) dissolved in 2 mL DMF was added to a suspension of 0.2959 g of NaH (7.40 mmol, 1.13 eq.) as a 60% by wt. dispersion in oil in 4 mL of DMF at 0° C. The addition occurred over a period of 10 minutes, followed by 30 minutes of additional reaction time. To this solution, 0.780 mL (6.56 mmol, 1.0 eq.) of benzyl bromide was added slowly and the resulting mixture stirred for 20 minutes at 0° C. TLC analysis (40:60 ethyl acetate:hexane on silica, CAM stain) indicated consumption of the starting material and the product with $R_f$=0.28. The majority of the DMF was removed by evaporation under reduced pressure. The resulting oil was dissolved in 5 mL of water and extracted three times with 15 mL of ethyl acetate. The organic extracts were combined, washed with 5 mL of brine, dried over anhydrous $Na_2SO_4$, filtered, and concentrated under reduced pressure. The resulting residue was then purified by silica gel column chromatography to obtain 0.997 g (3.95 mmol, 60.4% yield) of the desired product. Mass spec analysis (MALDI): exact mass 252.14 Da, observed 275.95 [M+Na]$^+$. HPLC showed one peak at 4.387 minutes for the purified product (method A).

Scheme 17:
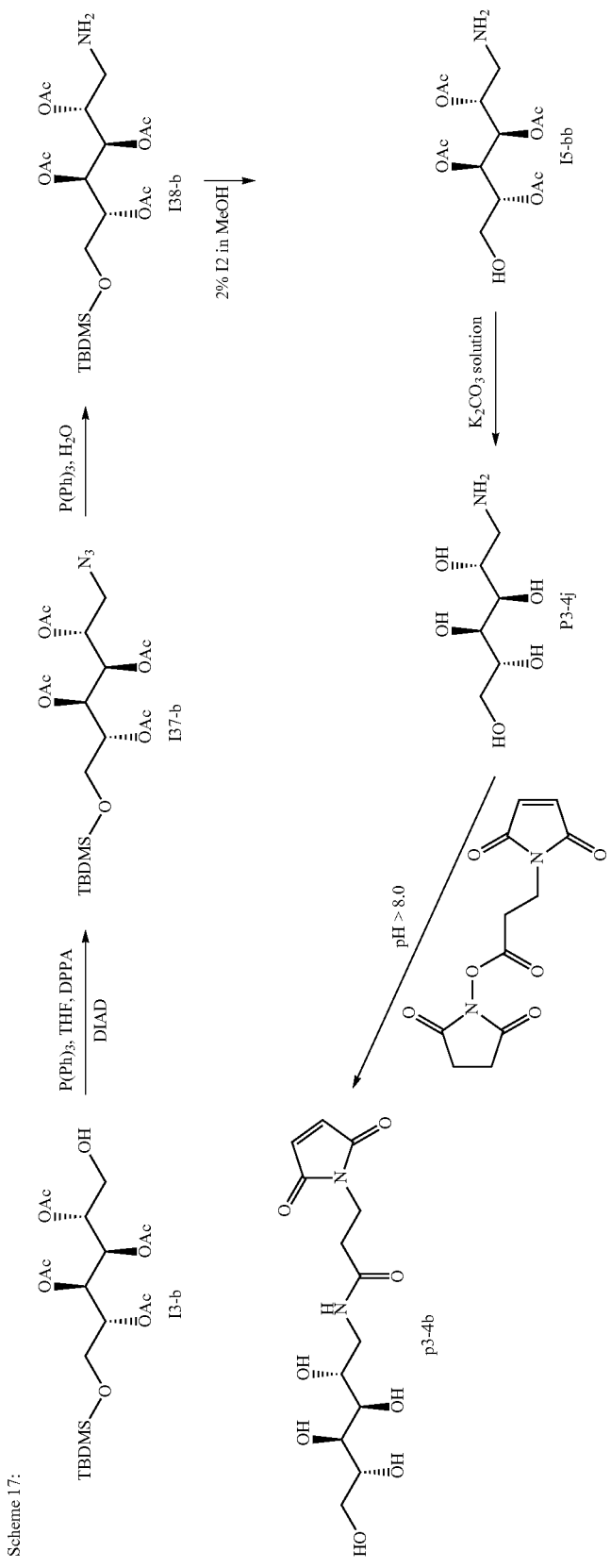

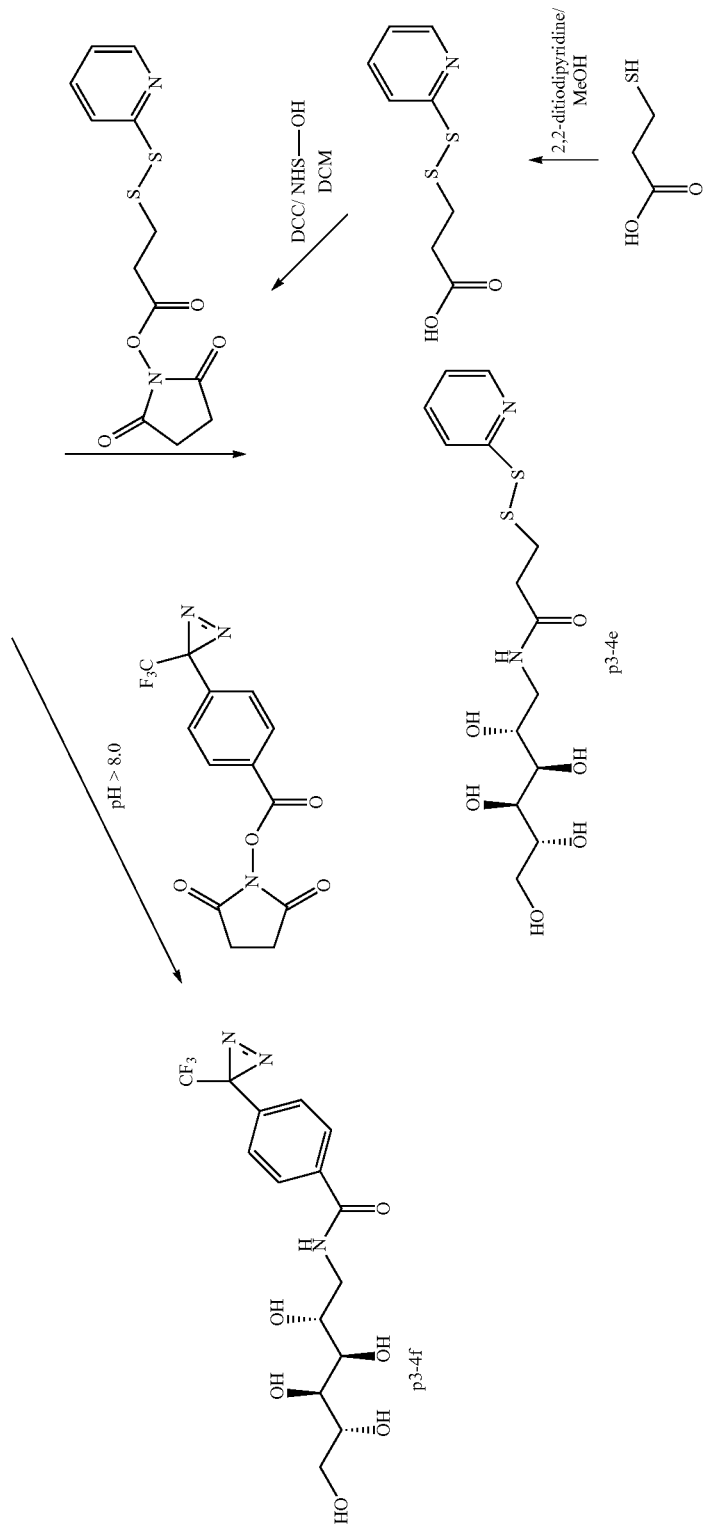

Example 6

Synthesis of Monofunctional SA Crosslinking Reagent p3-4f

Compound I37-b: Diisopropyl azodicarboxylate (DIAD) (178 µL, 0.906 mmol, 1.2 equiv.) was added dropwise via syringe to a solution of compound I3-b (350 mg, 0.753 mmol) and triphenylphosphine (238 mg, 0.906 mmol, 1.2 equiv.) in dry tetrahydrofuran (21 mL) under nitrogen at 0° C. After approximately one hour of stirring at 0° C. in the dark, diphenylphosphoryl azide (196 µL, 0.906 mmol, 1.2 equiv.) was added dropwise via syringe. The reaction was warmed to RT and stirred in the dark for 3 days. The reaction mixture was concentrated in vacuo and purified by silica gel column chromatography to obtain the desired product (0.294 g, 80% yield). TLC (EtOAc:hexanes=1:3, charring by PMA): Rf=0.52. Mass spec analysis (electrospray): exact mass 489.21, observed 490 $[M+H]^+$; 512 $[M+Na]^+$; 1001 $[2M+Na]^+$.

Compound I38-b: Triphenylphosphine (470 mg, 1.80 mmol, 3 equiv.) and deionized water (100 µL) were added to a solution of compound I37-b (294 mg, 0.600 mmol) in THF (10 mL). The reaction was stirred at RT overnight and then the mixture concentrated in vacuo. Toluene (~5 mL) was added and the mixture concentrated again in vacuo. The residue was purified by silica gel column chromatography to obtain the product (91 mg, 33%). TLC (EtOAc:hexanes=3:1, charring by Ninhydrin): Rf=0.17. Mass spec analysis (electrospray): exact mass 463.22, obtained 464 $[M+H]^+$; 486 $[M+Na]^+$; 949 $[2M+Na]^+$.

Compound I5-bb: TBDMS of I38-b is deprotected following a similar protocol as converting I2-a to I8-a using a 2% iodine in methanol solution. The crude product can be either purified by silica gel column chromatography or used directly for the next reaction if it is sufficiently pure (>90%).

NHS Ester of Trifluoromethyl Benzoic Acid:

20 mg (0.0869 mmole) of 4-(1-azi-2,2,2-trifluoromethyl) benzoic acid, 21.6 mg (0.1052 mmole) of DCC, 11 mg (0.0956 mmole) of N-hydroxysuccimide, and 435 µL of dimethylformamide (DMF) was added to a 1.5 mL ultracentrifuge tube. The mixture was vortexed for 30 seconds and then nutated at RT. HPLC indicated the completion of the reaction within an hour (starting material: $t_R$=3.73 minutes; NHS ester: $t_R$=3.99 minutes). The crude reaction mixture was used directly for the next step without purification. HPLC conditions: Xterra™ RP18 column, 5 nm, 4.6×250 mm; Buffer A: 0.1% TFA in water; Buffer B: 0.1% TFA in acetonitrile; Eluted with isocratic 60% B.

Compound p3-4j: $K_2CO_3$ solution (~1 M) in water is added to a flask containing compound I5-bb. If the compound is not completely soluble, a small amount of MeOH can be added. The progress of the reaction is monitored by TLC (charring by PMA). The reaction is normally done within 1 hr to obtain compound p3-4j, which is used directly for the next reaction without work up and purification.

Compound p3-4f: The reaction mixture of the NHS ester of trifluoromethyl benzoic acid is filtered and added directly into $K_2CO_3$ solution containing compound p3-4j (~1:1 molar ratio). The pH of the solution is checked. The optimal pH for this reaction is between pH 8.0 and 9.0. The progress of the reaction is monitored by TLC or HPLC; the amide coupling is normally complete within 1~4 hrs. After the reaction, the solution is passed through a C18 column to desalt (if sufficiently pure) or subjected directly to a preparative HPLC purification using a water/acetonitrile gradient system. The collected fractions are combined and lyophilized to obtain the product. The crude product can also be purified by silica gel chromatography (usually over 90% yield, if HPLC is employed the recovery is lower). The identity of the product is checked by mass spectrometry and the structure confirmed by $^1$HNMR.

Example 7

Synthesis of Monofunctional SA Crosslinking Reagent p3-4b

Compound p3-4b: Compound p3-4b is prepared following a similar protocol as compound p3-4f. First, the NHS ester is synthesized by following a similar protocol as trifluoromethyl benzoic acid. 3-maleimidopropionic acid (1.1 equiv. of compound I4-ba), N,N'-dicyclohexylcarbodiimide (DCC, 1.1 equiv.), and N-hydroxysuccinimide (1.1 equiv.) in DCM is added to a flask. Ice/water may be used if the scale of the reaction is over a few grams. After stirring the reaction for a few hours, a white solid precipitated out. After filtration, the organic solvent is evaporated under low pressure to produce an oil. The oil is added directly to the $K_2CO_3$ solution containing p3-4j following the same protocol as compound p3-4f. The product is purified by HPLC or silica gel chromatography (usually over 90% yield, if HPLC is employed the recovery is lower). The identity of the product is checked by mass spectrometry and the structure confirmed by $^1$HNMR.

Example 8

Synthesis of Monofunctional SA Crosslinking Reagent p3-4e

Dithiopyridine Propionic Acid: 2,2-dithiodipyridine in methanol (~1M solution) purged with N2 is added to an oven-dried three-necked flask under N2 and equipped with a stir bar at RT. 3-mercaptopropionic acid is added dropwise to this mixture. The solution turns yellow and is allowed to stir for 2~4 hrs. The solvent is removed in vacuo and the residue purified by silica gel column chromatography to obtain the desired product (usually quantitative yield). The identity of the product is checked by mass spectrometry and the structure confirmed by $^1$HNMR.

NHS Ester of Dithiopyridine Propionic Acid: NHS ester is synthesized following a similar protocol as trifluoromethyl benzoic acid and dichloromethane used as a solvent. The progress of the reaction is monitored by HPLC or TLC. After the reaction, the solid precipitate is filtered and the solvent removed in vacuo. The residue oil is used directly for the next reaction.

Compound p3-4e: The compound is synthesized as described for p3-4f using the NHS ester of dithiopyridine propionic acid and p3-4j as the starting materials. The identity of the product is checked by mass spectrometry and the structure confirmed by $^1$HNMR.

Example 9

Synthesis of Monofunctional SA Crosslinking Reagent p3-4a

Scheme 22:

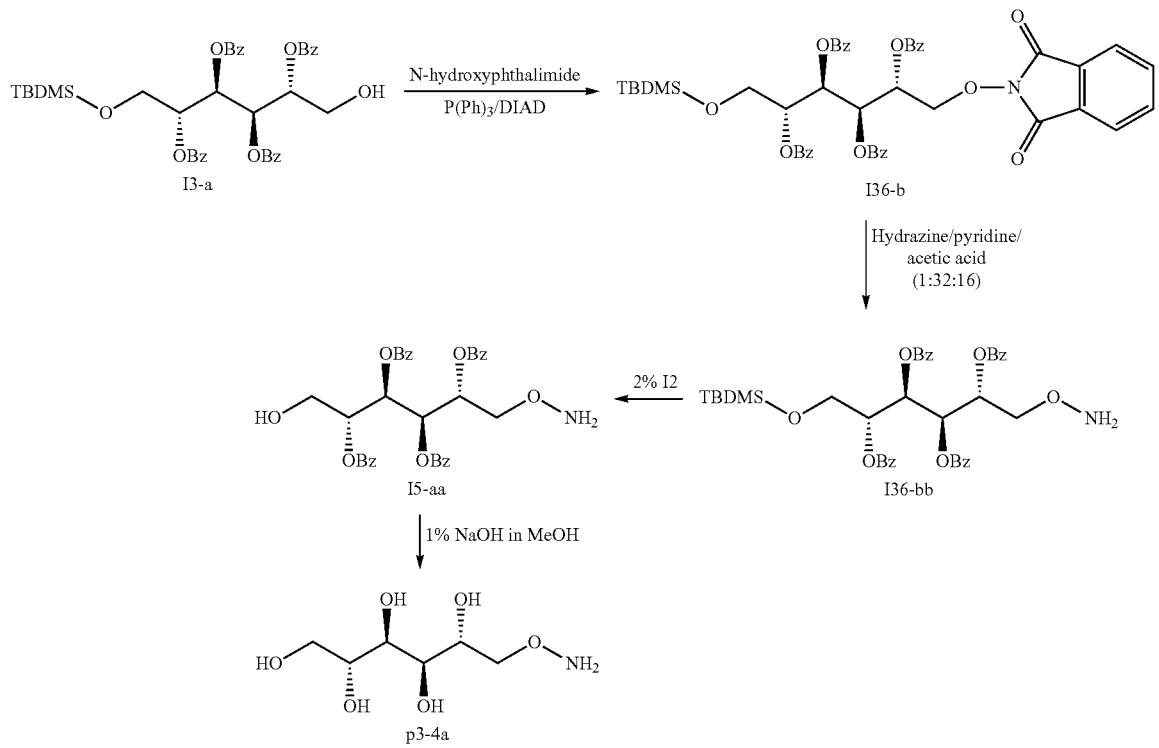

Compound I36-b: Diisopropyl azodicarboxylate (29 μL) was added dropwise via syringe to a solution of compound I3-a (70 mg, 0.098 mmol), N-hydroxyphthalimide (25 mg, 0.15 mmol, 1.5 equiv.), and triphenylphosphine (39 mg, 0.15 mmol, 1.5 equiv.) in THF (ACS grade, 1 mL) in an ice bath. The reaction was allowed to warm to RT overnight. The starting material was mostly consumed. The mixture was concentrated in vacuo and purified by silica gel column chromatography to obtain the desired product (71 mg, 84%). The ESI-MS m/z was consistent with [M−OBz]$^+$ and [M+H]$^+$ (736 and 858, respectively).

Compound I36-bb: Compound I36-b (70 mg, 0.082 mmol) was mixed with 500 μL of a hydrazine:pyridine:acetic acid (1:32:16, volume by volume) solution by vortexing. After approximately 10 minutes, the reaction was quenched with 10 mL of water, which resulted in an initial white turbidity, but then all turbidity dissolved. The reaction was extracted three times with 3 mL of dichloromethane. The crude combined organic phase was analyzed by mass spec (electrospray): exact mass 727.28, observed 606 [M−OBz]$^+$; 728 [M+H]$^+$; 1456 [2M+H]$^+$. An alternative method using tert-butyl N-hydroxycarbamate (BocN-OH) was also tested on a very small scale and resulted in the desired product as confirmed by mass spec.

Compound I5-aa: Compound I5-aa is prepared as described for converting I2-a to I8-a using a 2% iodine in methanol solution. The crude product can be either purified by silica gel column chromatography or used directly for the next reaction if it is sufficiently pure (>90%).

Compound p3-4a: Compound I5-aa (~50 mg) is added to a 10 mL reaction vial, followed by 1% NaOH in MeOH solution. The reaction mixture is stirred at RT and the progress of the reaction checked by TLC (UV and PMA charring). After completion, the MeOH is removed in vacuo. DCM is added into the residue solid. After mixing for a few minutes, the DCM layer is dried in vacuo to obtain the product. If the DCM layer contained some benzoic acid, the residue is redissolved in water and acidified to pH 2~3 using diluted HCl. The aqueous solution is extracted with DCM to eliminate the residual benzoic acid. The aqueous solution is adjusted to pH 8~10 using diluted NaOH. The aqueous solution is extracted three times with DCM. The DCM layers were combined and dried to obtain the product. The identity of the product is checked by mass spec and the structure confirmed by $^1$H-NMR.

Compound I5-b: A 2% solution of iodine in methanol (4 mL) was added to a solution of compound I4-ba (252 mg, 0.515 mmol) in methanol (2 mL). The reaction was stirred at RT overnight. The reaction was quenched by dropwise addition of 3% aqueous sodium thiosulfate until no brown color remained. The mixture was concentrated in vacuo, taken up in water (~20 mL), and extracted three times with 20 mL of dichloromethane. The combined organic layers were dried over sodium sulfate overnight, filtered, concentrated, and dried under vacuum to yield the product (176 mg, 91%), which was used for the next reaction without further purification. TLC (EtOAc:hexanes=3:2, charring by PMA): Rf=0.47. The ESI-MS m/z was consistent with [M+H]$^+$, 376; [M+Na]$^+$, 398; and [2M+Na]$^+$, 773.

Example 10

Synthesis of Homobifunctional SA Crosslinking Reagent p6-4aa

Scheme 19:

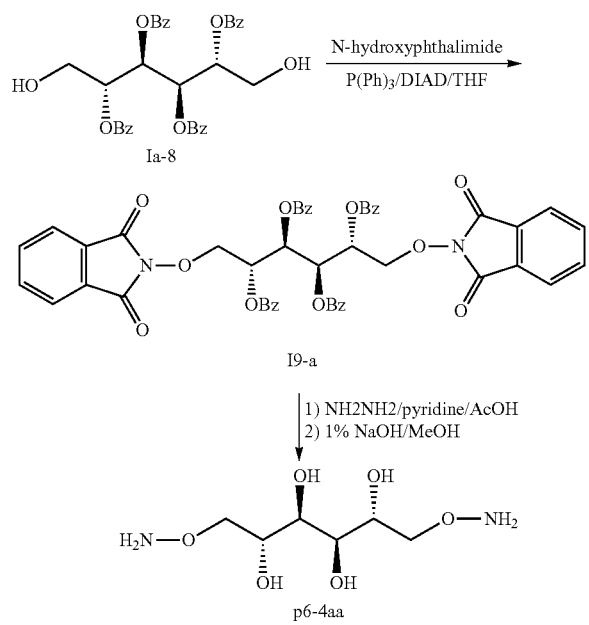

Compound I9-a: A solution of DIAD (49 µL, 3.0 equiv.) in THF (0.1 mL) was added slowly via syringe to a solution of compound k (49.5 mg, 0.083 mmol), N-hydroxyphthalimide (40.5 mg, 3.0 equiv.), and triphenylphosphine (65 mg, 3.0 equiv.) in THF (0.8 mL) in an ice bath under nitrogen. The solution quickly turned bright orange. After approximately 30 minutes, the reaction mixture was allowed to warm to RT and the orange color faded. The reaction was stirred overnight. The volatiles were removed in vacuo, and the residue was purified on a silica gel column to yield the product (31 mg, 42%) with acceptable purity (about 85%). HPLC (TFA05 method, detected by UV absorbance at 220 nm) retention time=9.20 min. Mass spec analysis (electrospray): exact mass 888.22 Da, obtained 766 [M–OBz]$^+$; 911 [M+Na]$^+$.

Compound p6-4aa: Phthalimide protecting groups and the Bz groups are removed and the product purified following the protocol described in example 9 to obtain compound p6-4aa.

Example 11

Synthesis of Homobifunctional SA Crosslinking Reagent p6-4bb

Scheme 20:

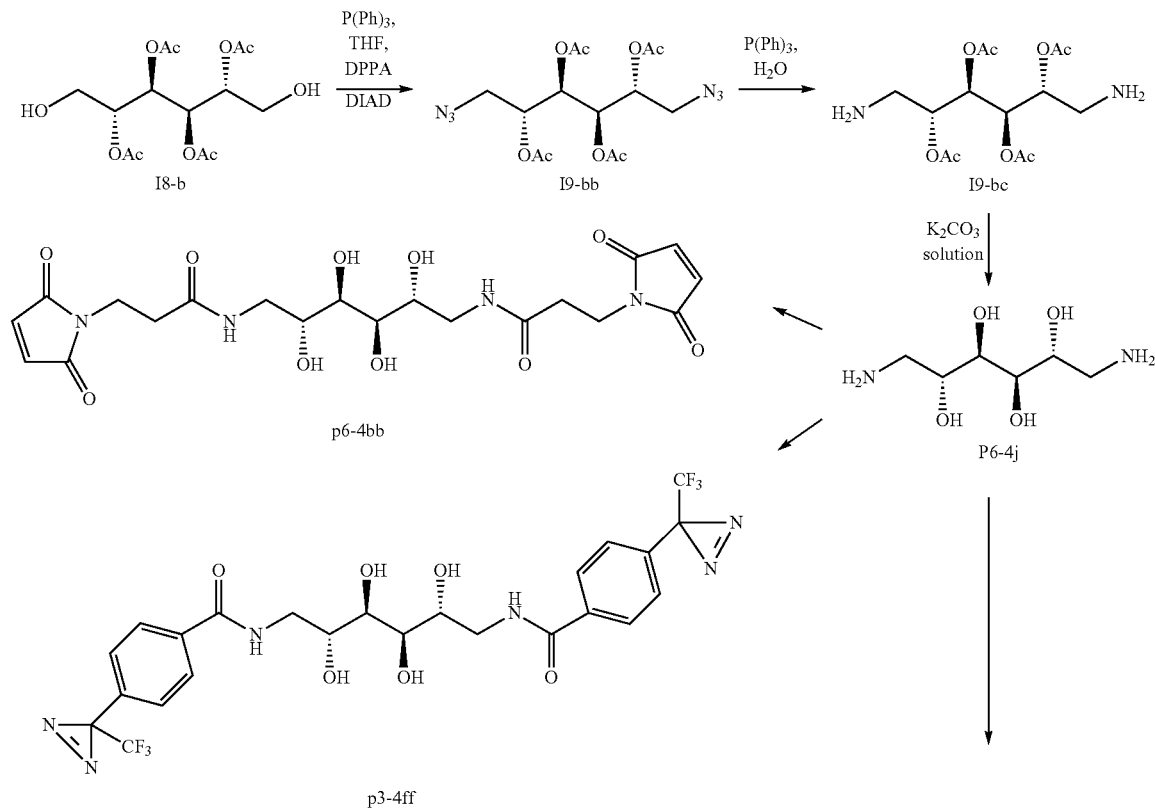

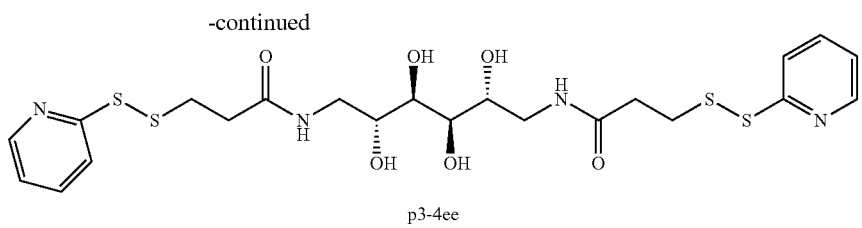

p3-4ee

Compound I9-bb: Diazide compound I9-bb is converted from protected di-hydroxyl mannitol (I8-b) following the same protocol as described for monoazide compound 37-b in example 6. The compound is purified by silica gel chromatography. The identity of the product is checked by mass spec and the structure confirmed by $^1$H-NMR. The purity is checked by TLC with charring (PMA).

Compound I9-bc: Diamine compound I9-bc is converted from the diazide compound I9-bb following the same protocol as described for monoamine compound 38-b in example 6. The compound is purified by silica gel chromatography. The identity of the product is checked by mass spec and the structure confirmed by $^1$H-NMR. The purity is checked by TLC with charring (PMA).

Compound p6-4j: The deprotection of the acetate group of diamine compound I9-bc is performed following the same protocol as described for compound p3-4j from I5-bb in example 6. After the completion of the deprotection, the mixture is used directly to carry out the next step.

Compound p6-4bb:

Homobifunctional maleimide compound p6-4bb is synthesized from p6-4j following the same protocol described for monofunctional maleimide compound p3-4b in example 7. The compound is purified by silica gel chromatography. The identity of the product is checked by mass spec and the structure confirmed by $^1$H-NMR. The purity is checked by TLC or HPLC.

Example 12

Synthesis of SA Crosslinking Reagent p6-4ff

Compound p6-4ff: Homobifunctional maleimide compound p6-4ff is synthesized from p6-4j following the same protocol as described for monofunctional maleimide compound p3-4f in example 6. The compound is purified by silica gel chromatography. The identity of the product is checked by mass spec and the structure confirmed by $^1$H-NMR. The purity is checked by TLC or HPLC.

Example 13

Synthesis of SA Crosslinking Reagent p6-444

Compound p6-4ee:

Homobifunctional maleimide compound p6-4ee is synthesized from p6-4j following the same protocol as described for monofunctional maleimide compound p3-4e in example 8. The compound is purified by silica gel chromatography. The identity of the product is checked by mass spec and the structure confirmed by $^1$H-NMR. The purity is checked by TLC or HPLC.

Example 14

Synthesis of Heterobifunctional Thrietol Crosslinking Reagent p2-2ab

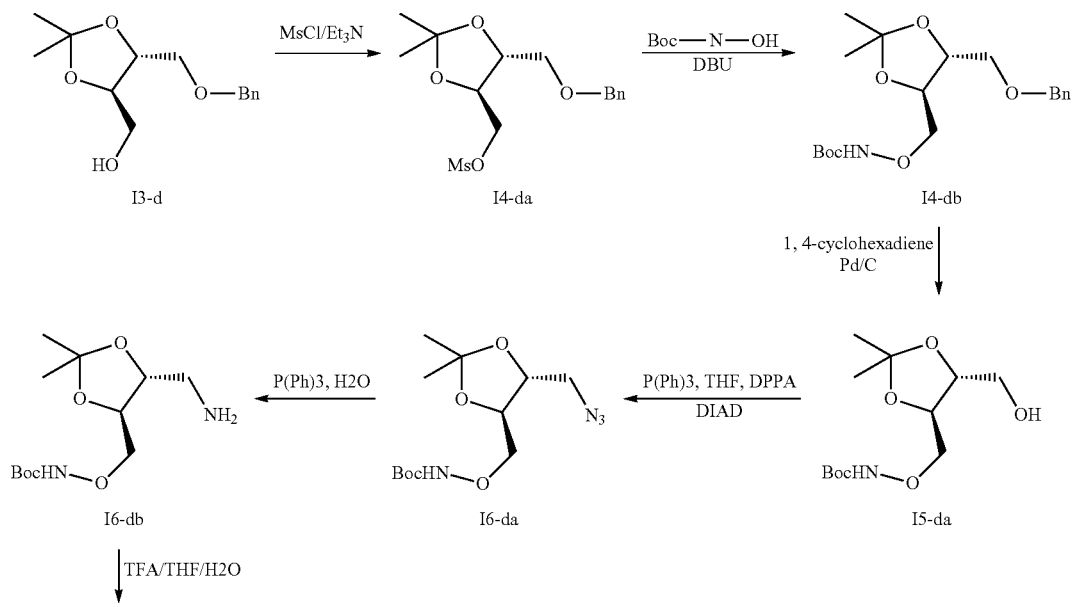

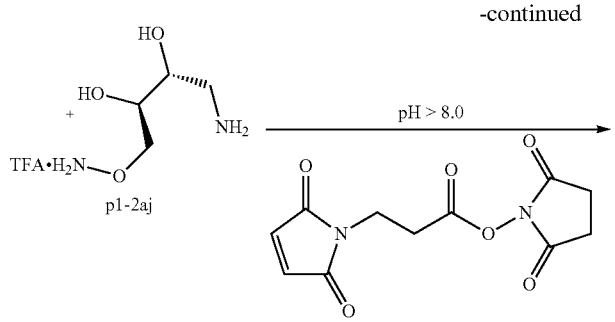
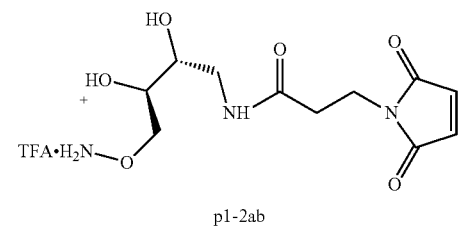

Compound I4-da: Methanesulfonyl chloride (75 μL) was added dropwise via a syringe to a stirred solution of compound I3-d (195 mg, 0.773 mmol) and triethylamine (300 μL, 2.8 equiv.) in dichloromethane (2 mL) in an ice bath. The reaction was stirred in the ice bath for one hour, then quenched with 2 M aqueous $NH_4Cl$ (~2 mL). The organic phase was separated out and washed again with 2 M aqueous $NH_4Cl$ (~2 mL). The combined aqueous layers were back-extracted three times with 3 mL of dichloromethane. The combined organic phase was washed with 2 mL of brine, dried over sodium sulfate, filtered, and concentrated to obtain the crude product (quantitative yield assumed) without further purification. TLC (EtOAc:hexanes=2:3, visualized by 254 nm UV or PMA charring): Rf=0.46.

Compound I4-db: A solution of compound I4-da (255 mg, 0.773 mmol) in diethyl ether (1 mL) was added via syringe to a stirred solution of DBU (175 μL, 1.5 equiv. with respect to compound I4-da) and N-Boc-hydroxylamine (145 mg, 1.4 equiv.) in diethyl ether (1 mL) in an ice bath under nitrogen. The reaction mixture was stirred at RT for 3 days. Slow conversion was observed, though the reaction profile was clean. The ether was evaporated and the reaction mixture re-dissolved in acetonitrile (2 mL) and heated to reflux overnight. Faster conversion was observed, though the reaction profile became significantly more complicated. The reaction mixture was concentrated and purified via silica gel chromatography to obtain the product (48 mg, 17% over two steps). TLC (EtOAc:hexanes=2:3, visualized by 254 nm UV or CAM charring): Rf=0.75. Mass spec analysis (electrospray): exact mass 367.20 Da, observed 368 [M+H]+; 390 [M+Na]+; 757 [2M+Na]+.

Compound I5-da: A 10-mL pear-shaped flask equipped with a stir bar was charged with 100 mg of 10% palladium on carbon, then purged twice with nitrogen. A solution of compound I4-db (40 mg, 0.109 mmol) and 1,4-cyclohexadiene (200 μL, approximately 20 equiv.) in 1:1 THF/MeOH (1 mL) was added via syringe. The mixture was stirred at RT. Slow conversion was observed, and additional excess 1,4-cyclohexadiene was added periodically. The reaction was not complete after one day of stirring; therefore, formic acid (50 μL) was used as an alternative hydrogen transfer reagent. After stirring for 2 days the reaction was complete. The mixture was carefully filtered through a Celite pad and concentrated to obtain the product (25 mg, 83%), which was used for the next step without further purification. TLC (EtOAc:hexanes=2:3, visualized by CAM charring): Rf=0.22. Mass spec analysis (electrospray): exact mass 277.15 Da, observed 278 [M+H]+; 300 [M+Na]+; 555 [2M+H]+; 577 [2M+Na]+.

Compound I6-da: The primary OH group in I5-da is converted to azide following the same protocol described for compound I37-b in example 6. The compound is purified by silica gel chromatography. The identity of the product is checked by mass spec and the structure confirmed by $^1$H-NMR. The purity is checked by TLC with charring (PMA).

Compound I6-db: The azide group in I6-da is reduced to an amine following the same protocol as described for compound I38-b in example 6. The compound is purified by silica gel chromatography. The identity of the product is checked by mass spec and the structure confirmed by $^1$H-NMR. The purity is checked by TLC with charring (PMA).

Compound p1-2aj: The acetonide (isopropylidene ketal) protection group and the Boc were simultaneously deprotected following the procedure in the literature (Leblanc, Y. et al. *J. Org. Chem.* 1986, 51, 789). Trifluoroacetic acid (0.2 M) is added to a stirred solution of compound I6-db in 4:1 THF/water at 0° C. The resulting solution is allowed to warm to RT and left overnight. The reaction is neutralized by the addition of concentrated ammonium hydroxide, and THF removed under reduced pressure to obtain the product.

Compound p1-2ab: The amine group of p1-2aj is coupled to the NHS ester of 3-maleimido propionic acid following the same protocol as described for compound p3-4b in example 7. The compound is purified by silica gel chromatography. The identity of the product is checked by mass spec and the structure confirmed by $^1$H-NMR. The purity is checked by TLC or HPLC.

Scheme 22:

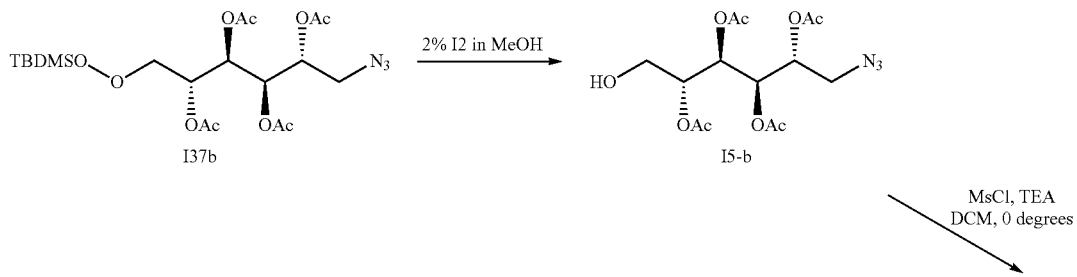

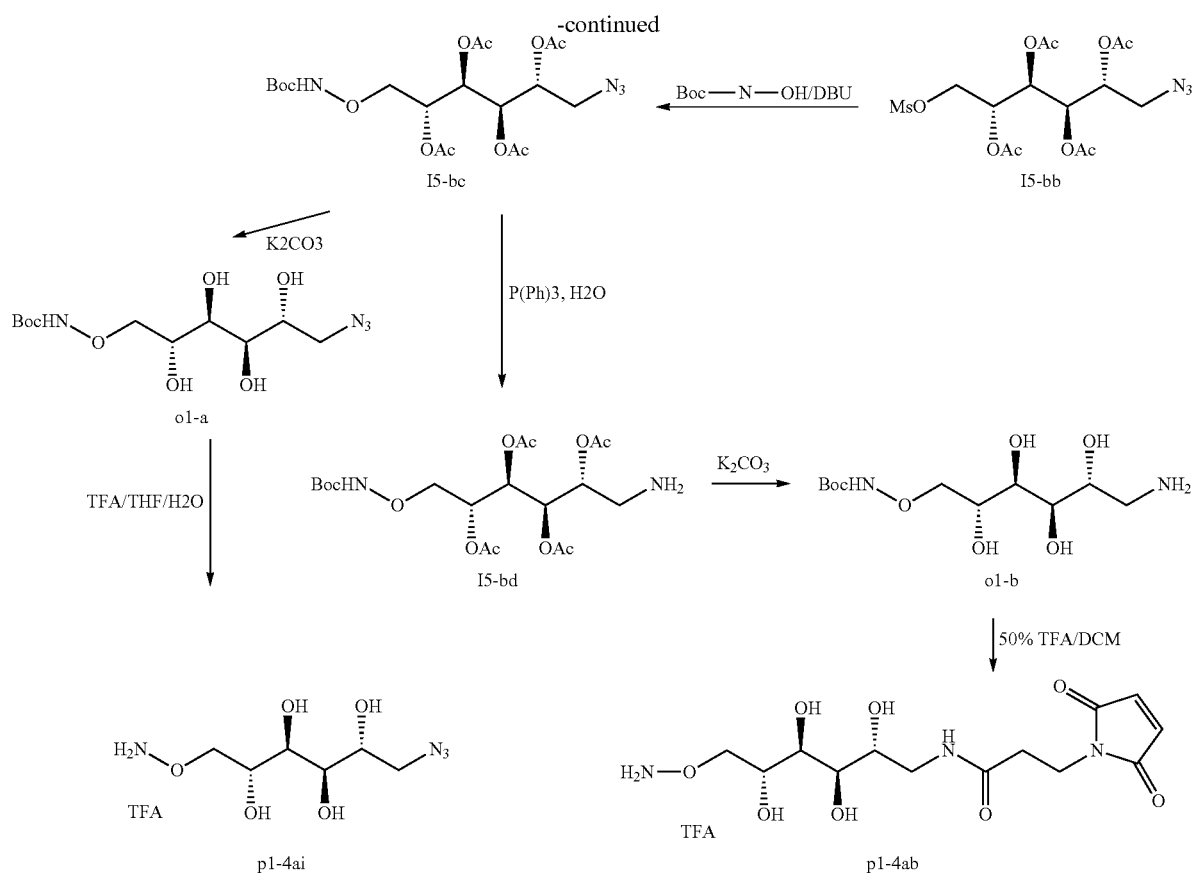

Example 15

Synthesis of Heterobifunctional Thrietol Crosslinking Reagent p2-2ab

Compound I5-b: A 2% solution of iodine in methanol (4 mL) was added to a solution of compound I37-b (252 mg, 0.515 mmol) in methanol (2 mL). The reaction was stirred at RT overnight. The reaction was quenched by the dropwise addition of 3% aqueous sodium thiosulfate until no brown color remained. The mixture was concentrated in vacuo, taken up in water (~20 mL), and extracted three times with 20 mL of dichloromethane. The combined organic layers were dried over sodium sulfate overnight, filtered, concentrated, and dried under vacuum to obtain the product (176 mg, 91%), which was used for the next reaction without further purification. TLC (EtOAc:hexanes=3:2, charring by PMA): Rf=0.47. Mass spec analysis (electrospray): exact mass 375.13 Da, obtained: 376 [M+H]$^+$; 398 [M+Na]$^+$; 773 [2M+Na]$^+$.

Compound I5-bb and I5-bc: The OH group of I5-b is converted to the Boc-protected aminooxy following the same protocol described for compound I4-db in example 11. The compound is purified by silica gel chromatography. The identity of the product is checked by mass spec and the structure confirmed by $^1$H-NMR. The purity is checked by TLC or HPLC.

Compound p1-4aj: The acetate of I5-bc is deprotected in K$_2$CO$_3$ solution following the protocol described for compound p3-4j in example 6. After deprotection, the solution is neutralized and extracted with DCM. The DCM layers were evaporated in vacuo and purified by silica gel chromatography to obtain compound o1-a. The Boc of o1-a is deprotected following the protocol described for compound p1-2aj. After evaporation of the solvent, a pure product is obtained. The identity of the product is checked by mass spec and the structure confirmed by $^1$H-NMR. The purity is checked by TLC or HPLC.

Example 16

Synthesis of Br-Substituted SA

Scheme 23:

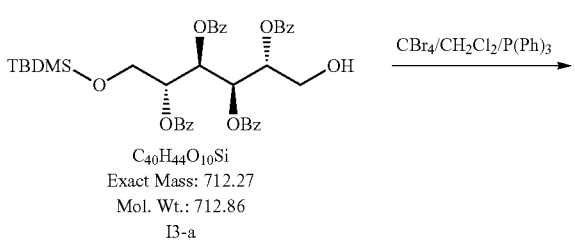

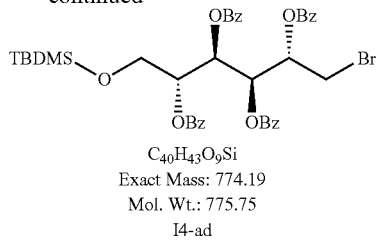

C$_{40}$H$_{43}$O$_9$Si
Exact Mass: 774.19
Mol. Wt.: 775.75
I4-ad

Compound I4-ad: A solution of carbon tetrabromide (300 mg, "may contain up to ca. 6% water," approximately 1.05 equiv.) in 1 mL dichloromethane was added to a solution of compound I3-a (505 mg, 0.84 mmol) in dichloromethane (3 mL) in an ice bath. A solution of triphenylphosphine (275 mg, 1.25 equiv.) in 1 mL dichloromethane was added. The reaction was stirred in an ice bath for approximately 2 hours, and then warmed to RT and stirred overnight. TLC indicated a trace amount of starting material remained, but the reaction profile was rather dirty. The reaction mixture was concentrated in vacuo and purified by silica gel column chromatography to obtain the product (209 mg, 37%). TLC (EtOAc: hexanes=1:1, visualized by UV 254 nm): Rf=0.82. The ESI-MS m/z was consistent with [M−OBz]$^+$, 539, 541; [M-Br]$^+$, 581; [M−OH]$^+$, 643, 645; [M+H]$^+$, 661, 663; [M+Na]$^+$, 683 and 685; and [2M+Na]$^+$, 1344, 1346, and 1348.

Example 17

Alkylation of an OH Group

Scheme 24:

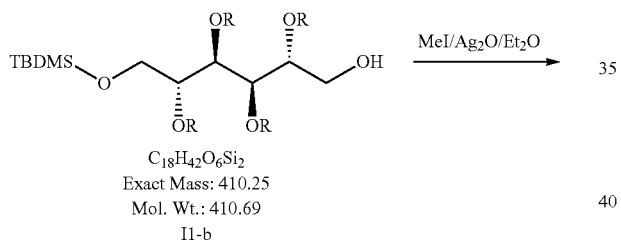

C$_{18}$H$_{42}$O$_6$Si$_2$
Exact Mass: 410.25
Mol. Wt.: 410.69
I1-b

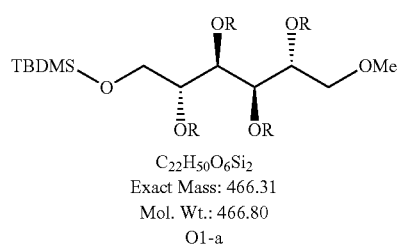

C$_{22}$H$_{50}$O$_6$Si$_2$
Exact Mass: 466.31
Mol. Wt.: 466.80
O1-a

R: one of them is TBDMS, and the rest of them are H

Compound O1-a: Methyl iodide (1.3 mL) was added to a stirred mixture of the starting material, I1-b (100 mg), silver (I) oxide (1.97 g), and crushed 4 A MS (500 mg) in diethyl ether (5 mL). The reaction was heated at reflux for 8 hr, then cooled to RT and stirred for 2 days. TLC indicated complete conversion, and ESI-MS data suggested the formation of the expected product: 467 [M+H]$^+$, 489 [M+Na]$^+$, 956 [2M+Na]$^+$. Note: in this reaction, the starting material was a byproduct of the silylation reaction of mannitol (Scheme 12). I1-b is a regional isomer of I1-a, as it has the same mass spec data but a lower Rf value because one of the TBDMS is coupled to the secondary OH group of the mannitol.

Example 18

Dimerization and Tetramerization of Threitol

Scheme 24:

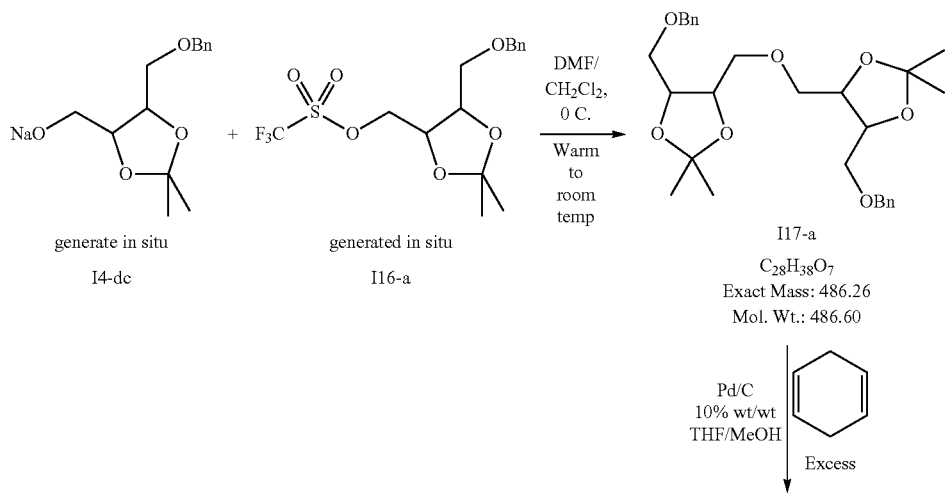

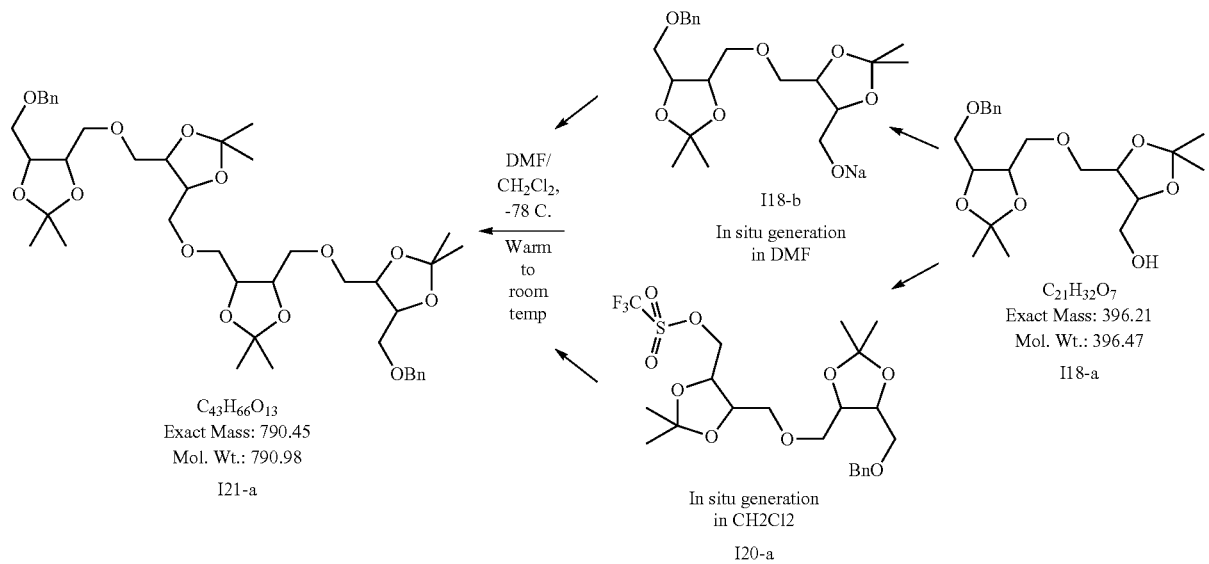

Compound I17-a: 0.1223 g (0.485 mmol, 1 eq.) of I3-d was dissolved in 2.1 mL of CH₂Cl₂ with 0.075 mL (0.538 mmol, 1.11 eq.) of triethylamine and cooled to −78° C. Next, 0.080 mL (0.475 mmol, 0.98 eq.) of trifluoromethanesulfonic anhydride was added and the mixture stirred at −78° C. for 30 minutes, then warmed to 0° C. for a period of 7 minutes before use. In a separate reaction flask, 0.0338 g (0.845 mmol, 1.7 eq.) of NaH as a 60% by wt. dispersion in oil was suspended in 3 mL of DMF at 0° C. Next, 0.1288 g (0.510 mmol, 1.05 eq.) of I3-d dissolved in 2 mL of DMF was added to the suspension. The resulting mixture was stirred for 20 minutes at 0° C. At the end of this period, the "triflate" solution was added slowly to the "alkoxide" mixture and the reaction warmed to RT. The reaction was quenched by the addition of 0.200 mL of water. The majority of the DMF and CH₂Cl₂ were removed by evaporation under reduced pressure. The resulting oil was dissolved in 5 mL of water and extracted three times with 15 mL of ethyl acetate. The organic extracts were combined, washed with 5 mL of brine, dried over anhydrous Na₂SO₄, filtered, and concentrated under reduced pressure. HPLC analysis of the residue indicated two peaks of almost equal area at 4.496 and 8.262 minutes. TLC analysis (25:75 ethyl acetate:hexane on silica, CAM stain) indicated the product with $R_f$=0.30 and a small amount of starting material with Rf=0.15. The resulting residue was purified by silica gel column chromatography to obtain 0.0564 g (0.116 mmol, 23.9% yield) of the desired product. Mass spec (turbo spray): expected m/z 487.3 [M+H], observed m/z 487.5; expected m/z 509.3 [M+Na], observed m/z 509.5; and expected m/z 995.6 [2M+Na], observed m/z 995.6. After purification, HPLC analysis indicated a single peak at 8.155 minutes.

In a separate experiment, THF solvent was used instead of DMF. A lower yield of 13% was obtained.

Compound I18-a: 0.050 g (0.12 mmol, 1 eq.) of I17-a was dissolved in 2 mL methanol and 2 mL THF. The solution was purged with nitrogen for 15 minutes to remove dissolved gasses, followed by the addition of 0.105 g of Pd/C 10% wt./wt. The system was sealed and purged with nitrogen gas. Next, 0.100 mL (1.06 mmol, 8.8 eq.) of 1,4-cyclohexadiene was added at RT. The mixture was stirred and the progress of the reaction monitored by TLC. After 1 hour, an additional 0.100 mL (1.06 mmol, 8.8 eq.) of 1,4-cyclohexadiene was added. After 2 hrs, an additional 0.100 mL (1.06 mmol, 8.8 eq.) of 1,4-cyclohexadiene was added. After 3 hours, an additional 0.400 mL (4.24 mmol, 35.3 eq.) of 1,4-cyclohexadiene was added and the reaction stirred overnight. TLC indicated consumption of the starting material and the presence of product with R=0.30 (40:60 ethyl acetate: hexane on silica). The Pd/C was removed by filtration of the reaction mixture through a Celite 545 pad, followed by the addition of 1 mL of MeOH and 0.75 mL of water to facilitate the transfer of the product through the Celite. The THF and MeOH were removed by evaporation under reduced pressure and the water removed by lyophilization. A total of 0.0365 g (0.092 mmol, 89% yield) of material was obtained. Mass spec (turbo spray): expected m/z 397.2 [M+H], observed m/z 397.5; expected m/z 419.2 [M+Na], observed m/z 419.5; and expected m/z 815.4 [2M+Na], observed m/z 815.8. Also present were signals consistent with a substance on which both benzyl protecting groups had been removed: expected m/z 307.2 [M+H], observed m/z 307.4; expected m/z 419.2 [M+H], observed m/z 419.5. HPLC indicated a main product peak at 5.627 minutes. This material was used in the next step without further purification.

Compound I21-a: The tetramer is prepared following the same protocol as described for compound I17-a from dimer I17-8. The compound is purified by silica gel chromatography. The identity of the product is checked by mass spec and the structure confirmed by ¹H-NMR. The purity is checked by TLC or HPLC.

Example 19

Synthesis of a Single MW SA Macromolecule (>20 KDa) Crosslinking Reagent Using TBDMS Protection

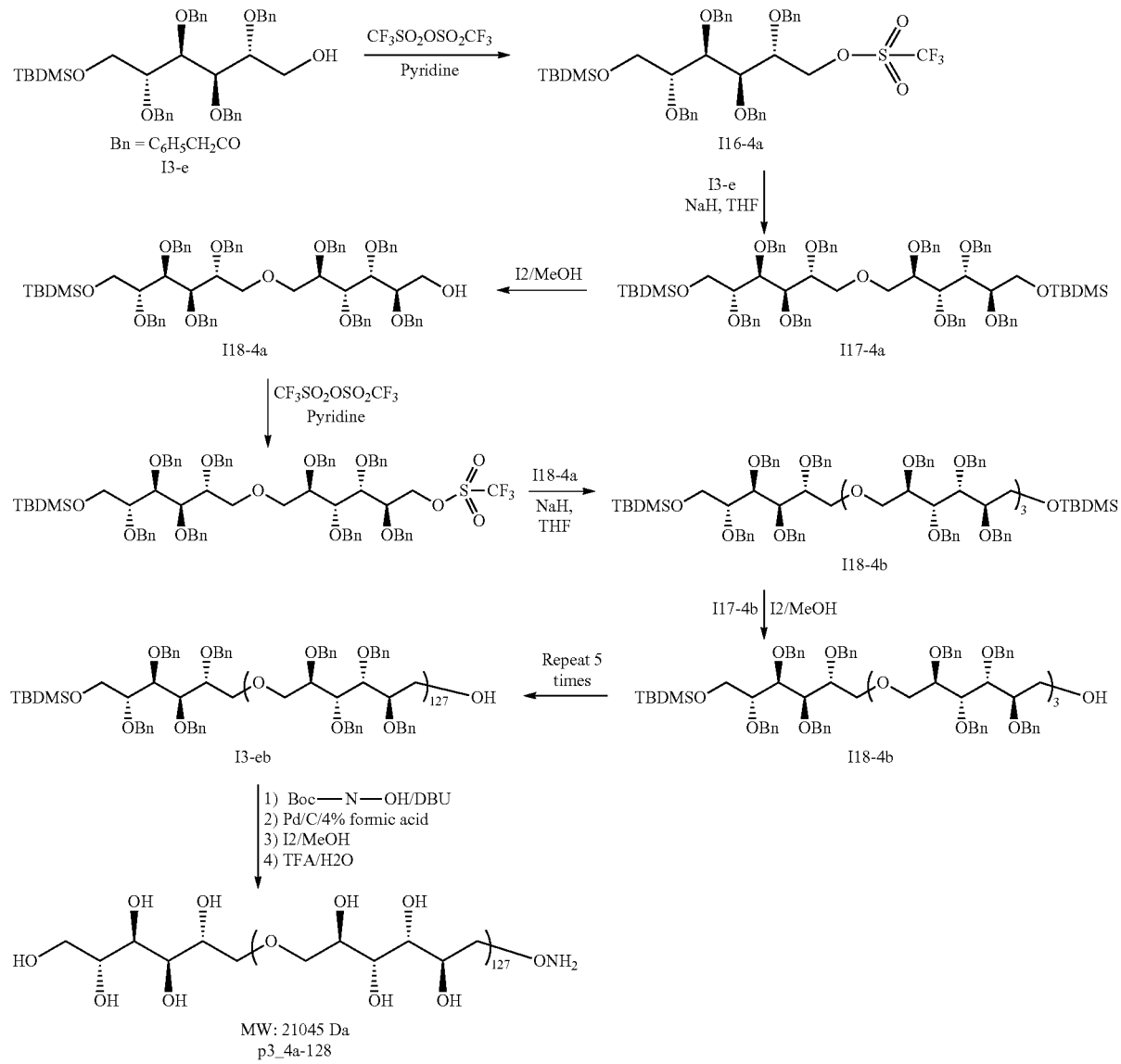

Scheme 25

Compound I3-e: Compound I3-e is prepared by benzylation of I1-a prepared following the same protocol as described for compound I5-d from I8-d (example 5). The compound is purified by silica gel chromatography. The identity of the product is checked by mass spec and the structure confirmed by $^1$H-NMR. The purity is checked by TLC or HPLC.

Compound p3_4a-128: Dimer I17-4a is prepared following a similar protocol as I17-a. I3-e reacted first with trifluoromethanesulfonic anhydride to form a triflate. Other good leaving groups, such as mesylate, can also be used here. Next, the triflate reacted with another I3-e in the presence of a base, such as NaH, lithium bis(trimethylsilyl) amide, or potassium tert-butoxide, in the presence of THF. In some cases, DMF may be used. After the coupling, the product is purified by silica gel chromatography and analyzed by HPLC and mass spec. One of the TBDMS groups of the dimer I17-4 is deprotected using 1% $I_2$ in MeOH following the same protocol as I3-a. The resulting dimer is activated with trifluoromethanesulfonic anhydride and reacted with another dimer in the presence of a base to form the tetramer I17-4b. After iodine deprotection of one of the TBDMS groups, the resulting material repeated the self-coupling and iodine deprotection cycle five times to obtain a mono-protected sugar alcohol with 128 SA units (I3-eb). The primary OH of I3-eb is converted to an aminooxy following the same protocol as described in I4-db in example 11. The final product is first debenzylated, then iodine is used to remove the TBDMS group, and finally TFA removed the Boc following previously described procedures in this patent. The final result is a aminooxy derivatized over a 20 KDa SA compound ready for conjugation through the aminooxy.

Example 20

Preparation of Other Monomers for Synthesizing Higher MW SAs Linked by an Amide Bond Fmoc Protection of D-Glucamine: D-glucamine (1.02 g, 5.52 mmol), Fmoc-OSu (1.99 g, 1.05 equiv.), and potassium carbonate (0.78 g, 1 equiv.) were suspended in DMF (40 mL). Water (40 mL) was added in small portions, generating heat. The reaction mixture briefly turned clear, and then a precipitate started to form. After stirring overnight, the reaction mixture was poured into 750 mL of water. Precipitate was collected by suction filtration and dried by lyophilization to obtain a yellow solid (1.75 g), of which approximately 40% was the desired material according to the HPLC peak area. HPLC (TFA05 method, detected by UV absorbance at 220 nm) retention time=5.10 min. The UV spectrum was characteristic of the Fmoc moiety. ESI-MS of the fraction collected from HPLC: m/z consistent with $[M+H]^+$, 404; $[M+Na]^+$, 426.

Fmoc Protection of D-Glucosamic Acid: Water (5 mL) was added to a stirred suspension of D-glucosamic acid (101.3 mg, 0.519 mmol), Fmoc-OSu (192 mg, 1.1 equiv.), and potassium bicarbonate (144 mg, 2 equiv.) in DMF (5 mL). Heat was generated. After sonication and the addition of more DMF (1 mL), the mixture briefly turned clear before white turbidity formed. The reaction was stirred at RT for 4 hours. The mixture was adjusted to pH 8 by the addition of 0.5 N HCl, and then concentrated in vacuo. The residue was taken up in water (~40 mL) and extracted three times with 15 mL of ethyl acetate. The aqueous layer was adjusted to pH 2.5 by the addition of 0.5 N HCl and extracted three times with 30 mL of ethyl acetate. The combined organic layers were dried over sodium sulfate, filtered, and concentrated to obtain the desired product (105 mg, 48%). HPLC (TFA05 method, detected by UV absorbance at 220 nm) retention time=5.06 min. The UV spectrum was characteristic of the Fmoc moiety. The ESI-MS m/z was consistent with $[M-OH]^+$, 400; $[M+H]^+$, 418; $[M+Na]^+$, 440.

The free OH groups of the above mentioned Fmoc-protected sugar alcohol amino acids are protected as an acetate ester or tButyl ester. The final monomer is used to assemble SA macromolecules linked by an amide bond using a standard Fmoc peptide solid phase synthesis strategy.

CONJUGATION EXAMPLES

Examples 21-26 illustrate the general methods and protocols for conjugating or modifying other molecules using sugar alcohol crosslinkers. The advantages of sugar alcohol crosslinkers over other crosslinkers are obvious in these examples because sugar alcohol crosslinkers are so hydrophilic that little or no organic solvent is needed for the reaction. Particularly in the cases of antibody-drug conjugate, the sugar alcohol link will greatly reduce the hydrophobicity of the drug and make it easy to react it with an antibody in the aqueous buffer after modification. One can also expect less aggregation and more stable antibody-drug conjugate.

Example 21

Synthesis of an Antibody-Drug Conjugate

The standard method for conjugating an antibody to a toxin is through a maleimide-NHS crosslinker (according to most published methods in the antibody-drug conjugate area). The disulfide bonds in the hinge region of the antibody can be selectively reduced to generate a half antibody containing sulfhydryl groups, which then react with a maleimide-modified toxin. Antibodies can also be thiolated at a surface amine to generate a sulfhydryl group, which can then be reacted with a maleimide-modified toxin. The second most popular method involves NHS ester coupling. For example, if the toxin has a free acid, it can be coupled to the surface amine of the antibody through the NHS ester activation method (simplified process).

CD33 Antibody-Doxorubicin: Commercially available CD33 antibody and doxorubicin are used to demonstrate the feasibility of synthesizing antibody-drug conjugates using a mannitol-based crosslinking reagent. In method a, the antibody is reduced at the hinge region to yield two half-antibody molecules, which react with maleimide-activated doxorubicin through a maleimide mannitol aminooxy cross-linking reagent. In method b, doxorubicin is reacted with carboxylic acid mannitol aminooxy, and then reacted with the surface amines of the antibody through EDC. After conjugation, the reaction mixtures are dialyzed or desalted to remove the unconjugated drug. Unconjugated (free) antibody is removed through preparative hydrophobic interaction chromatography (HIC) purification. The number of drug molecules loaded onto the antibody (antibody-drug ratio) is determined by HPLC analysis using a HIC column. The MW of the antibody-drug is analyzed by matrix-assisted laser desorption/ionization (MALDI) or electrospray mass spectrometry. The exact position of the labeling is determined by trypsin digestion of the antibody and analyzed by LC/MS-MS/MS. The percentage of aggregation is determined by gel filtration chromatography.

Example 22

Synthesis of Single Pure SA Macromolecules and Protein Conjugates

This example illustrates tetra-mannitol labeling of human granulocyte-colony stimulating factor (rhG-CSF). Recombinant rhG-CSF is prepared according to the literature (Souza, L M et al. *Science* 1986, 232, 61-65). A typical protocol for preparing single labeled rhG-CSF thorough the terminal amine is illustrated. A solution of rhG-CSF (5 mg/mL) in sodium phosphate buffer (pH 6.5) at 4° C. is added to a vial containing mannitol carboxymethyl-N-hydroxysuccinimidy ester (18 equiv.). After the SA molecule is dissolved, the reaction is stirred at 22° C. for 1 hr. Hydroxylamine (2 M, pH 7.3) is added to the reaction mixture to cleave any unstable SA labeling sites on rhG-CSF. After 1 hr, the reaction mixture is diluted with 1 mM HCl and the pH adjusted to 3.5 with 1M HCl. rhG-CSF-SA is purified by cation exchange chromatography. The site of SA labeling is determined by endoproteinase peptide mapping. The MW of the intact rhG-CSF-SA is determined by MALDI.

Example 23

Synthesis of Highly Loaded Therapeutic Agents on SA Macromolecules

Doxorubicin has a ketone group that easily reacts with aminooxy-containing SA macromolecules. An SA macromolecule containing multiple copies of aminooxy is reacted with doxorubicin to produce a highly loaded drug. Tetra-mannitol containing aminooxy in place of secondary OH groups reacts with doxorubicin, producing a highly loaded therapeutic agent.

Example 24

Synthesis of a Single Pure SA Macromolecule and Oligo Conjugates

An SA macromolecule (>20 KDa) can easily be attached to an oligo using the following procedure. A 5' or 3' terminal modified amine oligo is dissolved in sodium phosphate buffer (0.1 M, pH 8.0~9.0) at 10~20 mM concentration. An SA macromolecule bearing a single NHS ester is added directly into the oligo solution with a final concentration of SA macromolecule in the range of 1~2 mM. The vial is placed in a shaker at 37° C. for a few hours. The progress of the reaction can be checked by size-exclusion HPLC, anion exchange, or reversed-phase C18 chromatography. Depending on the size of the oligo, the reaction mixture can be desalted using gel filtration (Superdex™ 200) or ultrafiltration to remove the unreacted oligo. If the MWs of the oligo and SA are very close, a 1:1 ratio of the oligo and SA should be mixed together and the product purified by anion exchange chromatography. A 5' or 3' thiol modified oligo is also conjugated to an SA macromolecule (>20 KDa) bearing a single maleimide group at the termini following the standard protocol. The identity of the product is checked by MALDI-MS. Gel electrophoresis is used to analyze the reaction. Please note that sugar alcohols have no UV absorbance and may require a special detector, such as a pulsed electrochemical detector (PAD), refractive index detector, or light scattering detector. Other methods are spotting the sample in TLC and charring by CAM or PMA reagents.

Example 25

Synthesis of a Single Pure SA Macromolecule and Peptide Conjugates

An SA macromolecule (>20 KDa) can easily be attached to a thiol peptide using the following procedure. An SA macromolecule bearing a single maleimide group is mixed with 5~10 equivalents of thiol peptide in sodium phosphate buffer (0.1 M, pH 6.0) and mixed at RT. The progress of the reaction is checked by size-exclusion HPLC, anion exchange, cation exchange, or reversed-phase C18 chromatography. Depending on the size of the oligo, the reaction mixture is desalted using gel filtration (Superdex™ 200) or ultrafiltration to remove the unreacted peptide. If the MWs of the oligo and SA are very close, a 1:1 ratio of the peptide and SA should be mixed together and the product purified by anion or cation exchange chromatography. Other peptides, such as keto peptide, are also synthesized and react with a SA macromolecules (>20 KDa) bearing an aminooxy group under acidic conditions (usually acetic acid in MeOH) to obtain a SA-peptide conjugate.

Example 26

Synthesis of a HRP-Oligo Using a Sugar Alcohol Heterobifunctional Crosslinker A 5' or 3' modified amine oligo is first reacted with a sugar alcohol with an NHS-ester on one end and 2-pyridyldithiol on the other end (MW<500 Da) in sodium phosphate buffer (pH>8.0). The reaction is typically performed at 37° C. for 4 hr. The reacted oligo is desalted on a Sephedex™ G25 column and freeze-dried. The dried oligo is then dissolved in sodium phosphate buffer (pH>8.0) and reduced with DTT at 37° C. for 30 minutes. The reduced oligo is desalted and added directly into an HRP-bearing maleimide group. Maleimide-HRP is prepared by reacting HRP with an NHS-maleimide sugar alcohol crosslinker (MW<500 Da) or any other NHS-maleimide crosslinker. The oligo and HRP conjugation reaction is allowed to proceed at RT and its progress is monitored by gel filtration (or anion exchange) chromatography. The HRP-oligo conjugate is purified by gel filtration or anion exchange chromatography to obtain a single oligo-labeled HRP-containing sugar alcohol spacer.

The following list additional methods and examples for synthesizing various SA units, single MW SA polymers, and crosslinking reagents.

Example 19 described a specific method for synthesizing higher MW linear SA molecules using TBDMS protection strategy. However, in general it was found out the method is not practical or efficient to obtain higher order SA macromolecules. For example, the method uses trifluoromethanesulfonic acid anhydride to activate the free OH group. Trifluoromethanesulfonic acid anhydride is a very reactive reagent and the reaction conditions are very difficult to control. If not careful, side products are generated during the activation, despite using a dry ice/isopropanol bath (–80° C.). The method also uses a strong base, NaH, to deprotonate the hydroxyl group. Sometimes the TBDMS protecting group comes off during the coupling reaction, leaving unwanted side products.

To improve the overall yield so that a higher order SA macromolecule can be generated efficiently, a specific method for assembling the O-linked SA macromolecules was tested (Scheme 26, for general method please see FIG. 6). The method uses three sets of orthogonal protecting groups (benzyl ether, trityl or substituted trityl, and dimethylthiocarbamate) for the OH groups in the sugar alcohol monomers. Two sets of the sugar alcohol precursor units containing one of the primary OH groups protected by either a trityl or substituted trityl, or dimethylthiocarbamate (DMTC) group and the secondary OH groups are protected as benzyl ether, are synthesized. Iterate coupling of the sugar alcohol precursor units followed by selective deprotection of the trityl or dimethylthiocarbamate group of the resulting product efficiently generate higher order O-linked sugar alcohol marcomolecules.

Specifically, the method consists of:
(i) providing the first mono-SA unit having the general structural formula:

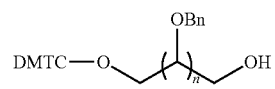

Wherein
n is an integer from 1 to about 8;
Bn represents a benzyl ether and DMTC is dimethylthiocarbamate.
(ii) providing the second mono-SA unit having the general structural formula:

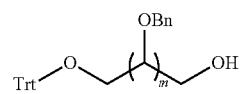

Wherein
m is an integer from 2 to about 8;
Bn represents a benzyl ether and Trt represents a trityl, or substituted trityl that having one or several functional groups such as methoxy on the aromatic ring.
(iii) substituting the primary OH group of the first mono-SA unit with a good leaving group such as mesylate ester.
(iv) deprotonate the free OH group of the second mono-SA unit in the presence of a base, such as NaH, LiHMDS, or potassium tert-butoxide (v) combining the first mono-SA unit with the second mono-SA unit under conditions that permit the condensation of these two units to form a dimer.
and (vi) deprotecting one of the primary OH groups of the dimer to provide a di-SA building block (two SA units) that can be utilized to build a higher MW SA molecule. Higher orders of SA building blocks (greater number of SA units) can be built following repetitive steps (i) to (vi) using r-SA building blocks, where r represents the number of SA units in one molecule.

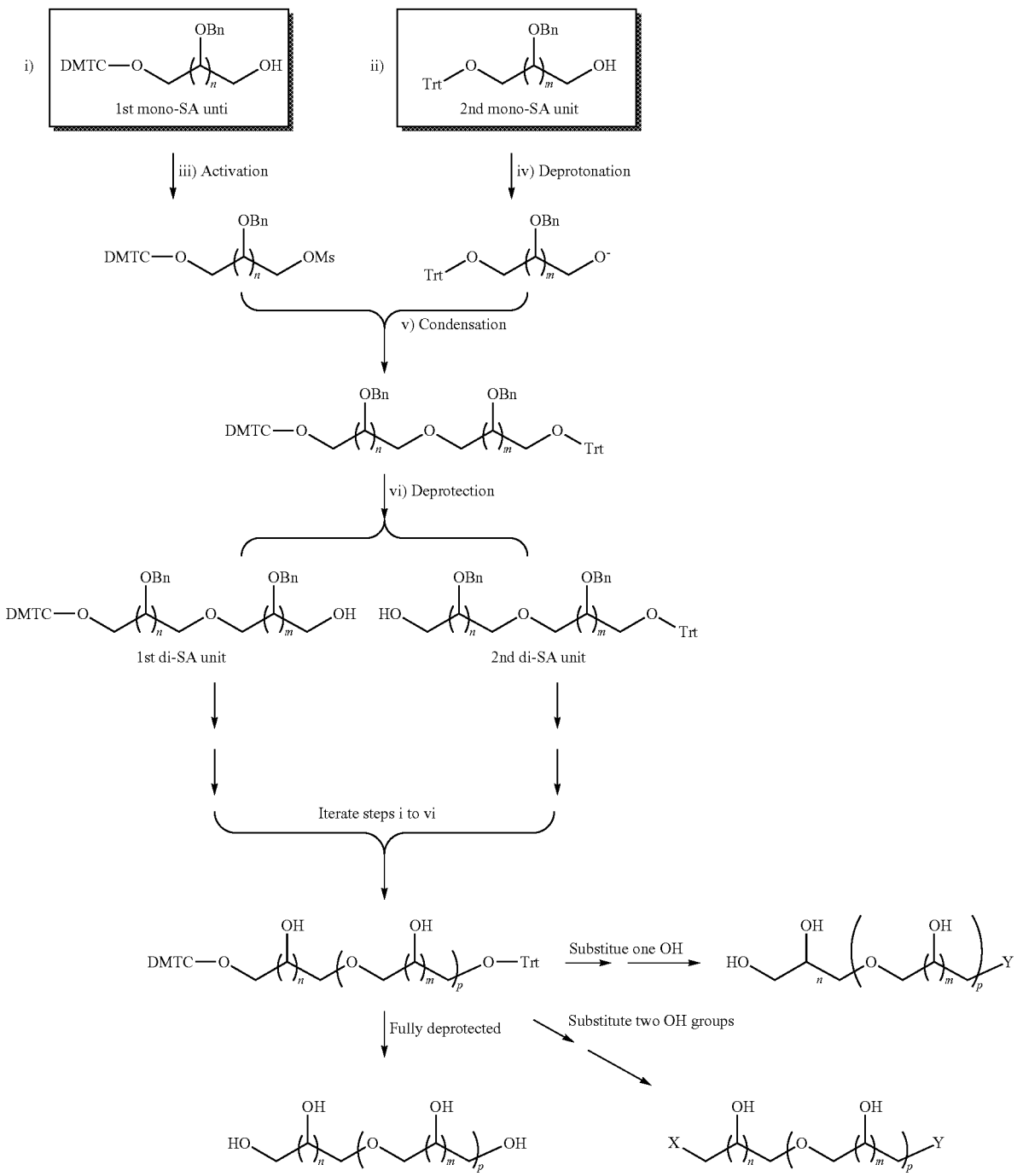

Scheme 26:

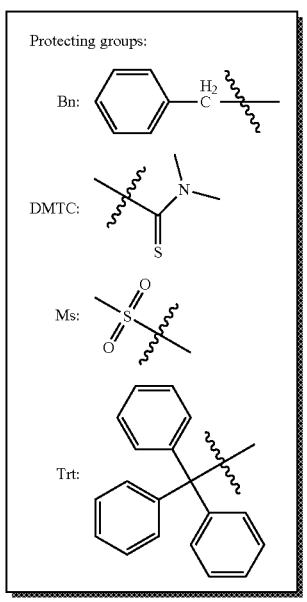

Scheme 27 describes the synthetic routes to obtain the first and second mono-SA unit for the coupling reaction in Scheme 26.

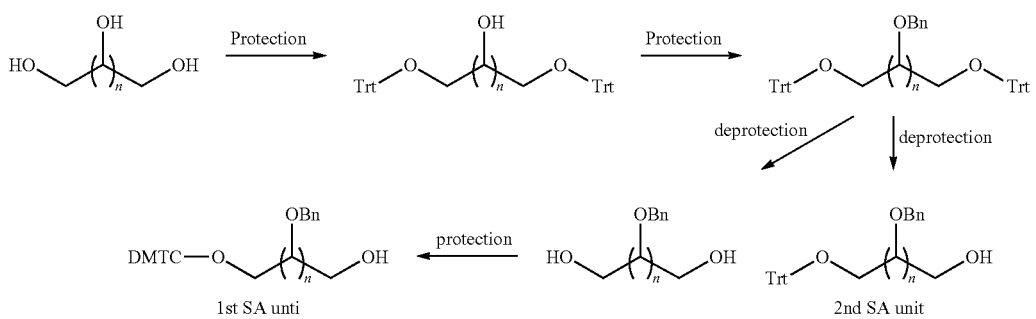

Higher MW linear SA molecules can be built by stepwise or convergent, or stepwise plus convergent methods depending on the heterogeneity of the secondary alcohol groups in the SA molecules. For example, tetra-SA building blocks containing different numbers and different kinds (different stereochemistry) of secondary OH groups on each SA unit can be built by coupling four different mono-SA units in a stepwise manner. Tetra-SA building blocks with different numbers and different kinds of secondary OH groups on each SA unit can also be built by coupling two units stepwise first, and then converging two of the di-SA building blocks together. Tetra-SA units with the same number and same kinds of secondary OH groups on each SA unit can be built by coupling two di-SA building blocks. In most cases, the low MW SA building blocks are built stepwise and the high MW SAs are assembled by convergence.

Functional groups X and Y can be assembled into the termini group by substituting the primary OH with desired crosslinking groups at the termini according to the methods described in this invention.

The following examples 27-39 describe specific methods of synthesizing varieties of low MW SA building units and using these SA units to assemble a single MW SA polymer. Three sets of orthogonal protecting groups (benzyl ether, trityl or substituted trityl, and dimethylthiocarbamate) for the OH groups have been described in details here. Other OH protecting groups can also be used for assembling SA molecules based on these methods, however the deprotection conditions for three protection groups (PG1, PG2, and PG3 in FIG. 6) have to be orthogonal to each other. An extensive description of protecting groups of typical art can be found in: Theodora W. Green and Peter G. M. Wuts, Protective Groups in Organic Synthesis, $2^{nd}$ ed., Wiley-Interscience, New York, 1991. Examples of OH protecting groups include, but are not limited to, alkyl, aryl, benzoyl, acetyl, benzyl, alkyl silyl, tetrahydropyranyl, tetrahydrofuranyl, and tetrahydrothiofuranyl.

Example 27

Synthesis of the First and Second Mono-SA Units for the Condensation Reactions Using Mannitol as an Example

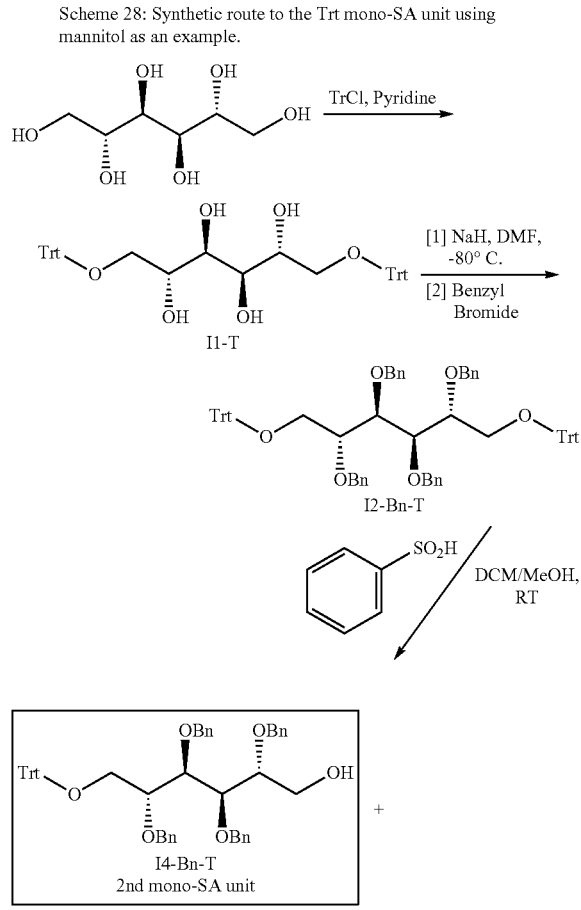

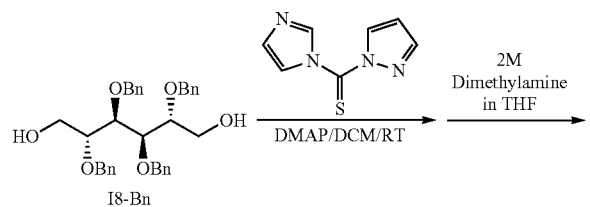

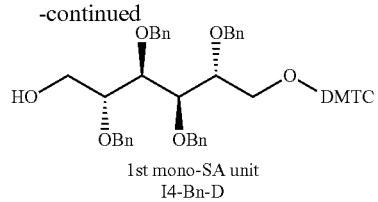

1st mono-SA unit
I4-Bn-D 1,6-di-O-trityl-D-mannitol (I1-T): Five grams (27.44 mmol) of D-mannitol, 60 mL of pyridine, and 134 mL of dichloromethane (DCM) was added to a 250 mL 3-neck round-shaped flask, followed by 16.9 g of triphenylmethyl chloride. The reaction mixture was refluxed for 12~24 hrs until all of the starting material disappeared. The reaction mixture was transferred to a 500 mL reparatory funnel and washed once with 100 mL of water. The water layer was back extracted three times with DCM. The DCM layers were combined and washed three times with brine. The DCM layers were dried over anhydrous $Na_2SO_4$, filtered, and concentrated under reduced pressure. The resulting residue was dissolved in a minimum amount of DCM and subjected to silica gel column chromatographic purification (EtOAc/hexanes) to obtain 16.4 g of the desired product (89.6% yield). Mass spec analysis (electrospray): exact mass 666.3, obtained mass 688.8 [M+Na]$^+$.

1,6-di-O-trityl-2,3,4,5-tetra-O-benzyl-D-mannitol (I2-Bn-T): 10.64 g (16 mmol) of 1,6-di-O-trityl-D-mannitol and 3.07 g of NaH (60% oil dispersion) were added into a 250 mL round-bottom flask. The flask was purged with $N_2$ and cooled in a dry ice/isopropanol bath, and then 133 mL of anhydrous DMF was added. After stirring for 5 min, 8.55 mL (72 mmol) of benzyl bromide was added slowly to the reaction mixture. The dry ice/iPrOH bath was removed and the reaction mixture stirred at RT for 3.5 hr and then concentrated under reduced pressure. 400 mL of EtOAc and 300 mL of deionized water were added to the residue. After separation, the water layer was back extracted twice with EtOAc. The combined EtOAc layers were washed three times with brine, dried over anhydrous $Na_2SO_4$, filtered, and concentrated under reduced pressure to obtain 18 g of desired product (yield: 109%). The product was used directly for the next reaction without further purification. Mass spec analysis (MALDI-TOF): exact mass: 1026.49, obtained: 1050.85 [M+Na]$^+$.

1-O-trityl-6-OH-2,3,4,5-tetra-O-benzyl-D-mannitol (I4-Bn-T) (2nd SA unit): 277 mL of DCM was added to a 1 L round-bottom flask containing 18 g (17.52 mmol) of 1,6-di-O-trityl-2,3,4,5-tetra-O-benzyl-D-mannitol. The reaction mixture was stirred for a few minutes until a clear solution was obtained, then 146 mL of MeOH was added, followed by 1.67 g (10.6 mmol) of benzene sulfonic acid. The reaction mixture was stirred at RT overnight and concentrated under reduced pressure and purified by silica gel chromatography (EtOAc/hexanes) to obtain 2.73 g of mono-trityl deprotected mannitol (1-O-trityl-2,3,4,5-tetra-O-benzyl-D-mannitol) (yield: 20%). Mass spec analysis (electrospray): exact mass 784.38, obtained mass 806.8 [M+Na]$^+$. $^1$H-NMR (500 MHz, $CDCl_3$): δ 7.48-7.53 (m, 6H, Trt-$\underline{H}$), 7.20-7.40 (m, 26H, aromatic H), 7.07 (dd, 3H, Trt-$\underline{H}$), 4.81 (d, 1H, —$C_6H_5$—C$\underline{H}_2$—), 4.70 (d, 1H, —$C_6H_5$—C$\underline{H}_2$—), 4.60 (dd, 3H, —$C_6H_5$—C$\underline{H}_2$—), 4.50 (d, 1H, —$C_6H_5$—C$\underline{H}_2$—), 4.43 (dd, 2H, —$C_6H_5$—C$\underline{H}_2$—), 4.12 (m, 1H, Trt-O—C$\underline{H}_2$—), 4.06 (m, 1H, Trt-O—C$\underline{H}_2$—), 3.90 (m, 2H, —C$\underline{H}_2$—OH), 3.80 (m, 1H, —C$\underline{H}$—), 3.71 (m, 1H, —C$\underline{H}$—), 3.65 (m, 1H, —C$\underline{H}$—), 3.40 (dd, 1H, —C$\underline{H}$—); $^{13}$C-DEPT135 (500 MHz, CDCl$_3$) 128.83, 128.50, 128.37, 128.28, 128.13, 127.80, 127.74, 127.70, 127.69, 127.50, 127.48, 127.45, 127.34, 126.97, 79.62 (—CH—), 78.91 (—CH—), 78.68 (—CH—), 78.40 (—CH—), 74.33 (—C$_6$H$_5$—CH$_2$), 73.82 (—C$_6$H$_5$—CH$_2$), 72.01 (—C$_6$H$_5$—CH$_2$—), 71.33 (—C$_6$H$_5$—CH$_2$), 62.51 (Trt-O—CH$_2$), 60.49 (CH$_2$—OH).

1,6-OH-2,3,4,5-tetra-O-benzyl-D-mannitol (I8-Bn): A total of 2.09 g of di-trityl deprotected mannitol (2,3,4,5-tetra-O-benzyl-D-mannitol) was obtained as a side product from the deprotection reaction of 18 g of 1,6-di-O-trityl-2,3,4,5-tetra-O-benzyl-D-mannitol (yield: 42%). Mass spec analysis (electrospray): exact mass 542.27, obtained mass 564.7 [M+Na]$^+$. $^1$H-NMR (500 MHz, CDCl$_3$): δ 7.28-7.4 (m, 20H, —C$_6$H$_5$—), 4.81 (d, 2H, —C$_6$H$_5$—CH$_2$—), 4.70 (d, 2H, —C$_6$H$_5$—CH$_2$—), 4.60 (d, 2H, —C$_6$H$_5$—CH$_2$—), 4.45 (d, 2H, —C$_6$H$_5$—CH$_2$—), 3.96 (m, 3H, —CH$_2$—), 3.96 (m, 1H, —CH$_2$—), 3.86 (m, 1H, —CH—), 3.84 (m, 1H, —CH—), 3.68-3.74 (m, 2H, —CH—); $^{13}$C-DEPT135 (500 MHz, CDCl$_3$) 128.56, 128.41, 127.97, 127.92, 127.77, 127.74, 79.71 (—CH—), 78.87 (—CH—), 74.50 (—C$_6$H$_5$—CH$_2$—), 71.53 (—C$_6$H$_5$—CH$_2$—), 60.45 (—CH$_2$—OH).

1-OH-6-O-DMTC-2,3,4,5-tetra-O-benzyl-D-mannitol (I4-Bn-D): 0.48 g (2.68 mmol) of 1,1'-thiocarbonyldiimidazole and 31 mg (0.24 mmol) of dimethylaminopyridine (DMAP) was added to a 50 mL round-bottom flask containing 1.32 g (2.44 mmol) of 1,6-OH-2,3,4,5-tetra-O-benzyl-D-mannitol. After flushing the flask with N$_2$, 13 mL of anhydrous DCM was added. The reaction was stirred at RT overnight and then the solvent removed under reduced pressure. 10.52 mL of 2M dimethylamine in THF was added to the residue. After overnight stirring at RT under N$_2$, the solvent was removed in vacuo and the residue chromatographed over silica gel (EtOAc/hexanes) to obtain 0.71 g of mono-DMTC protected mannitol (50% yield) and 0.54 g of di-DMTC protected mannitol. Mass spec analysis (electrospray): Mono-DMTC protected mannitol, exact mass 629.28, obtained mass 629.8; Di-DMTC protected mannitol, exact mass 716.3, obtained mass 716.7. $^1$H-NMR of 14-Bn-D (500 MHz, CDCl$_3$): δ 7.28-7.38 (m, 20H, —C$_6$H$_5$—), 5.13 (m, 0.5H), 4.61-4.79 (m, 6H, —C$_6$H$_5$—CH$_2$—), 4.40-4.48 (dd, 2H, —C$_6$H$_5$—CH$_2$—), 4.08 (m, 1H, —CH$_2$—), 3.97 (m, 3H, —CH$_2$—), 3.92 (m, 1H, —CH—), 3.84 (m, 1H, —CH—), 3.77 (m, 1H, —CH—), 3.70 (m, 1H, —CH—), 3.38 (s, 3H, —N—CH$_3$), 3.05 (s, 3H, —N—CH$_3$); $^{13}$C-DEPT135 (500 MHz, CDCl$_3$) 128.56, 128.44, 128.40, 128.36, 128.03, 127.97, 127.92, 127.86, 127.76, 127.74, 127.67, 127.64, 127.57, 79.71 (weak), 79.57 (—CH—), 78.88 (—CH—), 78.72 (—CH—), 78.63 (—CH—), 77.56 (—CH—), 77.22 (weak), 74.63 (—C$_6$H$_5$—CH$_2$—), 74.50 (weak), 74.33 (—C$_6$H$_5$—CH$_2$—, 71.69 (—C$_6$H$_5$—CH$_2$), 71.53 (weak), 71.38 (—C$_6$H$_5$—CH$_2$), 69.69 (—CH$_2$—O—S(O)—N), 60.45 (weak), 60.39 (—CH$_2$—OH), 42.83 (—N—CH$_3$), 37.79 (—N—CH$_3$).

Example 28

Synthesis of Dimer Using Mannitol as an Example

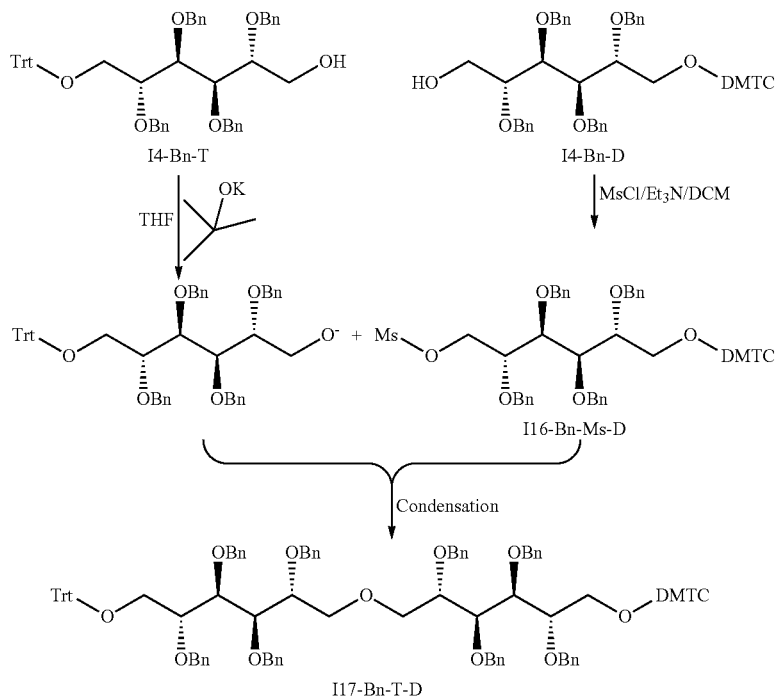

Scheme 30:

1-O-Ms-6-O-DMTC-2,3,4,5-tetra-O-benzyl-D-mannitol (I16-Bn-Ms-D): A 25 mL round-bottom flask containing 0.71 g (1.13 mmol) of 1-OH-6-O-DMTC-2,3,4,5-tetra-O-benzyl-D-mannitol was flushed with N$_2$, and 8.4 mL of anhydrous DCM and 237 µL of Et$_3$N were added. After cooling the reaction mixture in an ice/NaCl/water bath for a few minutes, 106 µL of MsCl was added slowly. After the addition, the ice/NaCl/water bath was removed and the reaction mixture stirred at RT for 1.5 hour. The solvent was removed under reduced pressure and the residue evaluated by silica gel column chromatography (EtOAc/hexanes) to obtain 0.73 g of mesylate product (90.7% yield). Mass spec analysis (electrospray): exact mass 707.26, obtained mass 707.7.

Fully Protected Dimer (di-SA) (I17-Bn-T-D): A 25 mL round-bottom flask containing 7.145 g (9.102 mmol) of 1-O-trityl-6-OH-2,3,4,5-tetra-O-benzyl-D-mannitol (2nd SA unit) was flushed with $N_2$ and 36 mL of THF was added. The entire content was cooled to below 0 degrees in an ice/NaCl/water bath, then 10.42 mL of 1M ButOK in THF was added. After 15 minutes, the reaction mixture was warmed to RT for 15 minutes and a solution of 3.786 g (5.354 mmol) of 1-O-Ms-6-O-DMTC-2,3,4,5-tetra-O-benzyl-D-mannitol in 34 mL of THF (0.2 M) added drop by drop. Fifteen minutes after the addition, the ice/NaCl/water bath was removed and the reaction mixture allowed to warm to RT and stirred overnight. The organic layer was concentrated in vacuo and the residue purified by silica gel chromatography (EtOAc/hexanes) to obtain 5.2125 g of the desired product (yield: 70%). $^1$H-NMR (500 MHz, $CDCl_3$): δ 7.40 (m, 6H, Trt-$\underline{H}$), 7.08-7.30 (m, 46H, aromatic H in Benzyl and Trt), 6.95 (m, 3H, Trt-$\underline{H}$), 5.02-5.04 (dd, 1H, $J_1$=2.5 Hz, $J_2$=12 Hz, —$C_6H_5$—$C\underline{H}_2$—), 4.96-4.99 (dd, 1H, $J_1$=2.6 Hz, $J_2$=12 Hz, 1H, —$C_6H_5$—$C\underline{H}_2$—), 4.72 (d, 1H, J=12 Hz, —$C_6H_5$—$C\underline{H}_2$—), 4.63 (s, 2H, —$C_6H_5$—$C\underline{H}_2$—), 4.48-4.58 (m, 9H, —$C_6H_5$—$C\underline{H}_2$—), 4.43 (m, 2H, —$C_6H_5$—$C\underline{H}_2$—), 4.36 (d, 1H, J=11.45 Hz, —$C\underline{H}_2$—), 4.30 (d, 1H, J=11.5 Hz, —$C\underline{H}_2$—), 4.26 (q, 1H, J=11.42 Hz, —$C\underline{H}_2$—), 4.20 (d, 1H, J=11.3 Hz, —$C\underline{H}_2$—), 4.12 (d, 1H, J=3.5 Hz, —$C\underline{H}_2$—), 4.02 (d, 1H, J=3.95 Hz, —$C\underline{H}$—), 3.98 (q, 1H, J=3.45 Hz, —$C\underline{H}$—), 3.92 (q, 1H, J=3.95 Hz, —$C\underline{H}_2$—), 3.86 (m, 2H, —$C\underline{H}$—), 3.82 (m, 2H, —$C\underline{H}$—), 3.55-3.57 (dd, 1H, $J_1$=2.3 Hz, $J_2$=10.7 Hz, —$C\underline{H}$—), 3.28 (s, 2H), 3.27 (s, 3H, —N—$C\underline{H}$), 3.0 (s, 2H), 2.90 (s, 3H, —N—$C\underline{H}_3$); $^{13}$C-DEPT135 (500 MHz, $CDCl_3$) 128.75 (weak), 128.59 (weak), 128.52, 128.46, 128.44, 128.41, 128.36, 128.34, 128.13, 128.08, 128.03, 127.94, 127.86, 127.80, 127.76, 127.74, 127.67, 127.64, 127.57, 127.27, 127.00, 85.79, 79.61, 79.57, 78.72, 78.63, 77.56, 77.23 (weak), 74.81 (—$C_6H_5$—$\underline{C}H_2$—), 74.63 (—$C_6H_5$—$\underline{C}H_2$—), 74.33 (—$C_6H_5$—$\underline{C}H_2$—), 73.73 (—$C_6H_5$—$\underline{C}H_2$—), 71.69 (—$C_6H_5$—$\underline{C}H_2$—), 71.48 (—$C_6H_5$—$\underline{C}H_2$—), 71.38 (—$C_6H_5$—$\underline{C}H_2$—), 69.69 (—$\underline{C}H_2$—O—), 68.56 (—$\underline{C}H_2$—O—), 65.43 ((—$\underline{C}H_2$—O—), 60.39 (—$\underline{C}H_2$—O—), 42.86 (weak), 42.83 (—N—$\underline{C}H_3$), 37.89 (N—$\underline{C}H_3$), 37.79.

Example 29

Synthesis of Di-SA Precursor Units for Further Coupling Using Mannitol as an Example Scheme 31: Deprotection of the trityl group to obtain the DMTC di-SA unit

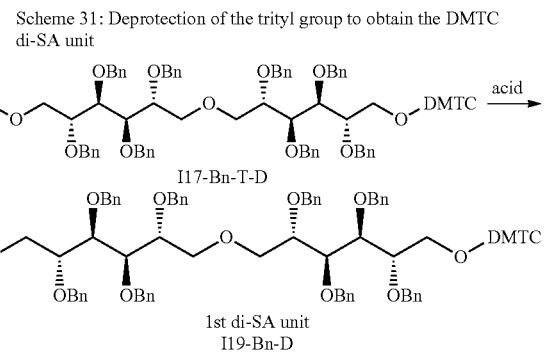

Compound I19-Bn-D (1$^{st}$ di-SA unit): Compound I19-Bn-D can be obtained by deprotecting the trityl group of compound I17-Bn-T-D using mild acid such as benzene sulfonic acid or acetic acid. However, the reaction should be monitored very carefully by TLC and HPLC to ensure the product formation. The product is analyzed by HPLC or TLC. The identity of the product can be confirmed by NMR or MS.

Scheme 32: Deprotection of the DMTC group to obtain Trt di-SA unit.

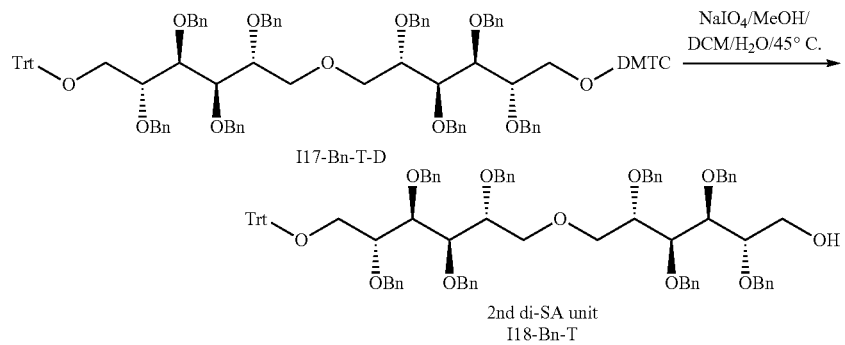

Compound I18-Bn-T (2$^{nd}$ di-SA unit): The DMTC group of the dimer was removed following a similar procedure as in the literature (Barma, D. K. et al. *Organic Letters*, 2003, 5, 4755-4757). 2 mL of THF, 1 mL of MeOH, 143 μL of deionized water, and 39.1 mg of $NaIO_4$ were added to a 25 mL flask containing 0.24 g (0.17 mmol) of compound I17-Bn-T-D. The reaction mixture was stirred at 45° C. The progress of the reaction was monitored by TLC (EtOAc/hexanes). After incubating overnight, TLC indicated that the reaction was very slow. More $NaIO_4$ was added in three batches at 4-hr intervals (total 141 mg) and the reaction mixture stirred at 45° C. for another day. 135 mg of $Na_2CO_3$ in 500 μL deionized water was added to quench the reaction. After 2 hrs, 25 mL of deionized water was added to the reaction mixture, which was extracted three times with 25 mL of EtOAc. The combined EtOAc layer was washed three times with 10 mL brine, dried over anhydrous $Na_2SO_4$, filtered, and concentrated under reduced pressure. The residue was purified by silica gel chromatography to obtain 0.082 g of deprotected dimer (yield: 37.4%) plus 0.047 g of starting material. $^1$H-NMR (500 MHz, $CDCl_3$): δ 7.38 (m, 6H, Trt-$\underline{H}$), 7.04-7.30 (m, 46H, aromatic H in Benzyl and Trt), 6.95 (m, 3H, Trt-H), 4.52-4.72 (m, 6H), 4.20-4.52 (m, 6H), 4.10-4.20 (m, 2H), 3.96-4.08 (m, 2H), 3.80 (m, 3H), 3.52 (m, 2H), 3.21 (m, 1H); $^{13}$C-DEPT135 (500 MHz, CDCl$_3$) 129.26, 129.20, 129.15, 128.87, 128.79, 128.59, 128.54, 128.47, 128.45, 128.41, 128.39, 128.38, 128.31, 128.28, 128.26, 128.17, 128.10, 128.01, 127.99, 127.96, 127.90, 127.84, 127.81, 127.78, 127.73, 127.66, 127.65, 127.63, 127.57, 127.52, 127.48, 127.41, 127.36, 127.27, 127.25, 127.13, 127.07, 127.01, 126.96 79.76, 79.65, 78.92, 78.82, 78.71, 78.43, 78.37, 78.03, 77.93, 77.63, 74.62 (—C$_6$H$_5$—CH$_2$—), 74.53 (—C$_6$H$_5$—CH$_2$—), 74.36 (—C$_6$H$_5$—CH$_2$—), 73.86 (—C$_6$H$_5$—CH$_2$—), 72.04 (—C$_6$H$_5$—CH$_2$—), 71.56 (—C$_6$H$_5$—CH$_2$—), 65.77 (weak, —CH$_2$—), 64.40 (weak, —CH$_2$—), 62.55 (—CH$_2$—), 60.52 (—CH$_2$—), 60.47 (—CH$_2$—), 36.57, 35.97

Deprotection of the benzyl groups of the dimer: The benzyl groups are easily removed by hydrogenation (H$_2$, 10% Pd/C) or using a hydrogen transfer reagent, such as formic acid or 1,4-cyclohexanediene in the presence of Pd/C (Synthesis, 1985, 76-77).

Example 30

Synthesis of the Trimer Using Mannitol as an Example

The trimer can be synthesized by coupling three mono-SA units together (see Scheme 33). This method has been shown to be inefficient. The reaction took a longer time and the product yield was only 11.5%.

1,6-O-Ms-2,3,4,5-tetra-O-benzyl-D-mannitol

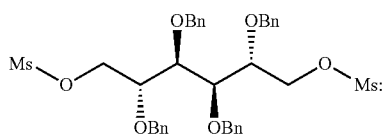

A 25 mL round-bottom flask containing 0.36 g (0.657 mmol) of 1-OH-6-O-DMTC-2,3,4,5-tetra-O-benzyl-D-mannitol was flushed with N$_2$ and 4.8 mL of anhydrous DCM and 275 µL of Et$_3$N added. After cooling the reaction mixture in an ice/NaCl/water bath for a few minutes, 122 µL of MsCl was added slowly. After the addition, the ice/NaCl/water bath was removed and the reaction mixture stirred at RT for 1.5 hrs. The solvent was removed under reduced pressure and the residue purified using silica gel column chromatography (EtOAc/hexanes) to obtain 0.449 g of mesylate product (97.7% yield). Mass spec analysis (electrospray): exact mass 698.22, obtained mass 720.6 [M+Na]$^+$.

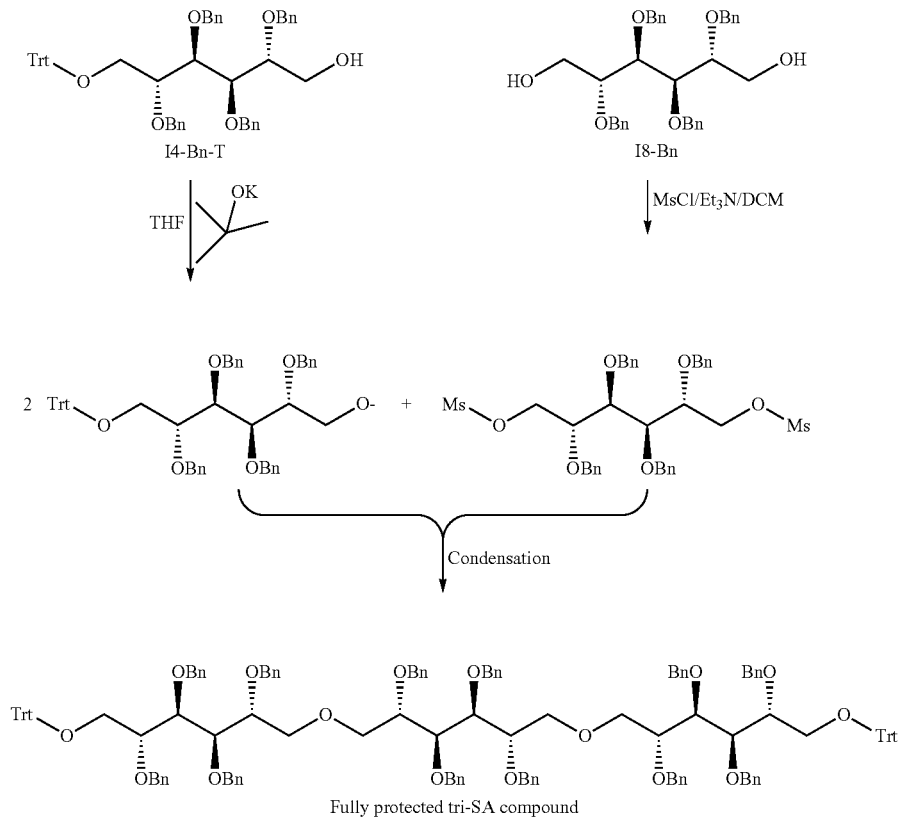

Scheme 33: Synthesis of tri-SA units by coupling three mono-SA unit together.

Fully Protected Tri-SA Compound:

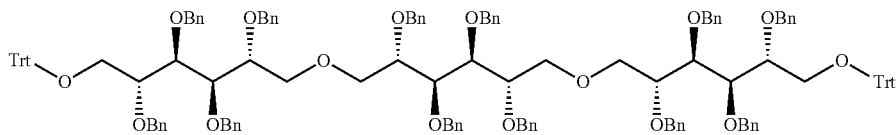

A 25 mL round-bottom flask containing 1.33 g (1.69 mmol) of 1-O-trityl-6-OH-2,3,4,5-tetra-O-benzyl-D-mannitol (2nd SA unit) was flushed with $N_2$ and 6 mL of THF added. The contents were cooled to below 0 degrees in an ice/NaCl/water bath, then 2.02 mL of 1M ButOK in THF was added. After 15 minutes, the reaction mixture was warmed to RT for 15 minutes and a solution of 0.42 g (0.6 mmol) of 1,6-O-Ms-2,3,4,5-tetra-O-benzyl-D-mannitol in 6 mL THF added drop by drop. Fifteen minutes after the addition, the ice/NaCl/water bath was removed and the reaction mixture allowed to warm to RT and stirred for 72 hrs. The organic layer was concentrated in vacuo and the residue purified by chromatography (EtOAc/hexanes) to obtain 0.143 g of the desired product (yield: 11.5%). $^1$H-NMR (500 MHz, CDCl$_3$): δ 7.34-7.41 (m, 12H, Trt-H), 7.00-7.30 (m, ~82H, aromatic H in Benzyl and Trt), 6.88 (m, 4H, Trt-H), 4.50-4.70 (m, 16H, —C$_6$H$_5$—C$\underline{H}_2$—), 4.20-4.44 (m, 14H, —C$_6$H$_5$—C$\underline{H}_2$—), 3.90-4.10 (m, 10H), 3.70-3.80 (m, 6H), 3.50-3.68 (m, 6H), 3.23 (m, 2H); $^{13}$C-DEPT135 (500 MHz, CDCl$_3$) 128.87, 128.47, 128.33, 128.29, 128.28, 128.26, 128.17, 128.12, 128.04, 127.84, 127.79, 127.73, 127.68, 127.61, 127.56, 127.50, 127.46, 127.40, 127.35, 127.27, 127.24, 127.22, 127.18, 126.92, 85.76 (—CH$_2$—), 80.50, 80.01, 79.01, 78.89, 78.62, 78.56, 78.46, 74.96 (—C$_6$H$_5$—C$\underline{H}_2$—), 73.97 (—C$_6$H$_5$—C$\underline{H}_2$—), 73.92 (—C$_6$H$_5$—C$\underline{H}_2$—), 73.86 (—C$_6$H$_5$—C$\underline{H}_2$—), 73.76 (—C$_6$H$_5$—C$\underline{H}_2$—), 72.00 (—C$_6$H$_5$—C$\underline{H}_2$—), 71.79 (—C$_6$H$_5$—C$\underline{H}_2$—), 71.67 (—C$_6$H$_5$—C$\underline{H}_2$—), 71.60 (—C$_6$H$_5$—C$\underline{H}_2$—), 71.46 (—C$\underline{H}_2$—), 71.33 (—C$\underline{H}_2$—), 69.38 (—C$\underline{H}_2$—), 67.07 (—C$\underline{H}_2$—), 62.58 (—C$\underline{H}_2$—), 60.41 (—C$\underline{H}_2$—).

Trimer formation by coupling one mono-SA unit and one di-SA unit: The trimer can also be prepared by coupling a pre-activated DMTC mono-SA unit (1-O-Ms-6-O-DMTC-2,3,4,5-tetra-O-benzyl-D-mannitol) with a Trt di-SA unit (Scheme 34) or coupling a pre-activated DMTC di-SA unit with a Trt mono-SA unit (Scheme 35). Because the trityl protected SA unit has to be in excess in order to push the coupling reaction to completion, the latter method using a Trt mono-SA unit is more preferable due to its availability compared to the Trt di-SA unit. The DMTC di-SA unit is activated the same way as the DMTC mono-SA unit, using MsCl. The resulting activated SA unit is coupled to the Trt SA unit in the presence of 1M ButOK following the same procedure as the dimer.

Scheme 34: Synthesis of tri-SA unit by coupling one mono-SA (DMTC protected) and one di-SA unit (Trityl or methoxy substituted trityl) together.

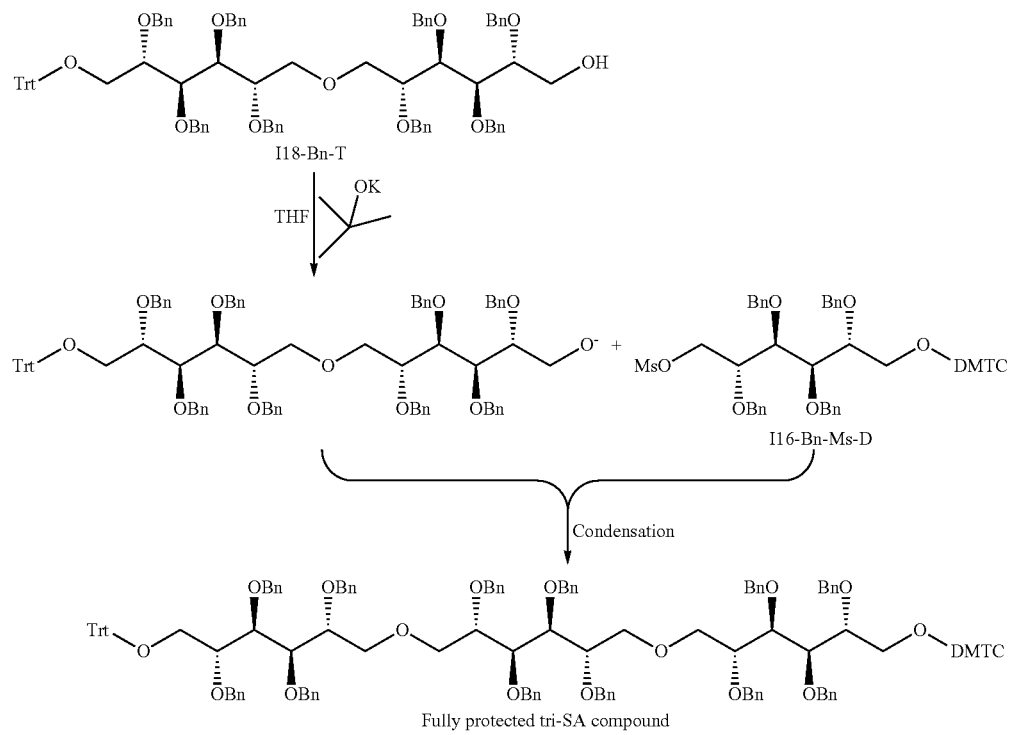

Fully protected tri-SA compound

Fully Protected Tri-SA Compound:

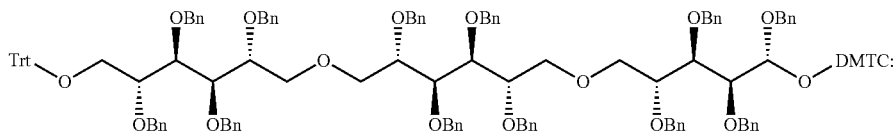

A 25 mL round-bottom flask containing 1.016 g (0.776 mmol) of trityl protected di-SA unit was flushed with $N_2$ and 5.2 mL of THF added. The entire content was cooled to below 0 degrees in an ice/NaCl/water bath, then 0.93 mL of 1M ButOK in THF was added. After 15 minutes, the reaction mixture was warmed to RT for 15 minutes and a solution of 0.637 g (0.9 mmol) of 1-O-Ms-6-O-DMTC-2,3,4,5-tetra-O-benzyl-D-mannitol (mono-SA unit) in 3.5 mL of THF was added drop by drop. Fifteen minutes after the addition, the ice/NaCl/water bath was removed and the reaction mixture allowed to warm to RT and stirred overnight. 20 mL of ethyl acetate was added and the organic layer was washed 8 times with 4 mL of brine. The organic layer was concentrated in vacuo and the residue purified by silica gel chromatography (EtOAc/hexanes) to obtain 0.21 g of the desired product (yield: 17%). $^1$H-NMR (500 MHz, $CDCl_3$): δ 7.39 (m, 15H, Trt-H), 7.3-7.1 (m, 80H, aromatic H in Benzyl and Trt), 5.05 (dd, 2H, -Benzyl-$CH_2$—), 4.8-4.05 (m, 17H, -Benzyl-$CH_2$ and alkyl H), 4.00-3.6 (m, 7H, alkyl), 3.55 (d, 1H, alkyl), 3.25 (s, 3H, N—$CH_3$), 2.87 (s, 3H, N—$CH_3$). $^{13}$C (500 MHz, $CDCl_3$): δ 187.02 (thioamide), 142.99, 137.63, 137.56, 137.41, 137.15, 127.77, 127.70, 127.48, 127.41, 127.39, 127.36, 127.31, 127.29, 127.21, 127.19, 127.08, 127.03, 126.99, 126.89, 126.88, 126.81, 126.69, 126.65, 126.62, 126.59, 126.52, 126.38, 126.28, 126.20, 126.18, 126.15, 125.98, 125.89, 85.66 (alkyl), 77.91 (alkyl), 77.28 (alkyl), 76.89 (alkyl), 76.27 (alkyl), 76.24 (alkyl), 76.02 (alkyl), 75.77 (alkyl), 73.29 (-Bn-$CH_2$), 73.08 (-Bn-$CH_2$), 72.88 (-Bn-$CH_2$), 70.73 (ether), 70.64 (ether), 70.33 (ether), 70.28 (ether), 68.39, 61.37, 41.73 (thioamide), 36.72 (thioamide).

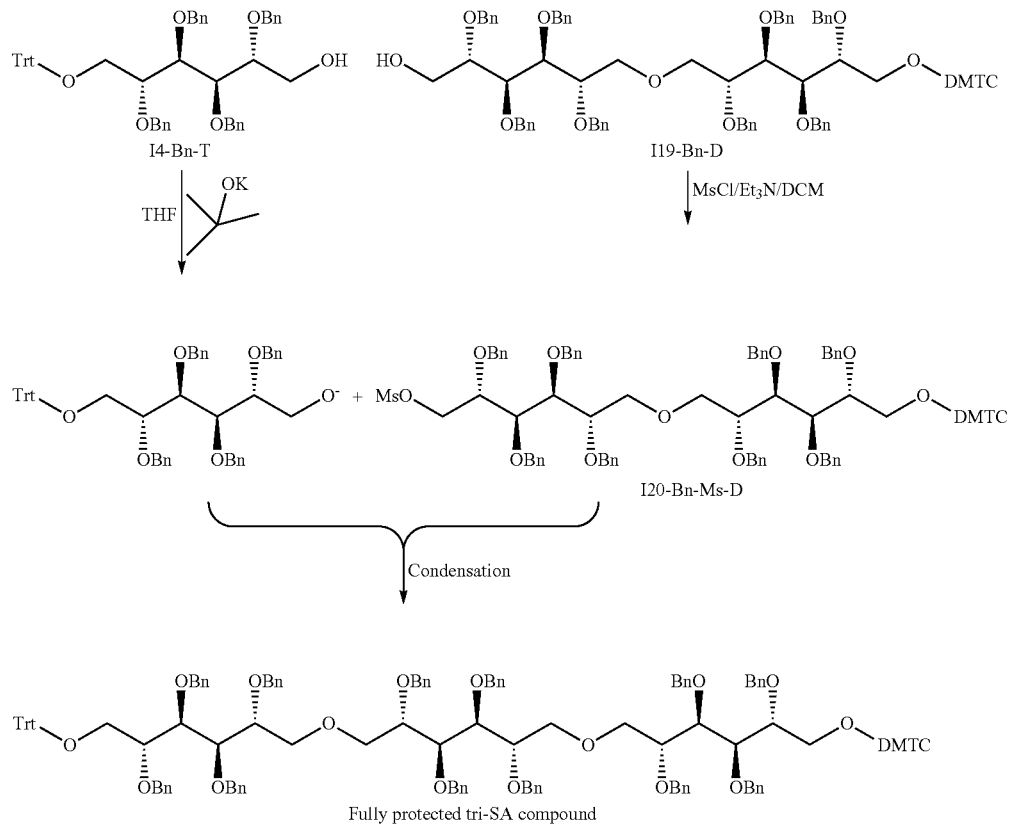

Scheme 35: Synthesis of tri-SA unit by coupling one mono-SA (trityl or methoxy substituted protected) and one di-SA unit (DMTC protected).

Fully protected tri-SA unit: tri-SA unit can also be synthesized by coupling one trityl protected mono-SA with one DMTC proted di-SA unit. The activation and coupling method are essentially the same as the ones described in scheme 33 and 34. The tri-SA compound is purified by silica gel chromatography. The identity of the product is checked by mass spec and the structure confirmed by $^1$H-NMR. The purity is checked by TLC or HPLC.

Example 31

Synthesis of Tri-SA Precursor Units for Further Coupling Using Mannitol as an Example Trt Tri-SA Unit:

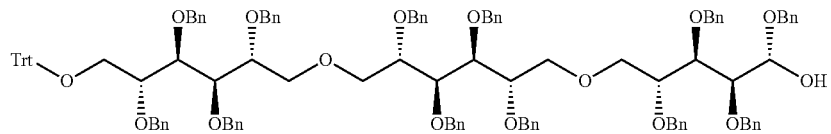

The Trityl tri-SA unit can be synthesized following the same protocol as described for example 29. The fully protected tri-SA compound is dissolved in a mixture of solvent such as THF, MeOH, and water. Oxidizing reagent such as NaIO4 is added. The reaction mixture is stirred at RT or elevated temperature for a few hours. The progress of the reaction is monitored by TLC or HPLC. After the completion of the reaction, the crude reaction mixture is worked up and purified by silica gel chromatography. The product is analyzed by HPLC or TLC. The identity of the product can be confirmed by NMR or MS.

DMTC Tri-SA Unit:

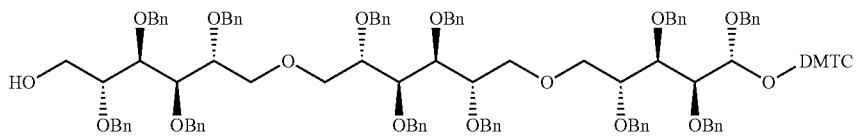

Trityl group can be removed using mild acid such as benzene sulfonic acid or acetic acid. However, the reaction should be monitored very carefully by TLC and HPLC to ensure the right product is formed. The product is analyzed by HPLC or TLC. The identity of the product can be confirmed by NMR or MS.

Example 32

Synthesis of the Tetramer Using Mannitol as an Example

Scheme 36:

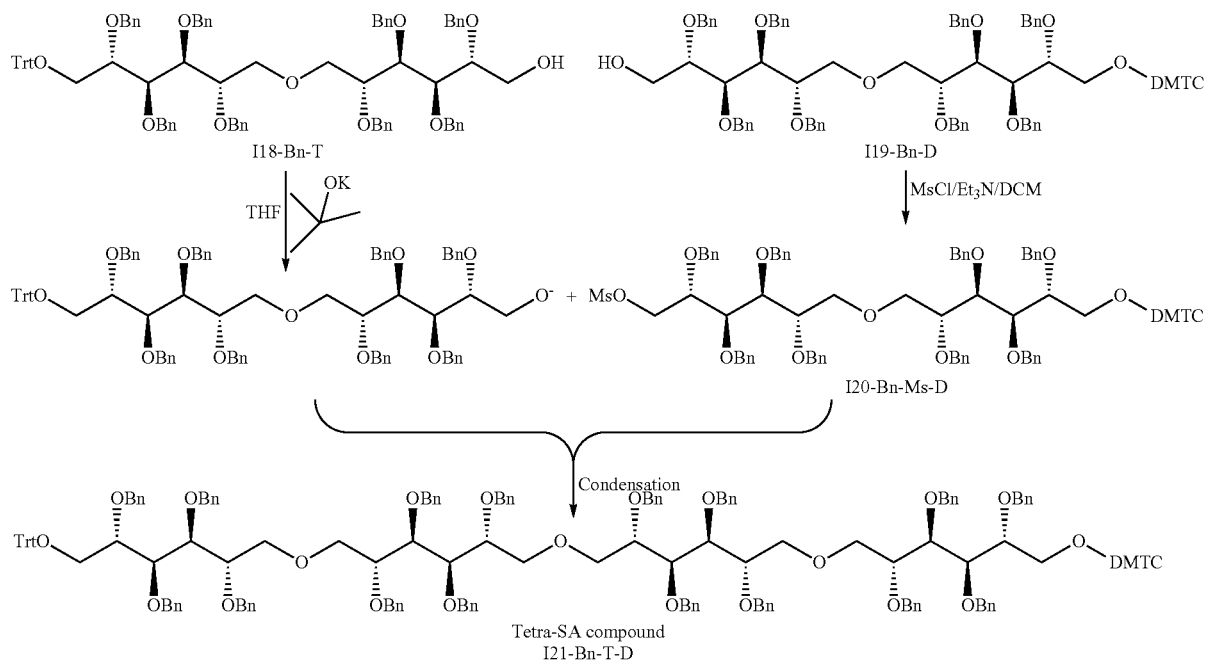

The tetramer SA molecule is synthesized by coupling two of the di-SA units. The first DMTC di-SA unit is activated the same way as the DMTC mono-SA unit, using MsCl. The resulting activated DMTC di-SA unit is coupled to the second Trt di-SA unit in the presence of 1M ButOK following the same procedure as the dimer to obtain the tetramer. The Trt tetra-SA precursor unit is obtained after oxidative cleavage of the DMTC group of the fully protected tetramer SA molecule following previous protocols and can be used for further coupling. The DMTC tetra-SA unit is obtained after mild acid cleavage of the fully protected tetramer SA molecule following previous protocols and can be used for further coupling. A fully deprotected tetramer SA molecule is obtained after mild acid cleavage of the Trt group, hydrogenation of the benzyl ether, and oxidative cleavage of the DMTC group following previous protocols.

Example 33

Synthesis of the Pentamer Using Mannitol as an Example group, hydrogenation of the benzyl ether, and oxidative cleavage of the DMTC group following previous protocols.

Example 34

Synthesis of the Hexamer Using Mannitol as an Example

The hexamer SA molecule is synthesized by coupling two of the tri-SA units or by coupling one Trt or substituted Trt di-SA unit with one Tetra DMTC tetra-SA. Similar to prior experiments, the first DMTC di-SA unit or tri-SA unit is activated using MsCl. The resulting activated DMTC SA unit is coupled to the Trt or substituted Trt SA unit in the presence of 1M ButOK following the same procedure as the dimer to obtain the hexamer. The Trt or substituted Trt hexa-SA precursor unit is obtained after oxidative cleavage of the DMTC group of the fully protected hexamer SA molecule following previous protocols and can be used for further coupling. The DMTC hexa-SA unit is obtained after mild acid cleavage of the fully protected hexamer SA molecule following previous protocols and can be used for

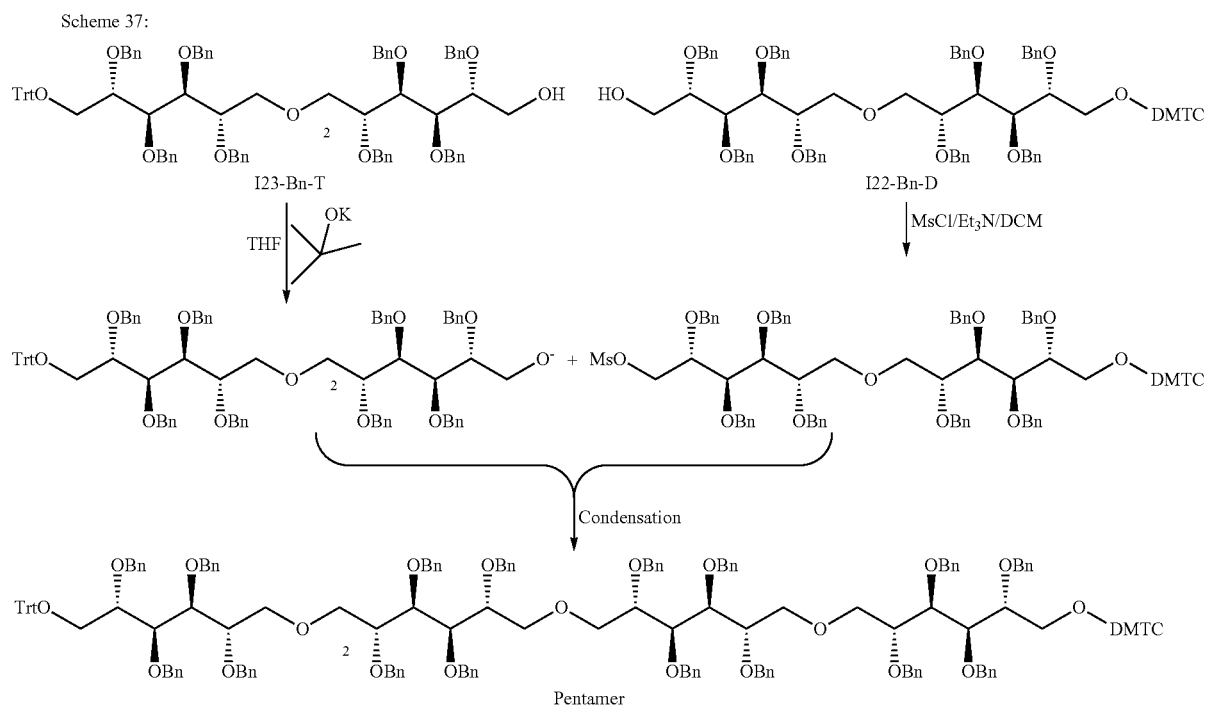

The pentamer SA molecule is synthesized by coupling one Trt or substituted Trt tri-SA unit with DMTC di-SA. The first DMTC di-SA unit is activated the same way as the DMTC mono-SA unit, using MsCl. The resulting activated DMTC di-SA unit is coupled to the Trt or substituted Trt tri-SA unit in the presence of 1M ButOK following the same procedure as the dimer to obtain the pentamer. The Trt or substituted Trt penta-SA precursor unit is obtained after oxidative cleavage of the DMTC group of the fully protected pentamer SA molecule following previous protocols and can be used for further coupling. The DMTC penta-SA unit is obtained after mild acid cleavage of the fully protected pentamer SA molecule following previous protocols and can be used for further coupling. A fully deprotected pentamer SA molecule is obtained after mild acid cleavage of the Trt further coupling. A fully deprotected hexamer SA molecule is obtained after mild acid cleavage of the Trt or substituted Trt group, hydrogenation of the benzyl ether, and oxidative cleavage of the DMTC group following previous protocols.

Example 35

Synthesis of the Heptamer Using Mannitol as an Example

The heptamer SA molecule is synthesized by coupling one Trt or substituted Trt tri-SA unit with one DMTC tetra-SA. Similar to prior experiments, the first DMTC tetra-SA unit is activated using MsCl and then coupled to the Trt or substituted Trt tri-SA unit in the presence of 1M ButOK following the same procedure as the dimer, to obtain the heptamer. The Trt or substituted Trt hepta-SA precursor unit is obtained after oxidative cleavage of the DMTC group of the fully protected heptamer SA molecule following previous protocols and can be used for further coupling. The DMTC hepta-SA unit is obtained after mild acid cleavage of the fully protected heptamer SA molecule following previous protocols and can be used for further coupling. A fully deprotected heptamer SA molecule is obtained after mild acid cleavage of the Trt group, hydrogenation of the benzyl ether, and oxidative cleavage of the DMTC group following previous protocols.

Example 36

Synthesis of the Octamer Using Mannitol as an Example

The octamer SA molecule is synthesized by coupling two of the tetra-SA units or by coupling any of the Trt or substituted Trt r1-SA unit with a DMTC r2-SA unit, where the combined value of r1 and r2 is 8 (r represents the number of SA units in one molecule). Similar to prior experiments, the first DMTC tetra-SA unit is activated using MsCl and then coupled to the Trt or substituted Trt tetra-SA unit in the presence of 1M ButOK following the same procedure as the dimer to obtain the heptamer. The Tri or substituted Trt octa-SA precursor unit is obtained after oxidative cleavage of the DMTC group of the fully protected octamer SA molecule following previous protocols and can be used for further coupling. The DMTC octa-SA unit is obtained after mild acid cleavage of the fully protected octamer SA molecule following previous protocols and can be used for further coupling. A fully deprotected octamer SA molecule is obtained after mild acid cleavage of the Trt or substituted Trt group, hydrogenation of the benzyl ether, and oxidative cleavage of the DMTC group following previous protocols.

Example 37

Synthesis of Nonamer Mannitol

The nonamer SA molecule is synthesized by coupling any of the Trt or substituted Trt r1-SA unit with a DMTC r2-SA unit, where the combined value of r1 and r2 is 9. In one example, the first DMTC tetra-SA unit is activated using MsCl and then coupled to the Trt or substituted Trt Penta-SA unit in the presence of 1M ButOK following the same procedure as the dimer to obtain the nonamer. The nonamer can then be selectively deprotected to obtain Trt or substituted Trt nona-SA unit and DMTC nona-SA unit for further coupling following previous protocols. A fully deprotected nonamer SA molecule is obtained after mild acid cleavage of the Trt or substituted Trt group, hydrogenation of the benzyl ether, and oxidative cleavage of the DMTC group following previous protocols.

Example 38

Synthesis of the Decamer Using Mannitol as an Example

The decamer SA molecule is synthesized by coupling two of the penta-SA units or by coupling any of the Trt or substituted Trt r1-SA unit with a DMTC r2-SA unit, where the combined value of r1 and r2 is 10. In one example, the first DMTC tetra-SA unit is activated using MsCl and then coupled to the Trt or substituted Trt hexa-SA unit in the presence of 1M ButOK following the same procedure as the dimer to obtain the nonamer. The decamer can then be selectively deprotected to obtain Trt or substituted Trt deca-SA unit and DMTC deca-SA unit for further coupling following previous protocols. A fully deprotected decamer SA molecule is obtained after mild acid cleavage of the Trt or substituted Trt group, hydrogenation of the benzyl ether, and oxidative cleavage of the DMTC group following previous protocols.

Example 39

Synthesis of the Single MW SA Polymer Using Mannitol as an Example

Depending on the total number of SA unit in the SA polymer, the single MW SA polymer is synthesized by coupling any of the Trt or substituted Trt r1-SA units with a DMTC r2-SA unit, where the combined value of r1 and r2 is the total number of the SA unit in the SA polymer. In one example, the first DMTC r2-SA unit is activated using MsCl and then coupled to the Trt r1-SA unit in the presence of 1M ButOK following the same procedure as the dimer to obtain the single MW SA polymer. The SA polymer can be selectively deprotected to obtain either Trt or DMTC protected SA polymer. Functional groups X and Y can then be assembled into the termini group by substituting the primary OH with desired crosslinking groups at the termini according to the methods described in this invention. A fully deprotected single MW SA polymer is obtained after mild acid cleavage of the Trt or substituted Trt group, hydrogenation of the benzyl ether, and oxidative cleavage of the DMTC group following previous protocols.

Example 40

Synthesis of Substituted Trityl Protected Mono-SA Units Using Mannitol as an Example Scheme 38: Synthetic route to the monomethoxy Trt mono-SA unit from mannitol.

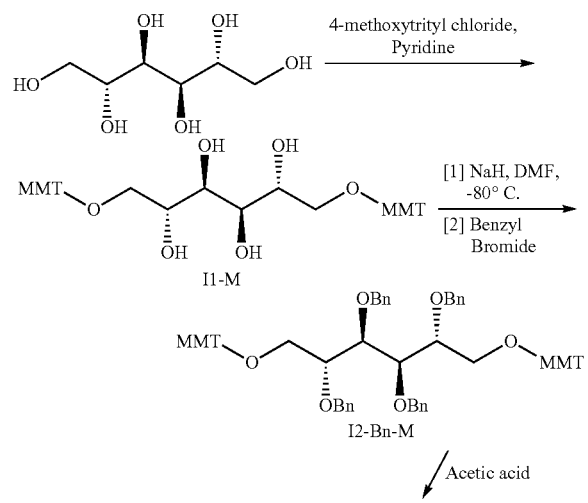

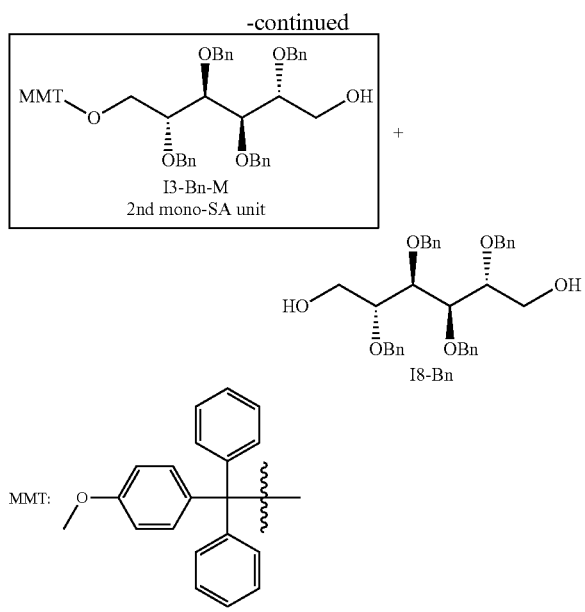

I3-Bn-M
2nd mono-SA unit 1,6-di-O-trityl-D-mannitol (I1-M): To a flask containing 1 g of D-mannitol (5.49 mmols) and 3.73 g of 4-methoxytrityl chloride (12.07 mmols) were added 26.7 mL anhydrous DCM. Once all material dissolved 13.35 mL of pyridine was added. The reaction mixture was refluxed for 5 hours then allowed to cool to RT overnight. The reaction was quenched with 25 mL of water then extracted 3 times with 7 mL of DCM buffered with 0.1% triethylamine. The organic fractions were combined then washed 3 times with 7 mL of brine. The DCM layers were dried over anhydrous $Na_2SO_4$, filtered, and concentrated under reduced pressure. The resulting residue was dissolved in a minimum amount of DCM and subjected to silica gel column chromatographic purification (EtOAc/hexanes) to obtain 3.2 g of the desired product (80% yield). $^1$H-NMR (500 MHz, $CDCl_3$): δ 7.34 (m, 6H, aromatic), 7.24 (m, 24H, aromatic), 6.71 (m, 4H, aromatic), 3.83 (s, 1H, —OH), 3.72 (s, 6H, $CH_3$), 3.687 (broad peak, 4H, CH2), 3.24 (m, 4H, —CH—), 2.88 (s, 1H, —OH), 2.62 (s, 1H, —OH). Mass spec analysis (MALDI-TOF): exact mass: 726.32, obtained: 749.86 $[M+Na]^+$.

1,6-di-O-MMT-2,3,4,5-tetra-O-benzyl-D-mannitol (I2-Bn-M): 4.95 g (6.8 mmol) of 1,6-di-O-MMT-D-mannitol and 2.18 g of NaH (60% oil dispersion) were added into a 250 mL round-bottom flask. The flask was purged with $N_2$ and cooled in a dry ice/isopropanol bath, and then 60 mL of anhydrous DMF was added. After stirring for 5 min, 5.24 g (30.66 mmol) of benzyl bromide was added slowly to the reaction mixture. The dry ice/iPrOH bath was removed and the reaction mixture stirred at RT for 3 hr. 200 mL of EtOAc and 50 mL of deionized water were added to the reaction mixture. After separation, the water layer was back extracted three times with EtOAc. The combined EtOAc layers were washed three times with brine, dried over anhydrous $Na_2SO_4$, filtered, and concentrated under reduced pressure. The resulting residue was dissolved in a minimum amount of DCM and subjected to silica gel column chromatographic purification (EtOAc/hexanes) to obtain 6.9 g of the desired product (94% yield). HPLC retention time: 4.851 min (5-95% ethyl acetate over 15 minutes, silica gel column). $^1$H-NMR (500 MHz, $CDCl_3$): δ 7.41 (m, 3H, aromatic), 7.33 (d, 1H, aromatic), 7.27-7.05 (m, 14H, aromatic), 4.70-4.20 (m, 8H, —$C_6H_5$—$CH_2$—), 4.04 (q, 1H, 3.78 (m, 2H, alkyl), 3.62 (s, 3H), 3.60 (dd, 1H, alkyl), other peaks from minor impurities such as MMTrityl-OH. 13C-NMR (500 MHz, $CDCl_3$): δ 158.71, 158.44, 147.11, 144.56, 139.19, 138.39, 137.85, 135.44, 130.47, 129.20, 128.53, 128.46, 128.36, 128.31, 128.22, 128.07, 127.93, 127.86, 127.81, 127.73, 127.69, 127.64, 127.44, 127.40, 127.29, 127.22, 127.13, 126.78, 113.19, 113.03, 79.67, 78.84, 77.25, 76.98, 76.74, 74.46, 74.29, 73.78, 71.88, 71.47, 71.26, 60.40, 55.22 ($CH_3$). Mass spec analysis (MALDI-TOF): exact mass: 1086.51, obtained: 1110.17 $[M+Na]^+$.

1-O-MMT-6-OH-2,3,4,5-tetra-O-benzyl-D-mannitol (2nd SA unit) (I3-Bn-M): To a flask containing 2.1 g of di-MMT protected D-mannitol (1.9343 mmols) in 9 mL of DCM was added 2.3 mL of glacial acetic acid and 19.3 mL of a 20% acetic acid in MeOH. The reaction mixture was stirred at RT for 23 hours and then cooled to 0 degree in an ice/water bath. 14.37 mL of triethylamine was then added slowly. The reaction mixture was then concentrated in vacuo, redissolved in DCM buffered with 0.1% triethylamine, and washed three times with 20 mL of water, then dried over dried over anhydrous $Na_2SO_4$, filtered, concentrated. The resulting residue was dissolved in a minimum amount of DCM and subjected to silica gel column chromatographic purification (EtOAc/hexanes) to obtain 0.374 g of the desired product (24% yield). HPLC retention time: 6.623 minutes (5-95% ethyl acetate, silica gel column). $^1$H-NMR (500 MHz, $CDCl_3$): δ 7.41 (m, 4H, aromatic), 7.28-7.07 (m, 40H, aromatic), 6.97 (q, 2H, aromatics), 4.70 (d, 1H, —$C_6H_5$—$CH_2$—), 4.55-4.62 (dd, 1H, —$C_6H_5$—$CH_2$—), 4.50-4.43 (m, 3H, —$C_6H_5$—$CH_2$—), 4.40 (d, 1H, —$C_6H_5$—$CH_2$—), 4.37-4.29 (m, 2H, —$C_6H_5$—$CH_2$—), 4.01-3.97 (m, 2H, -MMT-O—$CH_2$), 3.85 (m, 2H, —$CH_2$—OH), 3.83 (d, 1H, —CH—), 3.78 (m, 1H, —CH—), 1 3.75 (m, 1H, —CH—), 3.64 (s, 3H, $CH_3$), 3.62 (m, 1H, —CH—), other peaks from minor impurities such as MMTrityl-OH. $^{13}$C-NMR (500 MHz, $CDCl_3$): δ 158.71, 158.48, 147.09, 144.57, 139.18, 138.56, 138.40, 138.21, 137.94, 130.44, 129.18, 128.50, 128.44, 128.35, 128.30, 128.21, 128.06, 127.92, 127.84, 127.81, 127.71, 127.67, 127.63, 127.39, 127.11, 126.77, 113.17, 113.00, 79.65, 78.80, 77.24, 76.97, 76.72, 74.43, 71.48, 62.00, 60.38, 57.00, 56.00, 9.10 ($CH_3$). Mass spec analysis (MALDI-TOF): exact mass: 814.39, obtained: 837.83 $[M+Na]^+$.

Scheme 39: Synthetic route to the monomethoxy Trt mono-SA unit from tetra-Bn protected mannitol.

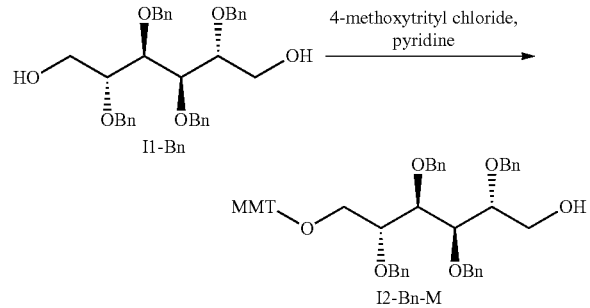

Compound I2-Bn-M: To a flask containing 7 g of tetra Bn protected D-mannitol (12.9 mmols) and 4.185 g of 4-methoxytrityl chloride (13.55 mmols) was added 432 mL of anhydrous DCM. Once all materials were dissolved, 31.4 mL of pyridine was added. The reaction mixture was refluxed for 4 hours then allowed to cool to RT overnight.

The reaction was diluted with 350 mL of DCM buffered with 0.1% triethylamine and 150 mL of water. The DCM layer was separated out from the aqueous layer. The aqueous layer was back extracted three times with DCM buffered with 0.1% triethylamine. The organic fractions were combined, and then washed 3 times with brine. The DCM layers were dried over anhydrous Na$_2$SO$_4$, filtered, and concentrated under reduced pressure. The resulting residue was dissolved in a minimum amount of DCM and subjected to silica gel column chromatographic purification (EtOAc/hexanes) to obtain 5.55 g of the desired product (53% yield). HPLC retention time: 6.664 min (5-95% ethyl acetate in 15 minutes, silica gel column).

Example 41

Synthesis SA Unit with Aminooxy Functional Group

Scheme 40:

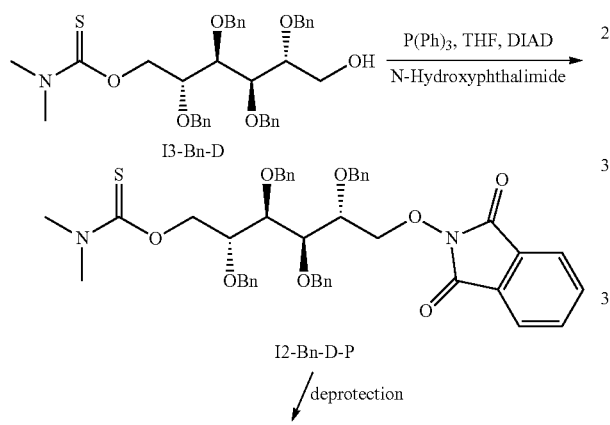

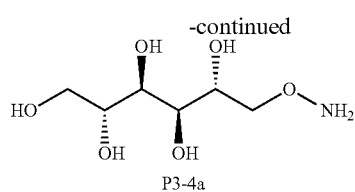

P3-4a

Compound I2-Bn-D-P: To a flask containing a 0.5 g of DMTC protected SA unit (I3-Bn-D) (0.794 mmols), 0.194 g of N-hydroxyphthalimide (0.191 mmols), and 0.312 g of triphenylphosphine (1.191 mmols) was added 8.09 mL of anhydrous THF. Once all materials were dissolved, the flask was cooled to −4 degrees in an ice/salt bath followed by addition of 249 μL of diethyl azodicarboxylate (1.578 mmols). The reaction was run for 3 hours before it was concentrated down then dissolved in 25 mL of diethyl ether. The organic layer was washed 3 times with 10 mL of saturated sodium bicarbonate. The organic layer was then dried over anhydrous Na$_2$SO$_4$, filtered, concentrated, and purified by silica gel column to obtain 0.4 g of desired product (65% yield). Mass spec analysis (MALDI-TOF): exact mass: 774.3, obtained: 797.7213 [M+Na]$^+$. $^1$H-NMR (500 MHz, CDCl$_3$): δ 7.69 (dd, 2H, phthalimide aromatic), 7.61 (dd, 2H, phthalimide aromatic), 7.26-7.12 (m, 20H, benzyl aromatics), 5.02-4.99 (dd, 1H, —C$_6$H$_5$—CH$_2$—), 4.84-4.80 (q, 2H, —C$_6$H$_5$—CH$_2$—), 4.64-4.51 (m, 6H, 5H —C$_6$H$_5$—CH$_2$— and 1H from —CH$_2$—O—), 4.45-4.43 (dd, 2H, —CH$_2$—O—), 4.35-4.32 (d, 1H, —CH$_2$—O—), 4.08 (m, 1H, alkyl), 4.05 (m, 1H, alkyl), 3.95 (q, 1H, alkyl), 3.89 (m, 1H, alkyl), 3.24 (s, 3H, —CH$_3$), 2.91 (s, 3H, —CH$_3$).

Compound p3-4a: A fully deprotected SA molecule is obtained after hydrazine cleavage of phthalimide group, hydrogenation of the benzyl ether, and oxidative cleavage of the DMTC group following previous protocols.

Example 42

Synthesis SA Unit with Heterobifunctional Crosslinking Group

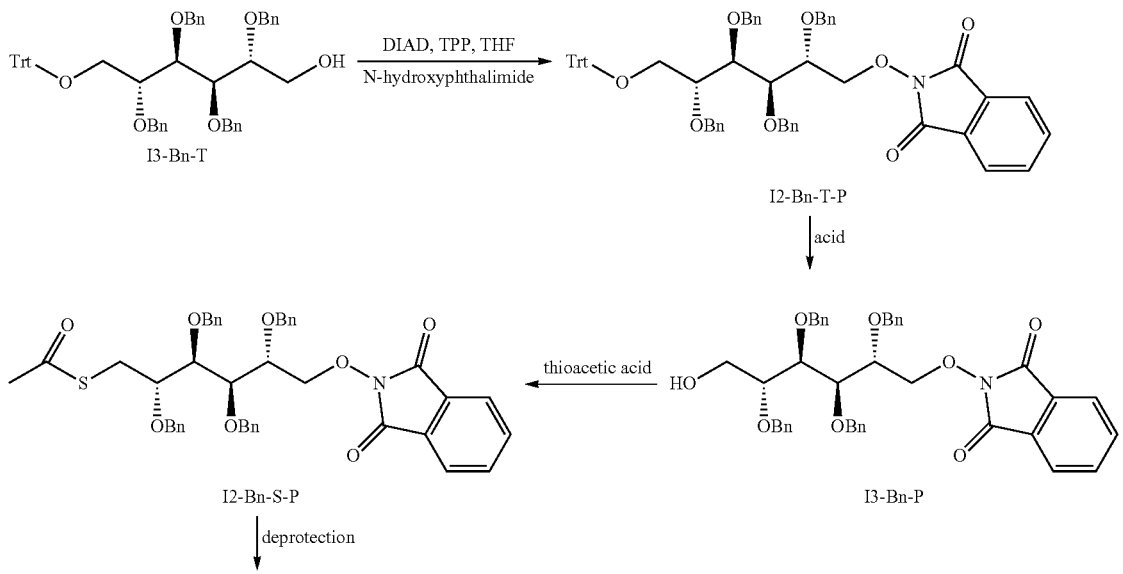

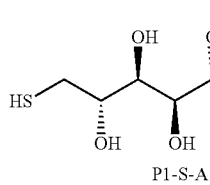

P1-S-A

→

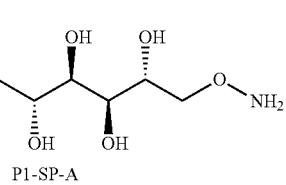

P1-SP-A

Compound I2-Bn-T-P: To a flask containing 0.5 g of Trityl protected SA compound (I3-Bn-T) (637 mmols), 0.156 g of N-hydroxyphthalimide (0.9554 mmols), and 0.25 g of triphenylphosphine (0.9554 mmols) was added 6.5 mL of anhydrous THF. Once all materials were dissolved, the flask was cooled to −4 degrees in an ice/salt bath, and then 222 uL of diethyl azodicarboxylate (1.274 mmols) was added. The reaction mixture was stirred for 24 hours before it was concentrated down then dissolved in 25 mL of diethyl ether. The organic layer was washed 3 times with saturated sodium bicarbonate. The organic layer was then dried over anhydrous sodium sulfate, concentrated, and purified by silica gel column to obtain 0.549 g of desired product (93% yield). $^1$H-NMR (500 MHz, CDCl$_3$): δ 7.701-7.673 (q, 2H, phthalimide aromatics), 7.629-7.604 (q, 2H, phthalmide aromatics), 7.40 (m, 6H, aromatics), 7.30-7.22 (m, 4H, aromatics), 7.19-7.08 (m, 23H, aromatics), 6.918 (m, 2H, aromatics), 4.814-4.755 (dd, 2H, CH$_2$), 4.69-4.60 (dd, 2H, CH$_2$), 4.51 (d, 1H, CH$_2$), 4.445 (m, 4H, 2CH$_2$), 4.32-4.299 (d, 1H CH$_2$), 4.14-4.09 (m, 2H, CH$_2$), 4.047 (m, 1H, CH), 3.812 (m, 1H, CH), 3.603-3.572 (dd, 1H, CH), 3.253 (q, 1H, CH). Mass spec analysis (MALDI-TOF): exact mass: 929.39, obtained: 953.97 [M+Na]$^+$.

Compound I3-Bn-P: To a flask containing 0.519 g of 12-Bn-T-P (0.5585 mmols) was added 9.3 mL of DCM. After stirred for few minutes, 2.5 mL of methanol was added slowly followed by the addition of 0.0486 g of benzene sulfonic acid (0.3072 mmols). After 5 hours the reaction mixture was concentrated down and then purified by silica gel column to obtain 0.193 g of the desired product (51% yield). Mass spec analysis (MALDI-TOF): exact mass: 687.28, obtained: 710.5086 [M+Na]$^+$. HPLC retention time: 4.763 min (5-95% ethyl acetate over 15 minutes, silica gel column). $^1$H-NMR (500 MHz, CDCl$_3$): δ 7.69 (dd, 2H, phthalimide aromatic), 7.62 (dd, 2H, phthalimide aromatics), 7.26-7.12 (m, 20H, benzyl aromatics), 4.82-4.79 (dd, 2H, —C$_6$H$_5$—CH$_2$—), 4.66-4.79 (m, 6H, —C$_6$H$_5$—CH$_2$—), 4.45-4.42 (dd, 2H, —CH$_2$—O-phthalmide), 4.33-4.31 (d, 1H, alkyl H), 4.18-4.15 (dd, 1H, alkyl H), 4.07-4.02 (m, 2H, —CH$_2$—OH), 3.94-3.92 (m, 1H, alkyl), 3.79 (m, 1H, alkyl H).

Compound I2-Bn-S-P: To a flask containing triphenylphosphine (0.0974 g, 0.3714 mmols) was added 800 μL of anhydrous tetrahydrofuran. Once all reagents were dissolved the flask was cooled to −4 degrees in an ice/salt bath then 0.0647 g of diethyl azodicarboxylate (0.0628 mmols) was added. The flask was left stirring at −4 degrees for 1 hour before 0.17 g of I3-Bn-P (0.2476 mmols) in 1 mL of anhydrous THF solution was added followed by 0.0377 g of thioacetic acid (0.0349 mmols). The reaction mixture was concentrated down after 3 hr, re-dissolved in DCM, and then washed 3 times with saturated NaHCO$_3$. The resulting organic fraction was then dried over anhydrous anhydrous Na$_2$SO$_4$, filtered, concentrated, and purified by silica gel column to obtain 0.1 g of the desired product (58% yield). HPLC retention time: 6.465 minutes (5-95% ethyl acetate over 15 minutes, silica gel column). Mass spec analysis (MALDI-TOF): exact mass: 745.27, obtained: 746.3 [M+H]$^+$. $^1$H-NMR (500 MHz, CDCl$_3$): δ 7.720-7.701 (q, 2H, phthalimide), 7.651-7.629 (q, 2H, phthalimide), 7.258-7.129 (m, 20H, OBn aromatics), 4.79 (d, 2H, CH$_2$), 4.65-4.59 (m, 4H, 2CH$_2$), 4.50 (dd, 2H, CH$_2$), 4.37 (dd, 1H, CH$_2$), 4.35 (d, 1H, CH$_2$), 3.98 (m, 2H, CH$_2$), 3.87 (t, 1H, CH), 3.72 (m, 1H, CH), 3.40 (dd, 1H, CH), 3.16 (dd, 1H, CH), 2.23 (s, 3H, CH$_3$).

Compound P1-S-A: A fully deprotected single thiol and aminooxy heterobifunctional SA crosslinking reagent is obtained after cleavage of the phthalimide group, hydrogenation of the benzyl ether, and acetal group following previous protocols.

Compound P1-SP-A: Thiol pyridone group can be attached to the free thiol following previous protocols to prevent the oxidation of free thiol group. It is convenient for any thiol specific conjugation reaction.

Thiol and aminooxy heterobifuncational SA polymer: Thiol and aminooxy heterobifuncational SA polymer with any length or MW can be made the same way as the monomer case (P1-S-A).

INCORPORATION BY REFERENCE

The entire disclosure of each of the publications and patent documents referred to herein is incorporated by reference in its entirety for all purposes to the same extent as if each individual publication or patent document were also individually denoted.

EQUIVALENTS

The invention may be embodied in other specific forms without departing from the spirit or essential characteristics thereof. The foregoing embodiments are therefore to be considered in all respects illustrative rather than limiting of the invention described herein. The scope of the invention is thus indicated by the appended claims rather than by the foregoing description, and all changes that come within the meaning and range of equivalent with the claims are intended to be embraced therein.

The invention claimed is:
1. A compound having a linear multimer sugar alcohol comprising three or more monomeric sugar alcohol unit B$^1$, where
  each monomeric sugar alcohol unit is bound to one or more other monomeric units through a linking group W formed by a reaction between the X, Y or Z portion of one monomeric unit with the X, Y or Z of another monomeric unit;

wherein
each $B^1$ has the chemical structural Formula XV:

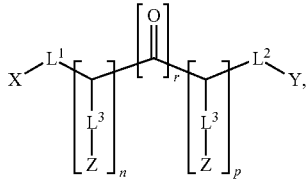
(XV)

wherein for each $B^1$, independently:
each of n and p is independently selected from 0 and an integer selected from 1 to about 12; and
n+p is between 1 and 12;
r is 0 or 1;
each of X and Y is independently selected from —OH, -J, —C(=O)-J, —C(=O)—CH$_2$-J, —NH—C(=O)—CH$_2$-J, —OR$^5$, —OR$^6$, —O-Mesyl, —O-Tosyl, NH—C(=O)—CH$_2$—O-Mesyl, —NH—C(=O)—CH$_2$—O-Tosyl, —SH, —S—S-tBuyl, —SR$^5$, —NHR$^5$, —NHR$^7$, —NH-Fmoc, —NH-Boc, —C(=O)H, —C(=O)OH, —N=C=S, —N=C=O, —N=N+=N—, —O—NH$_2$, —O—NH-Fmoc, —O—NH-Boc, —O—N-(Boc)$_2$, —O—N (-phthalimidyl), —NH—NH$_2$, —C(=O)—NH—NH$_2$, —NH—C(=S)—NH—NH$_2$, -toluenesulfonylhydrazide, a benzophenone, an aryl diazonium, a diazoalkane, a diazoacetyl, a diazirine, a diene, an alkene, a ketene, an alkene with allylic hydrogen, an epoxide, and an oxirane;
$R^5$ is $C_1$-$C_8$ alkyl;
$R^6$ is benzyl;
each $R^7$ is independently selected from the group consisting of trityl, MMT and DMT
each J is independently selected from the group consisting of Cl, Br and I;
each of $L^1$ and $L^2$ is $R^2$;
each W is independently selected from O, NH or a linking group formed by X and Y;
each $R^2$ is independently selected from —CH$_2$ or a bond;
each -$L^3$-Z is —OR$^1$, wherein each $R^1$ is independently selected from the group consisting of hydrogen, $C_1$-$C_8$ alkyl, benzoyl, acetyl, benzyl, $C_1$-$C_8$ alkyl silyl, cyclic ortho ester, acetate, tetrahydropyranyl, tetrahydrofuranyl, and tetrahydrothiofuranyl; and
at least in one of the $B^1$ unit, n+p+r is greater than 1.

2. The compound of claim 1, wherein
each X is —O—(C$_1$-C$_8$ alkyl);
at least one Y is —OH, -J, —N=N+=N⁻ or —O—NH$_2$, —NH—(C=O)—CH$_2$—Br, —SH,

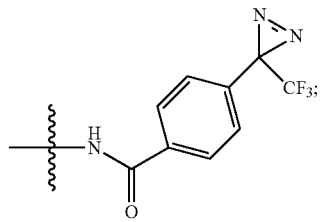 [SMILES: *NC(=O)c1ccc(C2(C(F)(F)F)N=N2)cc1]
and.

3. The compound of claim 1, wherein
$R^1$ is independently selected from the group consisting of hydrogen, $C_1$-$C_8$ alkyl, benzoyl, acetyl, and benzyl.
4. The compound of claim 3, wherein each $L^1$ and $L^2$ is —CH$_2$—.
5. The compound of claim 4, wherein each r is 0.
6. The compound of claim 1, wherein the molecular weight is from about 5 kDa to about 500 kDa.
7. The compound of claim 1, wherein the molecular weight of the compound is from about 10 kDa to about 100 kDa.
8. The compound of claim 1, wherein the molecular weight is from about 10 kDa to about 60 kDa.
9. The compound of claim 1, wherein the compound has a purity of greater than 90%.
10. The compound of claim 1, wherein the compound has a purity of greater than 95%.
11. The compound of claim 1, wherein the molecular weight of the compound is from about 10 kDa to about 60 kDa and the compound has a purity of greater than 95%.
12. The compound of claim 1, wherein W is —O—.
13. The compound of claim 1, wherein

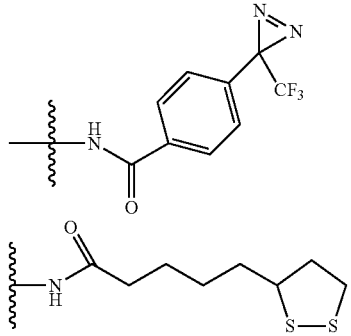

X and Y are different.
14. The compound of claim 13, wherein each -$L^3$-Z is —OH.
15. The compound of claim 14, wherein each $L^1$ and $L^2$ is —CH$_2$—.
16. The compound of claim 15, wherein each r is 0.

* * * * *